US009981033B2

(12) United States Patent
Mebatsion et al.

(10) Patent No.: US 9,981,033 B2
(45) Date of Patent: May 29, 2018

(54) PRRSV MINOR PROTEIN-CONTAINING RECOMBINANT VIRAL VECTORS AND METHODS OF MAKING AND USE THEREOF

(71) Applicant: MERIAL INC., Duluth, GA (US)

(72) Inventors: Teshome Mebatsion, Watkinsville, GA (US); Aemro Kassa, Watkinsville, GA (US); Taejoong Kim, Bogart, GA (US)

(73) Assignee: MERIAL INC., Duluth, GA (US)

( * ) Notice: Subject to any disclaimer, the term of this patent is extended or adjusted under 35 U.S.C. 154(b) by 0 days. days.

(21) Appl. No.: 15/190,740

(22) Filed: Jun. 23, 2016

(65) Prior Publication Data

US 2016/0375122 A1    Dec. 29, 2016

Related U.S. Application Data

(60) Provisional application No. 62/183,410, filed on Jun. 23, 2015.

(51) Int. Cl.
| | | |
|---|---|---|
| *A61K 39/12* | (2006.01) | |
| *C12N 7/00* | (2006.01) | |
| *C07K 14/08* | (2006.01) | |
| *C12N 15/86* | (2006.01) | |
| *A61K 39/00* | (2006.01) | |

(52) U.S. Cl.
CPC ............ *A61K 39/12* (2013.01); *C07K 14/082* (2013.01); *C12N 7/00* (2013.01); *C12N 15/86* (2013.01); *A61K 2039/5256* (2013.01); *A61K 2039/552* (2013.01); *C07K 2319/03* (2013.01); *C12N 2710/10043* (2013.01); *C12N 2770/10034* (2013.01); *C12N 2770/10051* (2013.01); *C12N 2840/203* (2013.01)

(58) Field of Classification Search
None
See application file for complete search history.

(56) References Cited

U.S. PATENT DOCUMENTS

| | | | |
|---|---|---|---|
| 6,495,138 | B1 | 12/2002 | van Nieuwstadt et al. |
| 7,465,455 | B2 | 12/2008 | Chang et al. |
| 8,142,788 | B2 | 3/2012 | Kim |
| 2008/0008722 | A1 | 1/2008 | Chang et al. |
| 2008/0019912 | A1 | 1/2008 | Harris |
| 2009/0208520 | A1 | 8/2009 | Kim |
| 2013/0142824 | A1 | 6/2013 | Ni et al. |
| 2014/0335118 | A1 | 11/2014 | Wang |
| 2016/0375122 | A1* | 12/2016 | Mebatsion ............... C12N 7/00 424/186.1 |

FOREIGN PATENT DOCUMENTS

| | | |
|---|---|---|
| CN | 103421817 A | 12/2013 |
| CN | 103992408 A | 8/2014 |
| WO | WO 96/04010 * | 2/1996 |
| WO | WO 99/39582 A1 | 8/1999 |
| WO | WO 00/03030 A2 | 1/2000 |
| WO | WO 2007/064742 A2 | 6/2007 |
| WO | WO 2012/108840 A1 | 8/2012 |

OTHER PUBLICATIONS

Dokland et al. (Virus Research. 2010; 154: 86-97).*
Cruz et al. (Virus Research. 2010; 154: 150-160).*
Lee et al. (Virology. 2006; 355: 30-43).*
Sequence alignment of SEQ ID No. 8 with GenEmbl access No. AF205184 by Levere et al. on Mar. 2000.*
Sequence alignment of SEQ ID No. 8 with GenEmbl access No. FJ629370 by Ellingson et al. in Vaccine vol. 28 No. 14 pp. 2679-2686 on Apr. 2010.*
Changhee Lee, D. Y. (2006). The small envelope protein of porcine reproductive and respiratory syndrome virus possesses ion channel protein-like properties. *Virology*, 30-43.
Charerntantanakul, W. (2012). Porcine reproductive and respiratory syndrome virus vaccines: Immunogenicity, efficacy and safety aspects. *World Journal of Virology*, 23-30.
Dea S, G. C. (2000). Current knowledge on the structural proteins of porcine reproductive and respiratory syndrome (PRRS) virus: comparison of the North American and European isolates. *Archives of Virology*, 659-688.
Dea, B. P. (1998). Immune response in pigs vaccinated with plasmid DNA encoding ORF5 of porcine reproductive and respiratory syndrome virus. Journal of General Virology, 989-999.
Dokland, T. (2010). The structural biology of PRRSV. *Virus Reserach*, 86-97.
Osorio et al. (2002). Passive Transfer of Virus-Specific Antibodies Confers Protection against Reproductive Failure Induced by a Virulent Strain of Porcine Reproductive and Respiratory Syndrome Virus and Establishes Sterilizing Immunity. *Virology*, 9-20.
Cruz, Jazmina et al. (2010). Vectored vaccines to protect against PRRSV. *Vir Res*, 150-160.
Ren, Jing-Qiang et al. (2014). Construction and immunogenicity of a DNA vaccine coexpressing GP3 and GP5 of genotype-I porcine reproductive and respiratory syndrome virus. *BMC Veterinary Research*, 1-11.
Li, Juan Li, M. P. (2012). Dissociation of porcine reproductive and respiratory syndrome virus neutralization from antibodies specific to major envelope protein surface epitopes. *Virology*, 367-376.
Lu, Z. (2012). Chimeric viruses containing the N-terminal ectodomains of GP5 and M proteins of porcine reproductive and respiratory syndrome virus do not change the cellular tropism of equine arteritis virus. *Virology*, 99-109.

(Continued)

*Primary Examiner* — Shanon A. Foley
(74) *Attorney, Agent, or Firm* — Judy Jarecki-Black; Richard Seeger; Merial Inc.

(57) ABSTRACT

The present invention encompasses recombinant porcine reproductive and respiratory syndrome virus (PRRSV) vaccines or compositions. In particular, the invention encompasses recombinant adenovirus vectors encoding and expressing PRRSV gp2, gp3, gp4, gp5a, gp5 and/or E antigens, proteins, epitopes or immunogens. Such vaccines or compositions can be used to protect animals from PRRSV.

20 Claims, 28 Drawing Sheets

(56) References Cited

OTHER PUBLICATIONS

Yu, Maorong et al. (2010). Subcellular localization and topology of porcine reproductive and respiratory syndrome virus E protein. *Virus Reserach,* 104-114.

Meng, X. (2000). Heterogeneity of porcine reproductive and respiratory syndrome virus: implications for current vaccine ef® cacy and future vaccine development. *Veterinary Microbiology 74* (2000) 309±329, 309-329.

Lopez, O. J. et al. (2007). Protection against Porcine Reproductive and Respiratory Syndrome Virus (PRRSV) Infection through Passive Transfer of PRRSV-Neutralizing Antibodies Is Dose Dependent. *linical and Vaccine Immunology,* 269-275.

Das, Phani et al. (2010). The Minor Envelope Glycoproteins GP2a and GP4 of Porcine Reproductive and Respiratory Syndrome Virus Interact with the Receptor CD163. *Journal of Virology,* 1731-1740.

Randall S. Prather, R. R. (2013). An Intact Sialoadhesin (Sn/SIGLEC1/CD169) Is Not Required for Attachment/Internalization of the Porcine Reproductive and Respiratory Syndrome Virus. *Journal of Virology,* 9538-9546.

Sakthivel Subramaniam, P. P. (2014). In vivo targeting of porcine reproductive and respiratory syndrome virus antigen through porcine DC-SIGN to dendritic cells elicits antigen-specific CD4T cell immunity in pigs. *Vaccine,* 6768-6775.

Tian D, W. Z.-D. (2012). Arterivirus minor envelope proteins are a major determinant of viral tropism in cell culture. *Journal of Virology,* 3701-3712.

Tjeerd G. Kimman, L. A.-Z. (2009). Challenges for porcine reproductive and respiratory syndrome virus (PRRSV) vaccinology. *Vaccine,* 3704-3718.

Yijun Du, F. A. (2010). Myristoylation of the small envelope protein of porcine reproductive and respiratory syndrome virus is nonessential for virus infectivity but promotes its growth. *Virus Research,* 294-299.

Z.S. Wang, X. X. (2011). Immunogenicity of the envelope GP3 protein of porcine reproductive and respiratory syndrome virus displayed on baculovirus. *Acta Virologica,* 139-146.

Zhang, J. H. (2012). Porcine Reproductive and Respiratory Syndrome Virus Vaccines: Current Status and Strategies to a Universal Vaccine. *Transboundary and Emerging Diseases,* 109-120.

Amonsin Alongkorn et al: "Comparative analysis of complete nucleotide sequence of porcine reproductive and respiratory syndrome virus (PRRSV) isolates in Thailand {US and EU genotypes)", Virology Journal, Biomed Central, London, GB, vo 1 • 6, No. 1, Sep. 16, 2009 (Sep. 16, 2009), p. 143, XP021059669.

Jiang W et al.: "Enhanced immune responses of mice inoculated recombinant adenoviruses expressing GP5 by fusion with GP3 and/or GP4 of PRRS virus" Virus Research, Amsterdam, NL, vol. 136, No. 1-2, Sep. 2008, pp. 50-57, XP022818917.

Nedzad Music et al: "The role of porcine reproductive and respiratory syndrome (PRRS) virus structural and non-structural proteins in virus pathogenesis", Animal Health Research Reviews, vo 1 . 11, No. 02 , Apr. 14, 2010 (Apr. 14, 2010), pp. 135-163, XP055299831.

* cited by examiner

E.
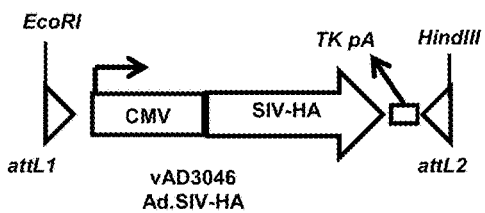
F.
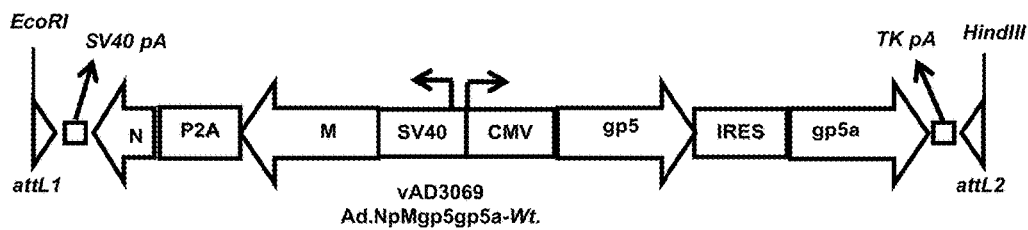
G.
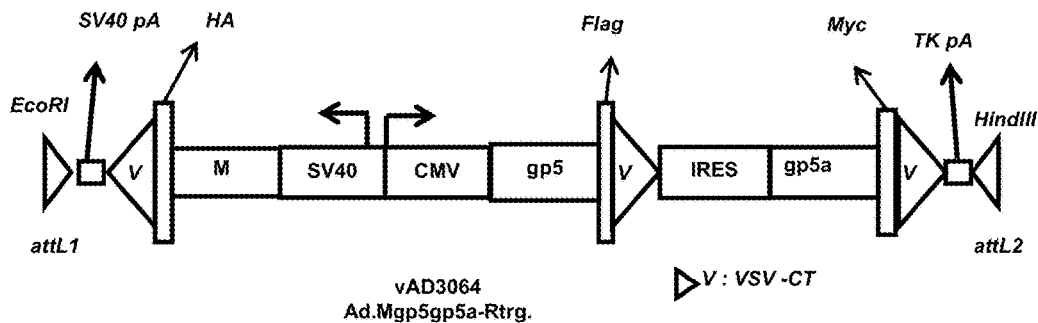
*FIG. 1 (Continued)*

Total protein Expression

Cell-surface Expression

| SEQ ID # | Type | Description |
|---|---|---|
| 1 | Polypeptide | PRRSV gp2 polypeptide, from VR2332, PRRSV Type II (entire viral sequence provided by Accession #:U87392.3, incorporated by reference in its entirety) |
| 2 | DNA/RNA | VR2332 PRRSV gp2 (12073..12843 of VR2332) |
| 3 | Polypeptide | VR2332 PRRSV gp3 polypeptide |
| 4 | DNA/RNA | VR2332 PRRSV gp3 (12696..13460 of VR2332) |
| 5 | Polypeptide | VR2332 PRRSV gp4 polypeptide |
| 6 | DNA/RNA | VR2332 PRRSV gp4 (13241..13777 of VR2332) |
| 7 | Polypeptide | VR2332 PRRSV E polypeptide |
| 8 | DNA/RNA | VR2332 PRRSV E (12078..12299 of VR2332) |
| 9 | DNA/RNA | VR2332 PRRSV gp2 (codon-optimized) |
| 10 | DNA/RNA | VR2332 PRRSV gp3 (codon-optimized) |
| 11 | DNA/RNA | VR2332 PRRSV gp4 (codon-optimized) |
| 12 | DNA/RNA | VR2332 PRRSV E (codon-optimized) |
| 13 | DNA/RNA | VR2332 PRRSV *rtg*-gp2 DNA (codon-optimized, re-targeted) |
| 14 | Polypeptide | VR2332 PRRSV *rtg*-gp2 polypeptide (gp2-myc-VSV) |
| 15 | DNA/RNA | VR2332 PRRSV *rtg*-gp3 DNA (codon-optimized, re-targeted) |
| 16 | Polypeptide | VR2332 PRRSV *rtg*-gp3 polypeptide (gp3-Flag-VSV) |
| 17 | DNA/RNA | VR2332 PRRSV *rtg*-gp4 DNA (codon-optimized, re-targeted) |
| 18 | Polypeptide | VR2332 PRRSV *rtg*-gp4 polypeptide (gp4-HA-VSV) |
| 19 | DNA/RNA | VR2332 PRRSV *rtg*-E (codon-optimized, re-targeted) |
| 20 | Polypeptide | VR2332 PRRSV *rtg*-E polypeptide |
| 21 | DNA/RNA | vAD3038 pre-recombination insert |
| 22 | DNA/RNA | vAD3041 pre-recombination insert |
| 23 | DNA/RNA | vAD3042 pre-recombination insert |
| 24 | DNA/RNA | vAD-*rtg*-gp234-E pre-recombination insert |
| 25 | DNA/RNA | vAD3033 pre-recombination insert |
| 26 | DNA/RNA | pAd5 Forward primer |
| 27 | DNA/RNA | pAd5 Reverse primer |
| 28 | DNA/RNA | Entire VR2332, PRRSV Type II sequence |
| 29 | DNA/RNA | Entire Lelystad PRRSV sequence (GenBank: A26843.1) |
| 30 | DNA/RNA | pAd/PL-DEST vector; attR1 site: 512-636; attR2 site: 2092-2216 |
| 31 | Polypeptide | PRRSV gp5a |
| 32 | Polypeptide | VR2332 PRRSV M (matrix protein) |
| 33 | Polypeptide | VR2332 PRRSV N (nucleocapsid protein) |

*FIG. 12*

| SEQ ID # | Type | Description |
|---|---|---|
| 34 | Polypeptide | ABO40192.1 PRRSV gp2 |
| 35 | Polypeptide | ACF93748.1 PRRSV gp2 |
| 36 | Polypeptide | AHA83141.1 PRRSV gp2 |
| 37 | Polypeptide | CAA01838.1 PRRSV gp2 |
| 38 | Polypeptide | AAE74522.1 PRRSV gp2 |
| 39 | Polypeptide | AAB54503.1 PRRSV gp2 |
| 40 | Polypeptide | AAE68461.1 PRRSV gp3 |
| 41 | Polypeptide | AAQ51784.1 PRRSV gp3 |
| 42 | Polypeptide | AAE74530.1 PRRSV gp3 |
| 43 | Polypeptide | CAA01839.1 PRRSV gp3 |
| 44 | Polypeptide | ABH73414.1 PRRSV gp3 |
| 45 | Polypeptide | AAE74526.1 PRRSV gp3 |
| 46 | Polypeptide | AAE74537.1 PRRSV gp4 |
| 47 | Polypeptide | AAE74538.1 PRRSV gp4 |
| 48 | Polypeptide | AAE74533.1 PRRSV gp4 |
| 49 | Polypeptide | CAA01840.1 PRRSV gp4 |
| 50 | Polypeptide | ABH73415.1 PRRSV gp4 |
| 51 | Polypeptide | AAE68462.1 PRRSV gp4 |
| 52 | Polypeptide | AGX46781.1 PRRSV E |
| 53 | Polypeptide | AED17147.1 PRRSV E |
| 54 | Polypeptide | AED17148.1 PRRSV E |
| 55 | Polypeptide | AGX46783.1 PRRSV E |
| 56 | Polypeptide | AED17156.1 PRRSV E |
| 57 | Polypeptide | AIS76359.1 PRRSV E |
| 58 | Polypeptide | ABU49670.1 PRRSV E |
| 59 | Polypeptide | VR2332 PRRSV gp5 |
| 60 | Polypeptide | CAA01841.1 PRRSV gp5 |
| 61 | Polypeptide | ADA15222.1 PRRSV gp5 |
| 62 | Polypeptide | AFS30909.1 PRRSV gp5a |
| 63 | Polypeptide | AGK45334.1 PRRSV gp5a |
| 64 | Polypeptide | AFU75332.1 PRRSV gp5a |
| 65 | Polypeptide | AGW23843.1 PRRSV gp5a |
| 66 | Polypeptide | *rtg*-gp5 of VR2332 PRRSV |
| 67 | DNA/RNA | *rtg*-gp5 of VR2332 PRRSV |
| 68 | Polypeptide | *rtg*-M of VR2332 PRRSV |
| 69 | DNA/RNA | *rtg*-M of VR2332 PRRSV |

*FIG. 12 (Continued)*

| SEQ ID # | Type | Description |
|---|---|---|
| 70 | DNA/RNA | Gp2 of PRRSV; Lelystad strain (portion of GenBank M96262.2) |
| 71 | Polypeptide | Gp2 of PRRSV; Lelystad strain |
| 72 | DNA/RNA | Gp3 of PRRSV; Lelystad strain (portion of GenBank M96262.2) |
| 73 | Polypeptide | Gp3 of PRRSV; Lelystad strain |
| 74 | DNA/RNA | Gp4 of PRRSV; Lelystad strain (portion of GenBank M96262.2) |
| 75 | Polypeptide | Gp4 of PRRSV; Lelystad strain |
| 76 | DNA/RNA | Gp4 of PRRSV; Lelystad strain (portion of GenBank M96262.2) |
| 77 | Polypeptide | Gp4 of PRRSV; Lelystad strain |
| 78 | DNA/RNA | M of PRRSV; Lelystad strain (portion of GenBank M96262.2) |
| 79 | Polypeptide | M of PRRSV; Lelystad strain |
| 80 | Polypeptide | Gp2 of PRRSV related to Lelystad strain |
| 81 | Polypeptide | Gp2 of PRRSV related to Lelystad strain |
| 82 | Polypeptide | Gp2 of PRRSV related to Lelystad strain |
| 83 | Polypeptide | Gp2 of PRRSV related to Lelystad strain |
| 84 | Polypeptide | Gp2 of PRRSV related to Lelystad strain |
| 85 | Polypeptide | Gp2 of PRRSV related to Lelystad strain |
| 86 | Polypeptide | Gp2 of PRRSV related to Lelystad strain |
| 87 | Polypeptide | Gp2 of PRRSV related to Lelystad strain |
| 88 | Polypeptide | Gp2 of PRRSV related to Lelystad strain |
| 89 | Polypeptide | Gp2 of PRRSV related to Lelystad strain |
| 90 | Polypeptide | Gp3 of PRRSV related to Lelystad strain |
| 91 | Polypeptide | Gp3 of PRRSV related to Lelystad strain |
| 92 | Polypeptide | Gp3 of PRRSV related to Lelystad strain |
| 93 | Polypeptide | Gp3 of PRRSV related to Lelystad strain |
| 94 | Polypeptide | Gp3 of PRRSV related to Lelystad strain |
| 95 | Polypeptide | Gp3 of PRRSV related to Lelystad strain |
| 96 | Polypeptide | Gp3 of PRRSV related to Lelystad strain |
| 97 | Polypeptide | Gp3 of PRRSV related to Lelystad strain |
| 98 | Polypeptide | Gp3 of PRRSV related to Lelystad strain |
| 99 | Polypeptide | Gp3 of PRRSV related to Lelystad strain |
| 100 | Polypeptide | Gp4 of PRRSV related to Lelystad strain |
| 101 | Polypeptide | Gp4 of PRRSV related to Lelystad strain |
| 102 | Polypeptide | Gp4 of PRRSV related to Lelystad strain |
| 103 | Polypeptide | Gp4 of PRRSV related to Lelystad strain |

*FIG. 12 (Continued)*

| SEQ ID # | Type | Description |
|---|---|---|
| 104 | Polypeptide | Gp4 of PRRSV related to Lelystad strain |
| 105 | Polypeptide | Gp4 of PRRSV related to Lelystad strain |
| 106 | Polypeptide | Gp4 of PRRSV related to Lelystad strain |
| 107 | Polypeptide | Gp4 of PRRSV related to Lelystad strain |
| 108 | Polypeptide | Gp4 of PRRSV related to Lelystad strain |
| 109 | Polypeptide | Gp4 of PRRSV related to Lelystad strain |
| 110 | Polypeptide | Gp5 of PRRSV related to Lelystad strain |
| 111 | Polypeptide | Gp5 of PRRSV related to Lelystad strain |
| 112 | Polypeptide | Gp5 of PRRSV related to Lelystad strain |
| 113 | Polypeptide | Gp5 of PRRSV related to Lelystad strain |
| 114 | Polypeptide | Gp5 of PRRSV related to Lelystad strain |
| 115 | Polypeptide | Gp5 of PRRSV related to Lelystad strain |
| 116 | Polypeptide | Gp5 of PRRSV related to Lelystad strain |
| 117 | Polypeptide | Gp5 of PRRSV related to Lelystad strain |
| 118 | Polypeptide | Gp5 of PRRSV related to Lelystad strain |
| 119 | Polypeptide | Gp5 of PRRSV related to Lelystad strain |
| 120 | Polypeptide | M of PRRSV related to Lelystad strain |
| 121 | Polypeptide | M of PRRSV related to Lelystad strain |
| 122 | Polypeptide | M of PRRSV related to Lelystad strain |
| 123 | Polypeptide | M of PRRSV related to Lelystad strain |
| 124 | Polypeptide | M of PRRSV related to Lelystad strain |
| 125 | Polypeptide | M of PRRSV related to Lelystad strain |
| 126 | Polypeptide | M of PRRSV related to Lelystad strain |
| 127 | Polypeptide | M of PRRSV related to Lelystad strain |
| 128 | Polypeptide | M of PRRSV related to Lelystad strain |
| 129 | Polypeptide | M of PRRSV related to Lelystad strain |
| 130 | Polypeptide | E of PRRSV related to Lelystad strain |
| 131 | Polypeptide | E of PRRSV related to Lelystad strain |
| 132 | Polypeptide | E of PRRSV related to Lelystad strain |
| 133 | Polypeptide | E of PRRSV related to Lelystad strain |
| 134 | Polypeptide | E of PRRSV related to Lelystad strain |
| 135 | Polypeptide | E of PRRSV related to Lelystad strain |
| 136 | Polypeptide | E of PRRSV related to Lelystad strain |
| 137 | Polypeptide | E of PRRSV related to Lelystad strain |
| 138 | Polypeptide | E of PRRSV related to Lelystad strain |
| 139 | Polypeptide | E of PRRSV related to Lelystad strain |

*FIG. 12 (Continued)*

ClustalW alignment of PRRSV gp2 polypeptide sequences

```
34 MKWGLCKAFSTKLANFLWMLSRNFWCPLLISSYFWPFCLASQSQVGWWSSVSDWFAPRYS  60
36 MKWGPYKAFLTKLANFLWMLSRSSWCPLLISLYFWPFCLASPSPVGWWSFASDWFAPRYS  60
35 MKWGLCKASLTKLANFLWMLSRNFWCPLLISSYFWPFCLASPSPVGWWSFASDWFAPRYS  60
38 MQWGPCKAFLTRSVNFLWMLSRSSWCPLLISSYFWPFCLASPLPAGWWSFASDWFAPRYS  60
37 MQWGHCG---VKSASCSWTPSLSSLLVWLILPFSLPYCLGSPSQDGYWSFFSEWFAPRFS  57
39 MQWGHCG---VKSASCSWTPSLSSLLVWLILXFSLPYCLGSPSQDGYWSFFSEWFAPRFS  57
   *:**       .: ..  *  *  .     **  : *:**.*    *:**  *:*****:*
34 VRALPFTLSNYRRSYEAFLSQCQVDIPTWGTKHPLGMFWHHKVSTLIDEMVSRRMYRIME 120
36 VRALPFTLSNYRRSYEAFLSQCQVDIPTWGTKHPLGMFWHHKVSTLIDEMVSRRMYRIME 120
35 VRALPFTLSNYRRSYEAFLSQCQVDIPTWGFKHPLGMLWHHKVSTLIDEMVSRRMYRTME 120
38 VRALPFTLSNYRRSYEAFLSQCQVDIPAWGTRHPLGMLWHHKVSTLIDEMVSRRMYRIME 120
37 VRALPFTLPNYRRSYEGLLPNCRPDVPQFAVKHPLGMFWHMRVSHLIDEMVSRRIYQTME 117
39 VRALPFTLPNYRRSYEGLLPNCRPDVPQFAVKHPLXMFWHMRVSHLIDEXVSRRIYQTME 117
   ********.*******.:*.:*: *:*  :. :*** *:** :** **** ****:*: **
34 KAGQAAWKQVVSEATLSRISSLDVVAHFQHLAAIEAETCKYLASRLPMLHNLRMTGSNVT 180
36 KAGQAAWKQVVSEATLSRISSLDVVAHFQHLAAIEAETCKYLASRLPMLHNLRMTGSNVT 180
35 KAGQAAWKQVVSEATLSRISGLDVVAHFQHLAAIEAETCKYLASRLPMLHNLRMTGSNVT 180
38 KAGQAAWKQVVSEATLSRISGLDVVAHFQHLAAIEAETCKYLASRLPMLHNLRITGSNVT 180
37 HSGQAAWKQVVGEATLTKLSGLDIVTHFQHLAAVEADSCRFLSSRLVMLKNLAVG--NVS 175
39 HSGQAAWKQVVGEATLTKLSGLDIVTHFQHLAAVEADSCRFLSSRLVMLKNLAVG--NVS 175
   :;**********.****:::*.**:*:*******:**::*::*:*** **:**  :  **:
34 IVYNSTLEQVVAIFPTPGSRPKLHDFQQWLIAVHSSIFSSVAASCTLFVVLWLRIPMLRT 240
36 IVYNSTLSQVFAIFPTPGSRPKLHDFQQWLIAVHSSIFSSVAASCTLFVVLWLRVPILHT 240
35 IVYNSTSNQVFAIFPTPGSRPKRHDFQQWLIAVHSSIFSSVAASCTLFVVLWLRIPMLRS 240
38 IVHNSTLNQVFAIFPTPGSRPKLHDFQQWLIAVHSSISSSVAASCTLFVVLWLRMPMLRS 240
37 LQYNTTLDRVELIFPTPGTRPKLTDFRQWLISVHASIFSSVASSVTLFIVLWLRIPALRY 235
39 LQYNTTLDRVELIFPTPGTRPKLTDFRQWLISVHASIFSSVASSVTLFIVLWLRIPALRY 235
    : :*:* ..:*  ******.*** **.****:**:** ****:* ***:*****:* *:
34 VFGFHWLGAIFLSNSQ 256
36 VFGFRWLGAIFLSNSQ 256
35 VFGFRWLGAIFLLNSR 256
38 VFGFRWLGAIFPSSSW 256
37 VFGFHWPTATHHSS-- 249
39 VFGFHWPTATHHSS-- 249
   ****:*   *  .  .
(34:36) Aligned. Score: 92.97
(34:35) Aligned. Score: 93.75
(34:38) Aligned. Score: 61.85
(34:37) Aligned. Score: 88.67
(34:39) Aligned. Score: 61.04
(36:35) Aligned. Score: 92.58
(36:38) Aligned. Score: 61.45
(36:37) Aligned. Score: 90.23
(36:39) Aligned. Score: 60.64
(35:38) Aligned. Score: 59.84
(35:37) Aligned. Score: 91.02
(35:39) Aligned. Score: 59.44
(38:37) Aligned. Score: 61.85
(38:39) Aligned. Score: 98.80
(37:39) Aligned. Score: 61.04
```

*FIG. 13*

ClustalW alignment of PRRSV gp3 polypeptide sequences

```
40  MVNSCTFLHIFLCCSFLYSLCCAVVAGSNTTYCFWFPLVRGNFSFELTVNYTVCPPCLTR  60
45  MANSCTFLYIFLCCSFLYSFCCAVVAGSNATYCFWFPLVRGNFSFELTVNYTVCPPCLTR  60
41  MANSCTFLYIFLCCSFLYSFCCAVVAGSNATYCFWFPLVRGNFSFELTVNYTVCPPCLTR  60
42  MANSCTFLHILLCCSFLYSFCCVVVTDANATFCFWFPLVRGNFSFELMVNYTVCPPCLTR  60
43  MAHQCARFHFFLCGFICYLVHSALASNSSSTLCFWFPLAHGNTSFELTINYTICMPCSTS  60
44  MAHQCARFHFFLCGFICYFVHSALASNSSSTLCFWFPLAHGNTSFELTINYTVCMPCPTS  60
    *.:.*: :::::**   : *   ..:.:.:.:* ******.:** **** :***;* ** *

40  QAAAEAYEPGRSLWCRIGYDRCGEDDHDELGFMVPSGLSSEGHLTSVYAWLAFLSFSYTA  120
45  QAATEAYEPGRSLWCRIGYDRCGEDDHDELGFVVPSGLSSEGHLTSVYAWLAFLSFSYTA  120
41  QAAAEAYEPGRSLWCRIGHDRCGEDDHDELGFVVPSGLSSEGHLTSAYAWLASLSFSYTA  120
42  QAAAQIYEPNRSLWCRIGNDRCGEDDHDELGFTVPPGLSKEVHLTSVYAWLAFLSFSYTA  120
43  QAARQRLEPGRNMWCKIGHDRCEERDHDELLMSIPSGYG-QLKLEGYYAWLAFLSFSYAA  119
44  QAALQRLEPGRNMWCKIGHDRCEERDQDELLMSIPSGYD-NLKLEGYYAWLAFLSFSYAA  119
    ***   :   **.*. :**:** *** *  *:***   :  :*.*  . : :*   .    ***** *****;*

40  QFHPEIFGIGNVSRVYVDIEHQLICAEHDGQNTTLPRHDNISAVFQTYYQHQVDGGNWFH  180
45  QFHPEIFGIGNVSQVYVDIRHQFICAVHDGQNATLPRHDNISAVFQTYYQHQVDGGNWFH  180
41  QFHPEIFGIGNVSRVYVDIKHQFICAVHDGQNTTLPHHDNISAVLQTYYQHQVDGGNWFH  180
42  QFHPEIFGIGNVSKVYVDINHQLICAVHDGQNTTLPRHDNISAVFQTYYQHQVDGGNWFH  180
43  QFHPELFGIGNVSRVFVDKRHQFICAEHDGHNSTVSTGHNISALYAAYYHHQIDGGNWFH  179
44  QFHPELFGIGNVSRVFVDKWHQFICAEHDGSNSTVSTGHNISALYAAYYHHQIDGGNWFH  179
    *****:********.*:*:**   **:*** *** *:*:.   .****:   :**:**:*.*******

40  LEWLRPFFSSWLVLNVSWFLRRSPANHVSVRLQTLRPTPPQRQALLSSKTSVALGIATR  240
45  LEWLRPFFSSWLVLNVSWFLRRSPASHVSVRLQTLRPTPPQRQALLSSKTSVALGIATR  240
41  LEWVRPFFSSWLVLNVSWFLRRSPASHVSVRVFQTSRPTPPQRQALLSSKTSVALGIATR  240
42  LEWLRPFFSSWLVLNVSWFLRRSPASHVSVRVFQTSRPTPPRQQISLSSRTSAALGMATR  240
43  LEWLRPLFSSWLVLNISWFLRRSPVSPVSRRIYQILRPTRPRLPVSWSFRTSIVSDLTGS  239
44  LEWLRPFFSSWLVLNISWFLRRSPVSPVSRRIYQILRPTRPQLPVSWSFRTSIVSDLMRS  239
    ***:**;********:********.. ** *: *  *** *:         *  :** . .:

40  PLRR---FAKS-----------LSAVRR  254
45  PLRR---FAKS-----------LSVVRR  254
41  PLRR---FAKS-----------LSAARR  254
42  PLRR---FAKS-----------LSAARR  254
43  QQRKRKFPSESRPNVVKPSVLPSTSR    265
44  QQRKGKFPSGSRPNAVKPSALPNISR    265
        *:   *..              *.   *

Sequences (1:2) Aligned. Score: 92.91
Sequences (1:3) Aligned. Score: 87.40
Sequences (1:4) Aligned. Score: 56.30
Sequences (1:5) Aligned. Score: 57.09
Sequences (1:6) Aligned. Score: 94.88
Sequences (2:3) Aligned. Score: 87.80
Sequences (2:4) Aligned. Score: 55.91
Sequences (2:5) Aligned. Score: 56.69
Sequences (2:6) Aligned. Score: 94.49
Sequences (3:4) Aligned. Score: 55.12
Sequences (3:5) Aligned. Score: 55.12
Sequences (3:6) Aligned. Score: 87.40
Sequences (4:5) Aligned. Score: 92.83
Sequences (4:6) Aligned. Score: 56.69
```

*FIG. 14*

ClustalW alignment of PRRSV gp4 polypeptide sequences

```
47 MAASLLFLMVGFKCLLVSQAFACKPCFSSSLADIKTNTTAAASFAVLQDISCLR-HRNSA 59
51 MAASLLFLMVGFKCLLVSQAFACKPCFSSSLADIKTNTTAAASFAVLQDISCLR-HRNSA 59
46 MASSLLFLMVGFKCLLVSQAFACKPCFSSSLADIKTNTTAAASFAVLQDIGCLR-HRDSA 59
48 MGASLLFLLVGFKCLLVSQAFACKPCFSSSLSDIKTNTTAAAGFAVLQDISCLR-HRNSA 59
49 MAAATLFFLAGAQHIMVSEAFACKPCFSTHLSDIETNTTAAAGFMVLQDINCFRPHGVSA 60
50 MAAAILFLLAGAQHIMVSEAFACKPCFSTHLSDIKTNTTAAAGFMVLQDINCFRPHEVSA 60
   *.::  **::.*  :  ::**:********:  *:**:*******.* *****.*:*  *   **

47 SE----AIRKIPQCRTAIGTPMYITITANVTDENYLHSSDLLMLSSCLFYASEMSEKGFEV 116
51 SE----AIRKIPQCRTAIGTPVYITTTANVTDENYLHSSDLLMLSSCLFYASEMSEKGFKV 116
46 SE----AIRKIPQCRTAIGTPVYITITANVTDENYLHSSDLLMLSSCLFYASEMSEKGFKV 116
48 SE----AIRKVPQCRTAIGTPVYITVTANVTDENYLHSSDLLMLSSCLFYASEMSEKGFKV 116
49 AQEKISFGKSSQCREAVGTPQYITITANVTDESYLNADLLMLSACLFYASEMSEKGFKV 120
50 TQREIPFRKSSQCREAVGTPQYITITANVTDESYLNADLLMLSACLFYASEMSEKGFKV 120
   ::     .: * .*** *:*** *** *******.**:..:******:************:*

47 VFGNVSGIVAVCVNFTSYVQHVREFTQR-SLMVDHVRLLHFMTPETMRWATVLACLFAIL 175
51 VFGNVSGIVAVCVNFTSYVQHVREFTQR-SLMVDHVRLLHFMTPETMRWATVLACLFAIL 175
46 VFGNVSGIVAVCVNFTSYVQHVREFTQR-SLVVDHVRLLHFMTPETMRWATVLACLFAIL 175
48 VFGNVSGIVAVCVNFTSYVQHVKEFTQR-SLVVDHVRLLHFMTPETMRWATVLACLFTIL 175
49 IFGNVSGVVSACVNFTDYVAHVTQHTQQHHLVIDHIRLLHFLTPSAMRWATTIACLFAIL 180
50 IFGNVSGVVSACVNFTDYVAHVTQHTQQHHLVIDHIRLLHFLTPSTMRWATTIACLFAIL 180
   :******:*:.*****.** ** :.**:   *::**:*****:**..:*****.:****:**

47 LAI 178
51 LAI 178
46 LAI 178
48 LAI 178
49 LAI 183
50 LAI 183
   ***

Sequences (1:2) Aligned. Score: 96.63
Sequences (1:3) Aligned. Score: 93.82
Sequences (1:4) Aligned. Score: 67.42
Sequences (1:5) Aligned. Score: 69.66
Sequences (1:6) Aligned. Score: 97.19
Sequences (2:3) Aligned. Score: 93.82
Sequences (2:4) Aligned. Score: 66.85
Sequences (2:5) Aligned. Score: 69.10
Sequences (2:6) Aligned. Score: 98.31
Sequences (3:4) Aligned. Score: 67.98
Sequences (3:5) Aligned. Score: 70.22
Sequences (3:6) Aligned. Score: 94.94
Sequences (4:5) Aligned. Score: 94.54
Sequences (4:6) Aligned. Score: 66.85
Sequences (5:6) Aligned. Score: 69.10
```

*FIG. 15*

ClustalW alignment of PRRSV E polypeptide sequences

```
53  MGSIQSLFDKIGQLFVDAFTEFLVSIVDIIIFLAILFGFTIAGWLVVFCIRLVCSAVFRA  60
54  MGSIQSLFDKIGQLFVDAFTEFLVSIVDIIIFLAILFGFTIAGWLVVFCIRLVSSAVFRA  60
52  MGSMQSLFDKIGQLFVDAFTEFLVSIVDIIIFLAILFGFTIAGWLVVFCIRLVCSAILRT  60
55  MGSMQSLFDKIGQLFVDAFTEFLVSIVDIIIFLAILFGFTIAGWLVVFCIRLVCSALRRP  60
57  MGSMQSLFDKIGQLFVDAFTEFLVSIVDIIIFLAILFGFTVAGWLVVFCIRLVFSAVLRA  60
56  MG----SLWSKISQLFVDAFTEFLVSVVDIAIFLAILFGFTVAGWLLVFLLRVVCSALLRS  57
58  MG----SLWSKISQLFVDAFTEFLVSVVDIVIFLAILFGFTVAGGLLVFFLRVVCSAILRS  57
    **    **:.**.***************:*** **********:** *:** :*:* **: *.

53  RPAIHPEQLQKIL  73
54  RPAIHPEQLQKIL  73
52  RPAIHPEQLQKIL  73
55  ---AH-EQLQKIL  69
57  RSTVHPEQLQKIL  73
56  RSAIHSPELSKVL  70
58  RSAIHSPELSKIL  70
         *   :*.*:*
```

```
Sequences (1:2) Aligned. Score: 94.52
Sequences (1:3) Aligned. Score: 93.15
Sequences (1:4) Aligned. Score: 82.61
Sequences (1:5) Aligned. Score: 72.86
Sequences (1:6) Aligned. Score: 90.41
Sequences (1:7) Aligned. Score: 74.29
Sequences (2:3) Aligned. Score: 98.63
Sequences (2:4) Aligned. Score: 81.16
Sequences (2:5) Aligned. Score: 70.00
Sequences (2:6) Aligned. Score: 90.41
Sequences (2:7) Aligned. Score: 70.00
Sequences (3:4) Aligned. Score: 79.71
Sequences (3:5) Aligned. Score: 68.57
Sequences (3:6) Aligned. Score: 90.41
Sequences (3:7) Aligned. Score: 68.57
Sequences (4:5) Aligned. Score: 63.77
Sequences (4:6) Aligned. Score: 89.86
Sequences (4:7) Aligned. Score: 60.87
Sequences (5:6) Aligned. Score: 71.43
Sequences (5:7) Aligned. Score: 92.86
Sequences (6:7) Aligned. Score: 71.43
```

*FIG. 16*

ClustalW alignment of PRRSV gp5a polypeptide sequences

```
63  MFKYVGELLDRGLLLAIAFFVVYRAVLFYCARQRQRKQQLLLPVDLQLDAM  51
64  MFKYVGEMLDRGLLLAIAFFVVYRAVLFHCARRRQRQQQLSSAIDLQLDAM  51
62  MFKYVGEVLDRVLLLAIAFFVVYRAVLSCCARQRQQQQQLSYSVDL-----  46
65  MFKYVGEMLDRGLLLTIAFFVVYRAVLVCCARQSRKRQQLPLTVDI-----  46
    *******:***  ***:***********    ***:  :::***   .:*:
```

Sequences (1:2) Aligned. Score: 80.43
Sequences (1:3) Aligned. Score: 80.43
Sequences (1:4) Aligned. Score: 73.91
Sequences (2:3) Aligned. Score: 84.31
Sequences (2:4) Aligned. Score: 76.09
Sequences (3:4) Aligned. Score: 71.74

PRRSV MINOR PROTEIN-CONTAINING RECOMBINANT VIRAL VECTORS AND METHODS OF MAKING AND USE THEREOF

CROSS-REFERENCE TO RELATED APPLICATIONS

This application claims priority to provisional application U.S. Ser. No. 62/183,410, filed on 23 Jun. 2015, and herein incorporated by reference in its entirety.

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention and does not reflect any view of the validity, patentability and/or enforceability of such cited patent documents. All sequences referenced herein by GenBank Accession numbers are herein incorporated by reference in their entirety, and said sequences are as set forth in GenBank at as of the filing date of the present application.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MER_15_265_ST25. The text file is 279 KB; it was created on 13 Jun. 2016; and it is being submitted electronically via EFS-Web, concurrent with the filing of the specification.

FIELD OF THE INVENTION

The present invention encompasses recombinant adenovirus-vectored PRRSV vaccines, compositions and methods of use.

SUMMARY OF THE INVENTION

PRRSV is devastating viral infection of pigs with huge economic importance (Derald J. Holtkamp, 2013). There is large variability in the antigenic characteristics of the different isolates and effective measures to prevent infections are limited. There are two major groups of vaccines available for PRRS, which are attenuated modified live virus (MLV) or killed virus vaccine. The MLV vaccines, although effective in a homologues challenge, fail to provide broader protection among the many circulating variants and have the potential to revert to wild-type resulting in fulminant infection. Besides, animals vaccinated with MLV vaccines continue to shed the virus and farms that use this vaccines cannot be PRRSV free. On the other side, the killed virus vaccines are much safer, but less effective than MLV vaccines. Therefore, the current options available to prevent infection are neither safe nor effective (Charerntantanakul, 2012) (Tjeerd G. Kimman, 2009). There has been a concerted effort to develop recombinant vaccines that can address the major drawbacks of current vaccines for much of the last 2 decades (Zhang, 2012). However, despite extensive effort, there is no single recombinant vaccine on the market licensed for prevention of PRRSV infection. Most recombinant vaccines that were evaluated in the past were based on one or combination of viral envelope proteins that are believed to be targets of neutralizing antibody response. However, lack of complete understanding of functional interaction either among the envelope proteins or with receptor on the target cells hampered the rational design of efficacious recombinant vaccines.

The viral envelope proteins of PRRSV are generally categorized into major and minor proteins based on abundance of proteins in the virion (Dokland, 2010) (Dea S, 2000). The major viral envelope proteins are gp5 (ORF 5) and M (ORF 6) and form a dimer. The minor envelope proteins are gp2 (ORF2), gp3 (ORF3), gp4 (ORF4) and E (ORF2b) and probably a newly identified viral protein gp5a (ORF 5a). The minor envelope proteins are believed to exist as multimers and they are implicated in direct interaction with receptor, CD163, and mediate viral entry (Phani B. Das, 2010).

Most of the previous attempts to develop recombinant vaccines have focused on major proteins, gp5, M or a combination (Dea, 1998). This is probably due to the fact that antibodies to major proteins are readily detected in PRRSV infected animals and assumed they might present neutralizing targets to the immune system. Besides, there is large degree of sequence variability in gp5 indicating these proteins are under immune selection pressure. However, depletion of gp5 specific antibodies from neutralizing sera indicated that these antibodies belong largely to a non-neutralizing fraction of the sera (Juan Li, 2012). Therefore, these have indicated to the presence of the primary neutralizing target on viral envelope proteins other than the major proteins and probably on minor proteins. Despite extensive effort to develop the major proteins as antigens in recombinant vaccines, ranging from purified recombinant proteins to vaccines delivered using a variety of vector platforms (Jazmina L. G. Cruza, 2010), none has made it to the market because of failure to afford robust protection.

Recently, the focus in developing recombinant PRRS vaccine has shifted to the minor proteins (Jing-Qiang Ren, 2014) (Sakthivel Subramaniam, 2014) (Z. S. WANG, 2011). This shift has been primarily driven by three recent findings. First, two of the minor proteins, gp2 and gp4 were shown to bind directly to CD163 receptor. Second, a swap of minor proteins but not major proteins with EAV (Equine arteritis Virus), also an arterivirus, altered the tropism of the virus, indicating the importance of minor proteins in interaction with receptor and directing virus to target cells (Lu Z1, 2012) (Tian D, 2012). Finally, knock-out mutants of CD163, which is the primary receptor for minor proteins, prevented virus infection, whereas similar knock-out for CD169, receptor for major proteins, did not affect viral entry (Randall S. Prather, 2013). Despite the increasing knowledge in the role of minor proteins in virus entry and as relevant target for neutralizing antibody response, none of the recombinant vaccines developed so far based on minor proteins resulted in protection of vaccinated animal from PRRS infection.

Here, we present that inclusion of another minor protein E to this combination of minor proteins resulted in a dramatically different protective response. Surprisingly, the presence of E protein together with gp2, gp3 and gp4 induced a robust immune response and reduced lung lesion from PRRS challenge. This is the first time that E protein has been shown as a critical component of protein complex that can induce protective immune response. This was achieved not only by identifying E protein as the essential component of the minor protein complex, but also by expressing all four proteins from a single vector platform that promoted formation of protein complex. This new finding will not only serve to further understand the critical interactions among viral proteins and cellular receptor but also paves the way toward achieving a universal recombinant PRRS vaccine that is actually free of live PRRSV.

In our hands, vaccination of animals with pooled plasmids expressing gp2, gp3 and gp4 failed to generate robust immune response (unpublished observation). The conclusion from this animal trial was that these proteins are presumed to exist as multimers and therefore expression of all the proteins simultaneously within a single cell to promote multimerization is required to form the correct conformation that presents a neutralizing epitope to the immune system. Subsequent biochemical assays also indicated this and all the proteins were placed in single vector to allow simultaneous expression. Surprisingly, in the animal trial reported here, we have found that this is also not sufficient to induce protective immune response. Rather, the critical factor for induction of protective immune response by these antigens was the modification introduced to re-target the proteins from intracellular compartments to the surface of the cells. Such a dramatic difference between the modified and unmodified proteins was entirely unexpected and will open new avenues to address similar challenges with a variety of viral targets. This is also the first time, to our knowledge; the immunogenicity of PRRSV envelope minor proteins was enhanced to a degree it can afford both protection from lung lesion against PRRS challenge as well as reduce level of serum viremia by simultaneously expressing all the minor proteins from a single vector and introducing modifications that enhanced cell surface expression.

REFERENCES

Changhee Lee, D. Y. (2006). The small envelope protein of porcine reproductive and respiratory syndrome virus possesses ion channel protein-like properties. *Virology*, 30-43.

Charerntantanakul, W. (2012). Porcine reproductive and respiratory syndrome virus vaccines: Immunogenicity, efficacy and safety aspects. *World Journal of Virology*, 23-30.

Dea S, G. C. (2000). Current knowledge on the structural proteins of porcine reproductive and respiratory syndrome (PRRS) virus: comparison of the North American and European isolates. *Archives of Virology*, 659-688.

Dea, B. P. (1998). Immune response in pigs vaccinated with plasmid DNA encoding ORF5 of porcine reproductive and respiratory syndrome virus. *Journal of General Virology*, 989-999.

Derald J. Holtkamp, J. K. (2013). Assessment of the economic impact of porcine reproductive and respiratory syndrome virus on united States Pork producers. *Journal of Swine Health and production*, 72-84.

Dokland, T. (2010). The structural biology of PRRSV. *Virus Research*, 86-97.

F. A. Osorio, J. A. (2002). Passive Transfer of Virus-Specific Antibodies Confers Protection against Reproductive Failure Induced by a Virulent Strain of Porcine Reproductive and Respiratory Syndrome Virus and Establishes Sterilizing Immunity. *Virology*, 9-20.

Jazmina L. G. Cruza, S. Z. (2010). Vectored vaccines to protect against PRRSV. *Virus Research*, 150-160.

Jing-Qiang Ren, W.-C. S.-J.-B.-L.-X.-P.-W.-Y. (2014). Construction and immunogenicity of a DNA vaccine coexpressing GP3 and GP5 of genotype-I porcine reproductive and respiratory syndrome virus. *BMC Veterinary Research*, 1-11.

Juan Li, M. P. (2012). Dissociation of porcine reproductive and respiratory syndrome virus neutralization from antibodies specific to major envelope protein surface epitopes. *Virology*, 367-376.

Lu Z1, Z. J. (2012). Chimeric viruses containing the N-terminal ectodomains of GP5 and M proteins of porcine reproductive and respiratory syndrome virus do not change the cellular tropism of equine arteritis virus. *Virology*, 99-109.

Maorong Yua, X. L. (2010). Subcellular localization and topology of porcine reproductive and respiratory syndrome virus E protein. *Virus Research*, 104-114.

Meng, X. (2000). Heterogeneity of porcine reproductive and respiratory syndrome virus: implications for current vaccine ef®cacy and future vaccine development. *Veterinary Microbiology* 74 (2000) 309±329, 309-329.

O. J. Lopez, M. F. (2007). Protection against Porcine Reproductive and Respiratory Syndrome Virus (PRRSV) Infection through Passive Transfer of PRRSV-Neutralizing Antibodies Is Dose Dependent. *Clinical and Vaccine Immunology*, 269-275.

Phani B. Das, P. D. (2010). The Minor Envelope Glycoproteins GP2a and GP4 of Porcine Reproductive and Respiratory Syndrome Virus Interact with the Receptor CD163. *Journal of Virology*, 1731-1740.

Randall S. Prather, R. R. (2013). An Intact Sialoadhesin (Sn/SIGLEC1/CD169) Is Not Required for Attachment/Internalization of the Porcine Reproductive and Respiratory Syndrome Virus. *Journal of Virology*, 9538-9546.

Sakthivel Subramaniam, P. P. (2014). In vivo targeting of porcine reproductive and respiratory syndrome virus antigen through porcine DC-SIGN to dendritic cells elicits antigen-specific CD4T cell immunity in pigs. *Vaccine*, 6768-6775.

Tian D, W. Z.-D. (2012). Arterivirus minor envelope proteins are a major determinant of viral tropism in cell culture. *Journal of Virology*, 3701-3712.

Tjeerd G. Kimman, L. A.-Z. (2009). Challenges for porcine reproductive and respiratory syndrome virus (PRRSV) vaccinology. *Vaccine*, 3704-3718.

Yijun Du, F. A. (2010). Myristoylation of the small envelope protein of porcine reproductive and respiratory syndrome virus is non-essential for virus infectivity but promotes its growth. *Virus Research*, 294-299.

Z. S. WANG, X. X. (2011). Immunogenicity of the envelope GP3 protein of porcine reproductive and respiratory syndrome virus displayed on baculovirus. *Acta Virologica*, 139-146.

Zhang, J. H. (2012). Porcine Reproductive and Respiratory Syndrome Virus Vaccines: Current Status and Strategies to a Universal Vaccine. *Transboundary and Emerging Diseases*, 109-120.

The present disclosure provides novel PRRSV vaccine compositions and methods of making and use thereof.

This disclosure is based, in part, upon the surprising and unexpected finding that inclusion of another PRRSV minor protein (E) to other combinations of minor proteins resulted in a dramatically different protective response. In some embodiments, sufficient portions of the E protein, for example, its transmembrane (TM), amino terminal (NT) or its carboxy terminal (CT) domain, may be used to elicit said protective response.

Surprisingly, the presence of E protein together with gp2, gp3 and gp4 induced a robust immune response and reduced lung lesion from PRRS challenge. This is the first time that E protein has been shown as a critical component of protein complex that can induce protective immune response.

As such, the disclosed vaccines were not merely achieved by identifying E protein as the essential component of the minor protein complex, but also, by expressing all four proteins from a single vector platform that promoted formation of protein complex.

In another aspect, the disclosure provides recombinant viral vectors expressing chimeric versions of PRRSV minor proteins, which contain different cellular localization determinants, as compared with their corresponding wild-type genes. In particular, a portion of VSV glycoprotein (G) and tissue plasminogen activator protein (tPA) has been added to cause the resulting chimeric gene products to localize to the cell surface. These recombinant vectors elicit safe and effective immune responses in the host animal against PRRSV. As such, modifications introduced to the PRRSV minor proteins to achieve their surface expression produced a similar effect as did co-expressing E protein along with gp2, gp3, and gp4.

Accordingly, this disclosure thus provides a roadmap for achieving a universal recombinant PRRS vaccine that is 100% free of live PRRSV.

The present invention more particularly relates to an adenovirus-vectored PRRSV vaccine or composition that comprises one or more engineered, recombinant adenovirus vectors that harbor and express certain PRRSV antigens, and optionally a pharmaceutically or veterinarily acceptable carrier, adjuvant, excipient, or vehicle. The PRRSV may be any strain, as the novel and inventive compositions and methods disclosed herein are universally applicable to all known and yet to be discovered PRRSV strains, for reasons discussed more fully below.

The PRRSV antigen includes PRRSV minor proteins (e.g. gp2, gp3, gp4, gp5a, gp5 or E), in any combination, and optionally includes additional PRRSV major proteins (e.g. gp5 or M). Similar to the other minor proteins, gp5a is relatively well-conserved, and is envisioned by Applicants to be an effective addition or substitution for the safe and effective recombinant viral vectors of the instant disclosure.

The PRRSV recombinant vectors may contain and express in an animal host at least the following combinations (in any order, and driven by any promoter element, PE, including the one indicated, and including elements such as IRES and 2A-peptides) of genes or components (rtg=re-targeted; CMV=cytomegalovirus promoter; SV40=simian virus 40 promoter; IRES=internal ribosomal entry site, self-cleaving 2A peptides derived from foot-and-mouth disease (FMD) virus, equine rhinitis A virus, Thosea asigna virus or porcine teschovirus-1): 1) (PE)gp2, (PE)gp3, (PE)gp4, (PE)E; 2) (PE)rtg gp2, (PE)gp3 and (PE)gp4; 3) (PE)rtg gp2, (PE)rtg gp3 and (PE)rtg gp4; 4) (PE)rtg gp2, (PE)rtg gp3, (PE)rtg gp4 and (PE)E; 5) (PE)rtg gp2, (PE)rtg gp3, (PE)rtg gp4 and (PE)rtg E; 6) (PE)rtg gp2, (PE)rtg gp4 and (PE)rtg E; 7) (PE)rtg gp2 and (PE)rtg gp4, 8) (M-(SV40)-(CMV)-gp5-(IRES)-gp5a; 9) gp2-(SV40)-(CMV)-E; 10) rtg gp2-(SV40)-(CMV)-E; 11) rtg gp2-(SV40)-(CMV)-rtg E; 12) (CMV)-E; 11) E-(p2A)-gp2-(SV40)-(CMV)-gp4; 12) rtg E-(p2A)-rtg gp2-(SV40)-(CMV)-rtg gp4; 13) (PE)gp2-(PE)gp4-(PE)E; 14) (PE)gp2-(PE)E; 15) (PE)gp2; 16) (PE) gp2-(PE)gp3; 16) (PE)gp2-(PE)gp4; 17) (PE)gp2-(PE)gp5a; 18) (PE)E; 19) (PE)E-(PE)gp3; 20) (PE)E-(PE)gp4; 19) (PE)E-(PE)gp5a; 20). In an advantageous embodiment, the vector contains and expresses at minimum (PE)gp2, (PE) gp4 and (PE)E, either wild-type or "rtg" versions thereof. The vector may also advantageously comprise gp2 plus any other gene encoding a PRRSV polypeptide.

The re-targeting may be accomplished by replacing existing gp2, gp3, gp4, gp5a, gp5 or E proteins transmembrane (TM) and cytoplasmic tail (CT) domains with, respectively, the TM and CT domains of VSV. In an embodiment, the gp5 and M proteins may also be subjected to the re-targeting procedure. The native PRRSV protein sequences may also or alternatively be replaced with the tPA signal sequence and either or both TM and CT of VSV (or those same elements from other suitable surface-expressed polypeptide). Alternatively, the re-targeting may be accomplished by replacing existing gp2, gp3, gp4, gp5a, E, gp5 or M protein CT domains with the CT domains of VSV (i.e. not changing the existing TM domains). Re-targeting of E may also be accomplished by replacing its cellular localization signals with that from a Type II membrane protein, or with VSV-G or combinations thereof, or the TM/CT domains of other surface glycoproteins.

Applicants further envision many alternative means of presenting the PRRSV antigens to the host animal's immune system. For example, the antigens could be displayed on the surface of virus-like particles (VLPs). In other embodiments, soluble versions of the antigens could be administered to the host animal, wherein oligomerization (including trimerization) of the proteins with each other, or additionally, with components of VSV-G, or other viral proteins or any oligomerization (including trimerization motifs) (e.g. motifs from bacterial GCN4, and the like). Moreover, the TM/CT domains of Type I viral surface glycoproteins are envisioned to accomplish the same purpose as, and are therefore interchangeable with, the corresponding domains from VSV-G.

Accordingly, now that the invention has been disclosed, the skilled person will recognize many alternative and functionally equivalent ways to accomplish substantially the same presentation of PRRSV minor proteins, including E, gp2, gp3, gp4, gp5a, major proteins, including gp5 and M, or combinations of minor and/or major proteins, to a host animal's immune system.

The invention also relates to a method of vaccinating an animal comprising administering to the animal an effective amount of one or more vaccines or compositions which may comprise an effective amount of an adenovirus-vectored PRRSV vaccine and optionally a pharmaceutically or veterinarily acceptable carrier, adjuvant, excipient, or vehicle. The administering may be subcutaneous, intranasal, intramuscular, transdermal, intradermal, mucosal, including oral, or any other administration.

The invention further relates to administration of the vaccine or composition using prime-boost protocol. The invention further encompasses a kit for performing a method of eliciting or inducing an immune response that may comprise any one of the recombinant Ad5 immunological compositions or vaccines, or inactivated immunological compositions or vaccines, and instructions for performing the method.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may be best understood in conjunction with the accompanying drawings, in which:

Figures 2, 3:
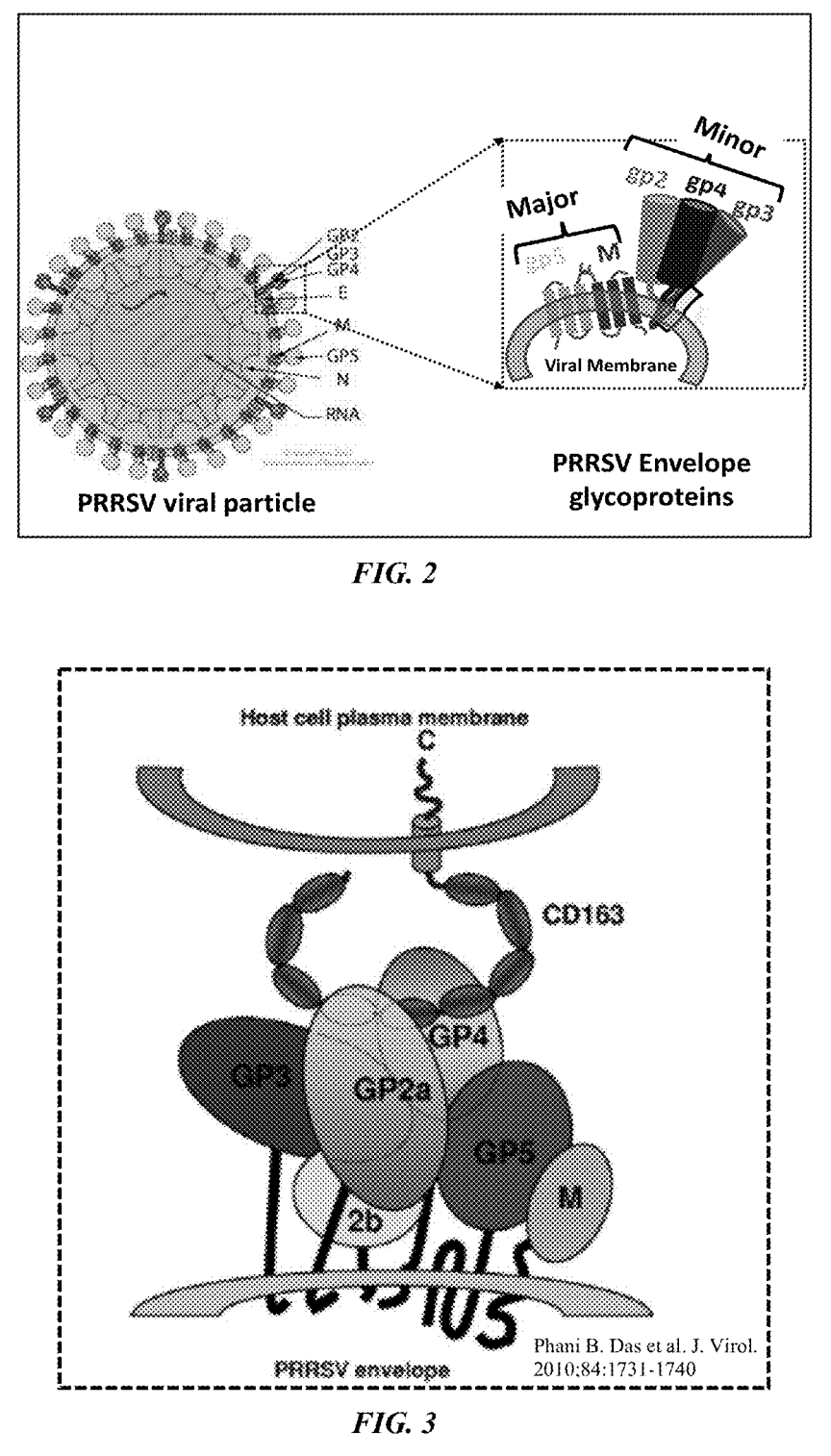

FIG. 2 is a schematic showing the arrangement of PRRSV "major" and "minor" proteins on the surface of a viral membrane;

FIG. 3 is a schematic showing the arrangement and interactions of the PRRSV "minor" proteins, as the current and disclosed evidence indicates these proteins are understood to interact with the host cell surface receptors (e.g. CD163);

FIG. 12 lists and describes the sequences present in the sequence listing;

FIG. 13 is a ClustalW alignment of the gp2 polypeptide sequences as set forth in SEQ ID NOs: 34-39;

FIG. 14 is a ClustalW alignment of the gp3 polypeptide sequences as set forth in SEQ ID NOs: 40-45;

FIG. 15 is a ClustalW alignment of the gp4 polypeptide sequences as set forth in SEQ ID NOs: 46-51;

FIG. 16 is a ClustalW alignment of the E polypeptide sequences as set forth in SEQ ID NOs: 52-58;

FIG. 17 is a ClustalW alignment of the gp5a polypeptide sequences as set forth in SEQ ID NOs: 62-65;

DETAILED DESCRIPTION

Figure 1:
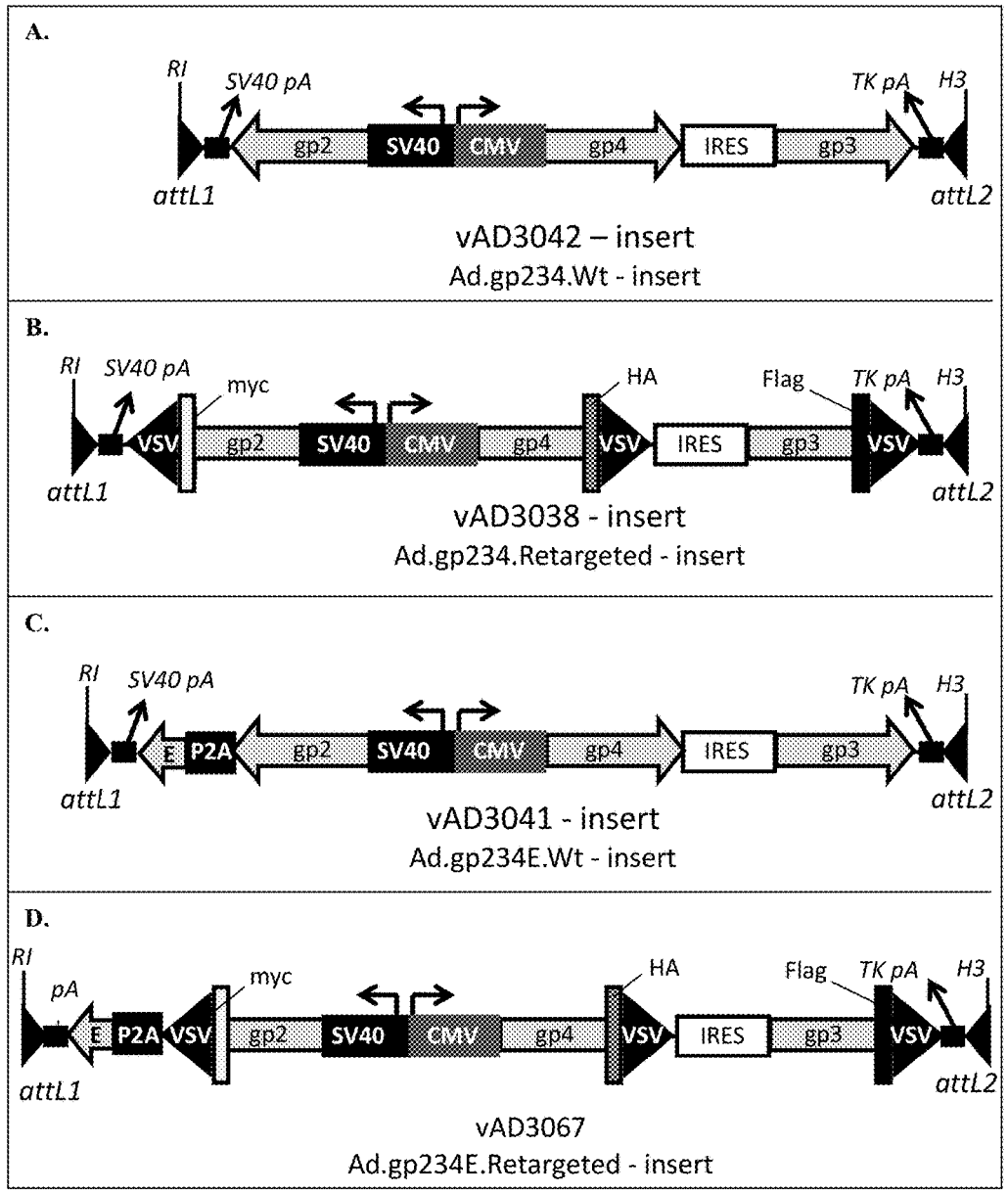
FIG. 1 presents maps of the inserts used to produce four different recombinant viral vectors expressing porcine reproductive and respiratory syndrome virus (PRRSV) minor viral envelope proteins. vAD3042 expresses codon-optimized, PRRSV gp2, gp3 and gp4 without E (A); vAD3038 expresses codon-optimized, re-targeted ("rtg") rtg-gp2, rtg-gp3 and rtg-gp4 without E (B); vAD3041 expresses codon-optimized, gp2, gp3, gp4 with E (C); vAD3067 expresses codon-optimized, rtg-gp2, rtg-gp3, rtg-gp4 with E (D); vAD3046 expresses codon-optimized Swine influenza virus hemagglutinin (SIV-HA) (E); vAD3069 expresses codon-optimized Nucleoprotein (Np or N), M, gp5 and gp5a (F); and vAD3064 expresses codon-optimized, rtg-M, rtg-gp5 and rtg-gp5a (G)

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

In the present invention, adenovirus 5 (Ad5), or another suitable vector, is used to deliver and express in vivo in an animal host selected PRRSV envelope proteins, to elicit in the animal a safe and effective immune response against experimental or natural challenge with virulent PRRSV.

While Ad5 was used to deliver the PRRSV proteins in the instant disclosure, any other suitable vector could be used. For example, baculovirus, poxvirus, including fowl poxvirus and canarypox virus may be used to deliver the novel and inventive combinations of genes disclosed herein. In another embodiment, porcine cytomegalovirus (PCMV), which is a herpesvirus found in the tissues throughout the body including the nose of newborn piglets where it causes inflammation (rhinitis), may be used as the vector.

The present invention thus relates to a vaccine or immunological composition that may comprise an effective amount of one or more engineered Ad5 vectors, or other suitable vectors, and optionally, a pharmaceutically or veterinarily acceptable carrier, adjuvant, excipient, or vehicle.

Accordingly, the present invention encompasses an engineered Ad5 vector, or other suitable vector, expressing PRRSV envelope protein(s), polypeptide(s), antigen(s), epitope(s) or immunogen(s), which elicit an immunogenic response in an animal. The PRRSV protein, polypeptide, antigen, epitope or immunogen includes at least one PRRSV minor protein, polypeptide, antigen, epitope or immunogen, selected from PRRSV gp2, gp3, gp4, gp5a and E.

As used herein, the term "PRRSV minor polypeptide, antigen, epitope or immunogen" refers to any minor polypeptide, antigen, epitope or immunogen of a porcine reproductive and respiratory syndrome virus. Currently, the minor polypeptides or components thereof include gp2, gp3, gp4, gp5a and E proteins, but there may be other proteins associated with the currently known minor proteins that could also be used effectively in the practice of the disclosed invention. In general, and as used herein, the term "ectodomain" refers to the domain or domains of a membrane protein that extend into the extracellular space. As such, any reference to percent identity to the ectodomain of a given protein is not intended to include a comparison to non-ectodomains, including transmembrane domains (TMDs) and cytoplasmic domains (CTDs), of said protein.

By "animal" is intended mammals, human, birds, and the like. The animal may be selected from the group consisting of equine (e.g., horse), canine (e.g., dogs, wolves, foxes, coyotes, jackals), feline (e.g., lions, tigers, domestic cats, wild cats, other big cats, and other feline including cheetahs and lynx), ovine (e.g., sheep), bovine (e.g., cattle, cow, buffalo), swine (pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

In the current invention, immunological protection of porcine animals against porcine reproductive and respiratory syndrome virus is of primary importance. However, the concepts disclosed herein will apply equally well to other viruses where, as here, the relatively low or limited expression of key "cell-entry-mediating" surface proteins renders vaccine development especially challenging. Accordingly, as disclosed herein, the re-targeting and/or chaperoning of such "minor envelope proteins" to a cell's surface has broad-reaching applications to all enveloped viruses.

In one embodiment, the Ad5 immunological composition or vaccine comprises one or more engineered Ad5 vectors, and optionally a pharmaceutical or veterinary acceptable excipient, adjuvant, carrier or vehicle. The engineered Ad5 vector may comprise a polynucleotide encoding a PRRSV minor protein, polypeptide, antigen, epitope or immunogen. The PRRSV protein, polypeptide, antigen, epitope or immunogen may be a gp2, gp3, gp4, gp5a, E, or any fragment thereof.

As used herein, the term "antigen" or "immunogen" means a substance that induces a specific immune response in a host animal. The antigen may comprise a whole organism, killed, attenuated or live; a subunit or portion of an organism; a recombinant vector containing an insert expressing an epitope, polypeptide, peptide, protein, or fragment thereof with immunogenic properties; a piece or fragment of nucleic acid capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also includes peptides and polypeptides that are immunologically active in the sense that once administered to the host, it is able to evoke an immune response of the humoral and/or cellular type directed against the protein. Preferably the protein fragment is such that it has substantially the same immunological activity as the complete, intact native protein. Thus, a protein fragment according to the invention comprises or consists essentially of or consists of at least one epitope or antigenic determinant. The term epitope, also known as antigenic determinant, is the part of a macromolecule recognized by the immune system and able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenyl-alanine, methionine, tryptophan; and (4) uncharged polar-glycine, asparagine, glutamine, cysteine, serine threonine and tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term "epitope" refers to the part of a macromolecule recognized by the immune system and able to induce an immune reaction of the humoral type (B cells) and/or cellular type (T cells). The term is also used interchangeably with "antigenic determinant" or "antigenic determinant site." Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. More often than not, an "immunological response" includes, but is not limited to, one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The term "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996).

For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. Immunogenic fragments, for purposes of the present invention, will usually include at least about 3 amino acids, about 5 amino acids, about 10-15 amino acids, about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of PRRSV protein or polypeptide. A polynucleotide encoding a fragment of the total protein or polypeptide comprises or consists essentially of or consists of a minimum of 15 nucleotides, advantageously about 30-45 nucleotides, and preferably about 45-75, at least 57, 87 or 150 consecutive or contiguous nucleotides of the sequence encoding the total protein or polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999), can be used in the practice of the invention, without undue experimentation.

A "polynucleotide" is a polymeric form of nucleotides of any length that contains deoxyribonucleotides, ribonucleotides, and analogs in any combination. Polynucleotides may have three-dimensional structure, and may perform any function, known or unknown. The term "polynucleotide" includes double-, single-, and triple-stranded helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The term "codon optimization" refers to the process of optimally configuring the nucleic acid sequence encoding a protein, polypeptide, antigen, epitope, domain or fragment for expression/translation in a selected host. In general, gene expression levels depend on many factors, such as promoter sequences and regulatory elements. One of the most important factors is the adaptation of the codon usage of the transcript gene to the typical codon usage of the host (Lithwich, G. and Margalit, H., Genome Res. 13, 2665-2673, 2003). Therefore, highly expressed genes in prokaryotic genomes under translational selection have a pronounced codon usage bias. This is because they use a small subset of codons that are recognized by the most abundant tRNA species (Ikemura, T., J. Mol. Biol. 151, 389-409, 1981). The force that modulates this codon adaptation is called translational selection and its strength is important in fast-growing bacteria (Rocha, E. P., Genome Res. 14, 2279-2286, 2004; Sharp, P. M. et al., Nucleic Acids Res. 33, 1141-1153). If a gene contains codons that are rarely used by the host, its expression level will not be maximal. This may be one of the limitations of heterologous protein expression (Gustafsson, C. et al., Trends Biotechnol. 22, 346-353, 2004) and the development of DNA vaccines (Ivory, C. and Chadee, K., Genet. Vaccines Ther. 2, 17, 2004). A high number of synthetic genes have been re-designed to increase their expression level. The Synthetic Gene Database (SGDB) (Wu, G. et al., Nucleic Acids Res. 35, D76-D79, 2007) contains information from more than 200 published experiments on synthetic genes. In the design process of a nucleic acid sequence that will be inserted into a new host to express a certain protein in optimal amounts, codon usage optimization is usually one of the first steps (Gustafsson, C., Trends Biotechnol. 22, 346-353, 2004). Codon usage optimization basically involves altering the rare codons in the target gene so that they more closely reflect the codon usage of the host without modifying the amino acid sequence of the encoded protein (Gustafsson, C., Trends Biotechnol. 22, 346-353, 2004). The information usually used for the optimization process is therefore the DNA or protein sequence to be optimized and a codon usage table (reference set) of the host.

There are several public web servers and stand-alone applications that allow some kind of codon optimization by anyone skilled in the art. 'GeneDesign' (Richardson, S. M. et al., Genome Res. 16, 550-556, 2006), 'Synthetic Gene Designer' (Wu, G. et al., Protein Expr. Purif. 47, 441-445, 2006) and 'Gene Designer' (Villalobos, A. et al., BMC Bioinformatics 7, 285, 2006) are packages that provide a platform for synthetic gene design, including a codon optimization step. With regard to the methods for codon usage optimization available in each server or program, the first programs developed used only the 'one amino acid-one codon' approach. More recent programs and servers now include further methods to create some codon usage variability. This variability reflects the codon usage variability of natural highly expressed genes and enables additional criteria to be introduced (such as the avoidance of restriction sites) in the optimization process. Most applications and web servers described herein provide three methods of codon optimization: a complete optimization of all codons, an optimization based on the relative codon usage frequencies of the reference set that uses a Monte Carlo approach and a novel approaches designed to maximize the optimization with the minimum changes between the query and optimized sequences.

In one embodiment, the nucleic acid sequence encoding the recombinant PRRSV minor protein, antigen, peptide, polypeptide, fragment, domain, or epitope is codon optimized for expression in animal. In another embodiment, the codon optimized sequences encode porcine PRRSV minor envelope proteins, antigens, peptides, polypeptides, fragments, domains, or epitopes for animal expression. In yet another embodiment, the codon optimized sequences encode PRRSV gp2, gp3, gp4, gp5a, gp5 or E proteins, antigens, peptides, polypeptides, fragments, domains, or epitopes for animal expression.

The following are non-limiting examples of polynucleotides: a gene or gene fragment, exons, introns, mRNA, tRNA, rRNA, siRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding a PRRSV minor envelope protein, antigen, epitope or immunogen. The complementary strand can be polymeric and of any length, and can contain deoxyribonucleotides, ribonucleotides, and analogs in any combination thereof.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

An "isolated" polynucleotide or polypeptide is one that is "substantially free" of the materials with which it is associated in its native environment. By "substantially free," it is meant that the polynucleotide or polypeptide is at least 50%, at least 70%, at least 80%, at least 90%, or at least 95% free of these materials. If the "isolated" polynucleotide or polypeptide is designated as being "nearly entirely free of contaminants," it is meant that the isolated polynucleotide or polypeptide is at least 98% free of these materials.

The invention further encompasses polynucleotides encoding functionally equivalent variants and derivatives of the PRRSV polypeptides and functionally equivalent fragments thereof that may enhance, decrease or not significantly affect inherent properties of the polypeptides encoded thereby. These functionally equivalent variants, derivatives, and fragments display the ability to retain the activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the PRRSV polynucleotide or polypeptide of interest.

In one aspect, the present invention provides PRRSV polypeptides, particularly PRRSV minor envelope polypeptides. In another aspect, the present invention provides a polypeptide having a sequence as set forth in SEQ ID NO: 1, 3, 5, 7, 14, 16, 18, 20, 31, 34-39, 40-45, 46-51, 52-58, 59-61, 62-66, 68, 71, 73, 75, 77, or 79-139, or variants or fragments thereof.

In another aspect, the present invention provides a polypeptide having at least 70%, at least 75%, at least 80%, at least 85%, at least 90%, at least 95%, 96%, 97%, 98% or 99% sequence identity to PRRSV gp2, gp3, gp4, gp5a, gp5 or E polypeptide of the invention, particularly to the polypeptide having a sequence as set forth in SEQ ID NO: 1, 3, 5, 7, 14, 16, 18, 20, 31, 34-39, 40-45, 46-51, 52-58, 59-61, 62-66, 68, 71, 73, 75, 77, or 79-139.

In yet another aspect, the present invention provides fragments and variants of the PRRSV gp2, gp3, gp4, gp5a, gp5 or E polypeptides identified above (SEQ ID NO: 1, 3, 5, 7, 14, 16, 18, 20, 31, 34-39, 40-45, 46-51, 52-58, 59-61, 62-66, 68, 71, 73, 75, 77, or 79-139) which may readily be prepared by one of skill in the art using well-known molecular biology techniques. Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 1, 3, 5, 7, 14, 16, 18, 20, 31, 34-39, 40-45, 46-51, 52-58, 59-61, 62-66, 68, 71, 73, 75, 77, or 79-139.

An immunogenic fragment of a PRRSV gp2, gp3, gp4, gp5a, gp5 or E polypeptide includes at least 8, 10, 15, or 20 consecutive amino acids, at least 21 amino acids, at least 23 amino acids, at least 25 amino acids, or at least 30 amino acids of the PRRSV gp2, gp3, gp4, gp5a, gp5 or E polypeptide having a sequence as set forth in SEQ ID NO: 1, 3, 5, 7, 14, 16, 18, 20, 31, 34-39, 40-45, 46-51, 52-58, 59-61, 62-66, 68, 71, 73, 75, 77, or 79-139, or variants thereof. In another embodiment, a fragment of the PRRSV gp2, gp3, gp4, gp5a, gp5 or E polypeptide includes a specific antigenic epitope found on a full-length PRRSV gp2, gp3, gp4, gp5a, gp5 or E polypeptide.

In another aspect, the present invention provides a polynucleotide encoding a PRRSV gp2, gp3, gp4, gp5a, gp5 or E polypeptide, such as a polynucleotide encoding a polypeptide having a sequence as set forth in SEQ ID NO: 1, 3, 5, 7, 14, 16, 18, 20, 31, 34-39, 40-45, 46-51, 52-58, 59-61, 62-66, 68, 71, 73, 75, 77, or 79-139. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 3, 5, 7, 14, 16, 18, 20, 31, 34-39, 40-45, 46-51, 52-58, 59-61, 62-66, 68, 71, 73, 75, 77, or 79-139, or a conservative variant, an allelic variant, a homolog or an immunogenic fragment comprising at least eight or at least ten consecutive amino acids of one of these polypeptides, or a combination of these polypeptides. The polynucleotide encoding the PRRSV gp2, gp3, gp4, gp5a, gp5 or E polypeptide may be codon-optimized for expression in a specific animal species.

In another aspect, the present invention provides a polynucleotide having a nucleotide sequence as set forth in SEQ ID NO: 2, 4, 6, 8, 9, 10, 11, 12, 13, 15, 17, 19, 21-24, 30, 67, 69, 70, 72, 74, 76, or 78, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to a polynucleotide having a sequence as set forth in SEQ ID NO: 2, 4, 6, 8, 9, 10, 11, 12, 13, 15, 17, 19, 21-24, 30, 67, 69, 70, 72, 74, 76, or 78, or a variant thereof.

In one aspect, the present invention provides PRRSV polypeptides, particularly PRRSV E polypeptide. In another aspect, the present invention provides a polypeptide having a sequence as set forth in SEQ ID NO: 7, 20, 52-58, or 130-139, and variant or fragment thereof.

In another aspect, the present invention provides a polypeptide having at least 70%, at least 75%, at least 80%, at least 85%, at least 90%, at least 95%, 96%, 97%, 98% or 99% sequence identity to a PRRSV E polypeptide of the invention, particularly to the polypeptides having a sequence as set forth in SEQ ID NO: 7, 20, 52-58, or 130-139.

In yet another aspect, the present invention provides fragments and variants of the PRRSV E polypeptides identified above (SEQ ID NO: 7, 20, 52-58, or 130-139) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 7, 20, 52-58, or 130-139.

An immunogenic fragment of a PRRSV E polypeptide includes at least 8, 10, 15, or 20 consecutive amino acids, at least 21 amino acids, at least 23 amino acids, at least 25 amino acids, or at least 30 amino acids of the PRRSV E polypeptide having a sequence as set forth in SEQ ID NO: 7, 20, 52-58, or 130-139, or variants thereof. In another embodiment, a fragment of a PRRSV E polypeptide includes a specific antigenic epitope found on a full-length PRRSV E polypeptide.

In another aspect, the present invention provides a polynucleotide encoding a PRRSV E polypeptide, such as a polynucleotide encoding a polypeptide having a sequence as set forth in SEQ ID NO: 7, 20, 52-58, or 130-139. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 7, 20, 52-58, or 130-139, or a conservative variant, an allelic variant, a homolog or an immunogenic fragment comprising at least eight or at least ten consecutive amino acids of one of these polypeptides, or a combination of these polypeptides. The polynucleotide encoding the PRRSV E polypeptide may be codon-optimized for expression in a specific animal species.

In another aspect, the present invention provides PRRSV polypeptides, particularly PRRSV gp2 polypeptide. In another aspect, the present invention provides a polypeptide having a sequence as set forth in SEQ ID NO: 1, 14, 34-39, or 80-89, and variant or fragment thereof.

In another aspect, the present invention provides a polypeptide having at least 70%, at least 75%, at least 80%, at least 85%, at least 90%, at least 95%, 96%, 97%, 98% or 99% sequence identity to a PRRSV gp2 polypeptide of the invention, particularly to the polypeptides having a sequence as set forth in SEQ ID NO: 1, 14, 34-39, or 80-89.

In yet another aspect, the present invention provides fragments and variants of the PRRSV gp2 polypeptides identified above (SEQ ID NO: 1, 14, 34-39, or 80-89) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 1, 14, 34-39, or 80-89.

An immunogenic fragment of a PRRSV gp2 polypeptide includes at least 8, 10, 15, or 20 consecutive amino acids, at least 21 amino acids, at least 23 amino acids, at least 25 amino acids, or at least 30 amino acids of the PRRSV gp2 polypeptide having a sequence as set forth in SEQ ID NO: 1, 14, 34-39, or 80-89, or variants thereof. In another embodiment, a fragment of a PRRSV gp2 polypeptide includes a specific antigenic epitope found on a full-length PRRSV gp2 polypeptide.

In another aspect, the present invention provides a polynucleotide encoding a PRRSV gp2 polypeptide, such as a polynucleotide encoding a polypeptide having a sequence as set forth in SEQ ID NO: 1, 14, 34-39, or 80-89. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 1, 14, 34-39, or 80-89, or a conservative variant, an allelic variant, a homolog or an immunogenic fragment comprising at least eight or at least ten consecutive amino acids of one of these polypeptides, or a combination of these polypeptides. The polynucleotide encoding the PRRSV gp2 polypeptide may be codon-optimized for expression in a specific animal species.

In another aspect, the present invention provides PRRSV polypeptides, particularly PRRSV gp3 polypeptide. In another aspect, the present invention provides a polypeptide having a sequence as set forth in SEQ ID NO: 3, 16, or 40-45, and variant or fragment thereof.

In another aspect, the present invention provides a polypeptide having at least 70%, at least 75%, at least 80%, at least 85%, at least 90%, at least 95%, 96%, 97%, 98% or 99% sequence identity to a PRRSV gp3 polypeptide of the invention, particularly to the polypeptides having a sequence as set forth in SEQ ID NO: 3, 16, or 40-45.

In yet another aspect, the present invention provides fragments and variants of the PRRSV gp3 polypeptides identified above (SEQ ID NO: 3, 16, or 40-45) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 3, 16, or 40-45.

An immunogenic fragment of a PRRSV gp3 polypeptide includes at least 8, 10, 15, or 20 consecutive amino acids, at least 21 amino acids, at least 23 amino acids, at least 25 amino acids, or at least 30 amino acids of the PRRSV gp3 polypeptide having a sequence as set forth in SEQ ID NO: 3, 16, or 40-45, or variants thereof. In another embodiment, a fragment of a PRRSV gp3 polypeptide includes a specific antigenic epitope found on a full-length PRRSV gp3 polypeptide.

In another aspect, the present invention provides a polynucleotide encoding a PRRSV gp3 polypeptide, such as a polynucleotide encoding a polypeptide having a sequence as set forth in SEQ ID NO: 3, 16, or 40-45. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 3, 16, or 40-45, or a conservative variant, an allelic variant, a homolog or an immunogenic fragment comprising at least eight or at least ten consecutive amino acids of one of these polypeptides, or a combination of these polypeptides. The polynucleotide encoding the PRRSV gp3 polypeptide may be codon-optimized for expression in a specific animal species.

In another aspect, the present invention provides PRRSV polypeptides, particularly PRRSV gp4 polypeptide. In another aspect, the present invention provides a polypeptide having a sequence as set forth in SEQ ID NO: 5, 18, or 46-51, and variant or fragment thereof.

In another aspect, the present invention provides a polypeptide having at least 70%, at least 75%, at least 80%, at least 85%, at least 90%, at least 95%, 96%, 97%, 98% or 99% sequence identity to a PRRSV gp4 polypeptide of the invention, particularly to the polypeptides having a sequence as set forth in SEQ ID NO: 5, 18, or 46-51.

In yet another aspect, the present invention provides fragments and variants of the PRRSV gp4 polypeptides identified above (SEQ ID NO: 5, 18, or 46-51) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO: 5, 18, or 46-51.

An immunogenic fragment of a PRRSV gp4 polypeptide includes at least 8, 10, 15, or 20 consecutive amino acids, at least 21 amino acids, at least 23 amino acids, at least 25 amino acids, or at least 30 amino acids of the PRRSV gp4 polypeptide having a sequence as set forth in SEQ ID NO: 5, 18, or 46-51, or variants thereof. In another embodiment, a fragment of a PRRSV gp4 polypeptide includes a specific antigenic epitope found on a full-length PRRSV gp4 polypeptide.

In another aspect, the present invention provides a polynucleotide encoding a PRRSV gp4 polypeptide, such as a polynucleotide encoding a polypeptide having a sequence as set forth in SEQ ID NO: 5, 18, or 46-51. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 5, 18, or 46-51, or a conservative variant, an allelic variant, a homolog or an immunogenic fragment comprising at least eight or at least ten consecutive amino acids of one of these polypeptides, or a combination of these polypeptides. The polynucleotide encoding the PRRSV gp4 polypeptide may be codon-optimized for expression in a specific animal species.

In another aspect, the present invention provides PRRSV polypeptides, particularly PRRSV gp5a polypeptide. In another aspect, the present invention provides a polypeptide having a sequence as set forth in SEQ ID NO:31 or 62-65, and variant or fragment thereof.

In another aspect, the present invention provides a polypeptide having at least 70%, at least 75%, at least 80%, at least 85%, at least 90%, at least 95%, 96%, 97%, 98% or 99% sequence identity to a PRRSV gp5a polypeptide of the invention, particularly to the polypeptides having a sequence as set forth in SEQ ID NO:31 or 62-65.

In yet another aspect, the present invention provides fragments and variants of the PRRSV gp5a polypeptides identified above (SEQ ID NO:31 or 62-65) which may readily be prepared by one of skill in the art using well-known molecular biology techniques.

Variants are homologous polypeptides having an amino acid sequence at least about 75%, 80%, 85%, 90%, 95%, 96%, 97%, 98%, or 99% identity to the antigenic polypeptides of the invention, particularly to the amino acid sequence as set forth in SEQ ID NO:31 or 62-65.

An immunogenic fragment of a PRRSV gp5a polypeptide includes at least 8, 10, 15, or 20 consecutive amino acids, at least 21 amino acids, at least 23 amino acids, at least 25 amino acids, or at least 30 amino acids of the PRRSV gp5a polypeptide having a sequence as set forth in SEQ ID NO: 31 or 62-65, or variants thereof. In another embodiment, a fragment of a PRRSV gp5a polypeptide includes a specific antigenic epitope found on a full-length PRRSV gp5a polypeptide.

In another aspect, the present invention provides a polynucleotide encoding a PRRSV gp5a polypeptide, such as a polynucleotide encoding a polypeptide having a sequence as set forth in SEQ ID NO: 31 or 62-65. In yet another aspect, the present invention provides a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 31 or 62-65, or a conservative variant, an allelic variant, a homolog or an immunogenic fragment comprising at least eight or at least ten consecutive amino acids of one of these polypeptides, or a combination of these polypeptides. The polynucleotide encoding the PRRSV gp5a polypeptide may be codon-optimized for expression in a specific animal species.

In another aspect, the present invention provides a polynucleotide having a nucleotide sequence as set forth in SEQ ID NO: 2, 4, 6, 8, 9, 10, 11, 12, 13, 15, 17, 19, 21-24, 30, 67, 69, 70, 72, 74, 76, or 78, or a variant thereof. In yet another aspect, the present invention provides a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 2, 4, 6, 8, 9, 10, 11, 12, 13, 15, 17, 19, 21-24, 30, 67, 69, 70, 72, 74, 76, or 78, or a variant thereof.

In some embodiments, the invention provides a safe and effective immunological or vaccine composition comprising: one or more recombinant viral vectors, comprising one or more heterologous polynucleotides, encoding one or more porcine reproductive and respiratory syndrome virus (PRRSV) gp2, gp3, gp4, gp5a, gp5 or E antigen, polypeptide, ectodomain, or variant thereof; and a pharmaceutically or veterinarily acceptable carrier. "Variant thereof" is intended to encompass immunologically equivalent versions of the antigens, polypeptides and ectodomains, including, for example, retargeted variants of the proteins as disclosed herein. "Immunologically equivalent" means the "variant thereof" is capable of eliciting a substantially similar immune response—as compared with the original comparator antigen, polypeptide or ectodomain—including a protective immune response.

In some embodiments of the composition the one or more vectors comprise a recombinant adenovirus 5 PRRSV (Ad5-PRRSV) vector, a recombinant baculovirus PRRSV vector, a recombinant porcine cytomegalovirus PRRSV vector or a recombinant poxvirus PRRSV vector.

In some embodiments, the one or more vectors comprise either: a nucleotide sequence encoding a PRRSV E antigen, polypeptide, ectodomain or variant thereof; or, a nucleotide sequence encoding a modified PRRSV gp2, gp3, gp4, gp5a, gp5 or M antigen, polypeptide, ectodomain, or variant thereof, wherein an existing cellular localization sequence of gp2, gp3, gp4, gp5a, gp5 or M has been replaced with a cell-surface expression determinant sequence from an heterologous gene. In some embodiments, the one or more vectors comprise a mixture of two vectors, a first vector expressing retargeted PRRSV minor proteins, and a second vector expressing re-targeted PRRSV major proteins.

In some embodiments, the recombinant vector(s) comprise a polynucleotide encoding an antigen, polypeptide or ectodomain having: at least 90% sequence identity to any one or more of SEQ ID NO: 1, 3, 5, 7, 14, 16, 18, 20, 31, 34-39, 40-45, 46-51, 52-58, 59-61, 62-66, 68, 71, 73, 75, 77, or 79-139; or, at least 90% sequence identity to an ectodomain sequence as set forth in a subsequence of SEQ ID NO: 1, 3, 5, 7, 14, 16, 18, 20, 31, 34-39, 40-45, 46-51, 52-58, 59-61, 62-66, 68, 71, 73, 75, 77, or 79-139.

In some embodiments, the recombinant Ad5-PRRSV vector comprises a polynucleotide having: at least 90% sequence identity to SEQ ID NO: 2, 4, 6, 8, 9, 10, 11, 12, 13, 15, 17, 19, 21-24, 30, 67, 69, 70, 72, 74, 76, or 78; or, at least 90% sequence identity to an ectodomain sequence encoded by a subsequence of SEQ ID NO: 2, 4, 6, 8, 9, 10, 11, 12, 13, 15, 17, 19, 21-24, 30, 67, 69, 70, 72, 74, 76, or 78.

In some embodiments, the composition or vaccine comprises one or two Ad5-PRRSV vectors. In some embodiments, the Ad5-PRRSV may expresses gp2 and E; gp2, gp4 and E; gp2, gp3, gp4 and E; rtg-gp2, rtg-gp3 and rtg-gp4; rtg-gp2 and E; rtg-gp2, rtg-gp4 and E; rtg-gp3 and E; rtg-gp4 and E; E alone; rtg-E alone; rtg-gp5, rtg-M.

In some embodiments, the Ad5-PRRSV recombinant vector comprises a polynucleotide encoding an antigen, polypeptide or ectodomain having at least 90% sequence identity to SEQ ID NO: 1, 3, 5, 7, 14, 16, 18, 20, 31, 34-39, 40-45, 46-51, 52-58, 59-61, 62-66, 68, 71, 73, 75, 77, or 79-139; or, comprises a polynucleotide encoding an ectodomain having at least 90% sequence identity to an ectodomain as set forth in a subsequence of SEQ ID NO: 1, 3, 5, 7, 14, 16, 18, 20, 31, 34-39, 40-45, 46-51, 52-58, 59-61, 62-66, 68, 71, 73, 75, 77, or 79-139.

In some embodiments, the recombinant Ad5-PRRSV vector comprises a polynucleotide having at least 90% sequence identity to SEQ ID NO: 2, 4, 6, 8, 9, 10, 11, 12, 13, 15, 17, 19, 21-24, 30, 67, 69, 70, 72, 74, 76, or 78; or, comprises a polynucleotide having at least 90% identity to an ectodomain sequence encoded by a subsequence of SEQ ID NO: 2, 4, 6, 8, 9, 10, 11, 12, 13, 15, 17, 19, 21-24, 30, 67, 69, 70, 72, 74, 76, or 78.

In some embodiments, the recombinant Ad5-PRRSV vector comprises one or more polynucleotides encoding one or more PRRSV gp2, gp3, gp4, gp5a, gp5 or E antigen, polypeptide, ectodomain, or variants thereof, or combinations thereof.

In some embodiments, the recombinant Ad5-PRRSV vector comprises one or more polynucleotides encoding one or more antigen, polypeptide or ectodomain having: (a) at least 90% sequence identity to a sequence set forth in SEQ ID NO: 1, 3, 5, 7, 14, 16, 18, 20, 31, 34-39, 40-45, 46-51, 52-58, 59-61, 62-66, 68, 71, 73, 75, 77, or 79-139; or, (b) at least 90% sequence identity to the ectodomain(s) encompassed by a sequence set forth in SEQ ID NO: 1, 3, 5, 7, 14, 16, 18, 20, 31, 34-39, 40-45, 46-51, 52-58, 59-61, 62-66, 68, 71, 73, 75, 77, or 79-139. By "ectodomain(s) encompassed by," it is intended that only the extracellular portion (i.e. not the transmembrane or cytoplasmic portion) of a given SEQ ID NO is to be subjected to the percent sequence identity limitation. For example, if a polypeptide consisting of 200 amino acids has an ectodomain spanning amino acids #20 to 100, a comparator polypeptide need only be 90% identical (i.e. in the case of 90% sequence identity language) across amino acids #20 to 100. Now that the invention has been disclosed, Applicants envision that the skilled person may routinely select from a wide variety of TMDs and CTDs to combine with the ectodomains of the disclosed individual and combinations of protective PRRSV polypeptides.

In some embodiments, the one or more polynucleotides have at least 90% sequence identity to a sequence as set forth in SEQ ID NO: 2, 4, 6, 8, 9, 10, 11, 12, 13, 15, 17, 19, 21-24, 30, 67, 69, 70, 72, 74, 76, or 78; or, the polynucleotides have at least 90% sequence identity across the length of an ectodomain encoded by a sequence as set forth in a subsequence of SEQ ID NO: 2, 4, 6, 8, 9, 10, 11, 12, 13, 15, 17, 19, 21-24, 30, 67, 69, 70, 72, 74, 76, or 78. The skilled person using routine techniques can comprehend or ascertain which polynucleotide sequences encode ectodomains.

In some embodiments, the Ad5-PRRSV vector comprises a polynucleotide encoding a PRRSV gp2 polypeptide having: (a) at least 90% sequence identity to a sequence as set forth in SEQ ID NO: 1, 14, 34-39, or 80-89 (gp2 protein); or (b) at least 90% sequence identity to an ectodomain sequence as set forth in a subsequence of SEQ ID NO: 1, 14, 34-39, or 80-89.

In some embodiments, the Ad5-PRRSV vector comprises a polynucleotide encoding a PRRSV E polypeptide having: (a) at least 90% sequence identity to a sequence as set forth in SEQ ID NO: 7, 20, 52-58, or 130-139 (E protein); or (b) at least 90% sequence identity to an ectodomain sequence as set forth in a subsequence of SEQ ID NO: 7, 20, 52-58, or 130-139.

In some embodiments, the Ad5-PRRSV vector comprises a polynucleotide encoding a PRRSV gp3 polypeptide having: (a) at least 90% sequence identity to a sequence as set forth in SEQ ID NO: 5, 18, 40-45, or 90-99 (gp3 protein); or (b) at least 90% sequence identity to an ectodomain sequence as set forth in a subsequence of SEQ ID NO: 5, 18, 40-45, or 90-99.

In some embodiments, the Ad5-PRRSV vector comprises two polynucleotides encoding PRRSV gp2 and E polypeptides having: (a) at least 90% sequence identity to one of the sequences as set forth in SEQ ID NO: 1, 14, 34-39, or 80-89 (gp2 protein) and one of the sequences as set forth in SEQ ID NO: 7, 20, 52-58, or 130-139 (E protein); or (b) at least 90% sequence identity to an ectodomain sequence as set forth in a subsequence of SEQ ID NO: 1, 14, 34-39, or 80-89 (gp2 protein) and an ectodomain sequence as set forth in a subsequence of SEQ ID NO: 7, 20, 52-58, or 130-139 (E protein).

In some embodiments, the Ad5-PRRSV vector comprises polynucleotides encoding PRRSV gp2, E and gp4 polypeptides having: (a) at least 90% sequence identity to one of the sequences as set forth in SEQ ID NO: 1, 14, 34-39, or 80-89 (gp2 protein), one of the sequences as set forth in SEQ ID NO: 7, 20, 52-58, or 130-139 (E protein) and one of the sequences as set forth in SEQ ID NO: 5, 18, 40-45, 90-99 (gp3 protein); or (b) at least 90% sequence identity to an ectodomain encompassed by one of the sequences as set forth in SEQ ID NO: 1, 14, 34-39, or 80-89 (gp2 protein), an ectodomain encompassed by one of the sequences as set forth in SEQ ID NO: 7, 20, 52-58, or 130-139 (E protein) and an ectodomain encompassed by one of the sequences as set forth in SEQ ID NO: 5, 18, 40-45, 90-99 (gp3 protein).

In another aspect, the disclosure provides a method of eliciting a protective immune response in an animal in need thereof against PRRSV comprising administering to the animal a recombinant Ad5-PRRSV vector expressing at least one gp2, gp3, gp4, gp5a, gp5 or E PRRSV antigen, and, a pharmaceutically or veterinarily acceptable carrier, adjuvant, excipient or vehicle.

In some embodiments of the method, the Ad5-PRRSV vector comprises one or more polynucleotides encoding one or more polypeptides having: (a) at least 90% sequence identity to one of the sequences as set forth in SEQ ID NO: 1, 14, 34-39, or 80-89 (gp2 protein) and SEQ ID NO: 7, 20, 52-58, or 130-139 (E protein); or (b) at least 90% sequence identity to the gp2 protein or E protein ectodomain(s) encompassed by the corresponding foregoing SEQ ID NOs.

The method of claim 24, wherein the Ad5-PRRSV vector comprises one or more polynucleotides encoding one or more polypeptides having at least 90% sequence identity to one of the sequences as set forth in SEQ ID NO: 1, 14, 34-39, or 80-89 (gp2 protein), one of the sequences as set forth in SEQ ID NO: 7, 20, 52-58, or 130-139 (E protein) and one of the sequences as set forth in SEQ ID NO: 5, 18, 40-45, 90-99 (gp3 protein); or (b) at least 90% sequence identity to gp2, E and gp3 ectodomains encompassed by the corresponding foregoing SEQ ID NOs.

In some embodiments, the administration is by oro-nasal, spray, drinking water, intramuscular, or subcutaneous administration, intradermal, transdermal. In some embodiments, the administration is a prime-boost. In some embodiments, the first vaccination is a mixture of two Ad5 vectors, the first expressing re-targeted PRRSV minor proteins and the second expressing PRRSV major proteins; and the boost comprises or consists essentially of either both vectors of the first vaccination, or either vector alone. In some embodiments, the animal in need of protection is a porcine animal.

In general, comparison of amino acid sequences is accomplished by aligning an amino acid sequence of a polypeptide of a known structure with the amino acid sequence of a polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

Alternatively or additionally, the term "homology" or "identity", for instance, with respect to a nucleotide or amino acid sequence, can indicate a quantitative measure of homology between two sequences. The percent sequence identity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur et al., 1983), for instance, using a window size of 20 nucleotides, a word length of 4 nucleotides, and a gap penalty of 4, and computer-assisted analysis and interpretation of the sequence data including alignment can be conveniently performed using commercially available programs (e.g., Vector NTI Software™, Invitrogen Inc. CA, USA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences. And, without undue experimentation, the skilled artisan can consult with many other programs or references for determining percent homology.

The invention further encompasses the PRRSV polynucleotides contained in a vector molecule or an expression vector and operably linked to a promoter element and optionally to an enhancer.

A "vector" refers to a recombinant DNA or RNA plasmid, bacteriophage, or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term "vector" includes vectors for cloning as well as viral vectors.

The term "engineered" or "recombinant" means a polynucleotide of semi-synthetic, or synthetic origin that either does not occur in nature or is linked to another polynucleotide in an arrangement not found in nature.

"Heterologous" means derived from a genetically distinct entity from the rest of the entity to which it is being compared. For example, a polynucleotide may be incorporated by genetic engineering techniques into a plasmid or vector derived from a different source, and is thus a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a PRRSV polypeptide, antigen, epitope or immunogen are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors. When the polynucleotide encodes a polypeptide fragment, e.g. a PRRSV peptide, advantageously, in the vector, an ATG is placed at 5' of the reading frame and a stop codon is placed at 3'. Other elements for controlling expression may be present, such as enhancer sequences, stabilizing sequences, such as intron and or untranslated 5' or 3' sequences and signal sequences permitting the secretion of the protein.

Methods for making and/or administering a vector or recombinants or plasmid for expression of gene products of the invention either in vivo or in vitro can be any desired method, e.g., a method which is by or analogous to the methods disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450; 6,312,683, and 6,596,279; U.S. patent application Ser. No. 12/753,597; WO 90/01543; WO91/11525; WO 94/16716; WO 96/39491; WO 98/33510; EP 265785; EP 0 370 573.

The present invention also relates to a composition or vaccine comprising vectors, such as expression vectors. The composition or vaccine can comprise, consist essentially of, or consist of one or more vectors, e.g., expression vectors, such as in vivo expression vectors, comprising, consisting essentially or consisting of (or expressing) one or more of PRRSV polypeptides, antigens, epitopes or immunogens. The vector contains and expresses a polynucleotide that comprises, consists essentially of, or consists of a polynucleotide coding for (or expressing) a PRRSV antigen, epitope or immunogen, in a pharmaceutically or veterinarily acceptable carrier, adjuvant, excipient or vehicle.

According to another embodiment, the vector or vectors in the composition or vaccine comprise, or consist essentially of, or consist of polynucleotide(s) encoding one or more proteins or fragment(s) thereof a PRRSV polypeptide, antigen, epitope or immunogen. The inventive composition or vaccine comprises, consists essentially of, or consists of, one or more vectors comprising, consisting essentially of, or consisting of, and advantageously also expressing, in vivo under appropriate conditions or suitable conditions or in a suitable host cell, polynucleotides from different PRRSV isolates encoding the same proteins and/or for different proteins.

The term plasmid covers any DNA transcription unit comprising a polynucleotide according to the invention and the elements necessary for its in vivo expression in a cell or cells of the desired host or target; and, in this regard, it is noted that a supercoiled plasmid and all of its topoisomers, open-circular plasmid, as well as linear forms of the plasmid, are intended to be within the scope of the invention.

Each plasmid comprises or contains or consists essentially of, in addition to the heterologous polynucleotide encoding a recombinant protein, antigen, epitope or immunogen, optionally fused with a polynucleotide encoding a heterologous peptide sequence, variant, analog or fragment, operably linked to a promoter or under the control of a promoter or dependent upon a promoter. In general, it is advantageous to employ a strong promoter that is functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter segment, which may or may not be associated with the enhancer segment. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart et al., 1985) or murine CMV-IE.

In more general terms, the promoter is either of a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

Functional sub-fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub-fragments.

Preferably, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., 1979).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

A “host cell” denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof. Host cells include, but are not limited to, baby hamster kidney (BHK) cells, colon carcinoma (Caco-2) cells, COST cells, HEK 293 cells, MCF-7 cells, MCF-10A cells, Madin-Darby canine kidney (MDCK) lines, mink lung (Mv1Lu) cells, MRC-5 cells, U937 cells, Chinese hamster ovary (CHO) cells, monkey Vero cells (cell line with the origin of the kidney of an African green monkey), quail (Quail muscle cell line QM7), chicken cell line DF1, and VERO cells. Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In one embodiment of the present invention, the vector is an Ad5 vector as described in US 2010/0255029 (incorporated herein by reference in its entirety).

Advantages of PRRSV vaccines based on the Ad5 vector include, but are not limited to, (1) induce a broad immunity, including humoral, cellular and mucosal responses (2) do not express all PRRSV proteins and therefore is compatible with the DIVA (differentiate infected from vaccinated animals) strategy, (3) induce rapid onset of immunity, and (4) production poses less risk for the environment than inactivated vaccines in case of accidental release.

One aspect of the invention relates to engineered or recombinant Ad5 vectors expressing PRRSV antigens. The antigen may be PRRSV minor envelope proteins, such as gp2, gp3, gp4, gp5a, or E protein, aforementioned. The engineered Ad5 vector may comprise one or more polynucleotides encoding one or more PRRSV antigens. In another aspect, the engineered Ad5 vector comprises one or more polynucleotides encoding a PRRSV gp2 antigen or variant thereof, a PRRSV E antigen or variant thereof, a PRRSV gp3 antigen or variant thereof, a PRRSV antigen or variant thereof, gp4 antigen or variant thereof, or a combination thereof.

In one embodiment, the invention provides for the administration of a therapeutically effective amount of a formulation for the delivery and expression of a protein, antigen, epitope or immunogen in a target cell. Determination of the prophylactically or therapeutically effective amount is routine experimentation for one of ordinary skill in the art. In another embodiment, the formulation comprises an expression vector comprising a polynucleotide that expresses a PRRSV minor envelope antigen, epitope or immunogen and a pharmaceutically or veterinarily acceptable carrier, vehicle, adjuvant or excipient. In another embodiment, the pharmaceutically or veterinarily acceptable carrier, vehicle, adjuvant or excipient facilitates transfection and/or improves preservation of the vector or protein.

The pharmaceutically or veterinarily acceptable carriers or vehicles or adjuvant or excipients are well known to the one skilled in the art. For example, a pharmaceutically or veterinarily acceptable carrier or vehicle or adjuvant or excipient can be sterile water, a 0.9% NaCl (e.g., saline) solution or a phosphate buffer. Other pharmaceutically or veterinarily acceptable carrier or vehicle or adjuvant or excipients that can be used for methods of this invention include, but are not limited to, poly-(L-glutamate) or polyvinylpyrrolidone. The pharmaceutically or veterinarily acceptable carrier or vehicle or adjuvant or excipients may be any compound or combination of compounds facilitating the administration of the vector (or protein expressed from an inventive vector in vitro); advantageously, the carrier, vehicle or adjuvant or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are but not exclusively suitable for plasmids, are those having the following formula:

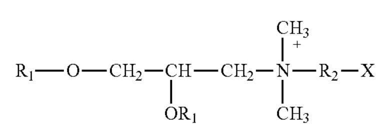

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

The plasmid mixture with the adjuvant is formed extemporaneously and/or contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio may be about 95:about 5 to about 5:about 95, or about 1:about 1, e.g., 1:1. The DMRIE or DMRIE-DOPE adjuvant: plasmid weight ratio can be between about 50:about 1 and about 1:about 10, such as about 10:about 1 and about 1:about 5, and advantageously about 1:about 1 and about 1:about 2, e.g., 1:1 and 1:2.

In another embodiment, pharmaceutically or veterinarily acceptable carrier, adjuvant, excipient, or vehicle may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (see, e.g., U.S. Pat. No. 6,358,500). Examples of other suitable emulsions are described in U.S. Pat. No. 7,371,395.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of cross linked acrylic or methacrylic acid, especially cross linked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers cross linked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are cross linked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or cross linked ethylene-maleic anhydride copolymers and they are, for example, cross linked by divinyl ether. Reference is also made to J. Fields et al., 1960.

With regard to structure, the acrylic or methacrylic acid polymers and EMA are preferably formed by basic units having the following formula:

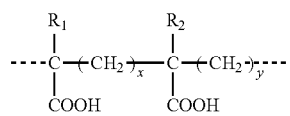

in which:
R1 and R2, which can be the same or different, represent H or CH3
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between 0.01 and 1.5% w/v, 0.05 to 1% w/v or 0.1 to 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α(IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNF□β), and transforming growth factor β (TGF□β). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a feline cytokine for preparations to be administered to a feline).

In another embodiment, the composition of the present invention may be prepared using the chemical or physical procedure as described by Stauffer et al. (Recent Patents on Anti-Infective Drug Discovery, 1, 291-296, 2006). Some of the inactivation techniques are summarized in the table below.

TABLE 1

Inactivation techniques

| Chemical | Physical | Combined |
|---|---|---|
| Ascorbic Acid | | Ascorbic Acid + UV |
| b-Propiolactone | Heat | Beta Propiolactone + UV |
| b-aminophenylketone | Pressure | Formalin + Heat |
| Diethylpyrocarbonate | UV | Formalin + UV |
| Ethylenimine | Non Ionic Detergents | Heat + Low Pressure |
| Formalin/Formaldehyde | | Pressure + Heat or Cold |
| Phenol | | Psoralen + UV |

The immunological composition and/or vaccine according to the invention comprise or consist essentially of or consist of an effective quantity to elicit a protective or therapeutic response of one or more expression vectors and/or polypeptides as discussed herein; and, an effective quantity can be determined from this disclosure, including the documents incorporated herein, and the knowledge in the art, without undue experimentation.

The compositions or vaccines of the present invention may be administered to an animal via drinking water, oro-nasal, sprays, aerosols, intranasal instillation, transdermal, subcutaneous, or intramuscular injection. Advantageously, the vaccines are administered by transdermal, oronasal, subcutaneous, intramuscular, spray or drinking water.

The present invention contemplates at least one administration to an animal of an efficient amount of the therapeutic composition made according to the invention. The therapeutic composition according to the invention can be administered by a needleless apparatus (as, for example with a Pigjet, Dermojet, Biojector, Vetjet or Vitajet apparatus (Bioject, Oreg., USA)).

In one embodiment of the invention, a prime-boost regimen can be employed, which is comprised of at least one primary administration and at least one booster administration using at least one common protein, polypeptide, antigen, epitope or immunogen. The immunological composition or vaccine used in primary administration is different in nature from those used as a booster. However, it is noted that the same composition can be used as the primary administration and the boost administration. This administration protocol is called "prime-boost".

In another aspect of the prime-boost protocol of the invention, a composition comprising the engineered Ad5 PRRSV vaccine or composition is administered followed by the administration of vaccine or composition comprising a recombinant viral vector that contains and expresses a PRRSV antigen in vivo, or an inactivated viral vaccine or composition comprising the PRRSV antigen, or a vaccine or composition comprising a PRRSV subunit (protein), or a DNA plasmid vaccine or composition that contains or expresses a PRRSV antigen. Likewise, a prime-boost protocol may comprise the administration of vaccine or composition comprising a recombinant viral vector that contains and expresses a PRRSV antigen in vivo, or an inactivated viral vaccine or composition comprising the PRRSV antigen, or a vaccine or composition comprising a PRRSV subunit (protein), or a DNA plasmid vaccine or composition that contains or expresses a PRRSV antigen, followed by the administration of a composition comprising the engineered Ad5 PRRSV vaccine or composition. It is noted that both the primary and the secondary administrations may comprise the composition comprising the engineered Ad5 PRRSV vaccine or composition. It is further noted that both the primary and the secondary administrations may comprise one or more compositions comprising the engineered vectors of the present invention.

A prime-boost protocol comprises at least one prime-administration and at least one boost administration using at least one common antigen. The vaccine or composition used in prime-administration may be different in nature from those used as a later booster vaccine or composition. The prime-administration may comprise one or more administrations. Similarly, the boost administration may comprise one or more administrations.

The various administrations are preferably carried out about 1 to about 6 weeks apart, or about 2 to about 4 weeks apart. Repeated booster every 2 to 6 weeks or an annual booster is also contemplated. The animals are preferably at least one day old at the time of the first administration.

The immunological composition and/or vaccine contains per dose from about $10^4$ to about $10^{11}$, advantageously from about $10^5$ to about $10^{10}$ and more advantageously from about $10^6$ to about $10^9$ viral particles of recombinant adenovirus expressing a PRRSV antigen, epitope or immunogen. In the case of immunological composition and/or vaccine based on a poxvirus, a dose can be between about $10^2$ pfu and about $10^9$ pfu. The immunological composition and/or vaccine contains per dose from about $10^2$ to about $10^7$, advantageously from about $10^3$ to about $10^5$ pfu of poxvirus or herpesvirus recombinant expressing the PRRSV antigen, epitope or immunogen.

The viral vector may be an attenuated avipox expression vector. In one embodiment, the avipox expression vector may be a fowlpox vector, for example, TROVAC®. In another embodiment, the avipox expression vector may be a canarypox vector, for example, ALVAC®. In still another embodiment, a baculovirus expression platform may be used. For example, the antigens may be produced in a baculovirus expression system using insect cell cultures as host, and the resulting recombinant polypeptides may be administered to the animals. Alternatively, the entire recombinant baculovirus may be administered as a vaccine. In general, the PRRSV antigen, epitope or immunogen may be a PRRSV minor envelope protein, such as gp2, gp3, gp4, gp5a, gp5 or E. Other viruses that may be used in methods of the invention include, but are not limited to, vaccinia viruses, such as an attenuated vaccinia virus, for instance NYVAC, adenoviruses and herpesviruses, including porcine CMV.

The efficacy of the vaccines may be tested about 2 to 4 weeks after the last immunization by challenging animals with a virulent strain of PRRSV. Both homologous and heterologous strains may be used for challenge to test the efficacy of the vaccine. The animal may be challenged by spray, intra-nasal, IM, intra-tracheal, and/or oral. The challenge viral challenge may be about $10^3$ to about $10^9$ virions or infectious units per dose, in a volume depending upon the route of administration. For example, if the administration is by spray, a virus suspension is aerosolized to generate about 1 to 200 µm droplets, if the administration is intra-nasal, intra-tracheal or oral, the volume of the challenge virus is about 0.05 to about 5 ml. Animals may be observed daily for 14 days following challenge for clinical signs and mortality. In addition, the groups of animals may be euthanized and evaluated for pathological findings. Oropharyngeal, tracheal or cloacal swabs may be collected from all animals post challenge for virus detection. The presence or absence of viral antigens in tissues may be evaluated by immunohistochemistry, viral isolation or titration, or nucleic acid detection such as reverse-transcriptase polymerase chain reaction (RT-PCR). Blood samples may be collected post-challenge and may be analyzed for the presence of anti-PRRSV gp2, gp3, gp4, gp5a, E virus-specific antibody. Alternatively, when the engineered vectors contain epitope tags, tag-specific antibodies may be used to detect the presence and location of recombinant vaccine polypeptides.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each immunization protocol, without any undue experimentation.

Another embodiment of the invention is a kit for performing a method of inducing an immunological or protective response against PRRSV in an animal comprising a recombinant Ad5 immunological composition or vaccine or an inactivated PRRSV immunological composition or vaccine and instructions for performing the method of delivery in an effective amount for eliciting an immune response in the animal.

Unless otherwise specifically recited, construction of nucleic acid inserts, plasmids and recombinant viral vectors was carried out using the standard molecular biology techniques known in the art, for example, described by J. Sambrook et al. (Molecular Cloning: A Laboratory Manual, 2nd Edition, Cold Spring Harbor Laboratory, Cold Spring Harbor, N.Y., 1989).

Particularly as to subject matter eligibility, the vectors disclosed herein do not result in the expression in the vaccinated animal of naturally-occurring levels of PRRSV proteins. Each gene's expression is driven by non-native heterologous promoter elements, and so, the ultimate amount of each cognate protein expressed will not be equivalent to that produced during natural PRRSV infection. Moreover, one important purpose of the disclosed expression system is to produce relatively high levels of PRRSV minor envelope proteins (native, modified or engineered), and to properly present the minor proteins to the host animal's immune system, to elicit in the animals a safe and protective immune response. The levels and presentation of the PRRSV minor envelope proteins typical of natural PRRSV infection fail to elicit a safe and effective immune response against the PRRSV minor proteins. Accordingly, both the disclosed vaccine compositions, and their ultimate disposition within the vaccinated animal, differ significantly in structure and function when compared to their closest naturally-occurring counterparts.

The invention is further illustrated by the following non-limiting examples.

EXAMPLES

Example 1—Construction and Testing of Plasmids Expressing PRRSV Genes

In order to increase visibility to the immune system, the PRRSV envelope proteins were re-targeted to the cell surface from intracellular compartments by introducing multiple changes while maintaining the extracellular domain (putative antibody binding site). The re-targeting of the envelope genes was initially attempted by removing the cytoplasmic and transmembrane domains of the native protein, which is probable site for the retention signal, and replacing them with similar domains from vesicular Stomatitis Virus glycoprotein (VSV-G), another viral protein known for cell surface expression. The signal sequence of the native envelope genes was also replaced with the signal sequence from tissue plasminogen activator (tPA), a well-characterized secretory protein, to promote entry of the modified proteins to the secretory pathway and eventual expression on the cell surface. Specific epitope tags were also inserted into each of the re-targeted proteins to track the expression and translocation of the proteins within the cell. The epitope tags Myc, Flag and HA flanked with linker sequences were inserted into gp2, gp3 and gp4, respectively (FIGS. 5A-5D).

Surface Expression of Re-Targeted Proteins.

Figure 6:
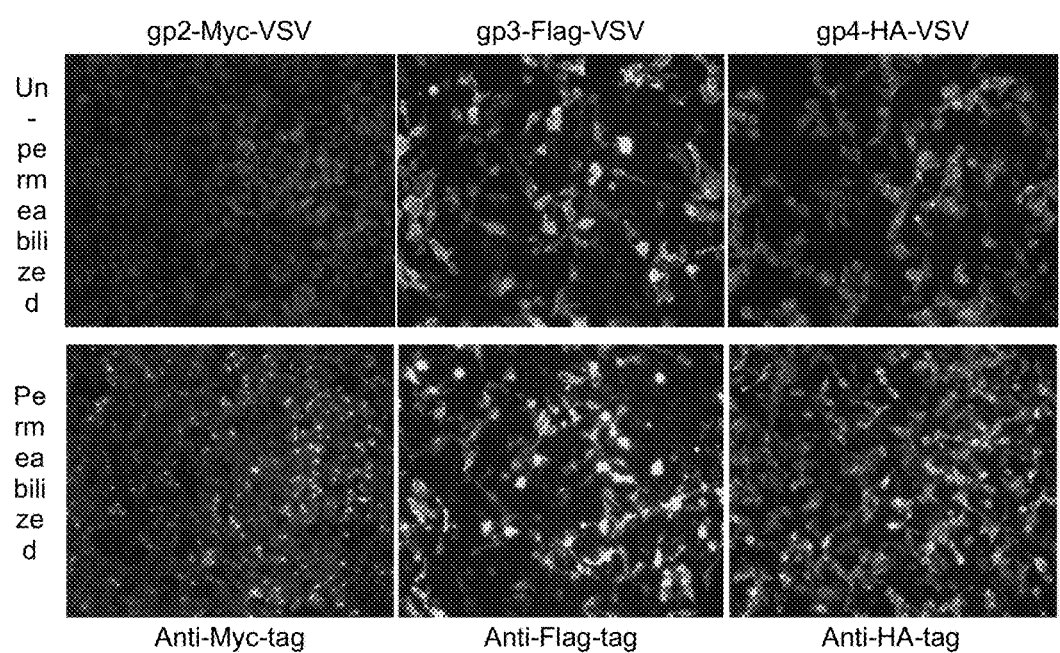
FIG. 6 presents immunofluorescence assay (IFA) images of fixed HEK 293T cells that had been transfected with epitope-tagged rtg-gp2, rtg-gp3 and rtg-gp4 proteins.

Each of the re-targeted genes was synthesized in its entirety and cloned into the expression plasmid with CMV promoter. The plasmids were transfected into HEK 293T cells and expression was detected in fixed cells by immunofluorescence assay (IFA) (FIG. 6). Cell surface and total protein expression was readily detected in cells transfected with both gp3-Flag-VSV and gp4-HA-VSV. However, expression in gp2-Myc-VSV-transfected cells was detected only after permeabilization of the cells, indicating the modifications introduced in gp2 were not sufficient to re-target the protein to the cells surface. Moreover, upon permeabilization, the staining for gp2-Myc-VSV was distinctly different from that of gp3 or gp4 modified (re-targeted) proteins. In the case of gp2-myc-VSV, the staining was more focal and intense, while in the gp3-Flag-VSV and gp4-HA-VSV it was diffuse throughout the cell. This indicated that the gp2-VSV-Myc protein was expressed, but might have folded improperly, becoming trapped in some sub-cellular compartment. There can be several reasons for inability of the modified gp2 to fold properly. First, these can be the requirement of other parts of the protein for proper folding, such as signal sequence, transmembrane or cytoplasmic tail that were removed in the process of modifying for surface expression. Second, it can also be due to incomplete removal of domains of gp2 that has still contained retention signal. Third, the misfolding might have been induced due to the presence of myc tag, which is not present in either modified gp3 or gp4. Fourth, it has been shown that the lack of expression of one of the minor proteins abrogates incorporation of all of the minor proteins into the virion; therefore, gp2 may require the presence of gp3 and gp4 to achieve proper folding.

Re-Targeted Proteins Interact to Form Oligomers.

Figure 7:
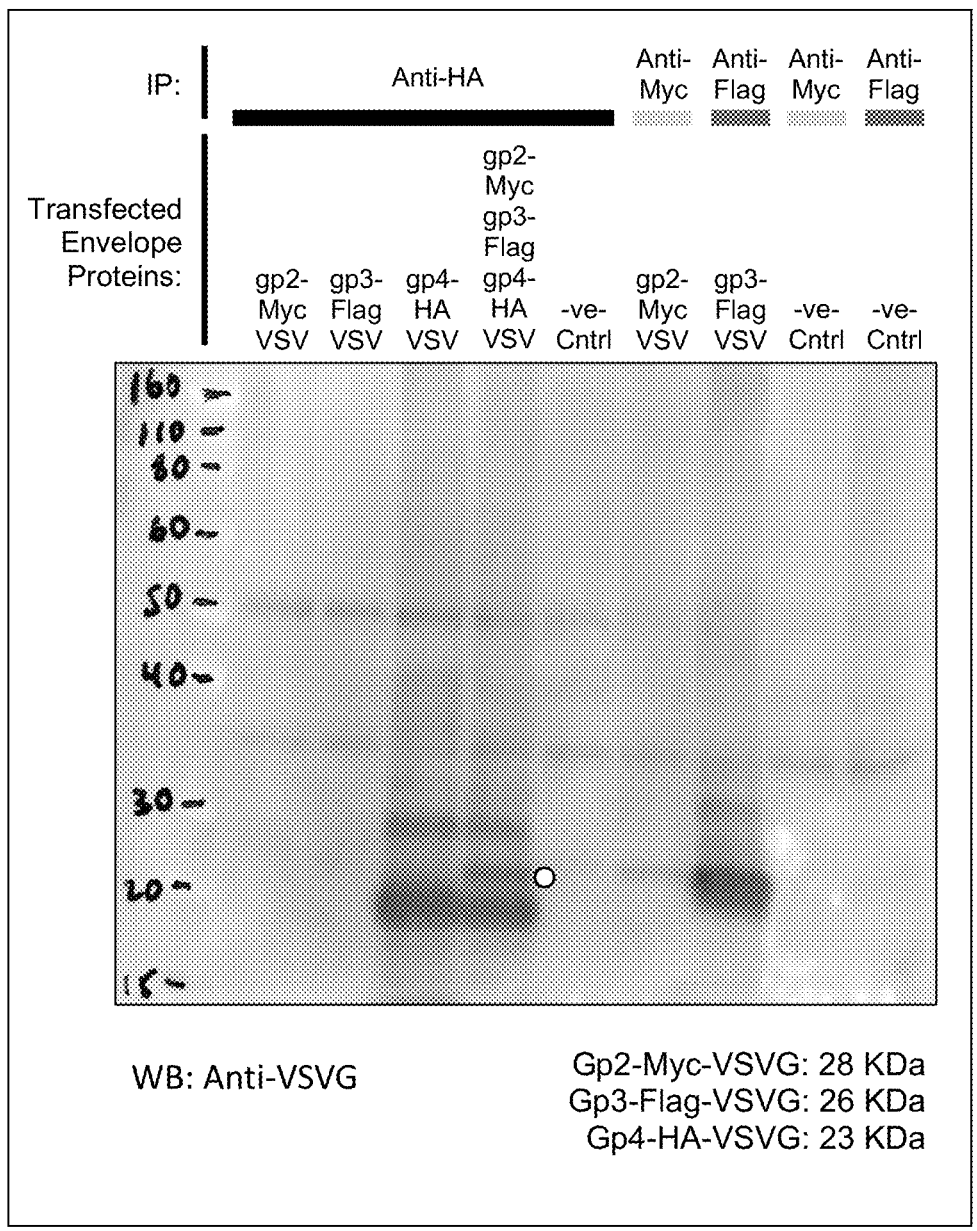
FIG. 7 shows an anti-VSVG Western Blot (WB) of co-immunoprecipitated (co-IP) lysates from HEK 293T cells transfected with plasmids coding for each of the individual re-targeted envelope proteins.

Interaction among minor proteins has been implicated by a functional assay and directly demonstrated by a biochemical assay. Plasmids coding for each of the re-targeted proteins were co-transfected to HEK-293T cells and interaction among the minor proteins was tested by co-immunoprecipitation (Co-IP) assay. As shown in FIG. 7, the anti-HA antibody pulls down specifically gp4-HA-VSV (lane 3) but not gp3-flag-VSV (lane 2) or gp2-myc-VSV (lane 1). However, when all the modified proteins were co-transfected, the same anti-HA antibody pulled down additional protein band other than gp4-HA-VSV (lane 4, red dot), indicating that the additional protein has direct interaction with gp4-HA-VSV but not the anti-HA antibody. The size of this band is similar to the gp2-Myc-VSV (lane 6) or gp3-Flag-VSV (lane 7), indicating that this protein interacting with gp4 can be gp2, gp3 or both. A subsequent probe of the additional band in the co-IP (lane 4) with anti-Flag or anti-Myc antibody turned out to be positive for both (not shown), indicating that this band contains both gp2 and gp3 proteins. Therefore, the conclusion from this and additional experiments is that the modifications introduced for surface expression of the gps did not alter their quaternary structure.

Re-Targeted Proteins Maintain Interaction with CD163 Receptor after Modification.

Figure 8:
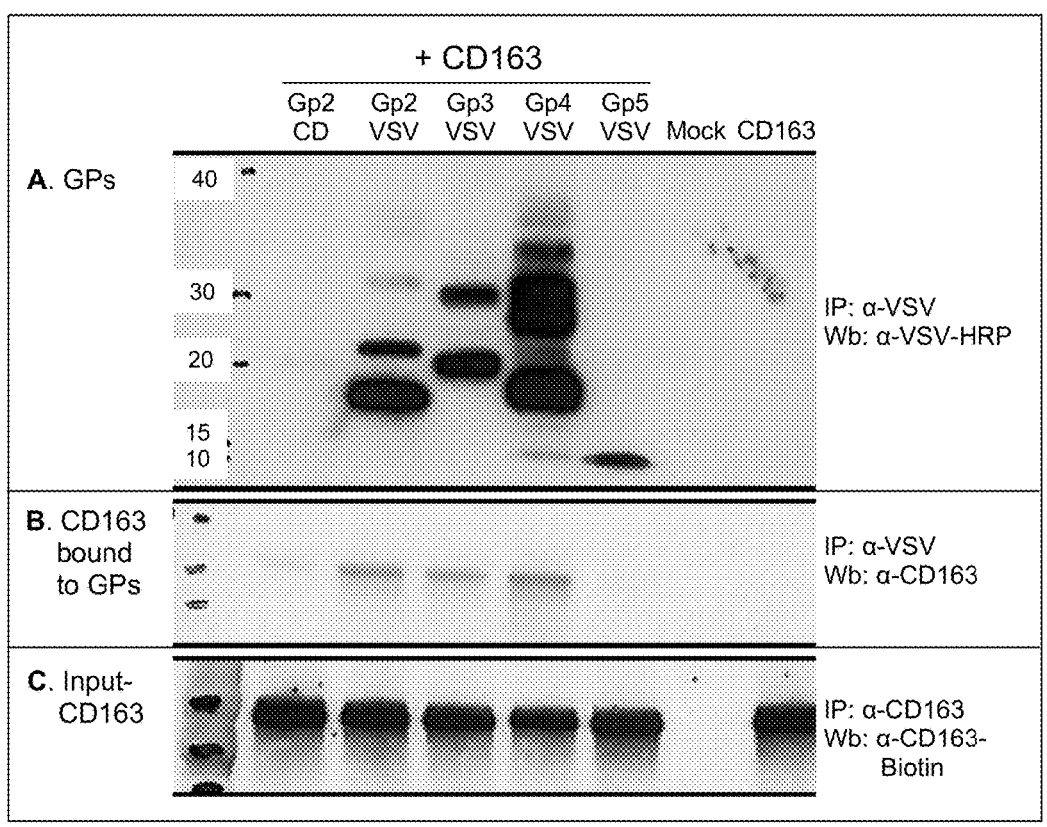
FIG. 8 shows several WBs of co-IP lysates from HEK 293T cells transfected with plasmids coding for each of the individual re-targeted envelope proteins or porcine CD16. IP: α-VSV, Wb: α-VSV-HRP (A); IP: α-VSV, Wb: α-CD163 (B); IP: α-CD163, Wb: α-CD163-Biotin (C)

The next step in ensuring the proper folding of the re-targeted protein was to show that they still maintain their capacity to interact with the receptor, porcine CD163. Each of the plasmids expressing the re-targeted proteins were co-transfected with plasmid expressing CD163 (domains 4-9), previously shown to be sufficient to mediate entry of virus into target cells. One portion of the cell lysate was immunoprecipitated with anti-VSV antibody (specific for the envelope proteins) and the other portion was immunoprecipitated with anti-CD163 antibody. The lysate precipitated with anti-CD163 antibody was probed with anti-CD163 antibody conjugated with Biotin to control for the input CD163 into each co-IP reaction (FIG. 8C). The lysate immunoprecipitated with anti-VSV was run in duplicates and one membrane was probed with anti-VSV-HRP (FIG. 8A), to measure the amount of modified gp, and the other membrane was probed with anti-CD163 (FIG. 8B) to measure the amount of CD163 co-immunoprecipitated with the modified envelope glycoproteins.

All the modified minor envelope glycoproteins do interact with CD163, whereas the modified gp5, a major glycoprotein used as negative control, had a much weaker or undetectable interaction with CD163.

Example 2—Animal Vaccination with Pooled PRRSV Envelope Gene-Expressing Plasmids Thirty-two, 3 weeks pigs were divided into 4 groups, of 8 animals each (Table 2).

TABLE 2

Study details.

| Group | No. Animals | Group | | Immunization (Days) | | | | Killed/DNA | Challenge |
|---|---|---|---|---|---|---|---|---|---|
| | | | | 0 | 14 | 28 | 42 | 63 | 84 |
| 1 | 8 | Wild-type PRRSV Gps | 1A | X | X | X | X | DNA (3) | X |
| | | | 1B | X | X | X | X | Killed (5) | X |
| 2 | 8 | Recombinant PRRSV | 2A | X | X | X | X | DNA (3) | X |
| | | Gps | 2B | X | X | X | X | Killed (5) | X |
| 3 | 8 | Mock DNA Imm. | 3A | X | X | X | X | DNA (3) | X |
| | | (Rabies G) | 3B | X | X | X | X | Killed (3) | X |
| 4 | 8 | Un-vaccinated | | | | | | | X |

The wild-type group received pool of 3 plasmids expressing the non-targeted gps, the recombinant group received pool of three plasmids expressing the re-targeted gps (i.e. FIGS. 5B to 5D), the Mock group received plasmid coding for the Rabies glycoprotein, while the unvaccinated group received only Tris-EDTA buffer. Each plasmid was at a concentration of about 1 μg/μL, and about 400 μg of each plasmid was administered at 200 μl per each ear lobe. After 4 immunizations, each group was further divided and boosted with either Killed vaccine, in TS6 adjuvant (U.S. Pat. No. 7,371,395 B2, to Merial, and herein incorporated by reference in its entirety), or received a 5th round of DNA immunization.

While there appeared to be a trend toward increased protection against lung lesions in animals vaccinated with either of the pooled plasmids, when compared to the rabies-G or unvaccinated groups, the mean among all groups was not statistically different. There was also no significant difference between groups receiving targeted vs. re-targeted plasmids.

Therefore, Applicants next set out to put all the genes within a single vector, to enable simultaneous expression within a single cell, to facilitate interaction/oligomerization of the PRRSV envelope proteins.

Example 3—Construction and Testing of Viral Vectors Expressing PRRSV Genes

Cells and Media. HEK 293 cells (ATCC) were maintained in MEM (Gibco #11095) with 10% Fetal Bovine serum (Moregate Batch #81827101) at 37° C. in 5% CO2. These cells were used to rescue the recombinant adenovirus (vAD3041, vAD3042, vAD3038, vAD3033, and vAD3067) and make virus stocks.

Construction of Viral Vectors and Immunogens.

The minor envelope proteins of PRRSV include gp2 (ORF2), gp3 (ORF3), gp4 (ORF4) and E (ORF2b). The DNA sequence of each of these proteins was obtained from GenBank Accession #U87392 (VR2332, PRRSV Type II). VR2332 (North American strain) represents one of two known major serotypes of PRRSV (Done et al., 1996). The other, prototype Lelystad, is representative of at least most strains that have been isolated in Western Europe. The codon-optimized sequences of each protein when constructed with appropriate promoter to express all proteins from single viral vector (FIG. 1). In each case, SV40 (Simian virus 40) and CMV (Cytomegalovirus) promoters drive expression of gp2 and gp4, respectively, in opposite directions, as indicated by arrows. It is envisioned that these promoters could be exchanged, such that SV40 could drive expression of gp4 and CMV could drive expression of gp2. Such variations will be obvious to the skilled person. Importantly, because of the disclosed critical role played by the PRRSV minor proteins in eliciting a safe and protective immune response, Applicants fully expect the following approaches to apply equally well to all PRRSV strains. Accordingly, codon-optimized versions of the Lelystad minor proteins may be prepared by routine methods, and the resulting sequences cloned into the recombinant vectors of the instant disclosure.

In all Ad5 PRRSV constructs, the expression of minor envelope glycoprotein gp3 is promoted by an Internal Ribosome Entry Site (IRES). Expression of minor envelope glycoprotein E in vAD3041 and vAD3067 (FIGS. 1C & 1D) is enabled by the presence of self-cleavage peptide (p2A), situated in the Ad5 constructs immediately following the gp2 coding region.

Further, the half-life of transcripts from SV40 and CMV promoters is enhanced by addition of poly A tails (pA) from SV40 or thymidine kinase (TK). The attL1 and attL2 sites (far left and right of each insert shown in FIG. 1) were used to insert the entire synthetic fragments into the adenoviral genome by LR recombination, Gateway Technology (Invitrogen) (thereby creating vAD3042, vAD3038, vAD3041 and vAD3067. The inserts of FIG. 1 were chemically synthesized (Genscript) to contain the appropriate restriction sites for cloning into the expression clone to generate recombinant Ad5 (Gateway Technology, Invitrogen). Once more, variations as to which element promotes expression of which particular PRRSV gene are contemplated, and are well within the reach of the skilled artisan reading this disclosure.

Accordingly, multiple combinations of minor proteins were assembled for recombination into the Ad5 vector: one containing only three of the minor proteins without E (vAD3042) (FIG. 1A; SEQ ID NO: 2); one containing rtg-gp2, rtg-gp3, rtg-gp4 proteins without E (vAD3038) (FIG. 1B; SEQ ID NO: 3); one containing all four codon-optimized minor proteins gp2, gp3, gp4 and E (vAD3041) (FIG. 1C; SEQ ID NO: 3); and one containing all four codon-optimized minor proteins rtg-gp2, rtg-gp3, rtg-gp4 and E (vAD3067) (FIG. 1D; SEQ ID NO: 4).

TABLE 3

Locations of features within the constructs

| Construct | Feature | Location |
|---|---|---|
| vAD3041 insert (4662 bp) | attL1 | 1-96 |
| | SV40 poly A | 97-314 (complementary) |
| | E ORF | 341-562 (complementary) |
| | P2A | 568-633 (complementary) |
| | gp2 ORF | 642-1412 (complementary) |
| | SV40 promoter | 1418-1785 (complementary) |
| | CMV promoter | 1806-2393 |
| | gp4 ORF | 2406-2942 |
| | IRES | 2949-3511 |
| | gp3 ORF | 3518-4282 |
| | TK poly A | 4295-4566 |
| | attL2 | 4567-4662 |
| vAD3042 insert (4662 bp) | attL1 | 1-96 |
| | SV40 poly A | 97-314 (complementary) |
| | gp2 ORF | 341-1111 (complementary) |
| | SV40 promoter | 1117-1484 (complementary) |
| | CMV promoter | 1505-2092 |
| | gp4 ORF | 2105-2641 |
| | IRES | 2648-3210 |
| | gp3 ORF | 3217-3981 |
| | TK poly A | 3994-4265 |
| | attL2 | 4266-4361 |
| vAD3038 insert (re-targeted vector) | attL1 | 1-96 |
| | SV40 poly A | 97-314 (complementary) |
| | gp2-Myc-VSV ORF | 333-1151 (complementary) |
| | SV40 promoter | 1163-1530 (complementary) |
| | CMV promoter | 1551-2138 |
| | gp4-HA-VSV ORF | 2148-2864 |
| | IRES | 2865-3427 |

TABLE 3-continued

Locations of features within the constructs

| Construct | Feature | Location |
|---|---|---|
| | gp3-Flag-VSV ORF | 3431-4192 |
| | TK poly A | 4199-4470 |
| | attL2 | 4471-4566 |
| vAD3067 insert (FIG. 1D) | attL1 | 1-96 |
| | SV40 poly A | 97-314 (complementary) |
| | E ORF | 341-562 (complementary) |
| | P2A | 568-633 (complementary) |
| | gp2-Myc-VSV ORF | 642-1460 (complementary) |
| | SV40 promoter | 1472-1839 (complementary) |
| | CMV promoter | 1860-2447 |
| | gp4-HA-VSV ORF | 2457-3173 |
| | IRES | 3174-3736 |
| | gp3-Flag-VSV ORF | 3740-4501 |
| | TK poly A | 4508-4779 |
| | attL2 | 4480-4575 |
| pAd/PL-DEST (Above transgene cassette inserts were placed between the attR1 and attR2 sites of pAD/PL-DEST) | Human Adenovirus 5 sequences | (wild type 1-458, includes 5'L-ITR and packaging signal): 1-458 |
| | attR1 site | 512-636 |
| | attR2 site | 2092-2216 |
| | Human Adenovirus 5 sequences | (wild type 3513-35935, E3 region deleted, includes 3'R-ITR): 2234-32782 |
| | PacI restriction site | 32788 and 34862 |
| | Plasmid backbone region | 32959-34705 including pUC origin, Ampicillin resistance gene |

Production of Virus.

The expression clones were generated by LR recombination of entry vector with destination vector using Gateway technology (Invitrogen). Recombinant adenovirus vAD3041, vAD3042 and vAD3038 were generated by transfection of linearized expression clones in HEK 293 cells with transfection reagent. After rescue of, each virus was harvested by freeze-thaw cycle and clarification the cell debris by centrifugation. For passage, each virus was inoculated into monolayer of HEK 293 cells and approximately 3-4 days post infection, virus was harvested by freeze-thaw cycle and clarification by centrifugation. Three passages were conducted to make virus stock, which was stored at −80° C. As a negative control, codon-optimized hemagglutinin (HA) gene of Swine Influenza Virus (SIV) was assembled similarly in Ad5 viral vectors (vAD3033).

Viral Titer.

HEK 293 cells were plated at a density of 7×10$^5$ cells per plate in three 96 well plates with MEM (Gibco #11095) media containing 2% FBS (Moregate Batch #81827101), non-essential amino acid (Gibco #11140), antibiotics-antimycotics (Gibco #15240). On the day of infection, each plate was infected with 100 μl per well of diluted virus from 10$^{-3}$ to 10$^{10}$. Virus titers were read on day 10 post infection and the average of three plates was used to calculate the titer. The Passage 3 stock titer of vAD3041 P.3 was 10$^{9.03}$ TCID$_{50}$ per ml, and that of vAD3042 P.3 was 10$^{8.90}$ TCID$_{50}$ per ml. The Passage 3 stock titer of vAD3038 P.3 was 10$^{9.93}$ TCID$_{50}$ per ml, and that of another batch of vAD3042 P.3 was 10$^{9.97}$ TCID$_{50}$ per ml.

Figure 4:
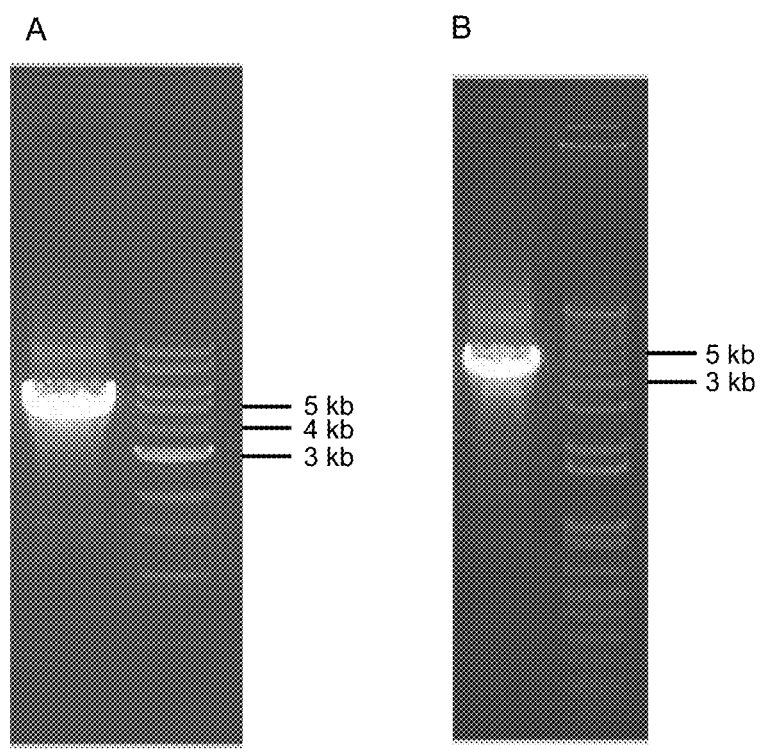
FIG. 4 is a gel image showing the PCR amplicon of the region of PRRSV minor protein inserted in vAD3041 passage 3 (A) and vAD3042 passage 3 (B)
Figure 5A:
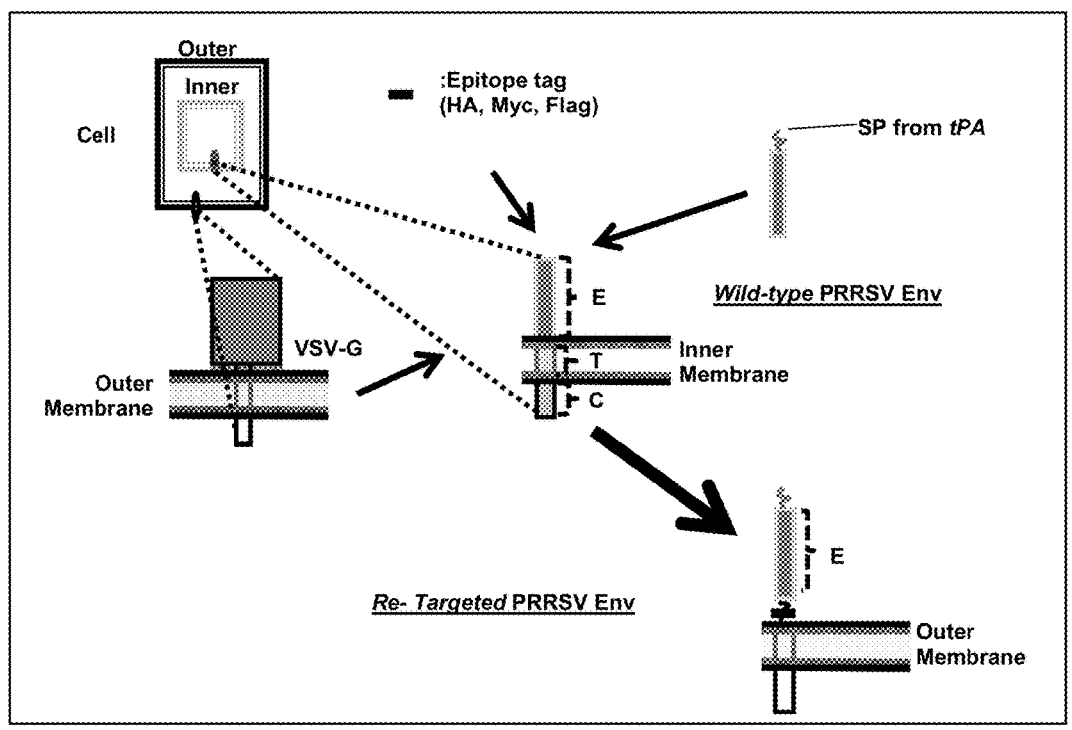
FIG. 5A presents the scheme used to re-target PRRSV envelope proteins to the cell surface.
Figure 5B:
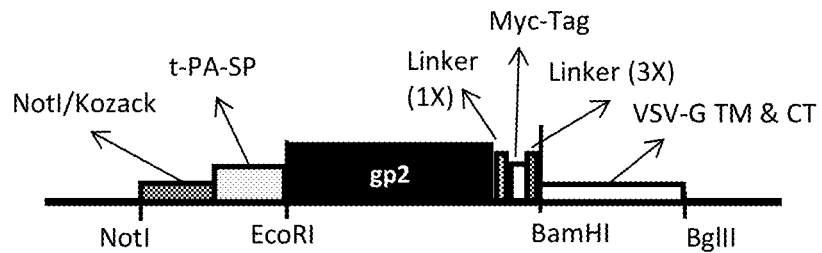
FIGS. 5B-5D present maps of the rtg-gp2, rtg-gp3 and rtg-gp4 proteins, wherein the endogenous TM and CT domains have been replaced with vesicular stomatitis virus-G (VSV-G) transmembrane (TM) and cytoplasmic tail (CT) domains, the signal sequence has been replaced, epitope tags have been added and linker sequences have been inserted.
Figure 5C:
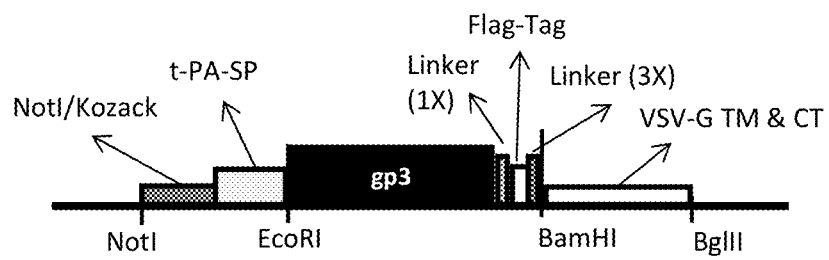
Figure 5D:
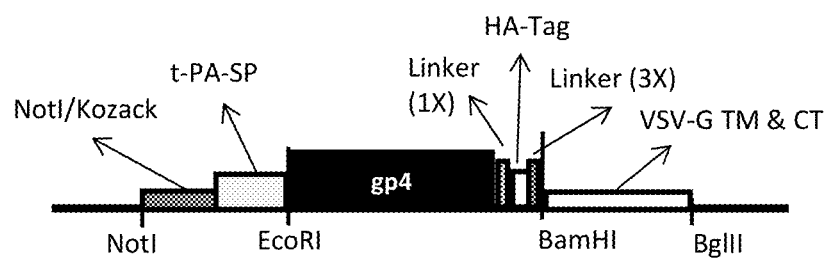

Viral DNA was extracted from each virus stock and amplified with primers pAd Forward (5'-GAC TTT GAC CGT TTA CGT GGA GAC-3') (SEQ ID NO: 26) and pAd Reverse (5'-CCT TAA GCC ACG CCC ACA CAT TTC-3') (SEQ ID NO: 27) using platinum PCR supermix High Fidelity (Invitrogen #12532) as directed. The PCR amplicons were the same size as expected: e.g. 4709 bp for vAD3041; 4408 bp for vAD3042 (FIG. 4). The nucleotide sequences of PCR amplicons from each recombinant adenovirus were identical as constructed in the entry vectors (described in FIG. 1), and there was no change in nucleotide sequence of transgene cassettes (PRRSV genes and promoter and poly A tails).

Expression of Re-Targeted Minor Envelope Proteins from Recombinant Adenovirus.

Figure 9A:
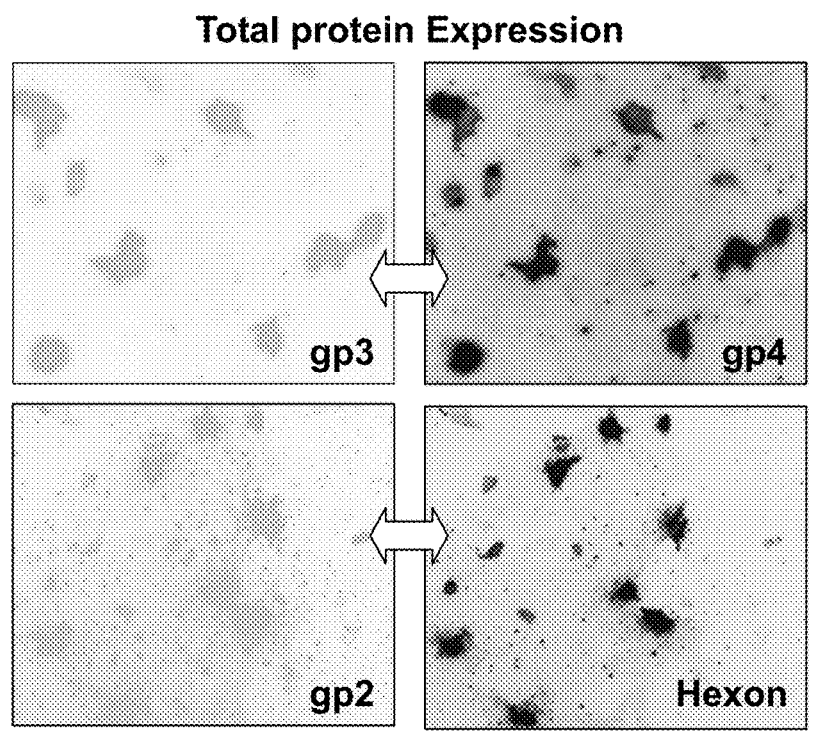
FIGS. 9A to 9C present dual-immunofluorescence assay (IFA) images of HEK 293 cells infected with vAD3038 (containing codon-optimized rtg-gp234); and stained simultaneously with two antibodies specific for indicated proteins and different fluorophore tags. Images were taken from identical optical field using filters specific for each fluorophore. Corresponding images are shown with arrow.
Figure 9B:
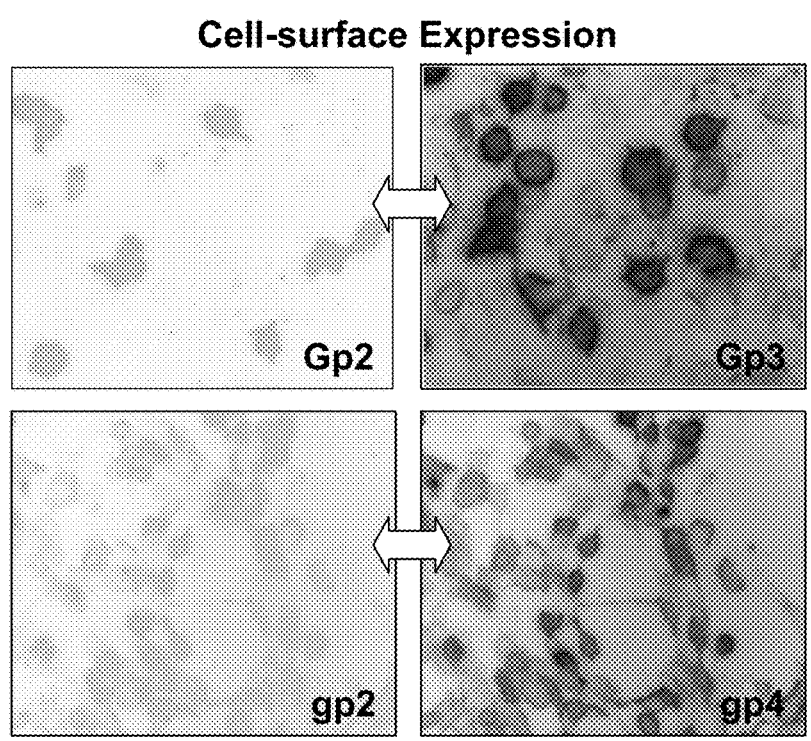

The simultaneous expression of each of the modified envelope proteins from the recombinant adenovirus within a single cell was confirmed by using dual-Immunofluorescence assay. The recombinant vAD3038 was used to infect confluent HEK293 monolayer at high MOI and cells were fixed after 48 hours and visualized by IFA for expression of the recombinant antigens. All the proteins were shown to express well including on the cell surface (FIGS. 9A & 9B).

Figure 9C:
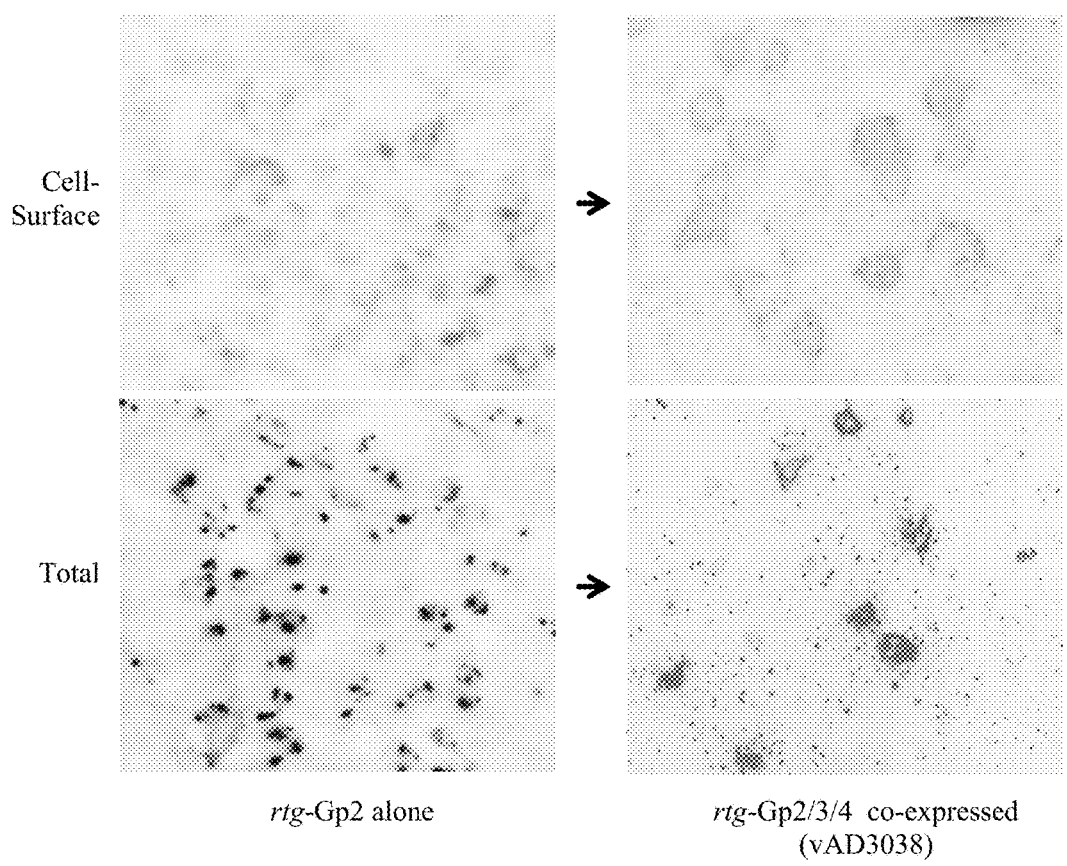
Figure 10:
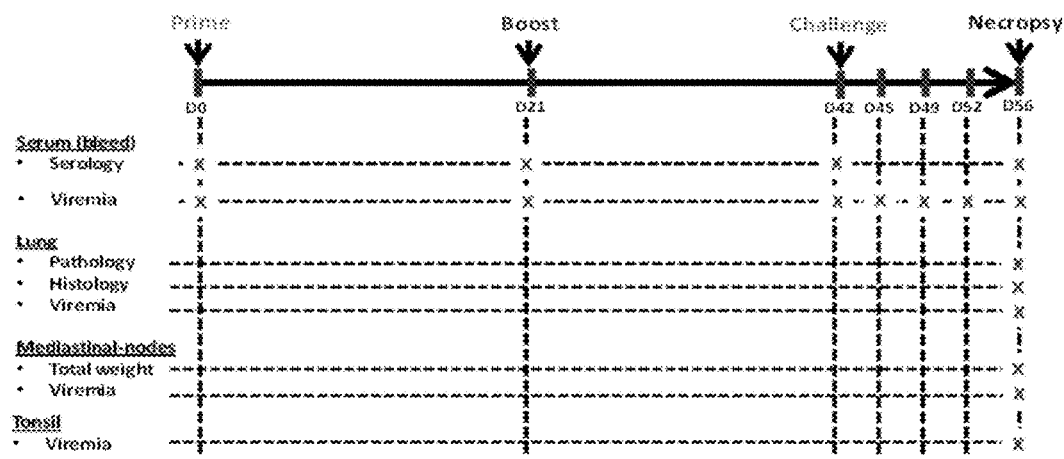
FIG. 10 is a chart detailing samples collected and time of collection throughout the study.

Importantly, the expression of gp2, which was defective when expressed alone, shown earlier as intense focal intracellular expression with no detectable surface expression, has improved with diffuse intracellular expression and distinct cell surface expression (FIG. 9C). This indicated that the proper folding and transport of modified gp2 might depend upon the co-expression of gp3 and/or gp4. This result suggests formation of the neutralizing epitope requires formation of higher order structure by interaction among the minor proteins.

Example 4—Clinical Trial Testing Safety and Efficacy of the Ad5 PRRSV Vaccines

Sixty (60) pigs were randomly divided into 4 groups, each containing 15 animals (Table 3). Group 1 received vAD3038, which expresses only gp2, gp3 and gp3, whereas Group 2 received vAD3041, which further expresses E. Group 3 received vAD3042, which expresses re-targeted gp2, gp3 and gp4, and Group 4 received vAD3033 that expresses SIV HA (negative control). Groups that received the adenoviral vaccines were primed by administering 1 ml of the preparation in each nostril, total 2 mL, approximately at a concentration of $10^{8-9}$ TCID$_{50}$/mL. These groups were boosted after 21 days by the same preparation administered intramuscularly. After 42 days of initiation of the experiment, all animals were challenged with PRRSV NADC20 strain intranasally. All animals were sacrificed after 2 weeks of challenge and examined for lesions in the lung and samples were collected for analysis of virus titer in tissues and sera, as indicated in FIG. 9.

TABLE 3

Vaccination trial scheme

| Group # | #/group | Prime Day 0 | Boost Day 21 | Challenge Day 42 |
|---|---|---|---|---|
| 1 | 15 | vAD3038 | vAD3038 | NADC20 |
| 2 | 15 | vAD3041 | vAD3041 | NADC20 |
| 3 | 15 | vAD3042 | vAD3042 | NADC20 |
| 4 | 15 | vAD3033 | vAD3033 | NADC20 |

Figure 11:
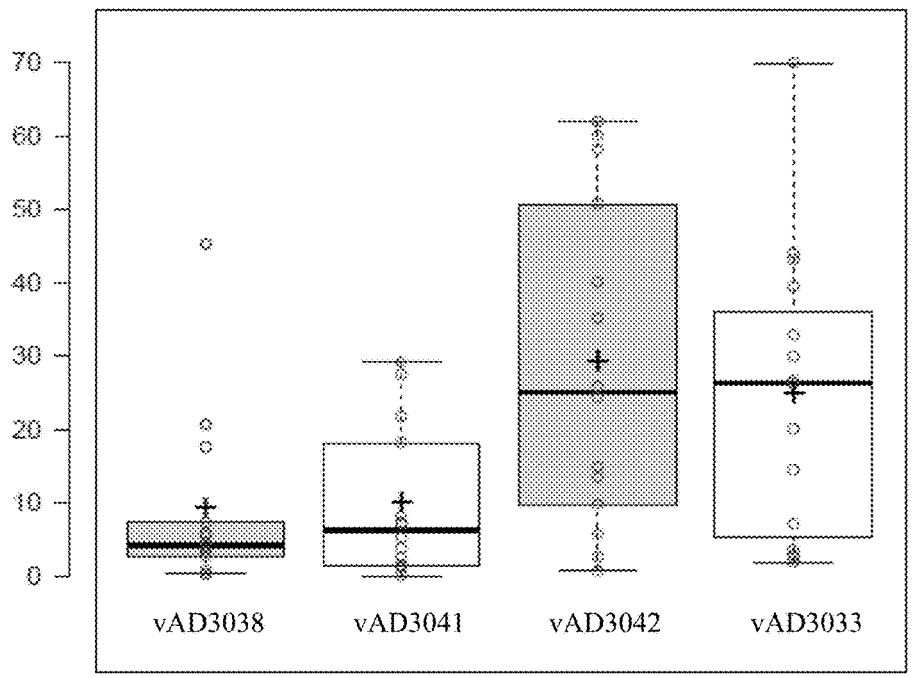
FIG. 11 is a graph showing the distribution of lung lesion scores among different groups. vAD3042 (Ad5 expressing codon-optimized, wild-type gp2, wild-type gp3 and wild-type gp4); vAD3041 (Ad5 expressing codon-optimized, wild-type gp2, wild-type gp3, wild-type gp4 and wild-type E); vAD3038 (Ad5 expressing codon-optimized, rtg-gp2, rtg-gp3 and rtg-gp4); and vAD3033 (Ad5 expressing a codon-optimized hemagglutinin (HA) gene of swine influenza virus (SIV), negative control). The median (cross-bar) and mean (+) and boxes represent the range between the $1^{st}$ and $3^{rd}$ inter-quartile range. The grey circles indicate the actual lung scores of each individual animal in each group.

In general, the data demonstrate that while vaccination with a single vector encoding the minor envelope proteins gp2, gp3 and gp4 (vAD3042) does not confer any significant advantage compared to the negative control, addition of E minor protein (vAD3041) makes a significant difference in protection against lung lesion from a PRRSV challenge. Moreover, re-targeting of the minor proteins (vAD3038) also makes a significant difference (FIG. 11).

Accordingly, the data and results disclosed herein support a generally-applicable model, wherein protection against PRRSV challenge is provided by antibodies directed against either one of the surface proteins (e.g. gp2), or the oligomeric structure of the surface formed and presented by the ternary/quaternary structure/arrangement of proteins. As such, these protective antibodies function, at least in part, by blocking the PRRSV infection by interfering with binding of the viral proteins to the cellular receptor(s).

Prior to this disclosure, the interaction of E protein with the rest of the minor proteins or other proteins in the virion was not known to be a prerequisite for elicitation of protective immunity. The instant vaccination trial has thus revealed a surprising and unexpected role for minor protein E, either alone or in combination with one or more of gp2, gp3 and gp4, in eliciting from porcine animals significantly higher protection against virulent PRRSV challenge.

It is envisioned by the Applicants, for example, that a neutralizing epitope may be, for example, located directly on the E protein, or it may induced by any one or combination of minor proteins in the presence of E protein. In view of the prior art references, this finding is entirely unexpected and surprising. Accordingly, this serendipitous discovery has not only identified a PRRSV-protective antigen composition, which serves as a basis to develop live-PRRSV-free vaccine, but it also opens up new areas of PRRSV research to elucidate protein-protein/virus-cell receptor interactions.

In view of the data and results, Applicants envision that other combinations of E+minor protein (e.g. E+gp2; E+gp2+gp3; E+gp2+gp4; and the like) will similarly overcome the problem of presenting a "neutralizing epitope" (defined herein as an epitope that is capable of eliciting in an animal a protective immune response, including the production of virus-neutralizing antibodies) to an animal's immune system. Moreover, the results indicate that re-targeting of the PRRSV minor proteins elicits a similarly surprising safe and protective immunity.

Applicants have thus revealed two major, yet related, approaches for overcoming the inability of separately-expressed gp2, gp3, and gp4 to present a virus-neutralizing epitope to a host animal's immune system, and elicit a protective immune response against virulent PRRSV challenge.

Moreover, this application discloses, for the first time, that the immunogenicity of PRRSV envelope minor proteins may be enhanced sufficiently to elicit protective immune responses. These inventive approaches are envisioned to have broad applicability to other viruses, particularly where cell localization plays a role in preventing virus neutralizing epitopes from being presented to the host's immune system.

Example 4—Clinical Trial Testing Safety and Efficacy of the Ad5 PRRSV Vaccines

Another study was conducted using the methods disclosed in Example 3, and Table 4 provides an overview. The adenoviral vectors had inserts according to the following: vAD3038 (Gp234-Rtrg); vAD3067 (Gp234-Rtrg+E-opt); vAD3064 (M-gp5-gp5a-Rtrg); vAD3041 (Gp234E); vAD3069 (Np-M-gp5-gp5a); vAD3046 (SIV-HA).

TABLE 4

Vaccination trial scheme (IM = intramuscular; IN = intranasal)

| Group # | # per group | Prime Day 0 | Boost Day 14 | Killed Vaccine Day 28 |
|---|---|---|---|---|
| 1 | 12 | vAD3038 (IN) | vAD3038 (IM) | Yes |
| 2 | 8 | vAD3067 (IM) | vAD3067 (IM) | Yes |
| 3 | 12 | vAD3067 (IN) | vAD3067 (IM) | Yes |
| 4 | 12 | (vAD3067 + vAD3064) (IN) | (vAD3067 + vAD3064) (IM) | Yes |
| 5 | 12 | (vAD3041 + vAD3069) (IN) | (vAD3041 + vAD3069) (IM) | Yes |
| 6 | 12 | vAD3038 (IN) | vAD3038 (IM) | No |
| 7 | 12 | vAD3046 (IN) | vAD3046 (IM) | No |

Summary.

Figure 18:
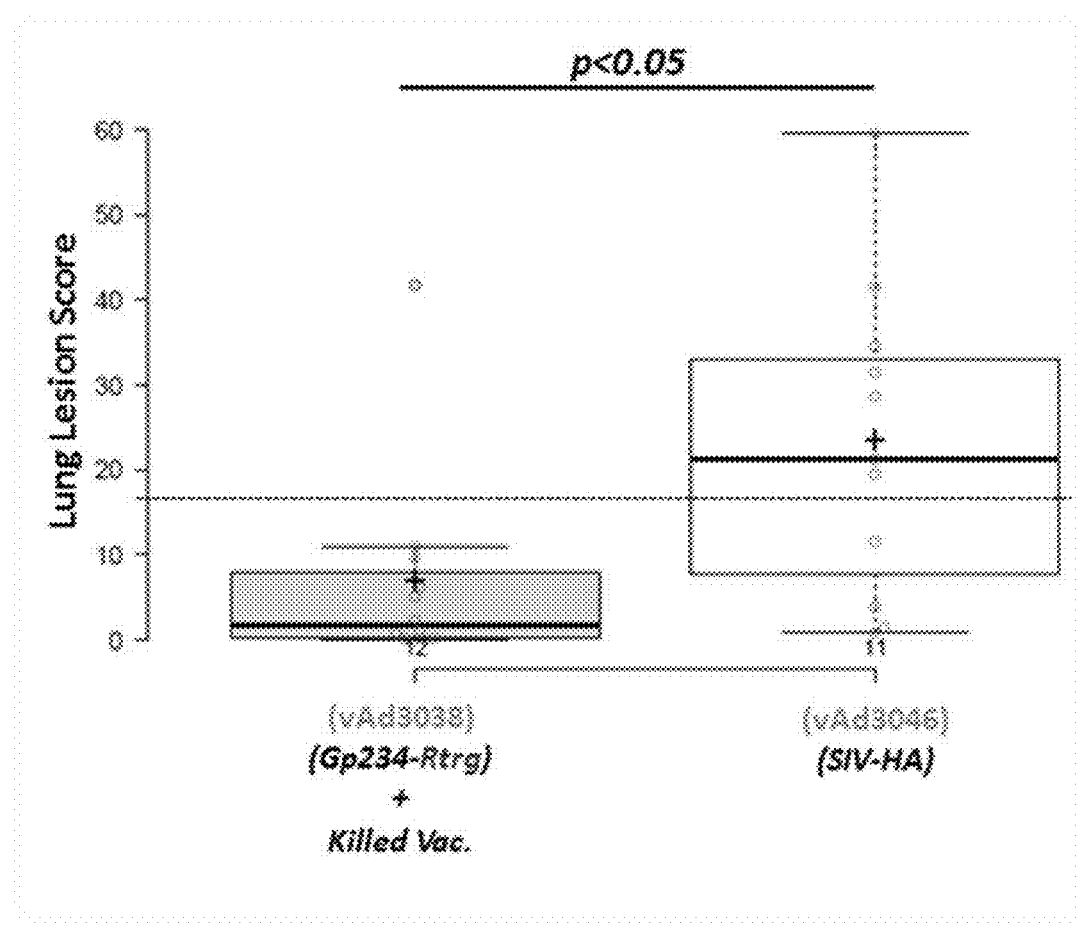
FIG. 18 is plot showing lung lesion scores for porcines administered either vAd3038 (Gp234-Rtrg+Killed Vaccine) or vAd3046 (SIV-HA)
Figure 19:
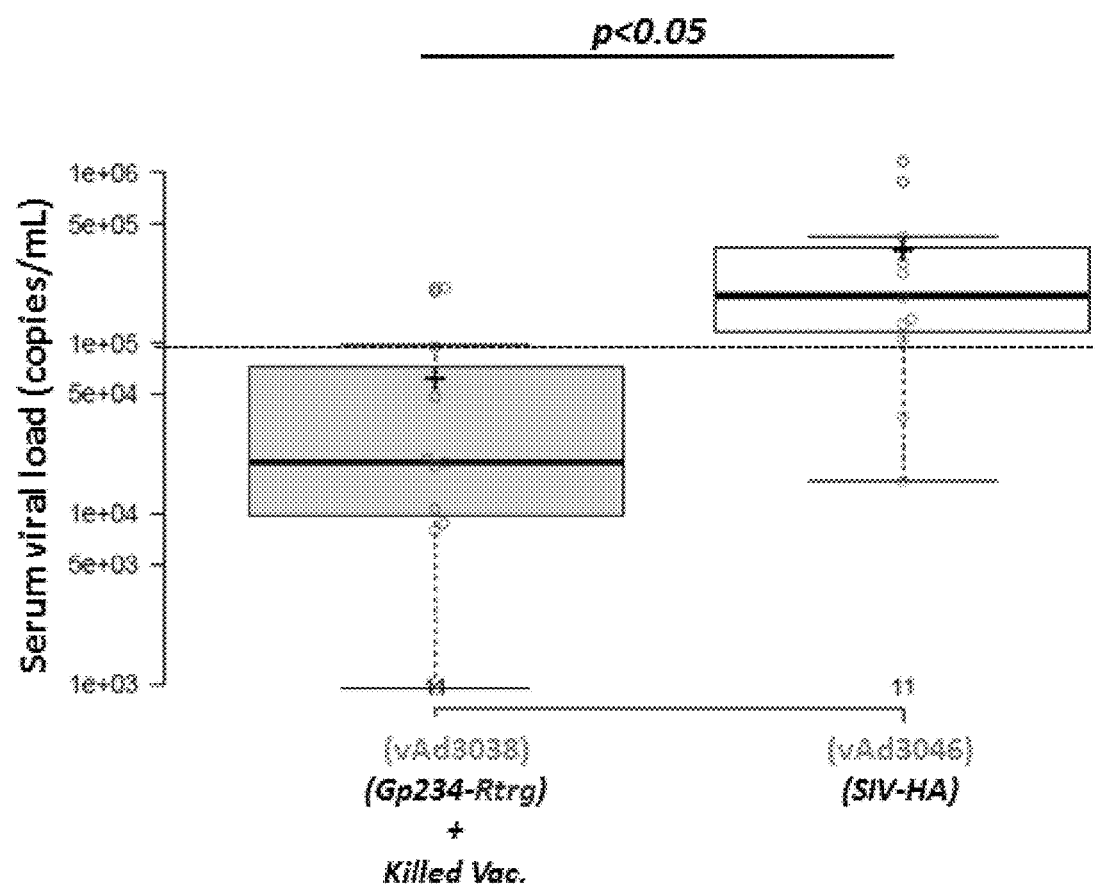
FIG. 19 is a plot showing serum viral load for porcines administered either vAd3038 (Gp234-Rtrg+Killed Vaccine) or vAd3046 (SIV-HA)
Figure 20:
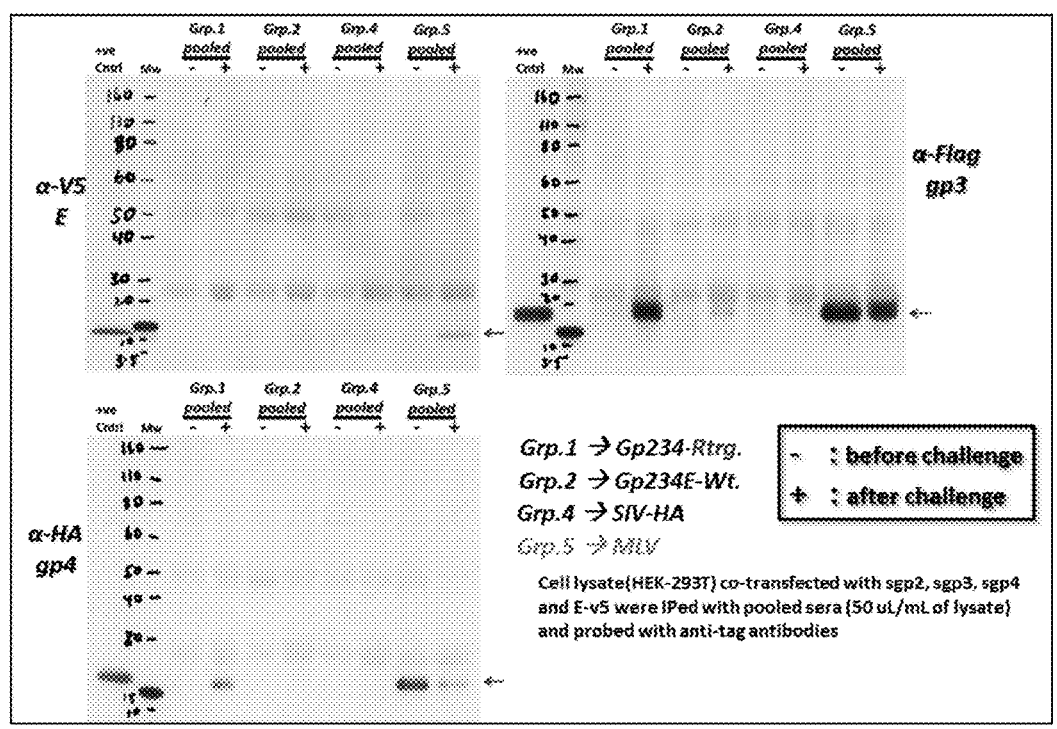
FIG. 20 compares the immune responses of Groups 1, 2, 4 and 5, before and after challenge. Western blots were probed with anti-V5 to visualize E protein levels (top left); anti-Flag to detect gp3 (right); and anti-HA to visualize gp4 protein levels (bottom left)
Figure 21:
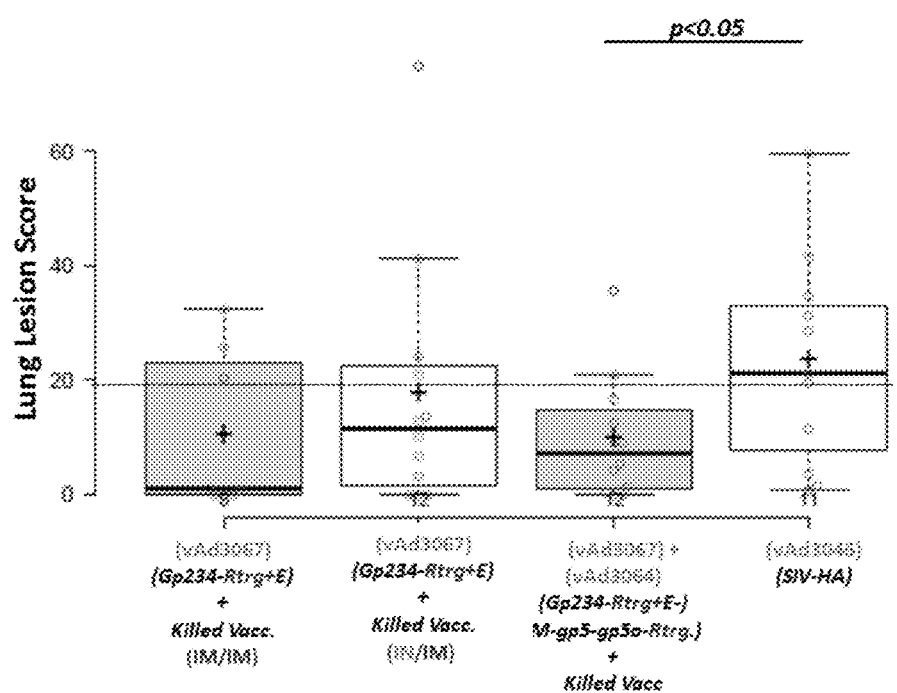
FIG. 21 is a plot showing lung lesion scores for porcines administered vAD3067 (IM/IM) followed by Killed vaccine, vAD3067 (IN/IM) followed by killed vaccine; vAD3067+vAD3064 (IN/IM) followed by killed vaccine; or vAD3046 followed by placebo. All killed vaccines were given once IM.
Figure 22:
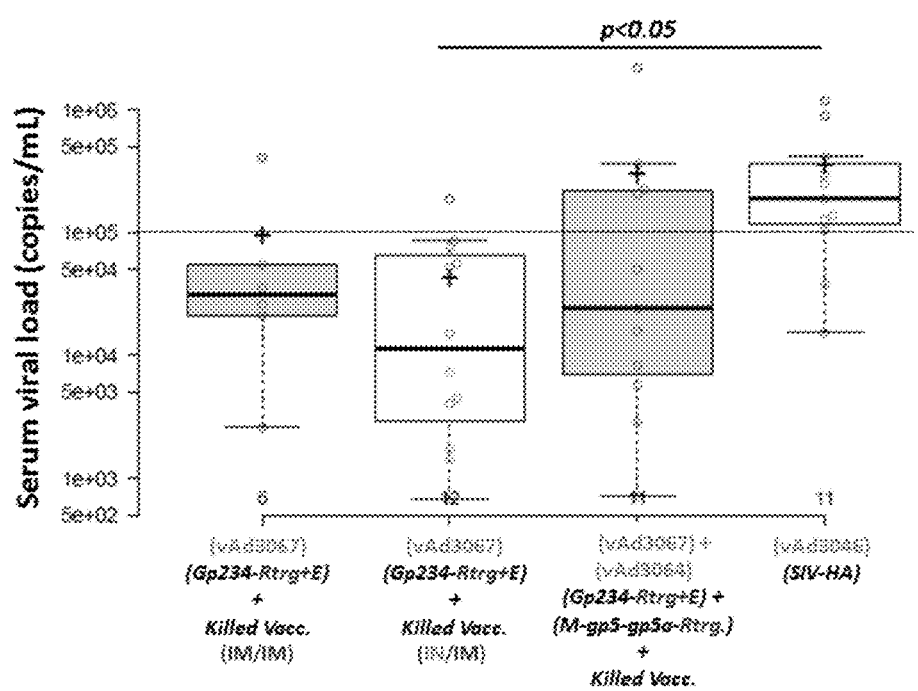
FIG. 22 is a plot serum viral load for porcines administered vAD3067 (IM/IM) followed by Killed vaccine, vAD3067 (IN/IM) followed by Killed vaccine; vAD3067+vAD3064 (IN/IM) followed by killed vaccine; or vAD3046 and placebo. All killed vaccines were given once IM.
Figure 23:
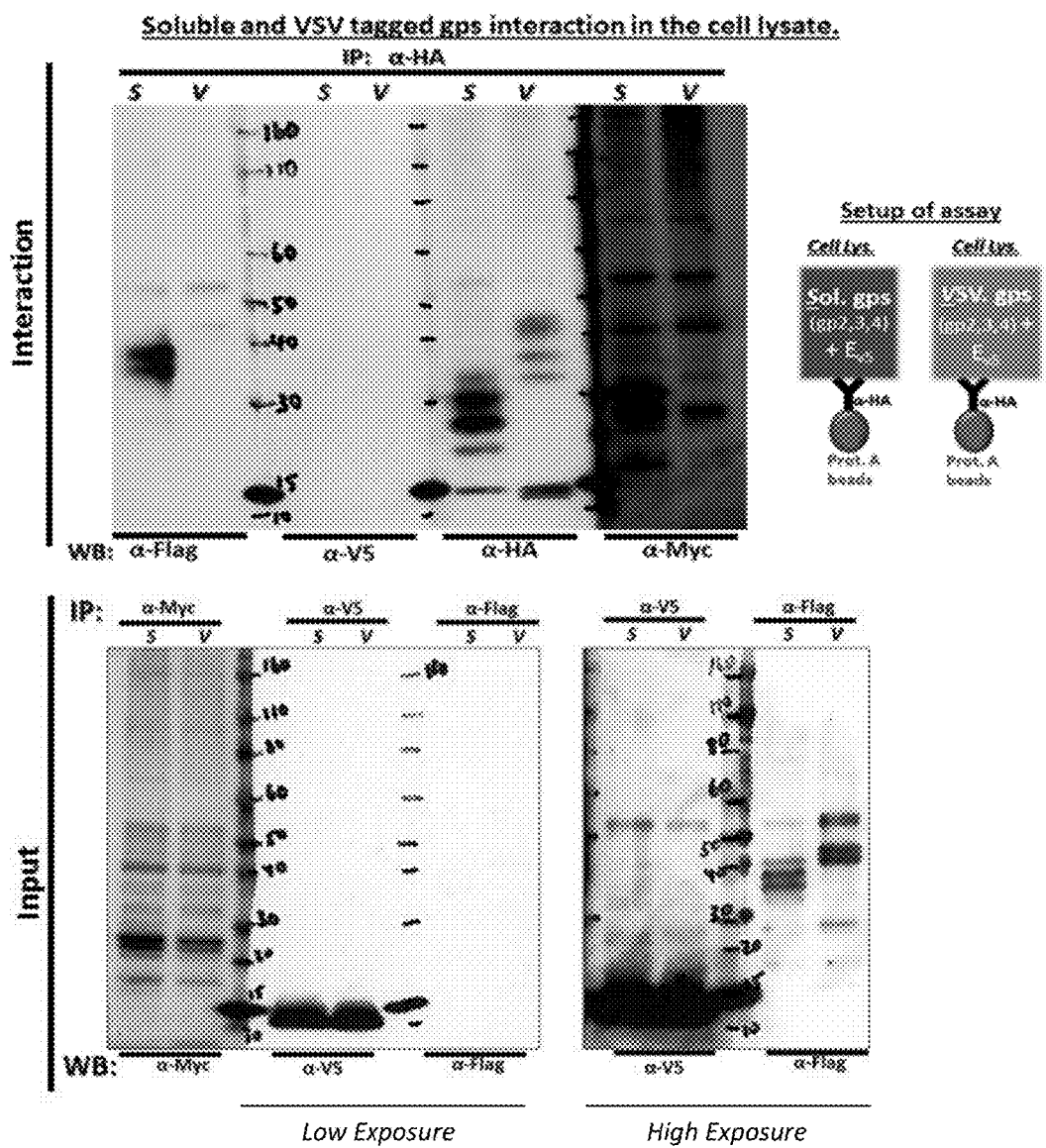
FIG. 23 shows the results of the immunoprecipitation study designed to interrogate the possible interaction between E and retargeted gp4 (no interaction observed). In the construct, the Flag tag is attached to gp3; the V5 tag is attached to E; the HA tag is attached to gp4; and, the Myc tag is attached to gp2. WB (Western blot), IP (immunoprecipitation), S (soluble gps) and V (VSV-tagged gps)
Figure 24:
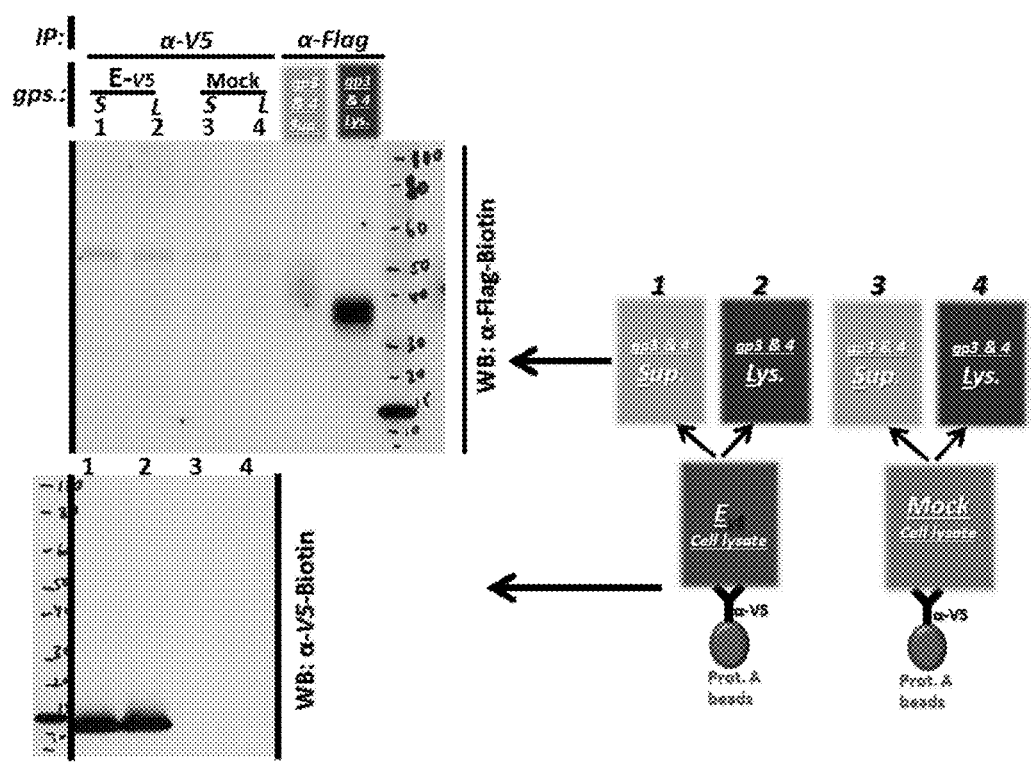
FIG. 24 shows the results of the IP study designed to interrogate the possible interaction between E and retargeted gp3 (no interaction observed).

The data demonstrated that vector-expressed, retargeted PRRSV minor envelope proteins boosted with killed vaccine lowered serum virus load in porcines and elicited in significant protection from lung lesion (FIGS. 18 & 19). These data could not have been predicted in advance of this study, even in view of the data presented in Example 3. Now that this study has been conducted, Applicants envision that the surprising protection from lung lesion and reduction in serum viral load may be attributable to a strong priming effect of the retargeted minor envelope proteins (FIG. 20). Also unpredictable was the finding that addition of E to retargeted minor envelope proteins showed no significant protection from lung lesion (FIGS. 21 & 22), in contrast to the opposite result disclosed in Example 3 (i.e. administration of the adeno construct containing E+Wt minor envelope proteins significantly reduced lung lesion). In view of the interaction data depicted in FIGS. 23 & 24, Applicants envision that this loss of protection from lung lesion could be caused by wild-type E negatively interacting with the retargeted minor envelope proteins (i.e. owing to the altered TM & CT domains, present in the retargeted proteins).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What is claimed is:

1. A safe and effective immunological or vaccine composition comprising: one or more recombinant viral vectors, comprising one or more heterologous polynucleotides, encoding porcine reproductive and respiratory syndrome virus (PRRSV) gp2, gp3, gp4, and E antigens, polypeptides, or ectodomains.

2. The composition of claim 1, further comprising a pharmaceutically or veterinarily acceptable carrier, and wherein the one or more vectors comprise a recombinant adenovirus 5 PRRSV (Ad5-PRRSV) vector, a recombinant baculovirus PRRSV vector, a recombinant porcine cytomegalovirus PRRSV vector or a recombinant poxvirus PRRSV vector.

3. The composition of claim 2, wherein the one or more vectors comprise: an Ad5-PRRSV vector.

4. The composition of claim 3, wherein the one or more vectors comprise a mixture of two vectors, a first vector expressing the gp2, gp3, and gp4 polypeptides, and a second vector expressing the E polypeptide.

5. The composition of claim 3, wherein the polynucleotide encodes:
   a. a PRRSV gp2 polypeptide having at least 90% sequence identity to SEQ ID NO: 1, 14, 34-39, 71, or 80-89;
   b. a PRRSV gp3 polypeptide having at least 90% sequence identity to SEQ ID NO: 3, 16, 4.0-45, 73, or 90-99;
   c. a PRRSV gp4 polypeptide having at least 90% sequence identity to SEQ ID NO: 5, 18, 46-51, 75, 77, or 100-109; and
   d. a PRRSV E polypeptide having at least 90% sequence identity to SEQ ID NO: 7, 52-58, or 130-139.

6. The composition of claim 5, wherein the recombinant PRRSV vector is an Ad5-PRRSV vector, which comprises a polynucleotide having:
   a. at least 90% sequence identity to a sequence as set forth in SEQ ID NO: 2, 4, 6, 8, 9, 10, 11, 12, 13, 15, 17, 21-23, 30, 70, 72, 74, or 76; or
   b. the sequence as set forth in SEQ ID NO: 2, 4, 6, 8, 9, 10, 11, 12, 13, 15, 17, 21-23, 30, 70, 72, 74, or 76.

7. The composition of claim 1, wherein the composition or vaccine comprises one or two recombinant Ad5-PRRSV vectors.

8. The composition of claim 7, wherein the recombinant Ad5-PRRSV vector expresses in vivo in an animal host wild type PRRSV gp2, gp3, gp4, and E polypeptides.

9. The composition of claim 8, wherein the gp2 polypeptide is has the sequence as set forth in SEQ ID NO: 1; the gp3 polypeptide has the sequence as set forth in SEQ ID NO: 3; the gp4 polypeptide has the sequence as set forth in SEQ ID NO: 5; and the E polypeptide has the sequence as set forth in SEQ ID NO: 7.

10. A recombinant Ad5-PRRSV vector comprising, or consisting essentially of, PRRSV gp2, gp3, gp4, and E antigen(s), polypeptide(s), or ectodomain(s).

11. The recombinant Ad5-PRRSV vector of claim 10, wherein the one or more polynucleotide encode(s):
   a. a PRRSV gp2 polypeptide having at least 90% sequence identity to SEQ ID NO: 1, 14, 34-39, 71, or 80-89;
   b. a PRRSV gp3 polypeptide having at least 90% sequence identity to SEQ ID NO: 3, 16, 40-45, 73, or 90-99;
   c. a PRRSV gp4 polypeptide having at least 90% sequence identity to SEQ ID NO: 5, 18, 46-51, 75, 77, or 100-109; and
   d. a PRRSV E polypeptide having at least 90% sequence identity to SEQ ID NO: 7, 52-58, or 130-139.

12. The recombinant Ad5-PRRSV vector of claim 10, wherein the one or more polynucleotides encode:
   a. a PRRSV gp2 polypeptide having the sequence as set forth in SEQ ID NO: 1, 14, 34-39, 71, or 80-89;
   b. a PRRSV gp3 polypeptide having the sequence as set forth in SEQ ID NO: 3, 16, 40-45, 73, or 90-99;
   c. a PRRSV gp4 polypeptide having the sequence as set forth in SEQ ID NO: 5, 18, 46-51, 75, 77, or 100-109; and
   d. a PRRSV E polypeptide having the sequence as set forth in SEQ ID NO: 7, 52-58, or 130-139.

13. The recombinant Ad5-PRRSV vector of claim 10, wherein the Ad5-PRRSV vector comprises a polynucleotide encoding:
   a. a PRRSV gp2 polypeptide having the sequence as set forth in SEQ ID NO: 1, 14, or 34-39;
   b. a PRRSV gp3 polypeptide having the sequence as set forth in SEQ ID NO: 3, 16, or 40-45;
   c. a PRRSV gp4 polypeptide having the sequence as set forth in SEQ ID NO: 5, 18, or 46-51; and
   d. a PRRSV E polypeptide having the sequence as set forth in SEQ ID NO: 7, or 52-58.

14. The recombinant Ad5-PRRSV vector of claim 10, wherein the Ad5-PRRSV vector comprises a polynucleotide encoding:
   a. a PRRSV gp2 polypeptide having the sequence as set forth in SEQ ID NO: 1;
   b. a PRRSV gp3 polypeptide having the sequence as set forth in SEQ ID NO: 3;
   c. a PRRSV gp4 polypeptide having the sequence as set forth in SEQ ID NO: 5; and
   d. a PRRSV E polypeptide having the sequence as set forth in SEQ ID NO: 7.

15. The recombinant Ad5-PRRSV vector of claim 10, wherein the Ad5-PRRSV vector comprises a polynucleotide encoding PRRSV polypeptides having the sequences as set forth in SEQ ID NO: 1, 3, 5, and 7, and no other PRRSV polypeptides.

16. The recombinant Ad5-PRRSV vector of claim 10, wherein the Ad5-PRRSV vector comprises polynucleotides comprising SEQ ID NO:21.

17. The recombinant Ad5-PRRSV vector of claim 10, wherein the Ad5-PRRSV vector comprises polynucleotides comprising SEQ ID NO:22.

18. A method of vaccinating an animal in need thereof against PRRSV comprising administering to the animal the recombinant Ad5-PRRSV vector of claim 10.

19. The method of claim 18, wherein the Ad5-PRRSV vector comprises one or more polynucleotides encoding:
   a. a PRRSV gp2 polypeptide having the sequence as set forth in SEQ ID NO: 1, 14, 34-39, 71, or 80-89;
   b. a PRRSV gp3 polypeptide having the sequence as set forth in SEQ ID NO: 3, 16, 40-45, 73, or 90-99;
   c. a PRRSV gp4 polypeptide having the sequence as set forth in SEQ ID NO: 5, 18, 46-51, 75, 77, or 100-109; and
   d. a PRRSV E polypeptide having the sequence as set forth in SEQ ID NO: 7, 52-58, or 130-139.

20. The method of claim 18, wherein the Ad5-PRRSV vector comprises one or more polynucleotides encoding:
   a. a PRRSV gp2 polypeptide having the sequence as set forth in SEQ ID NO: 1;
   b. a PRRSV gp3 polypeptide having the sequence as set forth in SEQ ID NO: 3;
   c. a PRRSV gp4 polypeptide having the sequence as set forth in SEQ ID NO: 5; and
   d. a PRRSV E polypeptide having the sequence as set forth in SEQ ID NO: 7.

\* \* \* \* \*

```
                       SEQUENCE LISTING

<160> NUMBER OF SEQ ID NOS: 139

<210> SEQ ID NO 1
<211> LENGTH: 256
<212> TYPE: PRT
<213> ORGANISM: Artificial Sequence
<220> FEATURE:
<223> OTHER INFORMATION: PRRS gp2

<400> SEQUENCE: 1

Met Lys Trp Gly Pro Cys Lys Ala Phe Leu Thr Lys Leu Ala Asn Phe
1               5                   10                  15

Leu Trp Met Leu Ser Arg Ser Ser Trp Cys Pro Leu Leu Ile Ser Leu
            20                  25                  30

Tyr Phe Trp Pro Phe Cys Leu Ala Ser Pro Ser Pro Val Gly Trp Trp
        35                  40                  45

Ser Phe Ala Ser Asp Trp Phe Ala Pro Arg Tyr Ser Val Arg Ala Leu
    50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Thr Lys His Pro Leu Gly
                85                  90                  95

Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Ile Leu Arg Thr
225                 230                 235                 240

Val Phe Gly Phe Arg Trp Leu Gly Ala Ile Phe Leu Ser Asn Ser Gln
                245                 250                 255

<210> SEQ ID NO 2
<211> LENGTH: 768
<212> TYPE: DNA
<213> ORGANISM: Artificial Sequence
<220> FEATURE:
<223> OTHER INFORMATION: VR2332 PRRSV gp2

<400> SEQUENCE: 2
atgaaatggg gtcc

-continued

| | |
|---|---|
| tcacggagtt cttggtgtcc attgttgata tcattatatt tttggccatt ttgtttggct | 120 |
| tcaccatcgc cggttggctg gtggtctttt gcatcagatt ggtttgctcc gcgatactcc | 180 |
| gtacgcgccc tgccattcac tctgagcaat acagaagat cttatgaggc ctttctttcc | 240 |
| cagtgccaag tggacattcc cacctgggga actaaacatc ctttggggat gctttggcac | 300 |
| cataaggtgt caaccctgat tgatgaaatg gtgtcgcgtc gaatgtaccg catcatggaa | 360 |
| aaagcagggc aggctgcctg gaaacaggtg gtgagcgagg ctacgctgtc tcgcattagt | 420 |
| agtttggatg tggtggctca ttttcagcat ctagccgcca ttgaagccga gacctgtaaa | 480 |
| tatttggcct cccggctgcc catgctacac aacctgcgca tgacagggtc aaatgtaacc | 540 |
| atagtgtata atagcacttt gaatcaggtg tttgctattt ttccaacccc tggttcccgg | 600 |
| ccaaagcttc atgattttca gcaatggtta atagctgtac attcctccat attttcctct | 660 |
| gttgcagctt cttgtactct ttttgttgtg ctgtggttgc gggttccaat actacgtact | 720 |
| gtttttggtt tccgctggtt aggggcaatt tttctttcga actcacag | 768 |

<210> SEQ ID NO 3
<211> LENGTH: 254
<212> TYPE: PRT
<213> ORGANISM: Artificial Sequence
<220> FEATURE:
<223> OTHER INFORMATION: PRRSV gp3

<400> SEQUENCE: 3

```
Met Val Asn Ser Cys Thr Phe Leu His Ile Phe Leu Cys Cys Ser Phe
1               5                   10                  15

Leu Tyr Ser Phe Cys Cys Ala Val Val Ala Gly Ser Asn Thr Thr Tyr
                20                  25                  30

Cys Phe Trp Phe Pro Leu Val Arg Gly Asn Phe Ser Phe Glu Leu Thr
            35                  40                  45

Val Asn Tyr Thr Val Cys Pro Pro Cys Leu Thr Arg Gln Ala Ala Thr
    50                  55                  60

Glu Ile Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Ile Pro Pro
                85                  90                  95

Gly Leu Ser Ser Glu Gly His Leu Thr Gly Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Leu Ile
    130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Ile Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240
```

```
Pro Leu Arg Arg Phe Ala Lys Ser Leu Ser Ala Val Arg Arg
            245                 250
```

<210> SEQ ID NO 4
<211> LENGTH: 762
<212> TYPE: DNA
<213> ORGANISM: Artificial Sequence
<220> FEATURE:
<223> OTHER INFORMATION: VR2332 PRRSV gp3 (12696..13460 of VR2332)

<400> SEQUENCE: 4

```
atggttaata gctgtacatt cctccatatt ttcctctgtt gcagcttctt gtactctttt     60
tgttgtgctg tggttgcggg ttccaatact acgtactgtt tttggtttcc gctggttagg    120
ggcaatttt  tctttcgaact cacagtgaat tacacggtgt gtccaccttg cctcacccgg   180
caagcagcca cagagatcta cgaacccggt aggtctcttt ggtgcaggat agggtatgac    240
cgatgtgggg aggacgatca tgacgagcta gggtttatga taccgcctgg cctctccagc    300
gaaggccact tgactggtgt ttacgcctgg ttggcgttct tgtccttcag ctacacggcc    360
cagttccatc ccgagatatt cgggataggg aatgtgagtc gagtttatgt tgacatcaaa    420
catcaactca tctgcgccga acatgacggg cagaacacca ccttgcctcg tcatgacaac    480
atttcagccg tgtttcagac ctattaccaa catcaagtcg acggcggcaa ttggtttcac    540
ctagaatggc ttcgtccctt cttttcctcg tggttggttt taaatgtctc ttggtttctc    600
aggcgttcgc ctgcaaacca tgtttcagtt cgagtcttgc agatattaag accaacacca    660
ccgcagcggc aagctttgct gtcctccaag acatcagttg ccttaggcat cgcgactcgg    720
cctctgaggc gattcgcaaa atccctcagt gccgtacggc ga                       762
```

<210> SEQ ID NO 5
<211> LENGTH: 178
<212> TYPE: PRT
<213> ORGANISM: Artificial Sequence
<220> FEATURE:
<223> OTHER INFORMATION: PRRSV gp4 polypeptide (VR2332)

<400> SEQUENCE: 5

```
Met Ala Ser Ser Leu Leu Phe Leu Val Val Gly Phe Lys Cys Leu Leu
1               5                   10                  15

Val Ser Gln Ala Phe Ala Cys Lys Pro Cys Phe Ser Ser Ser Leu Ala
            20                  25                  30

Asp Ile Lys Thr Asn Thr Thr Ala Ala Ala Ser Phe Ala Val Leu Gln
        35                  40                  45

Asp Ile Ser Cys Leu Arg His Arg Asp Ser Ala Ser Glu Ala Ile Arg
    50                  55                  60

Lys Ile Pro Gln Cys Arg Thr Ala Ile Gly Thr Pro Val Tyr Val Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160
```

Thr Met Arg Trp Ala Thr Val Leu Ala Cys Leu Phe Ala Ile Leu Leu
            165                 170                 175

Ala Ile

<210> SEQ ID NO 6
<211> LENGTH: 534
<212> TYPE: DNA
<213> ORGANISM: Artificial Sequence
<220> FEATURE:
<223> OTHER INFORMATION: VR2332 PRRSV gp4 (13241..13777 of VR2332)

<400> SEQUENCE: 6

```
atggcttcgt cccttctttt cctcgtggtt ggttttaaat gtctcttggt ttctcaggcg    60
ttcgcctgca aaccatgttt cagttcgagt cttgcagata ttaagaccaa caccaccgca   120
gcggcaagct ttgctgtcct ccaagacatc agttgcctta gcatcgcga ctcggcctct   180
gaggcgattc gcaaaatccc tcagtgccgt acggcgatag ggacacccgt gtatgttacc   240
atcacagcca atgtgacaga tgagaattat ttacattctt ctgatctcct catgctttct   300
tcttgccttt tctatgcttc tgagatgagt gaaaagggat ttaaggtggt atttggcaat   360
gtgtcaggca tcgtggctgt gtgtgtcaat tttaccagct acgtccaaca tgtcaaggag   420
tttacccaac gctccctggt ggtcgaccat gtgcggttgc tccatttcat gacacctgag   480
accatgaggt gggcaactgt tttagcctgt cttttgcca ttctgttggc aatt          534
```

<210> SEQ ID NO 7
<211> LENGTH: 73
<212> TYPE: PRT
<213> ORGANISM: Artificial Sequence
<220> FEATURE:
<223> OTHER INFORMATION: PRRSV E polypeptide (VR2332)

<400> SEQUENCE: 7

Met Gly Ser Met Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
            20                  25                  30

Leu Ala Ile Leu Phe Gly Phe Thr Ile Ala Gly Trp Leu Val Val Phe
        35                  40                  45

Cys Ile Arg Leu Val Cys Ser Ala Ile Leu Arg Thr Arg Pro Ala Ile
    50                  55                  60

His Ser Glu Gln Leu Gln Lys Ile Leu
65                  70

<210> SEQ ID NO 8
<211> LENGTH: 219
<212> TYPE: DNA
<213> ORGANISM: Artificial Sequence
<220> FEATURE:
<223> OTHER INFORMATION: VR2332 PRRSV E (12078..12299 of VR2332)

<400> SEQUENCE: 8

```
atggggtcca tgcaaagcct ttttgacaaa attggccaac ttttttgtgga tgctttcacg    60
gagttcttgg tgtccattgt tgatatcatt atattttttgg ccattttgtt tggcttcacc   120
atcgccggtt ggctggtggt cttttgcatc agattggttt gctccgcgat actccgtacg   180
cgccctgcca ttcactctga gcaattacag aagatctta                           219
```

<210> SEQ ID NO 9
<211> LENGTH: 768

<212> TYPE: DNA
<213> ORGANISM: Artificial Sequence
<220> FEATURE:
<223> OTHER INFORMATION: VR2332 PRRSV gp2 (codon-optimized)

<400> SEQUENCE: 9

| | | | | | |
|---|---|---|---|---|---|
| atgaaatggg | accctgtaa | ggctttcctg | actaaactcg | caaacttcct | ctggatgctc | 60 |
| tcacgatctt | cctggtgccc | tctgctcatc | tctctctact | ctggccatt | tgcctggcc | 120 |
| tccccctctc | cagtgggatg | gtggtcattc | gccagtgact | ggtttgctcc | ccgatattca | 180 |
| gtgcgggctc | tcccattcac | tctgagcaac | taccggcgct | cctatgaggc | atttctgagc | 240 |
| cagtgtcagg | tggacatccc | aacctggggc | acaaagcacc | ctctgggaat | gctctggcac | 300 |
| cataaagtga | gtacactgat | cgatgagatg | gtcagcagga | gaatgtacag | aattatggaa | 360 |
| aaggctggcc | aggccgcttg | gaaacaggtg | gtctctgaag | caaccctctc | acgaatcagc | 420 |
| tccctggacg | tggtcgccca | cttccagcat | ctcgcagcca | ttgaggcaga | aacatgcaag | 480 |
| tacctggcca | ccgcctgcc | tatgctccat | aacctgagga | tgactgggtc | caatgtgacc | 540 |
| atcgtctata | actctacact | gaatcaggtg | ttcgctattt | ttcctactcc | cggcagcagg | 600 |
| cccaaactcc | acgatttcca | gcagtggctg | atcgccgtgc | attcttcaat | tttcagtagc | 660 |
| gtcgctgcat | cctgtaccct | gtttgtggtc | ctgtggctcc | gggtgcccat | cctccgcaca | 720 |
| gtgttcgggt | tcggtggct | gggggctatt | tccctctcca | actcacag | | 768 |

<210> SEQ ID NO 10
<211> LENGTH: 762
<212> TYPE: DNA
<213> ORGANISM: Artificial Sequence
<220> FEATURE:
<223> OTHER INFORMATION: VR2332 PRRSV gp3 (codon-optimized)

<400> SEQUENCE: 10

| | | | | | |
|---|---|---|---|---|---|
| atggtcaatt | cctgtaccttt | cctccacatc | ttcctctgtt | gttcattcct | ctattccttc | 60 |
| tgttgcgctg | tcgtcgctgg | gtcaaacacc | acatactgct | tctggtttcc | actggtgaga | 120 |
| ggaaacttct | cctttgagct | cacagtcaat | tataccgtgt | gccctccatg | tctgacccga | 180 |
| caggcagcta | cagaaatcta | cgaacctggc | aggtctctgt | ggtgcagaat | ggctatgac | 240 |
| cgatgtggag | aggacgatca | cgatgaactg | gggttcatga | tccctccgg | cctgagctcc | 300 |
| gaaggacatc | tcacaggggt | ctacgcatgg | ctggccttcc | tctccttttc | ttatactgcc | 360 |
| cagttccacc | ccgaaatctt | cgggattggc | aacgtgtcca | gggtgtacgt | cgacatcaag | 420 |
| caccagctga | tttgtgccga | acatgacggc | cagaacacta | ccctgcctcg | gcatgataat | 480 |
| atcagcgccg | tgttccagac | ctactatcag | caccaggtgg | atggcggaaa | ttggtttcat | 540 |
| ctggagtggc | tccggcccctt | cttttcttca | tggctggtcc | tcaacgtgtc | atggttcctg | 600 |
| cggcgcagtc | ccgccaatca | cgtgagcgtc | cgggtgctgc | agattctccg | cccaactcca | 660 |
| cctcagaggc | aggctctgct | cagtagcaaa | acctcagtgg | cactgggcat | cgctacacga | 720 |
| cctctcagac | ggttcgctaa | gtccctctca | gcagtcagaa | gg | | 762 |

<210> SEQ ID NO 11
<211> LENGTH: 534
<212> TYPE: DNA
<213> ORGANISM: Artificial Sequence
<220> FEATURE:
<223> OTHER INFORMATION: VR2332 PRRSV gp4 (codon-optimized)

<400> SEQUENCE: 11

```
atggcttcat ctctcctctt cctcgtcgtg ggattcaaat gtctgctcgt gtctcaggcc    60
ttcgcttgta aaccctgctt ttccagtagc ctggctgaca tcaagactaa caccacagcc   120
gctgcatcat tcgcagtgct gcaggacatt agttgcctcc gacaccgaga tagtgccagc   180
gaggctatca ggaaaattcc ccagtgtaga acagcaatcg ggactccagt gtacgtcact   240
attaccgcca acgtgacaga cgaaaattat ctgcatagct ccgatctgct catgctgtct   300
tcatgcctct tctacgcttc cgagatgtct gaaaagggct tcaaagtggt ctttggcaac   360
gtctctggaa tcgtggccgt gtgcgtgaat tcaccagct atgtccagca cgtgaaggag   420
tttacacagc gatccctggt ggtcgatcac gtgcgcctgc tccacttcat gaccctgaa    480
accatgcggt gggctactgt cctcgcctgc ctgttcgcca ttctcctcgc tatt          534
```

<210> SEQ ID NO 12
<211> LENGTH: 219
<212> TYPE: DNA
<213> ORGANISM: Artificial Sequence
<220> FEATURE:
<223> OTHER INFORMATION: VR2332 PRRSV E (codon-optimized)

<400> SEQUENCE: 12

```
atggggtcta tgcagtcact gtttgataag attgggcagc tctttgtgga cgcctttacc    60
gagttcctgg tcagcattgt ggacatcatc attttcctgg ccatcctctt cggctttacc   120
attgctggat ggctggtggt cttttgcatc cggctcgtgt gtagcgccat cctcagaaca   180
agacctgcca tccactccga acagctccag aaaatcctc                          219
```

<210> SEQ ID NO 13
<211> LENGTH: 816
<212> TYPE: DNA
<213> ORGANISM: Artificial Sequence
<220> FEATURE:
<223> OTHER INFORMATION: VR2332 PRRSV rtg-gp2 DNA (codon-optimized,
      re-targeted)

<400> SEQUENCE: 13

```
atggatgcta tgaaacgggg actctgttgc gtgctgctgc tgtgcggagc cgtctttgtc    60
tcaccttcct caccaagccc tgtcgggtgg tggtcctttg cttctgactg gttcgcacca   120
cgatactccg tgcgggcact gccttttact ctctccaact accggcgctc ttatgaggcc   180
ttcctgtctc agtgccaggt ggacatccct acctggggaa caaagcaccc cctcgggatg   240
ctgtggcacc ataaagtgtc tacactgatc gatgagatgg tctcaaggag aatgtataga   300
attatgaaaa aggcaggcca ggccgcttgg aaacaggtgg tctcagaagc caccctgagt   360
cgaatcagct ccctcgatgt ggtcgctcac tttcagcatc tggcagccat tgaggccgaa   420
acctgtaagt acctcgctag ccgcctcccc atgctgcaca acctcaggat gactggcagt   480
aatgtgacca tcgtctataa cagcacactg aatcaggtgt tgctattttt ccccactcca   540
ggaagcaggc aaagctgca tgacttccag ggcggaagcg agcagaaact gatctccgag   600
gaggacctgg aggatcagg aggaagtgga ggatccgagc tggtggaagg tggttttct    660
tcatggaaga gtagcatcgc ctccttcttt ttcatcattg ggctgatcat tggcctgttc   720
ctcgtgctgc gggtcggaat ccatctgtgc atcaagctga acatacaaa gaaacgacag   780
atttacactg acattgagat gaatagactg ggcaaa                             816
```

<210> SEQ ID NO 14
<211> LENGTH: 272
<212> TYPE: PRT

<213> ORGANISM: Artificial Sequence
<220> FEATURE:
<223> OTHER INFORMATION: VR2332 PRRSV rtg-gp2 polypeptide (gp2-myc-VSV)

<400> SEQUENCE: 14

```
Met Asp Ala Met Lys Arg Gly Leu Cys Cys Val Leu Leu Cys Gly
1               5                   10                  15

Ala Val Phe Val Ser Pro Ser Pro Ser Pro Val Gly Trp Trp Ser
                20                  25                  30

Phe Ala Ser Asp Trp Phe Ala Pro Arg Tyr Ser Val Arg Ala Leu Pro
                35                  40                  45

Phe Thr Leu Ser Asn Tyr Arg Arg Ser Tyr Glu Ala Phe Leu Ser Gln
                50                  55                  60

Cys Gln Val Asp Ile Pro Thr Trp Gly Thr Lys His Pro Leu Gly Met
65                  70                  75                  80

Leu Trp His His Lys Val Ser Thr Leu Ile Asp Glu Met Val Ser Arg
                85                  90                  95

Arg Met Tyr Arg Ile Met Glu Lys Ala Gly Gln Ala Ala Trp Lys Gln
                100                 105                 110

Val Val Ser Glu Ala Thr Leu Ser Arg Ile Ser Ser Leu Asp Val Val
                115                 120                 125

Ala His Phe Gln His Leu Ala Ala Ile Glu Ala Glu Thr Cys Lys Tyr
                130                 135                 140

Leu Ala Ser Arg Leu Pro Met Leu His Asn Leu Arg Met Thr Gly Ser
145                 150                 155                 160

Asn Val Thr Ile Val Tyr Asn Ser Thr Leu Asn Gln Val Phe Ala Ile
                165                 170                 175

Phe Pro Thr Pro Gly Ser Arg Pro Lys Leu His Asp Phe Gln Gly Gly
                180                 185                 190

Ser Glu Gln Lys Leu Ile Ser Glu Glu Asp Leu Gly Gly Ser Gly Gly
                195                 200                 205

Ser Gly Gly Ser Glu Leu Val Glu Gly Trp Phe Ser Ser Trp Lys Ser
                210                 215                 220

Ser Ile Ala Ser Phe Phe Phe Ile Ile Gly Leu Ile Ile Gly Leu Phe
225                 230                 235                 240

Leu Val Leu Arg Val Gly Ile His Leu Cys Ile Lys Leu Lys His Thr
                245                 250                 255

Lys Lys Arg Gln Ile Tyr Thr Asp Ile Glu Met Asn Arg Leu Gly Lys
                260                 265                 270
```

<210> SEQ ID NO 15
<211> LENGTH: 759
<212> TYPE: DNA
<213> ORGANISM: Artificial Sequence
<220> FEATURE:
<223> OTHER INFORMATION: VR2332 PRRSV rtg-gp3 DNA (codon-optimized, re-targeted)

<400> SEQUENCE: 15

```
atggatgcta tgaaacgggg gctctgctgc gtcctcctcc tgtgcggggc tgtcttcgtc    60
tcaccctcct caaatacaac ctactgcttt tggttcccac tcgtgagagg caactttagc   120
ttcgagctga ctgtgaatta caccgtctgc cctccatgtc tgacccgaca ggccgctgca   180
gaaatctacg aacctggacg gtccctgtgg tgccgcattg ggtatgacag gtgtgaggaa   240
gacgatcacg atgagctggg ctttatggtg cctcctggac tcagctccga aggacatctg   300
acatcagtct acgcctggct cgcttttctg tccttctctt atactgctca gtttcaccc    360
```

```
gaaatcttcg gaattgggaa cgtgtctcgg gtgtacgtcg acatcaagca ccagctcatt    420
tgcgcagaac atgacggcca gaacaccaca ctgccaaggc acgataatat ctccgccgtg    480
ttccagacat actatcagca tcaggtcgac ggcggagggg gctctgatta taaggacgat    540
gacgataaag gagggtcagg cggaagtggg ggatccgagc tggtggaagg ctggttttct    600
tcatggaaga gtagcatcgc cagcttcttt ttcatcattg gcctcatcat tggactgttc    660
ctcgtgctgc gcgtcggaat ccacctgtgc atcaagctga agcatactaa gaagcggcag    720
atttacaccg acattgagat gaacagactg gggaaatga                          759
```

<210> SEQ ID NO 16
<211> LENGTH: 252
<212> TYPE: PRT
<213> ORGANISM: Artificial Sequence
<220> FEATURE:
<223> OTHER INFORMATION: VR2332 PRRSV rtg-gp3 polypeptide (gp3-Flag-VSV)

<400> SEQUENCE: 16

```
Met Asp Ala Met Lys Arg Gly Leu Cys Cys Val Leu Leu Cys Gly
1               5                   10                  15

Ala Val Phe Val Ser Pro Ser Ser Asn Thr Thr Tyr Cys Phe Trp Phe
            20                  25                  30

Pro Leu Val Arg Gly Asn Phe Ser Phe Glu Leu Thr Val Asn Tyr Thr
        35                  40                  45

Val Cys Pro Pro Cys Leu Thr Arg Gln Ala Ala Glu Ile Tyr Glu
    50                  55                  60

Pro Gly Arg Ser Leu Trp Cys Arg Ile Gly Tyr Asp Arg Cys Glu Glu
65                  70                  75                  80

Asp Asp His Asp Glu Leu Gly Phe Met Val Pro Pro Gly Leu Ser Ser
                85                  90                  95

Glu Gly His Leu Thr Ser Val Tyr Ala Trp Leu Ala Phe Leu Ser Phe
            100                 105                 110

Ser Tyr Thr Ala Gln Phe His Pro Glu Ile Phe Gly Ile Gly Asn Val
        115                 120                 125

Ser Arg Val Tyr Val Asp Ile Lys His Gln Leu Ile Cys Ala Glu His
    130                 135                 140

Asp Gly Gln Asn Thr Thr Leu Pro Arg His Asp Asn Ile Ser Ala Val
145                 150                 155                 160

Phe Gln Thr Tyr Tyr Gln His Gln Val Asp Gly Gly Gly Ser Asp
            165                 170                 175

Tyr Lys Asp Asp Asp Lys Gly Gly Ser Gly Gly Ser Gly Ser
        180                 185                 190

Glu Leu Val Glu Gly Trp Phe Ser Ser Trp Lys Ser Ser Ile Ala Ser
    195                 200                 205

Phe Phe Phe Ile Ile Gly Leu Ile Ile Gly Leu Phe Leu Val Leu Arg
210                 215                 220

Val Gly Ile His Leu Cys Ile Lys Leu Lys His Thr Lys Lys Arg Gln
225                 230                 235                 240

Ile Tyr Thr Asp Ile Glu Met Asn Arg Leu Gly Lys
                245                 250
```

<210> SEQ ID NO 17
<211> LENGTH: 714
<212> TYPE: DNA
<213> ORGANISM: Artificial Sequence
<220> FEATURE:

<223> OTHER INFORMATION: VR2332 PRRSV rtg-gp4 DNA (codon-optimized, re-targeted)

<400> SEQUENCE: 17

```
atggatgcta tgaaacgggg actgtgctgc gtgctgctgc tctgtggggc tgtcttcgtg      60
tcaccttctt gtaaaccttg cttttccagc tccctggctg acatcaagac taacaccaca     120
gccgctgcat cttttgcagt gctccaggac atttcatgcc tgcgacaccg agatagcgcc     180
tccgaggcta tcaggaaaat tcctcagtgt agaacagcaa tcggcactcc cgtgtacgtc     240
actattaccg ccaacgtgac agacgaaaat tatctgcatt ctagcgacct gctcatgctc     300
agtagctgcc tgttctacgc ctctgagatg tcagaaaagg gctttaaagt ggtcttcggg     360
aacgtgagcg gcatcgtggc cgtgtgcgtg aacttcacca gctatgtcca gcacgtgaag     420
gagttcacac agcgatccct ggtggtcgat cacgtccgcc tgctccatgg cggatcttac     480
ccctatgacg tgccagatta cgcaggagga gtggaggaa gcggaggatc cgagctggtg     540
gaaggatggt ttcctcttg aagtcaagt atcgccagct tcttttttcat cattggactc     600
atcattgggc tgttcctcgt cctgcgggtg ggaatccatc tgtgcatcaa gctgaagcat     660
acaaagaagc ggcagattta cactgacatt gagatgaata gactgggcaa atga           714
```

<210> SEQ ID NO 18
<211> LENGTH: 237
<212> TYPE: PRT
<213> ORGANISM: Artificial Sequence
<220> FEATURE:
<223> OTHER INFORMATION: VR2332 PRRSV rtg-gp4 polypeptide (gp4-HA-VSV)

<400> SEQUENCE: 18

```
Met Asp Ala Met Lys Arg Gly Leu Cys Cys Val Leu Leu Cys Gly
1               5                   10                  15

Ala Val Phe Val Ser Pro Ser Cys Lys Pro Cys Phe Ser Ser Leu
                20                  25                  30

Ala Asp Ile Lys Thr Asn Thr Thr Ala Ala Ala Ser Phe Ala Val Leu
            35                  40                  45

Gln Asp Ile Ser Cys Leu Arg His Arg Asp Ser Ala Ser Glu Ala Ile
        50                  55                  60

Arg Lys Ile Pro Gln Cys Arg Thr Ala Ile Gly Thr Pro Val Tyr Val
65                  70                  75                  80

Thr Ile Thr Ala Asn Val Thr Asp Glu Asn Tyr Leu His Ser Ser Asp
                85                  90                  95

Leu Leu Met Leu Ser Ser Cys Leu Phe Tyr Ala Ser Glu Met Ser Glu
                100                 105                 110

Lys Gly Phe Lys Val Val Phe Gly Asn Val Ser Gly Ile Val Ala Val
            115                 120                 125

Cys Val Asn Phe Thr Ser Tyr Val Gln His Val Lys Glu Phe Thr Gln
        130                 135                 140

Arg Ser Leu Val Val Asp His Val Arg Leu Leu His Gly Gly Ser Tyr
145                 150                 155                 160

Pro Tyr Asp Val Pro Asp Tyr Ala Gly Gly Ser Gly Gly Ser Gly Gly
                165                 170                 175

Ser Glu Leu Val Glu Gly Trp Phe Ser Ser Trp Lys Ser Ser Ile Ala
                180                 185                 190

Ser Phe Phe Phe Ile Ile Gly Leu Ile Gly Leu Phe Leu Val Leu
            195                 200                 205

Arg Val Gly Ile His Leu Cys Ile Lys Leu Lys His Thr Lys Lys Arg
```

```
                  210                 215                 220
Gln Ile Tyr Thr Asp Ile Glu Met Asn Arg Leu Gly Lys
225                 230                 235

<210> SEQ ID NO 19
<211> LENGTH: 10
<212> TYPE: DNA
<213> ORGANISM: Artificial Sequence
<220> FEATURE:
<223> OTHER INFORMATION: Place holder for: VR2332 PRRSV rtg-E
      (codon-optimized,
      re-targeted)
<220> FEATURE:
<221> NAME/KEY: misc_feature
<222> LOCATION: (1)..(10)
<223> OTHER INFORMATION: n is a, c, g, t or u

<400> SEQUENCE: 19 nnnnnnnnnn                                                              10

<210> SEQ ID NO 20
<211> LENGTH: 10
<212> TYPE: PRT
<213> ORGANISM: Artificial Sequence
<220> FEATURE:
<223> OTHER INFORMATION: Placeholder for: VR2332 PRRSV rtg-E polypeptide
<220> FEATURE:
<221> NAME/KEY: misc_feature
<222> LOCATION: (1)..(10)
<223> OTHER INFORMATION: Xaa can be any naturally occurring amino acid

<400> SEQUENCE: 20

Xaa Xaa Xaa Xaa Xaa Xaa Xaa Xaa Xaa Xaa
1               5                   10

<210> SEQ ID NO 21
<211> LENGTH: 4566
<212> TYPE: DNA
<213> ORGANISM: Artificial Sequence
<220> FEATURE:
<223> OTHER INFORMATION: vAD3038 insert cassette

<400> SEQUENCE: 21
aaataatgat tttatttttga ctgatagtga cctgttcgtt gcaacacatt gatgagcaat       60
gcttttttat aatgccaact tgtacaaaaa agcaggtcg actctagagg atccgaaaaa       120
acctcccaca cctcccccctg aacctgaaac ataaaatgaa tgcaattgtt gttgttaact       180
tgtttattgc agcttataat ggttacaaat aaagcaatag catcacaaat ttcacaaata       240
aagcattttt ttcactgcat tctagttgtg gtttgtccaa actcatcaat gtatcttatc       300
atgtctggat ccccaagctt ctcgagaccg gttcatttgc ccagtctatt catctcaatg       360
tcagtgtaaa tctgtcgttt ctttgtatgt ttcagcttga tgcacagatg gattccgacc       420
cgcagcacga ggaacaggcc aatgatcagc ccaatgatga aaagaaagga ggcgatgcta       480
ctcttccatg aagaaaacca cccttccacc agctcggatc ctccacttcc tcctgatcct       540
cccaggtcct cctcggagat cagtttctgc tcgcttccgc cctggaagtc atgcagcttt       600
ggcctgcttc ctggagtggg gaaaatagca acacctgat tcagtgtgct gttatagacg       660
atggtcacat tactgccagt catcctgagg ttgtgcagca tggggaggcg gctagcgagg       720
tacttacagg tttcggcctc aatggctgcc agatgctgaa agtgagcgac cacatcgagg       780
gagctgattc gactcagggt ggcttctgag accacctgtt tccaagcggc ctggcctgcc       840
ttttccataa ttctatacat tctccttgag accatctcat cgatcagtgt agacacttta       900
```

```
tggtgccaca gcatcccgag ggggtgcttt gttccccagg tagggatgtc cacctggcac    960
tgagacagga aggcctcata agagcgccgg tagttggaga gagtaaaagg cagtgcccgc   1020
acggagtatc gtggtgcgaa ccagtcagaa gcaaaggacc accacccgac agggcttggt   1080
gaggaaggtg agacaaagac ggctccgcac agcagcagca cgcaacagag tccccgtttc   1140
atagcatcca tggtttaatt aaagcttttt gcaaaagcct aggcctccaa aaaagcctcc   1200
tcactacttc tggaatagct cagaggccga ggcggcctcg gcctctgcat aaataaaaaa   1260
aattagtcag ccatggggcg gagaatgggc ggaactgggc ggagttaggg gcgggatggg   1320
cggagttagg ggcgggacta tggttgctga ctaattgaga tgcatgcttt gcatacttct   1380
gcctgctggg gagcctgggg actttccaca cctggttgct gactaattga gatgcatgct   1440
ttgcatactt ctgcctgctg gggagcctgg ggactttcca caccctaact gacacacatt   1500
ccacagccaa gctgtaccga gctcgaattc gctagcatcg atgcggccgc gttgacattg   1560
attattgact agttattaat agtaatcaat tacgggtca ttagttcata gcccatatat   1620
ggagttccgc gttacataac ttacggtaaa tggcccgcct ggctgaccgc ccaacgaccc   1680
ccgcccattg acgtcaataa tgacgtatgt tcccatagta acgccaatag ggactttcca   1740
ttgacgtcaa tgggtggact atttacggta aactgcccac ttggcagtac atcaagtgta   1800
tcatatgcca gtacgccccc tattgacgtc aatgacggt aaatggcccg cctggcatta   1860
tgcccagtac atgaccttat gggactttcc tacttggcag tacatctacg tattagtcat   1920
cgctattacc atggtgatgc ggttttggca gtacatcaat gggcgtggat agcggtttga   1980
ctcacgggga tttccaagtc tccaccccat tgacgtcaat gggagtttgt tttggcacca   2040
aaatcaacgg gactttccaa aatgtcgtaa caactccgcc ccattgacgc aaatgggcgg   2100
taggcgtgta cggtgggagg tctatataag cagagctctc tagaaccatg gatgctatga   2160
aacggggact gtgctgcgtg ctgctgctct gtggggctgt cttcgtgtca ccttcttgta   2220
aaccttgctt ttccagctcc ctggctgaca tcaagactaa caccacagcc gctgcatctt   2280
ttgcagtgct ccaggacatt tcatgcctgc gacaccgaga tagcgcctcc gaggctatca   2340
ggaaaattcc tcagtgtaga acagcaatcg gcactcccgt gtacgtcact attaccgcca   2400
acgtgacaga cgaaaattat ctgcattcta gcgacctgct catgctcagt agctgcctgt   2460
tctacgcctc tgagatgtca gaaaagggct ttaaagtggt cttcgggaac gtgagcggca   2520
tcgtggccgt gtgcgtgaac ttcaccagct atgtccagca cgtgaaggag ttcacacagc   2580
gatccctggt ggtcgatcac gtccgcctgc tccatggcgg atcttacccc tatgacgtgc   2640
cagattacgc aggaggaagt ggaggaagcg gaggatccga gctggtggaa ggatggtttt   2700
cctcttggaa gtcaagtatc gccagcttct ttttcatcat tggactcatc attgggctgt   2760
tcctcgtcct gcgggtggga atccatctgt gcatcaagct gaagcataca aagaagcggc   2820
agatttacac tgacattgag atgaatagac tgggcaaatg atgacccccc ccctaacgt   2880
tactggccga agccgcttgg aataaggccg gtgtgcgttt gtctatatgt tattttccac   2940
catattgccg tcttttggca atgtgagggc ccggaaacct ggccctgtct tcttgacgag   3000
cattcctagg ggtctttccc ctctcgccaa aggaatgcaa ggtctgttga atgtcgtgaa   3060
ggaagcagtt cctctggaag cttcttgaag acaaacaacg tctgtagcga ccctttgcag   3120
gcagcggaac cccccacctg cgacaggtg cctctgcggc caaaagccac gtgtataaga   3180
tacacctgca aaggcggcac aaccccagtg ccacgttgtg agttggatag ttgtggaaag   3240
```

| | |
|---|---:|
| agtcaaatgg ctctcctcaa gcgtattcaa caaggggctg aaggatgccc agaaggtacc | 3300 |
| ccattgtatg ggatctgatc tggggcctcg gtgcacatgc tttacatgtg tttagtcgag | 3360 |
| gttaaaaaac gtctaggccc cccgaaccac ggggacgtgg ttttcctttg aaaaacacga | 3420 |
| tgataatacc atggatgcta tgaaacgggg gctctgctgc gtcctcctcc tgtgcggggc | 3480 |
| tgtcttcgtc tcaccctcct caaatacaac ctactgcttt tggttcccac tcgtgagagg | 3540 |
| caactttagc ttcgagctga ctgtgaatta ccgtctgc cctccatgtc tgacccgaca | 3600 |
| ggccgctgca gaaatctacg aacctggacg gtccctgtgg tgccgcattg ggtatgacag | 3660 |
| gtgtgaggaa gacgatacg atgagctggg ctttatggtg cctcctggac tcagctccga | 3720 |
| aggacatctg acatcagtct acgcctggct cgcttttctg tccttctctt atactgctca | 3780 |
| gtttcacccc gaaatcttcg gaattgggaa cgtgtctcgg gtgtacgtcg acatcaagca | 3840 |
| ccagctcatt tgcgcagaac atgacggcca gaacaccaca ctgccaaggc acgataatat | 3900 |
| ctccgccgtg ttccagacat actatcagca tcaggtcgac ggcggagggg gctctgatta | 3960 |
| taaggacgat gacgataaag gagggtcagg cggaagtggg ggatccgagc tggtggaagg | 4020 |
| ctggttttct tcatggaaga gtagcatcgc cagcttcttt ttcatcattg gcctcatcat | 4080 |
| tggactgttc ctcgtgctgc gcgtcggaat ccacctgtgc atcaagctga agcatactaa | 4140 |
| gaagcggcag atttacaccg acattgagat gacagactg gggaaatgat gaggtaccgg | 4200 |
| gggaggctaa ctgaaacacg gaaggagaca ataccggaag gaacccgcgc tatgacggca | 4260 |
| ataaaaagac agaataaaac gcacgggtgt tgggtcgttt gttcataaac gcggggttcg | 4320 |
| gtcccagggc tggcactctg tcgataccc accgagaccc cattggggcc aatacgcccg | 4380 |
| cgtttcttcc ttttccccac cccacccccc aagttcgggt gaaggcccag ggctcgcagc | 4440 |
| caacgtcggg gcggcaggcc ctgccatagc cagctttctt gtacaaagtt ggcattataa | 4500 |
| gaaagcattg cttatcaatt tgttgcaacg aacaggtcac tatcagtcaa aataaaatca | 4560 |
| ttatttt | 4566 |

<210> SEQ ID NO 22
<211> LENGTH: 4662
<212> TYPE: DNA
<213> ORGANISM: Artificial Sequence
<220> FEATURE:
<223> OTHER INFORMATION: pAD3041 transgene cassette

<400> SEQUENCE: 22

| | |
|---|---:|
| aaataatgat tttattttga ctgatagtga acctgttcgtt gcaacacatt gatgagcaat | 60 |
| gcttttttat aatgccaact ttgtacaaaa aagcaggtcg actctagagg atccgaaaaa | 120 |
| acctcccaca cctccccctg aacctgaaac ataaaatgaa tgcaattgtt gttgttaact | 180 |
| tgtttattgc agcttataat ggttacaaat aaagcaatag catcacaaat ttcacaaata | 240 |
| aagcattttt ttcactgcat tctagttgtg gtttgtccaa actcatcaat gtatcttatc | 300 |
| atgtctggat ccccaagctt ctcgagaccg gtcctgcagg tcagaggatt ttctggagct | 360 |
| gttcggagtg gatggcaggt cttgttctga ggatggcgct acacacgagc cggatgcaaa | 420 |
| agaccaccag ccatccagca atggtaaagc cgaagaggat ggccaggaaa atgatgatgt | 480 |
| ccacaatgct gaccaggaac tcggtaaagg cgtccacaaa gagctgccca atcttatcaa | 540 |
| acagtgactg catagacccc atggtggagg tccagggttc tcctccacgt ctccagcctg | 600 |
| cttcagcagg ctgaagttag tagctccgct tcccctgcag gtcactgtga gttggagagg | 660 |
| aaaatagccc ccagccaccg aaacccgaac actgtgcgga ggatgggcac ccggagccac | 720 |

```
aggaccacaa acagggtaca ggatgcagcg acgctactga aaattgaaga atgcacggcg      780
atcagccact gctggaaatc gtggagtttg ggcctgctgc cgggagtagg aaaaatagcg      840
aacacctgat tcagtgtaga gttatagacg atggtcacat tggacccagt catcctcagg      900
ttatggagca taggcaggcg gctggccagg tacttgcatg tttctgcctc aatggctgcg      960
agatgctgga agtgggcgac cacgtccagg gagctgattc gtgagagggt tgcttcagag     1020
accacctgtt tccaagcggc ctggccagcc ttttccataa ttctgtacat tctcctgctg     1080
accatctcat cgatcagtgt actcacttta tggtgccaga gcattcccag agggtgcttt     1140
gtgccccagg ttgggatgtc cacctgacac tggctcagaa atgcctcata ggagcgccgg     1200
tagttgctca gagtgaatgg gagagcccgc actgaatatc ggggagcaaa ccagtcactg     1260
gcgaatgacc accatcccac tggagagggg gaggccaggc aaaatggcca gaagtagaga     1320
gagatgagca gagggcacca ggaagatcgt gagagcatcc agaggaagtt tgcgagttta     1380
gtcaggaaag ccttacaggg tccccatttc atggtggagc ttttgcaaa agcctaggcc       1440 tccaaaaaag cctcctcact acttctggaa tagctcagag gccgaggcgg cctcggcctc     1500
tgcataaata aaaaaaatta gtcagccatg gggcggagaa tgggcggaac tgggcggagt     1560
taggggcggg atgggcggag ttaggggcgg gactatggtt gctgactaat tgagatgcat     1620
gctttgcata cttctgcctg ctggggagcc tggggacttt ccacacctgg ttgctgacta     1680
attgagatgc atgctttgca tacttctgcc tgctggggag cctggggact tccacaccc      1740 taactgacac acattccaca gccaagctgt accgagctcg aattcgctag catcgatgcg     1800
gccgcgttga cattgattat tgactagtta ttaatagtaa tcaattacgg ggtcattagt     1860
tcatagccca tatatggagt tccgcgttac ataacttacg gtaaatggcc cgcctggctg     1920
accgcccaac gacccccgcc cattgacgtc aataatgacg tatgttccca tagtaacgcc     1980
aatagggact ttccattgac gtcaatgggt ggactattta cggtaaactg cccacttggc     2040
agtacatcaa gtgtatcata tgccaagtac gccccctatt gacgtcaatg acggtaaatg     2100
gcccgcctgg cattatgccc agtacatgac cttatgggac tttcctactt ggcagtacat     2160
ctacgtatta gtcatcgcta ttaccatggt gatgcggttt tggcagtaca tcaatgggcg     2220
tggatagcgg tttgactcac ggggatttcc aagtctccac cccattgacg tcaatgggag     2280
tttgttttgg caccaaaatc aacgggactt tccaaaatgt cgtaacaact ccgccccatt     2340
gacgcaaatg ggcggtaggc gtgtacggtg ggaggtctat ataagcagag ctctctagaa     2400
ccaccatggc ttcatctctc ctcttcctcg tcgtgggatt caaatgtctg ctcgtgtctc     2460
aggccttcgc ttgtaaaccc tgcttttcca gtagcctggc tgacatcaag actaacacca     2520
cagccgctgc atcattcgca gtgctgcagg acattagttg cctccgacac cgagatagtg     2580
ccagcgaggc tatcaggaaa attccccagt gtagaacagc aatcgggact ccagtgtacg     2640
tcactattac cgccaacgtg acagacgaaa attatctgca tagctccgat ctgctcatgc     2700
tgtcttcatg cctcttctac gcttccgaga tgtctgaaaa gggcttcaaa gtggtctttg     2760
gcaacgtctc tggaatcgtg gccgtgtgcg tgaatttcac cagctatgtc cagcacgtga     2820
aggagtttac acagcgatcc ctggtggtcg atcacgtgcg cctgctccac ttcatgaccc     2880
ctgaaaccat gcggtgggct actgtcctcg cctgcctgtt cgccattctc ctcgctattt     2940
gaagatctcc ccccccccta acgttactgg ccgaagccgc ttggaataag gccggtgtgc     3000
gtttgtctat atgttatttt ccaccatatt gccgtctttt ggcaatgtga gggcccggaa     3060
```

| | |
|---|---|
| acctggccct gtcttcttga cgagcattcc tagggggtctt tccccctctcg ccaaaggaat | 3120 |
| gcaaggtctg ttgaatgtcg tgaaggaagc agttcctctg gaagcttctt gaagacaaac | 3180 |
| aacgtctgta gcgaccctttt gcaggcagcg gaaccccca cctggcgaca ggtgcctctg | 3240 |
| cggccaaaag ccacgtgtat aagatacacc tgcaaaggcg gcacaacccc agtgccacgt | 3300 |
| tgtgagttgg atagttgtgg aaagagtcaa atggctctcc tcaagcgtat tcaacaaggg | 3360 |
| gctgaaggat gcccagaagg taccccattg tatgggatct gatctggggc ctcggtgcac | 3420 |
| atgctttaca tgtgtttagt cgaggttaaa aaacgtctag gccccccgaa ccacggggac | 3480 |
| gtggttttcc tttgaaaaac acgatgataa taccaccatg gtcaattcct gtaccttcct | 3540 |
| ccacatcttc ctctgttgtt cattcctcta ttccttctgt tgcgctgtcg tcgctgggtc | 3600 |
| aaacaccaca tactgcttct ggtttccact ggtgagagga aacttctcct ttgagctcac | 3660 |
| agtcaattat accgtgtgcc ctccatgtct gacccgacag gcagctacag aaatctacga | 3720 |
| acctggcagg tctctgtggt gcagaattgg ctatgaccga tgtggagagg acgatcacga | 3780 |
| tgaactgggg ttcatgatcc ctcccggcct gagctccgaa ggacatctca cagggtcta | 3840 |
| cgcatggctg gccttcctct ccttttctta tactgcccag ttccaccccg aaatcttcgg | 3900 |
| gattggcaac gtgccagggg tgtacgtcga catcaagcac cagctgattt gtgccgaaca | 3960 |
| tgacggccag aacactaccc tgcctcggca tgataatatc agcgccgtgt tccagaccta | 4020 |
| ctatcagcac caggtggatg gcggaaattg gtttcatctg gagtggctcc ggcccttctt | 4080 |
| ttcttcatgg ctggtcctca acgtgtcatg gttcctgcgg cgcagtcccg ccaatcacgt | 4140 |
| gagcgtccgg gtgctgcaga ttctccgccc aactccacct cagaggcagg ctctgctcag | 4200 |
| tagcaaaacc tcagtggcac tgggcatcgc tacacgacct tcagacggt tcgctaagtc | 4260 |
| cctctcagca gtcagaaggt gaagatctgg taccggggga ggctaactga aacacggaag | 4320 |
| gagacaatac cggaaggaac ccgcgctatg acggcaataa aaagacagaa taaaacgcac | 4380 |
| gggtgttggg tcgtttgttc ataaacgcgg ggttcggtcc cagggctggc actctgtcga | 4440 |
| taccccaccg agaccccatt ggggccaata cgcccgcgtt tcttcctttt ccccaccca | 4500 |
| ccccccaagt tcgggtgaag gcccagggct cgcagccaac gtcggggcgg caggccctgc | 4560 |
| catagccagc tttcttgtac aaagttggca ttataagaaa gcattgctta tcaatttgtt | 4620 |
| gcaacgaaca ggtcactatc agtcaaaata aaatcattat tt | 4662 |

<210> SEQ ID NO 23
<211> LENGTH: 4361
<212> TYPE: DNA
<213> ORGANISM: Artificial Sequence
<220> FEATURE:
<223> OTHER INFORMATION: vAD3042 transgene cassette

<400> SEQUENCE: 23

| | |
|---|---|
| aaataatgat tttattttga ctgatagtga cctgttcgtt gcaacacatt gatgagcaat | 60 |
| gcttttttat aatgccaact ttgtacaaaa aagcaggtcg actctagagg atccgaaaaa | 120 |
| acctcccaca cctcccccctg aacctgaaac ataaaatgaa tgcaattgtt gttgttaact | 180 |
| tgtttattgc agcttataat ggttacaaat aaagcaatag catcacaaat ttcacaaata | 240 |
| aagcattttt ttcactgcat tctagttgtg gtttgtccaa actcatcaat gtatcttatc | 300 |
| atgtctggat ccccaagctt ctcgagaccg tcctgcagg tcactgtgag ttggagagga | 360 |
| aaatagcccc cagccaccga aacccgaaca ctgtgcggag gatgggcacc cggagccaca | 420 |
| ggaccacaaa cagggtacag gatgcagcga cgctactgaa aattgaagaa tgcacggcga | 480 |

```
tcagccactg ctggaaatcg tggagtttgg gcctgctgcc gggagtagga aaaatagcga   540
acacctgatt cagtgtagag ttatagacga tggtcacatt ggacccagtc atcctcaggt   600
tatggagcat aggcaggcgg ctggccaggt acttgcatgt ttctgcctca atggctgcga   660
gatgctggaa gtgggcgacc acgtccaggg agctgattcg tgagagggtt gcttcagaga   720
ccacctgttt ccaagcggcc tggccagcct tttccataat tctgtacatt ctcctgctga   780
ccatctcatc gatcagtgta ctcactttat ggtgccagag cattcccaga gggtgctttg   840
tgccccaggt tgggatgtcc acctgacact ggctcagaaa tgcctcatag gagcgccggt   900
agttgctcag agtgaatggg agagcccgca ctgaatatcg gggagcaaac cagtcactgg   960
cgaatgacca ccatcccact ggagaggggg aggccaggca aaatggccag aagtagagag  1020
agatgagcag agggcaccag gaagatcgtg agagcatcca gaggaagttt gcgagtttag  1080
tcaggaaagc cttacagggt ccccatttca tggtggagct ttttgcaaaa gcctaggcct  1140
ccaaaaaagc ctcctcacta cttctggaat agctcagagg ccgaggcggc tcggcctct   1200 gcataaataa aaaaaattag tcagccatgg ggcggagaat gggcggaact gggcggagtt  1260
aggggcggga tgggcggagt taggggcggg actatggttg ctgactaatt gagatgcatg  1320
ctttgcatac ttctgcctgc tggggagcct ggggactttc cacacctggt tgctgactaa  1380
ttgagatgca tgctttgcat acttctgcct gctggggagc tggggacttt ccacaccct   1440 aactgacaca cattccacag ccaagctgta ccgagctcga attcgctagc atcgatgcgg  1500
ccgcgttgac attgattatt gactagttat taatagtaat caattacggg gtcattagtt  1560
catagcccat atatggagtt ccgcgttaca aacttacgg taaatggccc gcctggctga   1620
ccgcccaacg accccccgcc cattgacgtc aataatgacgt atgttcccat agtaacgcca  1680
atagggactt tccattgacg tcaatgggtg gactatttac ggtaaactgc ccacttggca  1740
gtacatcaag tgtatcatat gccaagtacg ccccctattg acgtcaatga cggtaaatgg  1800
cccgcctggc attatgccca gtacatgacc ttatgggact ttcctacttg gcagtacatc  1860
tacgtattag tcatcgctat taccatggtg atgcggtttt ggcagtacat caatgggcgt  1920
ggatagcggt ttgactcacg gggatttcca agtctccacc ccattgacgt caatgggagt  1980
ttgttttggc accaaaatca acgggacttt ccaaaatgtc gtaacaactc cgccccattg  2040
acgcaaatgg gcggtaggcg tgtacggtgg gaggtctata taagcagagc tctctagaac  2100
caccatggct tcatctctcc tcttcctcgt cgtgggattc aaatgtctgc tcgtgtctca  2160
ggccttcgct tgtaaaccct gctttttccag tagcctggct gacatcaaga ctaacaccac  2220
agccgctgca tcattcgcag tgctgcagga cattagttgc ctccgacacc gagatagtgc  2280
cagcgaggct atcaggaaaa ttccccagtg tagaacagca atcgggactc cagtgtacgt  2340
cactattacc gccaacgtga cagacgaaaa ttatctgcat agctccgatc tgctcatgct  2400
gtcttcatgc ctcttctacg cttccgagat gtctgaaaag ggcttcaaag tggtctttgg  2460
caacgtctct ggaatcgtgg ccgtgtgcgt gaatttcacc agctatgtcc agcacgtgaa  2520
ggagtttaca cagcgatccc tggtggtcga tcacgtgcgc ctgctccact tcatgacccc  2580
tgaaaccatg cggtgggcta ctgtcctcgc ctgcctgttc gccattctcc tcgctatttg  2640
aagatctccc ccccccctaa cgttactggc cgaagccgct tggaataagg ccggtgtgcg  2700
tttgtctata tgttatttc caccatattg ccgtcttttg gcaatgtgag ggcccggaaa  2760 cctgccctg tcttcttgac gagcattcct aggggtcttt cccctctcgc caaaggaatg  2820
```

```
caaggtctgt tgaatgtcgt gaaggaagca gttcctctgg aagcttcttg aagacaaaca    2880
acgtctgtag cgacccttig caggcagcgg aaccccccac ctggcgacag gtgcctctgc    2940
ggccaaaagc cacgtgtata agatacacct gcaaaggcgg cacaacccca gtgccacgtt    3000
gtgagttgga tagttgtgga aagagtcaaa tggctctcct caagcgtatt caacaagggg    3060
ctgaaggatg cccagaaggt accccattgt atgggatctg atctggggcc tcggtgcaca    3120
tgctttacat gtgtttagtc gaggttaaaa aacgtctagg ccccccgaac cacggggacg    3180
tggttttcct ttgaaaaaca cgatgataat accaccatgg tcaattcctg taccttcctc    3240
cacatcttcc tctgttgttc attcctctat tccttctgtt gcgctgtcgt cgctgggtca    3300
aacaccacat actgcttctg gtttccactg gtgagaggaa acttctcctt tgagctcaca    3360
gtcaattata ccgtgtgccc tccatgtctg acccgacagg cagctacaga aatctacgaa    3420
cctggcaggt ctctgtggtg cagaattggc tatgaccgat gtggagagga cgatcacgat    3480
gaactggggt tcatgatccc tcccggcctg agctccgaag acatctcac  aggggtctac    3540 gcatggctgg ccttcctctc cttttcttat actgcccagt tccaccccga aatcttcggg    3600
attggcaacg tgtccagggt gtacgtcgac atcaagcacc agctgatttg tgccgaacat    3660
gacggccaga acactaccct gcctcggcat gataatatca gcgccgtgtt ccagacctac    3720
tatcagcacc aggtggatgg cggaaattgg tttcatctgg agtggctccg gcccttcttt    3780
tcttcatggc tggtcctcaa cgtgtcatgg ttcctgcggc gcagtcccgc caatcacgtg    3840
agcgtccggg tgctgcagat tctccgccca actccaccic agaggcaggc tctgctcagt    3900
agcaaaacct cagtggcact gggcatcgct acacgacctc tcagacggtt cgctaagtcc    3960
ctctcagcag tcagaaggtg aagatctggt accgggggag gctaactgaa acacggaagg    4020
agacaatacc ggaaggaacc cgcgctatga cggcaataaa aagacagaat aaaacgcacg    4080
ggtgttgggt cgtttgttca taaacgcggg gttcggtccc agggctggca ctctgtcgat    4140
accccaccga gaccccattg gggccaatac gcccgcgttt cttccttttc cccaccccac    4200
cccccaagtt cgggtgaagg cccagggctc gcagccaacg tcggggcggc aggccctgcc    4260
atagccagct ttcttgtaca aagttggcat tataagaaag cattgcttat caatttgttg    4320
caacgaacag gtcactatca gtcaaaataa aatcattatt t                        4361
```

<210> SEQ ID NO 24
<211> LENGTH: 10
<212> TYPE: PRT
<213> ORGANISM: Artificial Sequence
<220> FEATURE:
<223> OTHER INFORMATION: Placeholder for: vAD-rtg-gp234-E
      pre-recombination insert

<400> SEQUENCE: 24

Asn Asn Asn Asn Asn Asn Asn Asn Asn Asn
1               5                   10

<210> SEQ ID NO 25
<211> LENGTH: 10
<212> TYPE: DNA
<213> ORGANISM: Artificial Sequence
<220> FEATURE:
<223> OTHER INFORMATION: Placeholder for: vAD3033 pre-recombination
      insert
<220> FEATURE:
<221> NAME/KEY: misc_feature
<222> LOCATION: (1)..(10)
<223> OTHER INFORMATION: n is a, c, g, t or u

<400> SEQUENCE: 25 nnnnnnnnnn                                                                 10

<210> SEQ ID NO 26
<211> LENGTH: 24
<212> TYPE: DNA
<213> ORGANISM: Artificial Sequence
<220> FEATURE:
<223> OTHER INFORMATION: pAd5 Forward primer

<400> SEQUENCE: 26
gactttgacc gtttacgtgg agac                                                 24

<210> SEQ ID NO 27
<211> LENGTH: 24
<212> TYPE: DNA
<213> ORGANISM: Artificial Sequence
<220> FEATURE:
<223> OTHER INFORMATION: pAd5 Reverse primer

<400> SEQUENCE: 27
ccttaagcca cgcccacaca tttc                                                 24

<210> SEQ ID NO 28
<211> LENGTH: 15411
<212> TYPE: DNA
<213> ORGANISM: Artificial Sequence
<220> FEATURE:
<223> OTHER INFORMATION: Entire VR2332, PRRSV Type II sequence

<400> SEQUENCE: 28
atgacgtata ggtgttggct ctatgccttg gcatttgtat tgtcaggagc tgtgaccatt          60
ggcacagccc aaaacttgct gcacagaaac acccttctgt gatagcctcc ttcaggggag         120
cttagggttt gtccctagca ccttgcttcc ggagttgcac tgctttacgg tctctccacc         180
cctttaacca tgtctgggat acttgatcgg tgcacgtgta cccccaatgc cagggtgttt         240
atggcggagg gccaagtcta ctgcacacga tgcctcagtg cacggtctct ccttcccctg         300
aacctccaag tttctgagct cggggtgcta ggcctattct acaggcccga gagccactc          360 cggtggacgt tgccacgtgc attccccact gttgagtgct ccccgccgg ggcctgctgg          420 ctttctgcaa tctttccaat cgcacgaatg accagtggaa acctgaactt ccaacaaaga         480
atggtacggg tcgcagctga gctttacaga gccggccagc tcacccctgc agtcttgaag         540
gctctacaag tttatgaacg gggttgccgc tggtacccca ttgttggacc tgtccctgga         600
gtggccgttt cgccaattc cctacatgtg agtgataaac ctttcccggg agcaactcac          660
gtgttgacca acctgccgct cccgcagaga cccaagcctg aagacttttg ccccttgag          720 tgtgctatgg ctactgtcta tgacattggt catgacgccg tcatgtatgt ggccgaaagg         780
aaagtctcct gggcccctcg tggcggggat gaagtgaaat tgaagctgt ccccggggag          840 ttgaagttga ttgcgaaccg gctccgcacc tccttcccgc ccaccacac agtggacatg          900 tctaagttcg ccttcacagc ccctgggtgt ggtgtttcta tgcgggtcga acgccaacac         960
ggctgccttc ccgctgacac tgtccctgaa ggcaactgct ggtggagctt gtttgacttg        1020
cttccactgg aagttcagaa caaagaaatt cgccatgcta accaatttgg ctaccagacc        1080
aagcatggtg tctctggcaa gtacctacag cggaggctgc aagttaatgg tctccgagca        1140
gtaactgacc taaacggacc tatcgtcgta cagtacttct ccgttaagga gagttggatc        1200
cgccatttga aactggcggg agaacccagc tactctgggt ttgaggacct cctcagaata        1260

```
agggttgagc ctaacacgtc gccattggct gacaaggaag aaaaaatttt ccggtttggc    1320
agtcacaagt ggtacggcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt    1500
ggttggcact gcatttccgc catcgccaac cggatggtga attccaaatt tgaaaccacc    1560
cttcccgaaa gagtgagacc tccagatgac tgggctactg acgaggatct tgtgaatgcc    1620
atccaaatcc tcagactccc tgcggcctta gacaggaacg gtgcttgtac tagcgccaag    1680
tacgtactta agctggaagg tgagcattgg actgtcactg tgaccctgg gatgtcccct     1740 tctttgctcc ctcttgaatg tgttcagggc tgttgtgggc acaagggcgg tcttggttcc    1800
ccagatgcag tcgaggtctc cggatttgac cctgcctgcc ttgaccggct ggctgaggtg    1860
atgcacctgc ctagcagtgc tatcccagcc gctctggccg aaatgtctgg cgattccgat    1920
cgttcggctt ctccggtcac caccgtgtgg actgtttcgc agttctttgc ccgtcacagc    1980
ggagggaatc accctgacca agtgcgctta gggaaaatta tcagcctttg tcaggtgatt    2040
gaggactgct gctgttccca gaacaaaacc aaccgggtca ccccggagga ggtcgcagca    2100
aagattgacc tgtacctccg tggtgcaaca aatcttgaag aatgcttggc caggcttgag    2160
aaagcgcgcc cgccacgcgt aatcgacacc tcctttgatt gggatgttgt gctccctggg    2220
gttgaggcgg caacccagac gatcaagctg ccccaggtca ccagtgtcg tgctctggtc     2280 cctgttgtga ctcaaaagtc cttggacaac aactcggtcc ccctgaccgc cttttcactg    2340
gctaactact actaccgtgc gcaaggtgac gaagttcgtc accgtgaaag actaaccgcc    2400
gtgctctcca gttggaaaaa ggttgttcga gaagaatatg gctcatgcc aaccgagcct     2460 ggtccacggc ccacactgcc acgcgggctc gacgaactca aagaccagat ggaggaggac    2520
ttgctgaaac tggctaacgc ccagacgact tcggacatga tggcctggc agtcgagcag     2580 gttgacctaa aaacttgggt caagaactac ccgcggtgga caccaccacc ccctccgcca    2640
aaagttcagc ctcgaaaaac gaagcctgtc aagagcttgc cggagagaaa gcctgtcccc    2700
gccccgcgca ggaaggttgg gtccgattgt ggcagcccgg tttcattagg cggcgatgtc    2760
cctaacagtt gggaagattt ggctgttagt agcccctttg atctcccgac cccacctgag    2820
ccggcaacac cttcaagtga gctggtgatt gtgtcctcac gcaatgcat cttcaggccg     2880 gcgacaccct tgagtgagcc ggctccaatt cccgcacctc gcggaactgt gtctcgaccg    2940
gtgacaccct tgagtgagcc gatccctgtg cccgcaccgc ggcgtaagtt tcagcaggtg    3000
aaaagattga gttcggcggc ggcaatccca ccgtaccagg acgagcccct ggatttgtct    3060
gcttcctcac agactgaata tgaggcctct ccccagcac cgccgcagag cggggcgtt     3120 ctgggagtag aggggcatga agctgaggaa accctgagtg aaatctcgga catgtcgggt    3180
aacattaaac ctgcgtccgt gtcatcaagc agctccttgt ccagcgtgag aatcacacgc    3240
ccaaaatact cagctcaagc catcatcgac tcgggcgggc cctgcagtgg gcatctccaa    3300
gaggtaaagg aaacatgcct tagtgtcatg cgcgaggcat gtgatgcgac taagcttgat    3360
gaccctgcta cgcaggaatg gctttctcgc atgtgggatc gggtggacat gctgacttgg    3420
cgcaacacgt ctgtttacca ggcgatttgc accttagatg gcaggttaaa gttcctccca    3480
aaaatgatac tcgagacacc gccgcccat ccgtgtgagt ttgtgatgat gcctcacacg     3540
cctgcacctt ccgtaggtgc ggagagcgac cttaccattg gctcagttgc tactgaagat    3600
```

```
gttccacgca tcctcgagaa aatagaaaat gtcggcgaga tggccaacca gggacccttg      3660
gccttctccg aggataaacc ggtagatgac caacttgtca acgaccccg gatatcgtcg       3720 cggaggcctg acgagagcac atcagctccg tccgcaggca caggtggcgc cggctctttt      3780
accgatttgc cgccttcaga tggcgcggat gcggacgggg gggggccgtt tcggacggta      3840 aaagaaaag ctgaaaggct cttgaccaa ctgagccgtc aggttttga cctcgtctcc         3900 catctccctg ttttcttctc acgccttttc taccctggcg gtggttattc tccgggtgat     3960
tggggttttg cagcttttac tctattgtgc ctcttttat gttacagtta cccagccttt      4020
ggtattgctc ccctcttggg tgtgttttct gggtcttctc ggcgcgttcg aatgggggtt     4080
tttggctgct ggttggcttt tgctgttggt ctgttcaagc ctgtgtccga cccagtcggc    4140
gctgcttgtg agtttgactc gccagagtgt agaaacatcc ttcattcttt tgagcttctc    4200
aaaccttggg accctgttcg cagccttgtt gtgggccccg tcggtctcgg tcttgccatt    4260
cttggcaggt tactgggcgg ggcacgctgc atctggcact ttttgcttag gcttggcatt    4320
gttgcagact gtatcttggc tggagcttac gtgctttctc aaggtaggtg taaaaagtgc    4380
tggggatctt gtataagaac tgctcctaat gaggtcgctt ttaacgtgtt tcctttcaca    4440
cgtgcgacca ggtcgtcact tatcgacctg tgcgatcggt tttgtgcgcc aaaaggaatg    4500
gacccatttt ttctcgccac tgggtggcgc gggtgctggg ccggccgaag ccccattgag    4560
caaccctctg aaaaacccat cgcgtttgcc caattggatg aaaagaagat tacggctagg    4620
actgtggtcg cccagcctta tgaccccaac caagccgtaa agtgcttgcg ggtattgcag    4680
tcgggtgggg cgatggtggc taaggcggtc ccaaaagtgg tcaaggtttc cgctgttcca    4740
ttccgagccc ccttctttcc cactggagtg aaagttgacc ctgattgcag ggtcgtggtt    4800
gaccctgaca ctttcactgc agctctccgg tctggctact ccaccacaaa cctcgtcctt    4860
ggtgtagggg actttgccca gctgaatgga ttaaaaatca ggcaaatttc caagccttca    4920
gggggaggcc cacatctcat ggctgccctg catgttgcct gctcgatggc tctgcacatg    4980
cttgctggga tttatgtgac tgcggtgggt tcttgcggca ccggcaccaa cgacccgtgg    5040
tgcgctaacc cgtttgccgt ccctggctac ggacctggct ctctctgcac gtccaggttg    5100
tgcatttccc aacacggcct taccctgccc ttgacagcac ttgtggcggg attcggtatt    5160
caagaaattg ccttggtcgt tttgattttt gtttccatcg gaggcatggc tcataggttg    5220
agctgtaagg ctgacatgct gtgtgttttg cttgcaattg ccagctatgt ttgggtacct    5280
cttacctggt tgctttgtgt gtttccttgc tggttgcgct gttttctttt gcaccccctc    5340
accatcctat ggttggtgtt tttcttgatt tctgtgaata tgccttcagg aatcttggcc    5400
atggtgttgt tggtttctct ttggcttctt ggtcgttata ctaatgttgc tggccttgtc    5460
accccctacg acattcatca ttacaccagt ggccccgcg gtgttgccgc cttggctacc    5520
gcaccagatg ggacctactt ggccgctgtc cgccgcgctg cgttgactgg ccgcaccatg    5580
ctgtttaccc cgtcccagct tgggtctctt cttgagggtg ctttcagaac tcgaaagccc    5640
tcactgaaca ccgtcaatgt gatcgggtcc tccatgggct ctggcggggt gtttaccatc    5700
gacgggaaag tcaagtgcgt aactgccgca catgtcctta cggcaattc agctcgggtt    5760 tccggggtcg gcttcaatca aatgcttgac tttgacgtaa agggagattt cgctatagct    5820
gattgcccga attggcaagg ggctgccccc aagacccaat tctgcacgga tggatggact    5880
ggccgtgcct attggctaac atcctctggc gtcgaacccg cgtcattgg aaaaggattc    5940 gccttctgct tcaccgcatg tggcgattcc gggtccccag tgatcaccga ggccggtgag    6000
```

| | |
|---|---|
| cttgtcggcg ttcacacggg atcgaataaa caagggggg gcattgttac gcgcccctca | 6060 |
| ggccagtttt gtaatgtggc acccatcaag ctaagcgaat taagtgaatt ctttgctggg | 6120 |
| cctaaggtcc cgctcggtga tgtgaaggtc ggcagccaca taattaaaga cataagcgag | 6180 |
| gtgccttcag atctttgtgc cttgcttgct gccaaacctg aactggaagg aggcctctcc | 6240 |
| accgtccaac ttctttgtgt gttttttctc ctgtggagaa tgatgggaca tgcctggacg | 6300 |
| cccttggttg ctgtgagttt ctttattttg aatgaggttc tcccagccgt cctggtccgg | 6360 |
| agtgttttct cctttggaat gtttgtgcta tcctggctca cgccatggtc tgcgcaagtt | 6420 |
| ctgatgatca ggcttctgac agcagctctt aacaggaaca gatggtcact tgcctttttc | 6480 |
| agcctcggtg cagtgaccgg ttttgtcgca gatcttgcgg ccactcaggg gcatccgttg | 6540 |
| caggcagtga tgaatttgag cacctatgca ttcctgcctc ggatgatggt tgtgacctca | 6600 |
| ccagtcccag tgatcacgtg tggtgtcgtg cacctacttg ccatcatttt gtacttgttt | 6660 |
| aagtaccgtg gcccgcacca tatccttgtt ggcgatggag tgttctctgc ggctttcttc | 6720 |
| ttgagatact ttgccgaggg aaagttgagg gaagggtgt cgcaatcctg cggaatgaat | 6780 |
| catgagtctc tgactggtgc cctcgctatg agactcaatg acgaggactt ggatttcctt | 6840 |
| atgaaatgga ctgattttaa gtgctttgtt tctgcgtcca acatgaggaa tgcagcgggt | 6900 |
| caatttatcg aggctgccta tgctaaagca cttagagtag aactggccca gttggtgcag | 6960 |
| gttgataaag ttcgaggtac tttggccaaa cttgaagctt ttgctgatac cgtggcacct | 7020 |
| caactctcgc ccggtgacat tgttgtcgct ctcggccaca cgcctgttgg cagtatcttc | 7080 |
| gacctaaagg ttggtagcac caagcatacc ctccaagcca ttgagaccag agtccttgct | 7140 |
| gggtccaaaa tgaccgtggc gcgcgtcgtc gacccgaccc ccacgccccc acccgcaccc | 7200 |
| gtgcccatcc ccctcccacc gaaagttctg agaatggcc caacgcttg gggggatgag | 7260 |
| gaccgtttga ataagaagaa gaggcgcagg atggaagccc tcggcatcta tgttatgggc | 7320 |
| gggaaaaagt accagaaatt tgggacaag aattccggtg atgtgtttta tgaggaggtc | 7380 |
| cataataaca cagatgagtg ggagtgtctc agagttggcg accctgccga ctttgaccct | 7440 |
| gagaagggaa ctctgtgtgg acatgtcacc attgaaaaca aggcttacca tgtttacacc | 7500 |
| tccccatctg gtaagaagtt cttggtcccc gtcaacccag agaatggaag agttcaatgg | 7560 |
| gaagctgcaa agctttccgt ggagcaggcc ctaggtatga tgaatgtcga cggcgaactg | 7620 |
| actgccaaag aactggagaa actgaaaaga ataattgaca aactccaggg cctgactaag | 7680 |
| gagcagtgtt taaactgcta gccgccagcg acttgacccg ctgtggtcgc ggcggcttgg | 7740 |
| ttgttactga acagcggta aaaatagtca aatttcacaa ccggaccttc accctgggac | 7800 |
| ctgtgaattt aaaagtggcc agtgaggttg agctaaaaga cgcggttgag cacaaccaac | 7860 |
| acccggttgc gagaccgatc gatggtggag ttgtgctcct gcgttccgcg gttccttcgc | 7920 |
| ttatagacgt cttgatctcc ggtgctgatg catctcccaa gttacttgcc catcacgggc | 7980 |
| cgggaaacac tgggatcgat ggcacgctct gggattttga gtccgaagcc actaaagagg | 8040 |
| aagtcgcact cagtgcgcaa ataatacagg cttgtgacat taggcgcggc gacgctcctg | 8100 |
| aaattggtct cccttacaag ctgtaccctg ttaggggtaa ccctgagcgg gtgaaaggag | 8160 |
| ttctgcagaa tacaaggttt ggagacatac cttacaaaac ccccagtgac actggaagcc | 8220 |
| cagtgcacgc ggctgcctgc cttacgccca acgccactcc ggtgactgat gggcgctccg | 8280 |
| tcttggccac gaccatgccc cccgggtttg agttatatgt accgaccata ccagcgtctg | 8340 |

```
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcacccccat ggccttctgt tcttacaaga ccagctaaag tttgaggaca    9180
tgctcaaggt tcaaccctg atcgtctatt cggacgacct cgtgctgtat gccgagtctc    9240
ccaccatgcc aaactatcac tggtgggttg aacatctgaa tttgatgctg ggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg acagctgtg    9480
cttgtttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttttag acgaggtgct ggaacaagtc ccgtataagc    9840
ccccacggac cgttatcatg catgtggagc agggtctcac ccccccttgat ccaggtagat    9900
accaaactcg ccgcggatta gtctctgtca ggcgtggaat taggggaaat gaagttggac    9960
taccagacgg tgattatgct agcaccgcct tgctccctac ctgcaaagag atcaacatgg    10020
tcgctgtcgc ttccaatgta ttgcgcagca ggttcatcat cggcccaccc ggtgctggga    10080
aaacatactg gctccttcaa caggtccagg atggtgatgt tatttacaca ccaactcacc    10140
agaccatgct tgacatgatt agggctttgg ggacgtgccg gttcaacgtc ccggcaggca    10200
caacgctgca attccccgtc ccctcccgca ccggtccgtg ggttcgcatc ctagccggcg    10260
gttggtgtcc tggcaagaat tccttcctag atgaagcagc gtattgcaat cccttgatg    10320
tttttgaggct tcttagtaaa actaccctca cctgtcctagg agacttcaag caactccacc    10380
cagtgggttt tgattctcat tgctatgttt ttgacatcat gcctcaaact caactgaaga    10440
ccatctggag gttggacag aatatctgtg atgccattca gccagattac agggacaaac    10500
tcatgtccat ggtcaacaca acccgtgtga cctacgtgga aaaacctgtc aggtatgggc    10560
aggtcctcac ccctaccac agggaccgag aggacgacgc catcactatt gactccagtc    10620
aaggcgccac attcgatgtg gttacattgc atttgcccac taaagattca ctcaacaggc    10680
aaagagccct tgttgctatc accagggcaa gacacgctat cttttgtgtat gacccacaca    10740
```

```
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
actggcccgt ggtgtcaacc cagaacaatg aaaagtggcc ggatcggctg gttgccagcc   11100
ttcgccctat ccataaatac agccgcgcgt gcatcggtgc cggctatatg gtgggccctt   11160
cggtgtttct aggcactcct ggggtcgtgt catactatct cacaaaattt gttaagggcg   11220
gggctcaagt gcttccggag acggttttca gcaccggccg aattgaggta gactgccggg   11280
aatatcttga tgatcgggag cgagaagttg ctgcgtccct cccacacggt ttcattggcg   11340
acgtcaaagg cactaccgtt ggaggatgtc atcatgtcac ctccagatac ctcccgcgcg   11400
tccttcccaa ggaatcagtt gcggtagtcg gggtttcaag ccccggaaaa gccgcgaaag   11460
cattgtgcac actgacagat gtgtacctcc cagatcttga agcctatctc cacccggaga   11520
cccagtccaa gtgctggaaa atgatgttgg acttcaaaga agttcgacta atggtctgga   11580
aagacaaaac agcctatttc caacttgaag gtcgctattt cacctggtat cagcttgcca   11640
gctatgcctc gtacatccgt gttcccgtca actctacggt gtacttggac ccctgcatgg   11700
gccccgccct ttgcaacagg agagtcgtcg ggtccaccca ctgggggggct gacctcgcgg   11760 tcacccctta tgattacggc gctaaaatta tcctgtctag cgcgtaccat ggtgaaatgc   11820 ccccggata caaaattctg gcgtgcgcgg agttctcgtt ggatgaccca gttaagtaca   11880
aacatacctg gggtttgaa tcggatacag cgtatctgta tgagttcacc ggaaacggtg   11940
aggactggga ggattacaat gatgcgtttc gtgcgcgcca ggaagggaaa atttataagg   12000
ccactgccac cagcttgaag ttttattttc ccccgggccc tgtcattgaa ccaactttag   12060
gcctgaattg aaatgaaatg gggtccatgc aaagccttt tgacaaaatt ggccaacttt   12120
ttgtggatgc tttcacgag ttcttggtgt ccattgttga tatcattata ttttgcca   12180 ttttgtttgg cttcaccatc gccggttggc tggtggctctt ttgcatcaga ttggtttgct   12240
ccgcgatact ccgtacgcgc cctgccattc actctgagca attacagaag atcttatgag   12300
gcctttcttt cccagtgcca agtggacatt cccacctggg gaactaaaca tccttttggg   12360
atgctttggc accataaggt gtcaaccctg attgatgaaa tggtgtcgcg tcgaatgtac   12420
cgcatcatgg aaaaagcagg gcaggctgcc tggaaacagg tggtgagcga ggctacgctg   12480
tctcgcatta gtagtttgga tgtggtggct cattttcagc atctagccgc cattgaagcc   12540
gagacctgta aatatttggc ctcccggctg cccatgctac acaacctgcg catgacaggg   12600
tcaaatgtaa ccatagtgta taatagcact ttgaatcagg tgtttgctat ttttccaacc   12660
cctggttccc ggccaaagct tcatgatttt cagcaatggt taatagctgt acattcctcc   12720
atattttcct ctgttgcagc ttcttgtact cttttttgttg tgctgtggtt gcgggttcca   12780
atactacgta ctgttttttgg tttccgctgg ttaggggcaa ttttttctttc gaactcacag   12840 tgaattacac ggtgtgtcca ccttgcctca cccggcaagc agccacagag atctacgaac   12900
ccggtaggtc tctttggtgc aggatagggt atgaccgatg tggggaggac gatcatgacg   12960 agctaggggtt tatgataccg cctggcctct ccagcgaagg ccacttgact ggtgtttacg   13020
cctggttggc gttcttgtcc ttcagctaca cggcccagtt ccatcccgag atattcggga   13080
```

```
tagggaatgt gagtcgagtt tatgttgaca tcaaacatca actcatctgc gccgaacatg    13140
acgggcagaa caccaccttg cctcgtcatg acaacatttc agccgtgttt cagacctatt    13200
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcagata ttaagaccaa caccaccgca gcggcaagct tgctgtcct    13380 ccaagacatc agttgcctta ggcatcgcga ctcggcctct gaggcgattc gcaaaatccc    13440
tcagtgccgt acggcgatag ggacacccgt gtatgttacc atcacagcca atgtgacaga    13500
tgagaattat ttacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttgcca ttctgttggc aatttgaatg tttaagtatg ttggagaaat    13800
gcttgaccgc gggctgttgc tcgcgattgc tttctttgtg gtgtatcgtg ccgttctgtt    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaaaggg    14280
gcaaagttga ggtcgaaggt catctgatcg acctcaaaag agttgtgctt gatggttccg    14340
tggcaacccc tataaccaga gtttcagcgg aacaatgggg tcgtccttag atgacttctg    14400
tcatgatagc acggctccac aaaaggtgct tttggcgttt tctattacct acacgccagt    14460
gatgatatat gccctaaagg tgagtcgcgg ccgactgcta gggcttctgc accttttgat    14520
cttcctgaat tgtgctttca ccttcgggta catgactttc gcgcactttc agagtacaaa    14580
taaggtcgcg ctcactatgg gagcagtagt tgcactcctt tgggggtgt actcagccat    14640 agaaacctgg aaattcatca cctccagatg ccgtttgtgc ttgctaggcc gcaagtacat    14700
tctggcccct gcccaccacg ttgaaagtgc cgcacggttt catccgattg cggcaaatga    14760
taaccacgca tttgtcgtcc ggcgtccgg ctccactacg gtcaacggca cattggtgcc    14820
cgggttaaaa agcctcgtgt tgggtggcag aaaagctgtt aaacagggag tggtaaacct    14880
tgtcaaatat gccaataac aacggcaagc agcagaagag aaagaagggg gatgccagc    14940 cagtcaatca gctgtgccag atgctgggta agatcatcgc tcagcaaaac cagtccagag    15000
gcaagggacc gggaaagaaa aataagaaga aaacccgga gaagccccat tttcctctag    15060
cgactgaaga tgatgtcaga catcacttta cccctagtga gcgcaattg tgtctgtcgt    15120 caatccagac cgcctttaat caaggcgctg ggacttgcac cctgtcagat tcaggagga    15180 taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat t              15411
```

<210> SEQ ID NO 29
<211> LENGTH: 15108
<212> TYPE: DNA
<213> ORGANISM: Artificial Sequence
<220> FEATURE:
<223> OTHER INFORMATION: Entire Lelystad PRRSV sequence (GenBank: A26843.1)

<400> SEQUENCE: 29

| | | | | | |
|---|---|---|---|---|---|
| gggtattccc | cctacataca | cgacacttct | agtgtttgtg | taccttggag | gcgtgggtac | 60 |
| agccccgccc | cacccct tgg | ccctgttct | agcccaacag | gtatccttct | ctctcggggc | 120 |
| gagtgcgccg | cctgctgctc | ccttgcagcg | ggaaggacct | cccgagtatt | tccggagagc | 180 |
| acctgcttta | cgggatctcc | accctttaac | catgtctggg | acgttctccc | ggtgcatgtg | 240 |
| caccccggct | gcccgggtat | tttggaacgc | cggccaagtc | ttttgcacac | ggtgtctcag | 300 |
| tgcgcggtct | cttctctctc | cagagcttca | ggacactgac | ctcggtgcag | ttggcttgtt | 360 |
| ttacaagcct | agggacaagc | ttcactggaa | agtccctatc | ggcatccctc | aggtggaatg | 420 |
| tactccatcc | gggtgctgtt | ggctctcagc | tgttttccct | ttggcgcgta | tgacctccgg | 480 |
| caatcacaac | ttcctccaac | gacttgtgaa | ggttgctgat | gttttgtacc | gtgacggttg | 540 |
| cttggcacct | cgacaccttc | gtgaactcca | agtttacgag | cgcggctgca | actggtaccc | 600 |
| gatcacgggg | cccgtgcccg | ggatgggttt | gtttgcgaac | tccatgcacg | tatccgacca | 660 |
| gccgttccct | ggtgccaccc | atgtgttgac | taactcgcct | ttgcctcaac | aggcttgtcg | 720 |
| gcagccgttc | tgtccatttg | aggaggctca | ttctagcgtg | tacaggtgga | agaaatttgt | 780 |
| ggttttcacg | gactcctccc | tcaacggtcg | atctcgcatg | atgtggacgc | cggaatccga | 840 |
| tgattcagcc | gccctggagg | tactaccgcc | tgagttagaa | cgtcaggtcg | aaatcctcat | 900 |
| tcggagtttt | cctgctcatc | accctgtcga | cctggccgac | tgggagctca | ctgagtcccc | 960 |
| tgagaacggt | ttttccttca | acacgtctca | ttcttgcggt | caccttgtcc | agaaccccga | 1020 |
| cgtgtttgat | ggcaagtgct | ggctctcctg | ctttttgggc | cagtcggtcg | aagtgcgctg | 1080 |
| ccatgaggaa | catctagctg | acgccttcgg | ttaccaaacc | aagtggggcg | tgcatggtaa | 1140 |
| gtacctccag | cgcaggcttc | aagttcgcgc | cattcgtgct | gtagtcgatc | ctgatggtcc | 1200 |
| cattcacgtt | gaagcgctgt | cttgccccca | gtcttggatc | aggcacctga | ctctggatga | 1260 |
| tgatgtcacc | ccaggattcg | ttcgcctgac | atcccttcgc | attgtgccga | acacagagcc | 1320 |
| taccacttcc | cggatctttc | ggtttggagc | gcataagtgg | tatggcgctg | ccggcaaacg | 1380 |
| ggctcgtgct | aagcgtgccg | ctaaaagtga | aaggattcg | gctcccaccc | ccaaggttgc | 1440 |
| cctgccggtc | cccacctgtg | gaattaccac | ctactctcca | ccgacagacg | ggtcttgtgg | 1500 |
| ttggcatgtc | cttgccgcca | taatgaaccg | gatgataaat | ggtgacttca | cgtcccctct | 1560 |
| gactcagtac | aacagaccag | aggatgattg | gcttctgat | tatgatcttg | ttcaggcgat | 1620 |
| tcaatgtcta | cgactgcctg | ctaccgtggt | tcggaatcgc | gcctgtccta | acgccaagta | 1680 |
| ccttataaaa | cttaacggag | ttcactggga | ggtagaggtg | aggtctggaa | tggctcctcg | 1740 |
| ctcccttct | cgtgaatgtg | tggttggcgt | ttgctctgaa | ggctgtgtcg | caccgccttta | 1800 |
| tccagcagac | gggctaccta | aacgtgcact | cgaggcttg | gcgtctgctt | acagactacc | 1860 |
| ctccgattgt | gttagctctg | gtattgctga | cttcttgct | aatccacctc | tcaggaatt | 1920 |
| ctggaccctc | gacaaaatgt | tgacctcccc | gtcaccagag | cggtccggct | tctctagttt | 1980 |
| gtataaaatta | ctattagagg | ttgttccgca | aaaatgcggt | gccacggaag | gggctttcat | 2040 |
| ctatgctgtt | gagaggatgt | tgaaggattg | tccgagctcc | aaacaggcca | tggcccttct | 2100 |

```
ggcaaaaatt aaagttccat cctcaaaggc cccgtctgtg tccctggacg agtgtttccc    2160
tacggatgtt ttagccgact tcgagccagc atctcaggaa aggccccaaa gttccggcgc    2220
tgctgttgtc ctgtgttcac cggatgcaaa agagttcgag gaagcagccc cggaagaagt    2280
tcaagagagt ggccacaagg ccgtccactc tgcactcctt gccgagggtc ctaacaatga    2340
gcaggtacag gtggttgccg gtgagcaact gaagctcggc ggttgtggtt tggcagtcgg    2400
gaatgctcat gaaggtgctc tggtctcagc tggtctaatt aacctggtag gcgggaattt    2460
gtccccctca gaccccatga agaaaaacat gctcaatagc cgggaagacg aaccactgga    2520
tttgtcccaa ccagcaccag cttccacaac gaccctgtg agagagcaaa cacccgacaa    2580
cccaggttct gatgccggtg ccctccccgt caccgttcga aatttgtcc cgacggggcc    2640 tatactctgt catgttgagc actgcggcac ggagtcgggc gacagcagtt cgcctttgga    2700
tctatctgat gcgcaaaccc tggaccagcc tttaaatcta tccctggccg cttggccagt    2760
gagggccacc gcgtctgacc ctggctgggt ccacggtagg cgcgagcctg tctttgtaaa    2820
gcctcgaaat gctttctctg atggcgattc agcccttcag ttcggggagc tttctgaatc    2880
cagctctgtc atcgagtttg accggacaaa agatgctccg gtggttgacg ccctgtcga    2940 cttgacgact tcgaacgagg ccctctctgt agtcgatcct ttcgaatttg ccgaactcaa    3000
gcgcccgcgt ttctccgcac aagccttaat tgaccgaggc ggtccacttg ccgatgtcca    3060
tgcaaaaata aagaaccggg tatatgaaca gtgcctccaa gcttgtgagc ccggtagtcg    3120 tgcaaccccca gccaccaggg agtggctcga caaaatgtgg gatagggtgg acatgaaaac    3180
ttggcgctgc acctcgcagt tccaagctgg tcgcattctt gcgtccctca aattcctccc    3240
tgacatgatt caagcacac cgcctcctgt tcccaggaag aaccgagcta gtgacaatgc    3300
cggcctgaag caactggtgg cacagtggga taaggaaatt gagtgtgacc ccccccaaa    3360 accggttggg ccagtgcttg accagatcgt ccctccgcct acggatatcc agcaagaaga    3420
tgtcaccccc tccgatgggc cacccccatgc gccggatttt cctagtcgag tgagcacggg    3480
cgggagttgg aaaggcctta tgcttttccgg caccgtctc gcggggtcta tcagccagcg    3540
ccttatgaca tgggtttttg aagttttctc ccacctccca gcttttatgc tcacactttt    3600
ctcgccgcgg ggctctatgg ctccaggtga ttggttgttt gcaggtgtcg ttttacttgc    3660
tctcttgctc tgtcgttctt acccgatact cggatgcctt cccttattgg gtgtcttttc    3720
tggttctttg cggcgtgttc gtctgggtgt ttttggttct tggatggctt ttgctgtatt    3780
tttattctcg actccatcca acccagtcgg ttcttcttgt gaccacgatt cgccggagtg    3840
tcatgctgag ctttggctc ttgagcagcg ccaactttgg gaacctgtgc gcggccttgt    3900
ggtcggcccc tcaggcctct tatgtgtcat tcttggcaag ttactcggtg gtcacgttac    3960
tctctggcat gttctcctac gtttatgcat gcttgcagat ttggcccttt ctcttgttta    4020
tgtggtgtcc caggggcgtt gtcacaagtg ttggggaaag tgtataagga cagctcctgc    4080
ggaggtggct cttaatgtat tcctttctc gcgcgccacc cgtgtctctc ttgtatcctt    4140
gtgtgatcga ttccaaacgc caaaaggggt tgatcctgtg cacttggcaa cgggttggcg    4200
cgggtgctgc cgtggtgaga gccccatcca tcaaccacac caaaagccca tagcttatgc    4260
caatttggat gaaaagaaaa tgtctgccca acggtggtt gctgtcccat acgatcccag    4320
tcaggctatc aaatgcctga agttctgcca ggcgggaggg gccatcgtgg accagcctac    4380
acctgaggtc gttcgtgtgt ccgagatccc cttctcagcc ccatttttcc caaaagttcc    4440
```

```
agtcaaccca gattgcaggg ttgtggtaga ttcggacact tttgtggctg cggttcgctg    4500
cggttactcg acagcacaac tggttctggg ccggggcaac tttgccaagt taaatcagac    4560 ccccccagg aactctatct ccaccaaaac gactggtggg gcctcttaca cccttgctgt     4620
ggctcaagtg tctgcgtgga ctcttgttca tttcatcctc ggtctttggt tcacatcacc    4680
tcaagtgtgt ggccgaggaa ccgctgaccc atggtgttca aatcctttt catatcctac     4740 ctatggcccc ggagttgtgt gctcctctcg actttgtgtg tctgccgacg gggtcaccct    4800
gccattgttc tcagccgtgg cacaactctc cggtagagag gtggggattt ttattttggt    4860
gctcgtctcc ttgactgctt tggcccaccg catggctctt aaggcagaca tgttagtggt    4920
cttttcggct ttttgtgctt acgcctggcc catgagctcc tggttaatct gcttctttcc    4980
tatactcttg aagtgggtta cccttcaccc tcttactatg ctttgggtgc actcattctt    5040
ggtgttttgt ctgccagcag ccggcatcct ctcactaggg ataactggcc ttctttgggc    5100
aattggccgc tttacccagg ttgccggaat tattacacct tatgacatcc accagtacac    5160
ctctgggcca cgtggtgcag ctgctgtggc cacagcccca gaaggcactt atatggccgc    5220
cgtccggaga gctgctttaa ctgggcgaac tttaatcttc accccgtctg cagttggatc    5280
ccttctcgaa ggtgctttca ggactcataa accctgcctt aacaccgtga atgttgtagg    5340
ctcttccctt ggttccggag gggttttcac cattgatggc agaagaactg tcgtcactgc    5400
tgcccatgtg ttgaacggcg acacagctag agtcaccggc gactcctaca accgcatgca    5460
cactttcaag accaatggtg attatgcctg gtcccatgct gatgactggc agggcgttgc    5520
ccctgtggtc aaggttgcga aggggtaccg cggtcgtgcc tactggcaaa catcaactgg    5580
tgtcgaaccc ggtatcattg gggaagggtt cgccttctgt tttactaact gcggcgattc    5640
ggggtcaccc gtcatctcag aatctggtga tcttattgga atccacaccg gttcaaacaa    5700
acttggttct ggtcttgtga caacccctga aggggagacc tgcaccatca aagaaaccaa    5760
gctctctgac ctttccagac attttgcagg cccaagcgtt cctcttgggg acattaaatt    5820
gagtccggcc atcatccctg atgtaacatc cattccgagt gacttggcat cgctcctagc    5880
ctccgtccct gtagtggaag gcggcctctc gaccgttcaa cttttgtgtg tcttttttcct   5940 tctctggcgc atgatgggcc atgcctggac acccattgtt gccgtgggct tcttttttgct   6000 gaatgaaatt cttccagcag ttttggtccg agccgtgttt tcttttgcac tcttttgtgct   6060 tgcatgggcc acccctggt ctgcacaggt gttgatgatt agactcctca cggcatctct     6120
caaccgcaac aagcttttctc tggcgttcta cgcactcggg ggtgtcgtcg ttttggcagc   6180
tgaaatcggg acttttgctg gcagattgtc tgaattgtct caagctcttt cgacatactg    6240
cttcttacct agggtccttg ctatgaccag ttgtgttccc accatcatca ttggtggact    6300 ccatacccctc ggtgtgattc tgtggttatt caaataccgg tgcctccaca acatgctggt   6360
tggtgatggg agttttttcaa cgccccttctt cctacggtat tttgcagagg gtaatctcag  6420
aaaaggtgtt tcacagtcct gtggcatgaa taacgagtcc ctaacggctg ctttagcttg    6480
caagttgtca caggctgacc ttgattttttt gtccagctta acgaacttca agtgctttgt   6540
atctgcttca aacatgaaaa atgctgccgg ccagtacatt gaagcagcgt atgccaaggc    6600
cctgcgccaa gagttggcct ctctagttca gattgacaaa atgaaaggag ttttgtccaa    6660
gctcgaggcc tttgctgaaa cagccacccc gtcccttgac ataggtgacg tgattgttct    6720
gcttgggcaa catcctcacg gatccatcct cgatattaat gtggggactg aaaggaaaac    6780
tgtgtccgtg caagagaccc ggagcctagg cggctccaaa ttcagtgttt gtactgtcgt    6840
```

```
gtccaacaca cccgtggacg ccttgaccgg catcccactc cagacaccaa cccctctttt   6900
tgagaatggt ccgcgtcatc gcagcgagga agacgatctt aaagtcgaga ggatgaagaa   6960
acactgtgta tccctcggct tccacaacat caatggcaaa gtttactgca aaatttggga   7020
caagtctacc ggtgacacct tttacacgga tgattcccgg tacacccaag accatgcttt   7080
tcaggacagg tcagccgact acagagacag ggactatgag ggtgtgcaaa ccaccccca    7140 acagggattt gatccaaagt ctgaaacccc tgttggcact gttgtgatcg gcggtattac   7200
gtataacagg tatctgatca aaggtaagga ggttctggtc cccaagcctg caactgcct    7260 tgaagctgcc aagctgtccc ttgagcaagc tctcgctggg atgggccaaa cttgcgacct   7320
tacagctgcc gaggtggaaa agctaaagcg catcattagt caactccaag gtttgaccac   7380
tgaacaggct ttaaactgtt agccgccagc ggcttgaccc gctgtggccg cggcggccta   7440
gttgtgactg aaacggcggt aaaaattata aataccaca gcagaacttt caccttaggc    7500
cctttagacc taaagtcac ttccgaggtg gaggtaaaga atcaactga gcagggccac     7560 gctgttgtgg caaacttatg ttccggtgtc atcttgatga gaccctcaccc accgtccctt  7620 gtcgacgttc ttctgaaacc cggacttgac acaatacccg gcattcaacc agggcatggg   7680
gccgggaata tgggcgtgga cggttctatt tgggattttg aaaccgcacc cacaaaggca   7740
gaactcgagt tatccaagca aataatccaa gcatgtgaag ttaggcgcgg ggacgccccg   7800
aacctccaac tcccttacaa gctctatcct gttagggggg atcctgagcg gcataaaggc   7860
cgccttatca ataccaggtt tggagattta ccttacaaaa ctcctcaaga caccaagtcc   7920
gcaatccacg cggcttgttg cctgcacccc aacggggccc ccgtgtctga tggtaaatcc   7980
acactaggta ccactcttca acatggtttc gagctttatg tccctactgt gcctatagt    8040 gtcatggagt accttgattc acgccctgac accccttta tgtgtactaa acatggcact    8100
tccaaggctg ctgcagagga cctccaaaaa tacgacctat ccacccaagg atttgtcctg   8160
cctggggtcc tacgcctagt acgcagattc atctttggcc atattggtaa ggcgccgcca   8220
ttgttcctcc catcaaccta tcccgccaag aactctatgg cagggatcaa tggccagagg   8280
ttcccaacaa aggacgttca gagcatacct gaaattgatg aaatgtgtgc ccgcgctgtc   8340
aaggagaatt ggcaaactgt gacaccttgc accctcaaga aacagtactg ttccaagccc   8400
aaaaccagga ccatcctggg caccaacaac tttattgcct tggctcacag atcggcgctc   8460
agtggtgtca cccaggcatt catgaagaag gcttggaagt ccccaattgc cttggggaaa   8520
aacaaattca aggagctgca ttgcactgtc gccggcaggt gtcttgaggc cgacttggcc   8580
tcctgtgacc gcagcacccc cgccattgta agatggtttg ttgccaacct cctgtatgaa   8640
cttgcaggat gtgaagagta cttgccctagc tatgtgctta attgctgcca tgacctcgtg   8700
gcaacacagg atggtgcctt cacaaaacgc ggtggcctgt cgtccgggga ccccgtcacc   8760
agtgtgtcca acaccgtata ttcactggta atttatgccc agcacatggt attgtcggcc   8820
ttgaaaatgg gtcatgaaat tggtcttaag ttcctcgagg aacagctcaa gttcgaggac   8880
ctccttgaaa ttcagcctat gttggtatac tctgatgatc ttgtcttgta cgctgaaaga   8940
cccacatttc ccaattacca ctggtgggtc gagcaccttg acctgatgct gggtttcaga   9000
acggacccaa agaaaaccgt cataactgat aaacccagct tcctcggctg cagaattgag   9060
gcagggcgac agctagtccc caatcgcgac cgcatcctgg ctgctcttgc atatcacatg   9120
aaggcgcaga acgcctcaga gtattatgcg tctgctgccg caatcctgat ggattcatgt   9180
```

```
gcttgcattg accatgaccc tgagtggtat gaggacctca tctgcggtat tgcccggtgc    9240
gcccgccagg atggttatag cttcccaggt ccggcatttt tcatgtccat gtgggagaag    9300
ctgagaagtc ataatgaagg gaagaaattc cgccactgcg catctgcga cgccaaagcc     9360 gactatgcgt ccgcctgtgg gcttgatttg tgtttgttcc attcgcactt tcatcaacac    9420
tgccctgtca ctctgagctg cggtcaccat gccggttcaa aggaatgttc gcagtgtcag    9480
tcacctgttg gggctggcag atcccctctt gatgccgtgc taaaacaaat tccatacaaa    9540
cctcctcgta ctgtcatcat gaaggtgggt aataaaacaa cggccctcga tccggggagg    9600
taccagtccc gtcgaggtct cgttgcagtc aagaggggta ttgcaggcaa tgaagttgat    9660 cttctgatg gggactacca agtggtgcct cttttgccga cttgcaaaga cataaacatg      9720
gtgaaggtgg cttgcaatgt actactcagc aagttcatag tagggccacc aggttccgga    9780
aagaccacct ggctactgag tcaagtccag gacgatgatg tcatttacac acccacccat    9840
cagactatgt ttgatatagt cagtgctctc aaagtttgca ggtattccat tccaggagcc    9900
tcaggactcc ctttcccacc acctgccagg tccgggccgt gggttaggct tattgccagc    9960
gggcacgtcc ctggccgagt atcatacctc gatgaggctg gatattgtaa tcatctggac    10020
attcttagac tgcttttccaa aacacccctt gtgtgtttgg gtgaccttca gcaacttcac   10080
cctgtcggct ttgattccta ctgttatgtg ttcgatcaga tgcctcagaa gcagctgacc    10140
actatttaca gatttggccc taacatctgc gcacgcatcc agccttgtta cagggagaaa    10200
cttgaatcta aggctaggaa cactagggtg gttttacca cccggcctgt ggcctttggt      10260
caggtgctga caccatacca taaagatcgc atcggctctg cgataaccat agattcatcc    10320 caggggcca cctttgatat tgtgacattg catctaccat cgccaaagtc cctaaataaa      10380
tcccgagcac ttgtagccat cactcgggca agacacgggt tgttcattta tgaccctcat    10440
aaccagctcc aggagttttt caacttaacc cctgagcgca ctgattgtaa ccttgtgttc    10500
agccgtgggg atgagctggt agttctgaat gcggataatg cagtcacaac tgtagcgaag    10560
gcccttgaga caggtccatc tcgatttcga gtatcagacc cgaggtgcaa gtctctctta    10620
gccgcttgtt cggccagtct ggaagggagc tgtatgccac taccgcaagt ggcacataac    10680
ctggggtttt acttttcccc ggacagtcca acatttgcac ctctgccaaa agagttggcg    10740
ccacattggc cagtggttac ccaccagaat aatcgggcgt ggcctgatcg acttgtcgct    10800
agtatgcgcc caattgatgc ccgctacagc aagccaatgg tcggtgcagg gtatgtggtc    10860
agtatgcgcc caattgatgc ccgctacagc aagccaatgg tcggtgcagg gtatgtggtc    10920
aggggtgagc cccaggcctt gccagaaaca ctcgtttcaa cagggcgtat agccacagat    10980
tgtcgggagt atctcgacgc ggctgaggaa gaggcagcaa aagaactccc ccacgcattc    11040
attggcgatg tcaaaggtac cacggttggg gggtgtcatc acattacatc aaaataccta    11100
cctaggtccc tgcctaagga ctctgttgcc gtagttggag taagttcgcc cggcagggct    11160
gctaaagccg tgtgcactct caccgatgtg tacctccccg aactccggcc atatctgcaa    11220
cctgagacgg catcaaaatg ctggaaactc aaattagact tcagggacgt ccgactaatg    11280
gtctggaaag gagccaccgc ctatttccag ttggaagggc ttacatggtc ggcgctgccc    11340
gactatgcca ggtttattca gctgcccaag gatgccgttg tatacattga tccgtgtata    11400
ggaccggcaa cagccaaccg taaggtcgtg cgaaccacag actggcgggc cgacctggca    11460
gtgacaccgt atgattacgg tgcccagaac attttgacaa cagcctggtt cgaggacctc    11520 ggccgcagt ggaagatttt tggggttgcag ccctttaggc gagcatttgg ctttgaaaac    11580
```

```
actgaggatt gggcaatcct tgcacgccgt atgaatgacg gcaaggacta cactgactat    11640
aactggaact gtgttcgaga acgcccacac gccatctacg ggcgtgctcg tgaccatacg    11700
tatcattttg ccccctggcac agaattgcag gtagagctag gtaaaccccg gctgccgcct   11760
gggcaagtgc cgtgaattcg gggtgatgca atggggtcac tgtggagtaa aatcagccag    11820
ctgttcgtgg acgccttcac tgagttcctt gttagtgtgg ttgatattgc cattttccttc   11880
gccatactgt ttgggttcac cgtcgcagga tggttactgg tctttcttct cagagtggtt   11940
tgctccgcgc ttctccgttc gcgctctgcc attcactctc ccgaactatc gaaggtccta   12000
tgaaggcttg ttgcccaact gcagaccgga tgtcccacaa tttgcagtca agcacccatt    12060
gggyatgttt tggcacatgc gagtttccca cttgattgat gagatggtct ctcgtcgcat    12120
ttaccagacc atggaacatt caggtcaagc ggcctggaag caggtggttg gtgaggccac    12180
tctcacgaag ctgtcagggc tcgatatagt tactcatttc caacacctgg ccgcagtgga    12240
ggcggattct tgccgctttc tcagctcacg actcgtgatg ctaaaaaatc ttgccgttgg    12300
caatgtgagc ctacagtaca acaccacgtt ggaccgcgtt gagctcatct tccccacgcc    12360
aggtacgagg cccaagttga ccgatttcag acaatggctc atcagtgtgc acgcttccat    12420
ttttcctct gtggcttcat ctgttacctt gttcatagtg ctttggcttc gaattccagc     12480
tctacgctat gttttggtt tccattggcc cacggcaaca catcattcga gctgaccatc     12540
aactacacca tatgcatgcc ctgttctacc agtcaagcgg ctcgccaaag gctcgagccc    12600
ggtcgtaaca tgtggtgcaa aatagggcat gacaggtgtg aggagcgtga ccatgatgag    12660
ttgttaatgt ccatcccgtc cgggtacgga caactcaaac ttgagggtta ttatgcttgg    12720
ctggcttttt tgtcctttc ctacgcggcc caattccatc cggagttgtt cgggatagggg   12780
aatgtgtcgc gcgtcttcgt ggacaagcga caccagttca tttgtgccga gcatgatgga    12840
cacaattcaa ccgtatctac cggacacaac atctccgcat tatatgcggc atattaccac    12900
caccaaatag acgggggcaa ttggttccat ttggaatggc tgcggccact cttttcttcc    12960
tggctggtgc tcaacatatc atggtttctg aggcgttcgc ctgtaagccc tgtttctcga    13020
cgcatctatc agatattgag accaacacga ccgcggctgc cggtttcatg gtccttcagg    13080
acatcaattg tttccgacct cacggggtct cagcagcgca agagaaaatt ccttcggaa     13140
agtcgtccca atgtcgtgaa gccgtcggta ctccccagta catcacgata acggctaacg    13200
tgaccgacga atcatacttg tacaacgcgg acctgctgat gctttctgcg tgccttttct    13260
acgcctcaga aatgagcgag aaaggcttca agtcatctt tgggaatgtc tctggcgttg     13320
tttctgcttg tgtcaatttc acagattatg tggcccatgt gacccaacat acccagcagc    13380
atcatctggt aattgatcac attcggttgc tgcatttcct gacaccatct gcaatgaggt    13440
gggctacaac cattgcttgt ttgttcgcca ttctcttggc aatatgagat gttctcacaa    13500
attggggcgt tcttgactc cgcactcttg cttctggtgg cttttttttgc tgtgtaccgg    13560
cttgtcctgg tcctttgccg atggcaacgg cgacagctcg atataccaat acatatataa    13620
cttgacgata tgcgagctga atgggaccga ctggttgtcc agccattttg gttgggcagt    13680
cgagaccttt gtgctttacc cggttgccac tcatatcctc tcactgggtt ttctcacaac    13740
aagccatttt tttgacgcgc tcggtctcgg cgctgtatcc actgcaggat tgttggcgg    13800
gcggtacgta ctctgcagcg tctacggcgc ttgtgctttc gcagcgttcg tatgtttttgt   13860
catccgtgct gctaaaaatt gcatggcctg ccgctatgcc cgtacccggt ttaccaactt    13920
```

| | | | | |
|---|---|---|---|---|
| cattgtggac gaccggggga gagttcatcg atggaagtct ccaatagtgg tagaaaaatt | 13980 |
| gggcaaagcc gaagtcgatg gcaacctcgt caccatcaaa catgtcgtcc tcgaaggggt | 14040 |
| taaagctcaa cccttgacga ggacttcggc tgagcaatgg gaggcctaga cgattttttgc | 14100 |
| aacgatccta tcgccgcaca aaagctcgtg ctagccttta gcatcacata cacacctata | 14160 |
| atgatatacg cccttaaggt gtcacgcggc cgactcctgg ggctgttgca catcctaata | 14220 |
| tttctgaact gttcctttac attcggatac atgacatatg tgcattttca atccaccaac | 14280 |
| cgtgtcgcac ttaccctggg ggctgttgtc gcccttctgt ggggtgttta cagcttcaca | 14340 |
| gagtcatgga gtttatcac ttccagatgc agattgtgtt gccttggccg gcgatacatt | 14400 |
| ctggcccctg cccatcacgt agaaagtgct gcaggtctcc attcaatctc agcgtctggt | 14460 |
| aaccgagcat acgctgtgag aaagcccgga ctaacatcag tgaacggcac tctagtacca | 14520 |
| ggacttcgga gcctcgtgct gggcggcaaa cgagctgtta acgaggagt ggttaacctc | 14580 |
| gtcaagtatg gccggtaaaa accagagcca gaagaaaaag aaaagtacag ctccgatggg | 14640 |
| gaatggccag ccagtcaatc aactgtgcca gttgctgggt gcaatgataa agtcccagcg | 14700 |
| ccagcaacct aggggaggac aggccaaaaa gaaaaagcct gagaagccac attttccct | 14760 |
| ggctgctgaa gatgacatcc ggcaccacct cacccagact gaacgctccc tctgcttgca | 14820 |
| atcgatccag acggctttca atcaaggcgc aggaactgcg tcgctttcat ccagcgggaa | 14880 |
| ggtcagtttt caggttgagt ttatgctgcc ggttgctcat acagtgcgcc tgattcgcgt | 14940 |
| gacttctaca tccgccagtc agggtgcaag ttaatttgac agtcaggtga atggccgcga | 15000 |
| tggcgtgtgg cctctgagtc acctattcaa ttagggcgat cacatggggg tcatacttaa | 15060 |
| ttcaggcagg aaccatgtga ccgaaattaa aaaaaaaaaa aaaaaaaa | 15108 |

<210> SEQ ID NO 30
<211> LENGTH: 34864
<212> TYPE: DNA
<213> ORGANISM: Artificial Sequence
<220> FEATURE:
<223> OTHER INFORMATION: pAd/PL-DEST vector; attR1 site: 512-636; attR2 site: 2092-2216
<220> FEATURE:
<221> NAME/KEY: misc_feature
<222> LOCATION: (34060)..(34060)
<223> OTHER INFORMATION: n is a, c, g, or t

<400> SEQUENCE: 30

| | | | | |
|---|---|---|---|---|
| catcatcaat aatataccttt attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt ttccgcgttc | 420 |
| cgggtcaaag ttggcgtttt attattatag tcagtcgaag cttggatccg gtacctctag | 480 |
| aattctcgag cggccgctag cgacatcgat cacaagtttg tacaaaaaag ctgaacgaga | 540 |
| aacgtaaaat gatataaata tcaatatatt aaattagatt ttgcataaaa aacagactac | 600 |
| ataatactgt aaaacacaac atatccagtc actatggcgg ccgcattagg caccccaggc | 660 |
| tttacacttt atgcttccgg ctcgtataat gtgtggattt tgagttagga tccggcgaga | 720 |

```
tttcaggag  ctaaggaagc  taaaatggag  aaaaaaatca  ctggatatac  caccgttgat   780
atatcccaat  ggcatcgtaa  agaacatttt  gaggcatttc  agtcagttgc  tcaatgtacc   840
tataaccaga  ccgttcagct  ggatattacg  gccttttttaa  agaccgtaaa  gaaaaataag   900
cacaagtttt  atccggcctt  tattcacatt  cttgcccgcc  tgatgaatgc  tcatccggaa   960
ttccgtatgg  caatgaaaga  cggtgagctg  gtgatatggg  atagtgttca  cccttgttac  1020
accgttttcc  atgagcaaac  tgaaacgttt  tcatcgctct  ggagtgaata  ccacgacgat  1080
ttccggcagt  ttctacacat  atattcgcaa  gatgtggcgt  gttacggtga  aaacctggcc  1140
tatttcccta  aagggtttat  tgagaatatg  ttttttcgtct  cagccaatcc  ctgggtgagt  1200
ttaccagtt   ttgatttaaa  cgtggccaat  atggacaatt  tcttcgcccc  cgttttcacc  1260
atgggcaaat  attatacgca  aggcgacaag  gtgctgatgc  cgctggcgat  tcaggttcat  1320
catgccgtct  gtgatggctt  ccatgtcggc  agaatgctta  atgaattaca  acagtactgc  1380
gatgagtggc  agggcgggc   gtaaacgcgt  ggatccggct  tactaaaaac  cagataacag  1440
tatgcgtatt  tgcgcgctga  tttttgcggt  ataagaatat  atactgatat  gtatacccga  1500
agtatgtcaa  aaagaggtgt  gctatgaagc  agcgtattac  agtgacagtt  gacagcgaca  1560
gctatcagtt  gctcaaggca  tatatgatgt  caatatctcc  ggtctggtaa  gcacaaccat  1620
gcagaatgaa  gcccgtcgtc  tgcgtgccga  acgctggaaa  gcggaaaatc  aggaagggat  1680
ggctgaggtc  gcccggttta  ttgaaatgaa  cggctcttttt  gctgacgaga  cagggggctg  1740
gtgaaatgca  gtttaaggtt  tacacctata  aaagagagag  ccgttatcgt  ctgtttgtgg  1800
atgtacagag  tgatattatt  gacacgcccg  ggcgacggat  ggtgatcccc  ctggccagtg  1860
cacgtctgct  gtcagataaa  gtctcccgtg  aactttaccc  ggtggtgcat  atcgggggatg  1920
aaagctggcg  catgatgacc  accgatatgg  ccagtgtgcc  ggtctccgtt  atcggggaag  1980
aagtggctga  tctcagccac  cgcgaaaatg  acatcaaaaa  cgccattaac  ctgatgttct  2040
ggggaatata  aatgtcaggc  tcccttatac  acagccagtc  tgcaggtcga  ccatagtgac  2100
tggatatgtt  gtgttttaca  gtattatgta  gtctgttttt  tatgcaaaat  ctaatttaat  2160
atattgatat  ttatatcatt  ttacgtttct  cgttcagctt  tcttgtacaa  agtggtgatc  2220
gattcgacag  atcactgaaa  tgtgtgggcg  tggcttaagg  gtgggaaaga  atatataagg  2280
tggggggtctt  atgtagtttt  gtatctgttt  tgcagcagcc  gccgccgcca  tgagcaccaa  2340
ctcgtttgat  ggaagcattg  tgagctcata  tttgacaacg  cgcatgcccc  catgggccgg  2400
ggtgcgtcag  aatgtgatgg  gctccagcat  tgatggtcgc  cccgtcctgc  cgcaaaactc  2460
tactaccttg  acctacgaga  ccgtgtctgg  aacgccgttg  gagactgcag  cctccgccgc  2520
cgcttcagcc  gctgcagcca  ccgcccgcgg  gattgtgact  gactttgctt  tcctgagccc  2580
gcttgcaagc  agtgcagctt  cccgttcatc  cgcccgcgat  gacaagttga  cggctctttt  2640
ggcacaattg  gattctttga  cccgggaact  taatgtcgtt  tctcagcagc  tgttggatct  2700
gcgccagcag  gtttctgccc  tgaaggcttc  ctcccctccc  aatgcggttt  aaaacataaa  2760
taaaaaacca  gactctgttt  ggatttggat  caagcaagtg  tcttgctgtc  tttatttagg  2820
ggttttgcgc  gcgcggtagg  cccgggacca  gcggtctcgg  tcgttgaggg  tcctgtgtat  2880
tttttccagg  acgtggtaaa  ggtgactctg  gatgttcaga  tacatgggca  taagcccgtc  2940
tctggggtgg  aggtagcacc  actgcagagc  ttcatgctgc  ggggtggtgt  tgtagatgat  3000
ccagtcgtag  caggagcgct  gggcgtgtg   cctaaaaatg  tctttcagta  gcaagctgat  3060
tgccaggggc  aggcccttgg  tgtaagtgtt  tacaaagcgg  ttaagctggg  atgggtgcat  3120
```

```
acgtggggat atgagatgca tcttggactg tattttagg ttggctatgt tcccagccat    3180
atccctccgg ggattcatgt tgtgcagaac caccagcaca gtgtatccgg tgcacttggg    3240
aaatttgtca tgtagcttag aaggaaatgc gtggaagaac ttggagacgc ccttgtgacc    3300
tccaagattt tccatgcatt cgtccataat gatggcaatg ggcccacggg cggcggcctg    3360
ggcgaagata tttctgggat cactaacgtc atagttgtgt tccaggatga gatcgtcata    3420
ggccatttt acaaagcgcg ggcggagggt gccagactgc ggtataatgg ttccatccgg    3480
cccaggggcg tagttaccct cacagatttg catttcccac gctttgagtt cagatggggg    3540
gatcatgtct acctgcgggg cgatgaagaa aacggtttcc ggggtagggg agatcagctg    3600
ggaagaaagc aggttcctga gcagctgcga cttaccgcag ccggtgggcc cgtaaatcac    3660
acctattacc gggtgcaact ggtagttaag agagctgcag ctgccgtcat ccctgagcag    3720
gggggccact tcgttaagca tgtccctgac tcgcatgttt tccctgacca aatccgccag    3780
aaggcgctcg ccgcccagcg atagcagttc ttgcaaggaa gcaaagtttt tcaacggttt    3840
gagaccgtcc gccgtaggca tgcttttgag cgtttgacca agcagttcca ggcggtccca    3900
cagctcggtc acctgctcta cggcatctcg atccagcata tctcctcgtt tcgcggggttg   3960
gggcggcttt cgctgtacgg cagtagtcgg tgctcgtcca gacgggccag ggtcatgtct    4020
ttccacgggc gcagggtcct cgtcagcgta gtctgggtca cggtgaaggg gtgcgctccg    4080
ggctgcgcgc tggccagggt gcgcttgagg ctggtcctgc tggtgctgaa gcgctgccgg    4140
tcttcgccct gcgcgtcggc caggtagcat ttgaccatgg tgtcatagtc cagcccctcc    4200
gcggcgtggc ccttggcgcg cagcttgccc ttggaggagg cgccgcacga ggggcagtgc    4260
agacttttga gggcgtagag cttgggcgcg agaaataccg attccgggga gtaggcatcc    4320
gcgccgcagg ccccgcagac ggtctcgcat tcccgagccc aggtgagctc tggccgttcg    4380
gggtcaaaaa ccaggtttcc cccatgcttt ttgatgcgtt tcttacctct ggtttccatg    4440
agccggtgtc cacgctcggt gacgaaaagg ctgtccgtgt ccccgtatac agacttgaga    4500
ggcctgtcct cgagcggtgt tccgcggtcc tcctcgtata gaaactcgga ccactctgag    4560
acaaaggctc gcgtccaggc cagcacgaag gaggctaagt gggaggggta gcggtcgttg    4620
tccactaggg ggtccactcg ctccagggtg tgaagacaca tgtcgccctc ttcggcatca    4680
aggaaggtga ttggtttgta ggtgtaggcc acgtgaccgg tgttcctga aggggggcta    4740
taaaaggggg tgggggcgcg ttcgtcctca ctctcttccg catcgctgtc tgcgagggcc    4800
agctgttggg gtgagtactc cctctgaaaa gcgggcatga cttctgcgct aagattgtca    4860
gtttccaaaa acgaggagga tttgatattc acctggcccg cggtgatgcc tttgagggtg    4920
gccgcatcca tctggtcaga aaagacaatc ttttgttgt caagcttggt ggcaaacgac    4980
ccgtagaggg cgttggacag caacttggcg atggagcgca gggtttggtt tttgtcgcga    5040
tcggcgcgct ccttggccgc gatgtttagc tgcacgtatt cgcgcgcaac gcaccgccat    5100
tcgggaaaga cggtggtgcg ctcgtcgggc accaggtgca cgcgccaacc gcggttgtgc    5160
agggtgacaa ggtcaacgct ggtggctacc tctccgcgta ggcgctcgtt ggtccagcag    5220
aggcggccgc ccttgcgcga gcagaatggc ggtagggggt ctagctgcgt ctcgtccggg    5280
gggtctgcgt ccacggtaaa gaccccgggc agcaggcgcg cgtcgaagta gtctatcttg    5340
catccttgca agtctagcgc ctgctgccat gcgcgggcgg caagcgcgcg ctcgtatggg    5400
ttgagtgggg gaccccatgg catggggtgg gtgagcgcgg aggcgtacat gccgcaaatg    5460
```

```
tcgtaaacgt agaggggctc tctgagtatt ccaagatatg tagggtagca tcttccaccg   5520
cggatgctgg cgcgcacgta atcgtatagt tcgtgcgagg gagcgaggag gtcgggaccg   5580
aggttgctac gggcgggctg ctctgctcgg aagactatct gcctgaagat ggcatgtgag   5640
ttggatgata tggttggacg ctggaagacg ttgaagctgg cgtctgtgag acctaccgcg   5700
tcacgcacga aggaggcgta ggagtcgcgc agcttgttga ccagctcggc ggtgacctgc   5760
acgtctaggg cgcagtagtc cagggtttcc ttgatgatgt catacttatc ctgtcccttt   5820
tttttccaca gctcgcggtt gaggacaaac tcttcgcggt ctttccagta ctcttggatc   5880
ggaaacccgt cggcctccga acggtaagag cctagcatgt agaactggtt gacggcctgg   5940
taggcgcagc atccctttc tacgggtagc gcgtatgcct gcgcggcctt ccggagcgag    6000
gtgtgggtga gcgcaaaggt gtccctgacc atgactttga ggtactggta tttgaagtca   6060
gtgtcgtcgc atccgccctg ctcccagagc aaaaagtccg tgcgcttttt ggaacgcgga   6120
tttggcaggg cgaaggtgac atcgttgaag agtatctttc ccgcgcgagg cataaagttg   6180
cgtgtgatgc ggaagggtcc cggcacctcg gaacggttgt taattacctg ggcggcgagc   6240
acgatctcgt caaagccgtt gatgttgtgg cccacaatgt aaagttccaa gaagcgcggg   6300
atgcccttga tggaaggcaa ttttttaagt tcctcgtagg tgagctcttc aggggagctg   6360
agcccgtgct ctgaaagggc ccagtctgca agatgagggt tggaagcgac gaatgagctc   6420
cacaggtcac gggccattag catttgcagg tggtcgcgaa aggtcctaaa ctggcgacct   6480
atggccattt tttctggggt gatgcagtag aaggtaagcg ggtcttgttc ccagcggtcc   6540
catccaaggt tcgcggctag gtctcgcgcg gcagtcacta gaggctcatc tccgccgaac   6600
ttcatgacca gcatgaaggg cacgagctgc ttcccaaagg cccccatcca agtataggtc   6660
tctacatcgt aggtgacaaa gagacgctcg gtgcgaggat gcgagccgat cgggaagaac   6720
tggatctccc gccaccaatt ggaggagtgg ctattgatgt ggtgaaagta aagtccctg    6780
cgacgggccg aacactcgtg ctggcttttg taaaaacgtg cgcagtactg gcagcggtgc   6840
acgggctgta catcctgcac gaggttgacc tgacgaccgc gcacaaggaa gcagagtggg   6900
aatttgagcc cctcgcctgg cgggtttggc tggtggtctt ctacttcggc tgcttgtcct   6960
tgaccgtctg gctgctcgag gggagttacg gtggatcgga ccaccacgcc gcgcgagccc   7020
aaagtccaga tgtccgcgcg cggcggtcgg agcttgatga caacatcgcg cagatgggag   7080
ctgtccatgg tctggagctc ccgcggcgtc aggtcaggcg ggagctcctg caggtttacc   7140
tcgcatagac gggtcagggc gcgggctaga tccaggtgat acctaatttc caggggctgg   7200
ttggtggcgg cgtcgatggc ttgcaagagg ccgcatcccc gcggcgcgac tacggtaccg   7260
cgcggcgggc ggtgggccgc gggggtgtcc ttggatgatg catctaaaag cggtgacgcg   7320
ggcgagcccc cggaggtagg gggggctccg gacccgccgg gagaggggc  aggggcacgt   7380
cggcgccgcg cgcgggcagg agctggtgct gcgcgcgtag gttgctggcg aacgcgacga   7440
cgcggcggtt gatctcctga atctggcgcc tctgcgtgaa gacgacgggc ccggtgagct   7500
tgagcctgaa agagagttcg acagaatcaa tttcggtgtc gttgacggcg gcctggcgca   7560
aaatctcctg cacgtctcct gagttgtctt gataggcgat ctcggccatg aactgctcga   7620
tctcttcctc ctggagatct ccgcgtccgg ctcgctccac ggtggcggcg aggtcgttgg   7680
aaatgcgggc catgagctgc gagaaggcgt tgaggcctcc ctcgttccag acgcggctgt   7740
agaccacgcc cccttcggca tcgcgggcgc gcatgaccac ctgcgcgaga ttgagctcca   7800
cgtgccgggc gaagacggcg tagtttcgca ggcgctgaaa gaggtagttg agggtggtgg   7860
```

```
cggtgtgttc tgccacgaag aagtacataa cccagcgtcg caacgtggat tcgttgatat    7920 ccccccaaggc ctcaaggcgc tccatggcct cgtagaagtc cacggcgaag ttgaaaaact   7980
gggagttgcg cgccgacacg gttaactcct cctccagaag acggatgagc tcggcgacag    8040
tgtcgcgcac ctcgcgctca aaggctacag gggcctcttc ttcttcttca atctcctctt    8100
ccataagggc ctccccttct tcttcttctg gcggcggtgg gggagggggg acacggcggc    8160
gacgacggcg caccgggagg cggtcgacaa agcgctcgat catctcccg cggcgacggc     8220 gcatggtctc ggtgacggcg cggccgttct cgcgggggcg cagttggaag acgccgcccg    8280
tcatgtcccg gttatgggtt ggcgggggc tgccatgcgg cagggatacg gcgctaacga     8340
tgcatctcaa caattgttgt gtaggtactc cgccgccgag ggacctgagc gagtccgcat    8400
cgaccggatc ggaaaacctc tcgagaaagg cgtctaacca gtcacagtcg caaggtaggc    8460
tgagcaccgt ggcgggcggc agcgggcggc ggtcggggtt gtttctggcg gaggtgctgc    8520
tgatgatgta attaaagtag gcggtcttga gacggcggat ggtcgacaga agcaccatgt    8580
ccttgggtcc ggcctgctga atgcgcaggc ggtcggccat gccccaggct tcgttttgac    8640
atcggcgcag gtcttttgtag tagtcttgca tgagcctttc taccggcact tcttcttctc    8700
cttcctcttg tcctgcatct cttgcatcta tcgctgcggc ggcggcggag tttggccgta    8760 ggtgcgccc tcttcctccc atgcgtgtga ccccgaagcc cctcatcggc tgaagcaggg     8820
ctaggtcggc gacaacgcgc tcggctaata tggcctgctg cacctgcgtg agggtagact    8880
ggaagtcatc catgtccaca aagcggtggt atgcgcccgt gttgatggtg taagtgcagt    8940
tggccataac ggaccagtta acggtctggt gacccggctg cgagagctcg gtgtacctga    9000
gacgcgagta agccctcgag tcaaatacgt agtcgttgca agtccgcacc aggtactggt    9060
atcccaccaa aaagtgcggc ggcggctggc ggtagagggg ccagcgtagg gtggccgggg    9120
ctccgggggc gagatcttcc aacataaggc gatgatatcc gtagatgtac ctggacatcc    9180
aggtgatgcc ggcggcggtg gtggaggcgc gcggaaagtc gcggacgcgg ttccagatgt    9240
tgcgcagcgg caaaaagtgc tccatggtcg ggacgctctg gccggtcagg cgcgcgcaat    9300
cgttgacgct ctagaccgtg caaaaggaga gcctgtaagc gggcactctt ccgtggtctg    9360
gtggataaat tcgcaagggt atcatggcgg acgaccgggg ttcgagcccc gtatccggcc    9420
gtccgccgtg atccatgcgg ttaccgcccg cgtgtcgaac ccaggtgtgc gacgtcagac    9480
aacgggggag tgctccttttt ggcttccttc caggcgcggc ggctgctgcg ctagcttttt   9540
tggccactgg ccgcgcgcag cgtaagcggt taggctggaa agcgaaagca ttaagtggct    9600
cgctccctgt agccggaggg ttattttcca agggttgagt cgcgggaccc ccggttcgag    9660
tctcggaccg gccggactgc ggcgaacggg ggtttgcctc cccgtcatgc aagacccccgc   9720 ttgcaaattc ctccggaaac agggacgagc cccttttttg cttttcccag atgcatccgg    9780
tgctgcggca gatgcgcccc cctcctcagc agcggcaaga gcaagagcag cggcagacat    9840
gcagggcacc ctcccctcct cctaccgcgt caggagggc gacatccgcg gttgacgcgg     9900
cagcagatgg tgattacgaa cccccgcggc gccgggcccg gcactacctg gacttggagg    9960
agggcgaggg cctggcgcgg ctaggagcgc cctctcctga gcgtaccca agggtgcagc     10020 tgaagcgtga tacgcgtgag gcgtacgtgc cgcggcagaa cctgtttcgc gaccgcgagg    10080
gagaggagcc cgaggagatg cgggatcgaa agttccacgc agggcgcgag ctgcggcatg    10140
gcctgaatcg cgagcggttg ctgcgcgagg aggactttga gcccgacgcg cgaaccggga    10200
```

| | |
|---|---|
| ttagtcccgc gcgcgcacac gtggcggccg ccgacctggt aaccgcatac gagcagacgg | 10260 |
| tgaaccagga gattaacttt caaaaaagct ttaacaacca cgtgcgtacg cttgtggcgc | 10320 |
| gcgaggaggt ggctatagga ctgatgcatc tgtgggactt tgtaagcgcg ctggagcaaa | 10380 |
| acccaaatag caagccgctc atggcgcagc tgttccttat agtgcagcac agcagggaca | 10440 |
| acgaggcatt cagggatgcg ctgctaaaca tagtagagcc cgagggccgc tggctgctcg | 10500 |
| atttgataaa catcctgcag agcatagtgg tgcaggagcg cagcttgagc ctggctgaca | 10560 |
| aggtggccgc catcaactat tccatgctta gcctgggcaa gttttacgcc cgcaagatat | 10620 |
| accatacccc ttacgttccc atagacaagg aggtaaagat cgaggggttc tacatgcgca | 10680 |
| tggcgctgaa ggtgcttacc ttgagcgacg acctgggcgt ttatcgcaac gagcgcatcc | 10740 |
| acaaggccgt gagcgtgagc cggcggcgcg agctcagcga ccgcgagctg atgcacagcc | 10800 |
| tgcaaagggc cctggctggc acgggcagcg gcgatagaga ggccgagtcc tactttgacg | 10860 |
| cgggcgctga cctgcgctgg gccccaagcc gacgcgccct ggaggcagct ggggccggac | 10920 |
| ctgggctggc ggtggcaccc gcgcgcgctg gcaacgtcgg cggcgtggag gaatatgacg | 10980 |
| aggacgatga gtacgagcca gaggacggcg agtactaagc ggtgatgttt ctgatcagat | 11040 |
| gatgcaagac gcaacggacc cggcggtgcg ggcggcgctg cagagccagc cgtccggcct | 11100 |
| taactccacg gacgactggc gccaggtcat ggaccgcatc atgtcgctga ctgcgcgcaa | 11160 |
| tcctgacgcg ttccggcagc agccgcaggc caaccggctc tccgcaattc tggaagcggt | 11220 |
| ggtcccggcg cgcgcaaacc ccacgcacga aaggtgctg gcgatcgtaa acgcgctggc | 11280 |
| cgaaaacagg gccatccggc ccgacgaggc cggcctggtc tacgacgcgc tgcttcagcg | 11340 |
| cgtggctcgt tacaacagcg gcaacgtgca gaccaacctg gaccggctgg tgggggatgt | 11400 |
| gcgcgaggcc gtgcgcagc gtgagcgcgc gcagcagcag ggcaacctgg gctccatggt | 11460 |
| tgcactaaac gccttcctga gtacacagcc cgccaacgtg ccgcggggac aggaggacta | 11520 |
| caccaacttt gtgagcgcac tgcggctaat ggtgactgag acaccgcaaa gtgaggtgta | 11580 |
| ccagtctggg ccagactatt ttttccagac cagtagacaa ggcctgcaga ccgtaaacct | 11640 |
| gagccaggct ttcaaaaact tgcaggggct gtgggggtg cgggctccca caggcgaccg | 11700 |
| cgcgaccgtg tctagcttgc tgacgcccaa ctcgcgcctg ttgctgctgc taatagcgcc | 11760 |
| cttcacggac agtggcagcg tgtcccggga cacatacctg ggtcacttgc tgacactgta | 11820 |
| ccgcgaggcc ataggtcagg cgcatgtgga cgagcatact ttccaggaga ttacaagtgt | 11880 |
| cagccgcgcg ctggggcagg aggacacggg cagcctggag gcaaccctaa actacctgct | 11940 |
| gaccaaccgg cggcagaaga tcccctcgtt gcacagttta aacagcgagg aggagcgcat | 12000 |
| tttgcgctac gtgcagcaga gcgtgagcct taacctgatg cgcgacgggg taacgcccag | 12060 |
| cgtggcgctg gacatgaccg cgcgcaacat ggaaccgggc atgtatgcct caaaccggcc | 12120 |
| gtttatcaac cgcctaatgg actacttgca tcgcgcggcc gccgtgaacc ccgagtattt | 12180 |
| caccaatgcc atcttgaacc cgcactggct accgccccct ggtttctaca ccgggggatt | 12240 |
| cgaggtgccc gagggtaacg atggattcct ctgggacgac atagacgaca cgtgttttc | 12300 |
| cccgcaaccg cagaccctgc tagagttgca acagcgcgag caggcagagg cggcgctgcg | 12360 |
| aaaggaaagc ttccgcaggc caagcagctt gtccgatcta ggcgctgcgg cccgcggtc | 12420 |
| agatgctagt agcccatttc caagcttgat agggtctctt accagcactc gcaccacccg | 12480 |
| cccgcgcctc ctgggcgagg aggagtacct aaacaactcg ctgctgcagc cgcagcgcga | 12540 |
| aaaaaacctg cctccggcat ttcccaacaa cgggatagag agcctagtgg acaagatgag | 12600 |

```
tagatggaag acgtacgcgc aggagcacag ggacgtgcca ggcccgcgcc cgcccacccg   12660
tcgtcaaagg cacgaccgtc agcggggtct ggtgtgggag gacgatgact cggcagacga   12720
cagcagcgtc ctggatttgg gagggagtgg caacccgttt gcgcaccttc gccccaggct   12780
ggggagaatg tttaaaaaa aaaaaagcat gatgcaaaat aaaaaactca ccaaggccat   12840
ggcaccgagc gttggttttc ttgtattccc cttagtatgc ggcgcgcggc gatgtatgag   12900
gaaggtcctc ctccctccta cgagagtgtg gtgagcgcgg cgccagtggc ggcggcgctg   12960
ggttctccct tcgatgctcc cctggacccg ccgtttgtgc ctccgcggta cctgcggcct   13020
accgggggga gaaacagcat ccgttactct gagttggcac ccctattcga caccacccgt   13080
gtgtacctgg tggacaacaa gtcaacggat gtggcatccc tgaactacca gaacgaccac   13140
agcaactttc tgaccacggt cattcaaaac aatgactaca gcccggggga ggcaagcaca   13200
cagaccatca atcttgacga ccggtcgcac tggggcggcg acctgaaaac catcctgcat   13260
accaacatgc caaatgtgaa cgagttcatg tttaccaata agtttaaggc gcgggtgatg   13320
gtgtcgcgct tgcctactaa ggacaatcag gtggagctga atacgagtg ggtggagttc   13380 acgctgcccg agggcaacta ctccgagacc atgaccatag accttatgaa caacgcgatc   13440
gtggagcact acttgaaagt gggcagacag aacggggttc tggaaagcga catcggggta   13500
aagtttgaca cccgcaactt cagactgggg tttgaccccg tcactggtct tgtcatgcct   13560
ggggtatata caaacgaagc cttccatcca gacatcattt tgctgccagg atgcggggtg   13620
gacttcaccc cagccgcct gagcaacttg ttgggcatcc gcaagcggca acccttccag   13680 gagggctttta ggatcaccta cgatgatctg gagggtggta acattcccgc actgttggat   13740
gtggacgcct accaggcgag cttgaaagat gacaccgaac agggcgggg tggcgcaggc   13800 ggcagcaaca gcagtggcag cggcgcggaa gagaactcca acgcggcagc cgcggcaatg   13860
cagccggtgg aggacatgaa cgatcatgcc attcgcggcg acaccttttgc cacacgggct   13920 gaggagaagc gcgctgaggc cgaagcagcg gccgaagctg ccgcccccgc tgcgcaaccc   13980
gaggtcgaga agcctcagaa gaaaccggtg atcaaacccc tgacagagga cagcaagaaa   14040
cgcagttaca acctaataag caatgacagc accttcaccc agtaccgcag ctggtaccct   14100
gcatacaact acggcgaccc tcagaccgga atccgctcat ggaccctgct ttgcactcct   14160
gacgtaacct gcggctcgga gcaggtctac tggtcgttgc cagacatgat gcaagacccc   14220
gtgaccttcc gctccacgcg ccagatcagc aactttccgg tggtgggcgc cgagctgttg   14280
cccgtgcact ccaagagctt ctacaacgac caggccgtct actcccaact catccgccag   14340
tttacctctc tgacccacgt gttcaatcgc tttcccgaga accagatttt ggcgcgcccg   14400
ccagccccca ccatcaccac cgtcagtgaa aacgttcctg ctctcacaga tcacgggacg   14460
ctaccgctgc gcaacagcat cggaggagtc cagcgagtga ccattactga cgccagacgc   14520
cgcacctgcc cctacgttta caaggccctg ggcatagtct cgccgcgcgt cctatcgagc   14580 cgcactttt gagcaagcat gtccatcctt atatcgccca gcaataacac aggctggggc   14640
ctgcgcttcc caagcaagat gtttggcggg gccaagaagc gctccgacca acacccagtg   14700
cgcgtgcgcg ggcactaccg cgcgccctgg ggcgcgcaca aacgcggccg cactgggcgc   14760
accaccgtcg atgacgccat cgacgcggtg gtggaggagg cgcgcaacta cacgcccacg   14820
ccgccaccag tgtccacagt ggacgcggcc attcagaccg tggtgcgcgg agcccggcgc   14880
tatgctaaaa tgaagagacg gcggaggcgc gtagcacgtc gccaccgccg ccgacccggc   14940
```

```
actgccgccc aacgcgcggc ggcggccctg cttaaccgcg cacgtcgcac cggccgacgg    15000
gcggccatgc gggccgctcg aaggctggcc gcgggtattg tcactgtgcc ccccaggtcc    15060
aggcgacgag cggccgccgc agcagccgcg gccattagtg ctatgactca gggtcgcagg    15120
ggcaacgtgt attgggtgcg cgactcggtt agcggcctgc gcgtgcccgt gcgcacccgc    15180
cccccgcgca actagattgc aagaaaaaac tacttagact cgtactgttg tatgtatcca    15240
gcggcggcgg cgcgcaacga agctatgtcc aagcgcaaaa tcaaagaaga gatgctccag    15300
gtcatcgcgc cggagatcta tggccccccg aagaaggaag agcaggatta caagcccccga   15360 aagctaaagc gggtcaaaaa gaaaagaaa gatgatgatg atgaacttga cgacgaggtg     15420
gaactgctgc acgctaccgc gcccaggcga cgggtacagt ggaaaggtcg acgcgtaaaa    15480
cgtgttttgc gacccggcac caccgtagtc tttacgcccg tgagcgctc cacccgcacc    15540 tacaagcgcg tgtatgatga ggtgtacggc gacgaggacc tgcttgagca ggccaacgag    15600
cgcctcgggg agtttgccta cggaaagcgg cataaggaca tgctggcgtt gccgctggac    15660
gagggcaacc caacacctag cctaaagccc gtaacactgc agcaggtgct gcccgcgctt    15720
gcaccgtccg aagaaaagcg cggcctaaag cgcgagtctg gtgacttggc acccaccgtg    15780
cagctgatgg tacccaagcg ccagcgactg gaagatgtct tggaaaaaat gaccgtggaa    15840
cctgggctgg agcccgaggt ccgcgtgcgg ccaatcaagc aggtggcgcc gggactgggc    15900
gtgcagaccg tggacgttca gatacccact accagtagca ccagtattgc caccgccaca    15960
gagggcatgg agacacaaac gtccccggtt gcctcagcgg tggcggatgc cgcggtgcag    16020
gcggtcgctg cggccgcgtc caagacctct acggaggtgc aaacggaccc gtggatgttt    16080
cgcgtttcag ccccccggcg cccgcgcggt tcgaggaagt acggcgccgc cagcgcgcta    16140
ctgcccgaat atgccctaca tccttccatt gcgcctaccc ccggctatcg tggctacacc    16200
taccgcccca gaagacgagc aactacccga cgccgaacca ccactggaac ccgccgccgc    16260
cgtcgccgtc gccagcccgt gctggcccccg atttccgtgc gcagggtggc tcgcgaagga    16320
ggcaggaccc tggtgctgcc aacagcgcgc taccaccccca gcatcgttta aaagccggtc    16380
tttgtggttc ttgcagatat ggccctcacc tgccgcctcc gtttcccggt gccgggattc    16440
cgaggaagaa tgcaccgtag gaggggcatg gccggccacg gcctgacggg cggcatgcgt    16500
cgtgcgcacc accggcggcg gcgcgcgtcg caccgtcgca tgcgcggcgg tatcctgccc    16560
ctccttattc cactgatcgc cgcggcgatt ggcgccgtgc ccggaattgc atccgtggcc    16620
ttgcaggcgc agagacactg attaaaaaca agttgcatgt ggaaaaatca aaataaaaag    16680
tctggactct cacgctcgct tggtcctgta actattttgt agaatggaag acatcaactt    16740
tgcgtctctg gccccgcgac acggctcgcg cccgttcatg ggaaactggc aagatatcgg    16800
caccagcaat atgagcggtg gcgccttcag ctggggctcg ctgtggagcg gcattaaaaa    16860
tttcggttcc accgttaaga actatggcag caaggcctgg aacagcagca caggccagat    16920
gctgagggat aagttgaaag agcaaaattt ccaacaaaag gtggtagatg gcctggcctc    16980
tggcattagc ggggtggtgg acctggccaa ccaggcagtg caaaataaga ttaacagtaa    17040
gcttgatccc cgccctcccg tagaggagcc tccaccggcc gtggagacag tgtctccaga    17100
ggggcgtggc gaaaagcgtc cgcgccccga cagggaagaa actctggtga cgcaaataga    17160
cgagcctccc tcgtacgagg aggcactaaa gcaaggcctg cccaccaccc gtcccatcgc    17220
gcccatggct accggagtgc tgggccagca cacacccgta acgctggacc tgcctcccccc   17280 cgccgacacc cagcagaaac ctgtgctgcc aggcccgacc gccgttgttg taacccgtcc    17340
```

```
tagccgcgcg tccctgcgcc gcgccgccag cggtccgcga tcgttgcggc ccgtagccag   17400
tggcaactgg caaagcacac tgaacagcat cgtgggtctg ggggtgcaat ccctgaagcg   17460
ccgacgatgc ttctgaatag ctaacgtgtc gtatgtgtgt catgtatgcg tccatgtcgc   17520
cgccagagga gctgctgagc cgccgcgcgc ccgctttcca agatggctac cccttcgatg   17580
atgccgcagt ggtcttacat gcacatctcg ggccaggacg cctcggagta cctgagcccc   17640
gggctggtgc agtttgcccg cgccaccgag acgtacttca gcctgaataa caagtttaga   17700
aaccccacgg tggcgcctac gcacgacgtg accacagacc ggtcccagcg tttgacgctg   17760
cggttcatcc ctgtggaccg tgaggatact gcgtactcgt acaaggcgcg gttcacccta   17820
gctgtgggtg ataaccgtgt gctggacatg gcttccacgt actttgacat ccgcggcgtg   17880
ctggacaggg gccctacttt taagcccctac tctggcactg cctacaacgc cctggctccc   17940
aagggtgccc caaatccttg cgaatgggat gaagctgcta ctgctcttga aataaaccta   18000
gaagaagagg acgatgacaa cgaagacgaa gtagacgagc aagctgagca gcaaaaaact   18060
cacgtatttg ggcaggcgcc ttattctggt ataaatatta caaggagggg tattcaaata   18120
ggtgtcgaag gtcaaacacc taaatatgcc gataaaacat ttcaacctga acctcaaata   18180
ggagaatctc agtggtacga aactgaaatt aatcatgcag ctgggagagt ccttaaaaag   18240
actaccccaa tgaaaccatg ttacggttca tatgcaaaac ccacaaatga aaatggaggg   18300
caaggcattc ttgtaaagca acaaaatgga aagctagaaa gtcaagtgga aatgcaattt   18360
ttctcaacta ctgaggcgac cgcaggcaat ggtgataact tgactcctaa agtggtattg   18420
tacagtgaag atgtagatat agaaacccca gacactcata tttcttacat gcccactatt   18480
aaggaaggta actcacgaga actaatgggc caacaatcta tgcccaacag gcctaattac   18540
attgctttta gggacaattt tattggtcta atgtattaca acagcacggg taatatgggt   18600
gttctggcgg gccaagcatc gcagttgaat gctgttgtag atttgcaaga cagaaacaca   18660
gagctttcat accagctttt gcttgattcc attggtgata gaaccaggta ctttctatg   18720 tggaatcagg ctgttgacag ctatgatcca gatgttagaa ttattgaaaa tcatggaact   18780
gaagatgaac ttccaaatta ctgctttcca ctggaggtg tgattaatac agagactctt   18840
accaaggtaa aacctaaaac aggtcaggaa aatggatggg aaaaagatgc tacagaattt   18900
tcagataaaa atgaaataag agttggaaat aattttgcca tggaaatcaa tctaaatgcc   18960
aacctgtgga gaaatttcct gtactccaac atagcgctgt atttgcccga caagctaaag   19020
tacagtcctt ccaacgtaaa aatttctgat aacccaaaca cctacgacta catgaacaag   19080
cgagtggtgg ctcccgggtt agtggactgc tacattaacc ttggagcacg ctggtcccctt   19140 gactatatgg acaacgtcaa cccatttaac caccaccgca atgctggcct gctctaccgc   19200
tcaatgttgc tgggcaatgg tcgctatgtg cccttccaca tccaggtgcc tcagaagttc   19260
tttgccatta aaaacctcct tctcctgccg ggctcataca cctacgagtg aacttcagg   19320 aaggatgtta acatggttct gcagagctcc ctaggaaatg acctaagggt tgacggagcc   19380
agcattaagt ttgatagcat ttgcctttac gccaccttct tccccatggc ccacaacacc   19440
gcctccacgc ttgaggccat gcttagaaac gacaccaacg accagtcctt taacgactat   19500
ctctccgccg ccaacatgct ctaccctata cccgccaacg ctaccaacgt gcccatatcc   19560
atcccctccc gcaactgggc ggctttccgc ggctgggcct tcacgcgcct taagactaag   19620 gaaacccat cactgggctc gggctacgac ccttattaca cctactctgg ctctataccc   19680
```

```
tacctagatg gaacctttta cctcaaccac acctttaaga aggtggccat tacctttgac    19740
tcttctgtca gctggcctgg caatgaccgc ctgcttaccc ccaacgagtt tgaaattaag    19800
cgctcagttg acggggaggg ttacaacgtt gcccagtgta acatgaccaa agactggttc    19860
ctggtacaaa tgctagctaa ctacaacatt ggctaccagg gcttctatat cccagagagc    19920
tacaaggacc gcatgtactc cttctttaga aacttccagc ccatgagccg tcaggtggtg    19980
gatgatacta aatacaagga ctaccaacag gtgggcatcc tacaccaaca caacaactct    20040
ggatttgttg gctaccttgc ccccaccatg cgcgaaggac aggcctaccc tgctaacttc    20100
ccctatccgc ttataggcaa gaccgcagtt gacagcatta cccagaaaaa gtttcttttgc   20160
gatcgcaccc tttggcgcat cccattctcc agtaacttta tgtccatggg cgcactcaca    20220
gacctgggcc aaaaccttct ctacgccaac tccgcccacg cgctagacat gacttttgag    20280
gtggatccca tggacgagcc cacccttctt tatgttttgt ttgaagtctt tgacgtggtc    20340
cgtgtgcacc ggccgcaccg cggcgtcatc gaaaccgtgt acctgcgcac gcccttctcg    20400
gccggcaacg ccacaacata agaagcaag caacatcaac aacagctgcc gccatgggct    20460
ccagtgagca ggaactgaaa gccattgtca aagatcttgg ttgtgggcca tatttttttgg  20520
gcacctatga caagcgcttt ccaggctttg tttctccaca caagctcgcc tgcgccatag    20580
tcaatacggc cggtcgcgag actgggggcg tacactggat ggcctttgcc tggaacccgc    20640
actcaaaaac atgctacctc tttgagccct ttggcttttc tgaccagcga ctcaagcagg    20700
tttaccagtt tgagtacgag tcactcctgc gccgtagcgc cattgcttct tcccccgacc    20760
gctgtataac gctggaaaag tccacccaaa gcgtacaggg gcccaactcg gccgcctgtg    20820
gactattctg ctgcatgttt ctccacgcct ttgccaactg gccccaaaact cccatggatc    20880
acaaccccac catgaacctt attaccgggg tacccaactc catgctcaac agtccccagg    20940
tacagcccac cctgcgtcgc aaccaggaac agctctacag cttcctggag cgccactcgc    21000
cctacttccg cagccacagt gcgcagatta ggagcgccac ttcttttttgt cacttgaaaa    21060
acatgtaaaa ataatgtact agagacactt tcaataaagg caaatgcttt tatttgtaca    21120
ctctcggggtg attatttacc cccacccttg ccgtctgcgc cgtttaaaaa tcaaaggggt   21180
tctgccgcgc atcgctatgc gccactggca gggacacgtt gcgatactgg tgtttagtgc    21240
tccacttaaa ctcaggcaca accatccgcg gcagctcggt gaagttttca ctccacaggc    21300
tgcgcaccat caccaacgcg tttagcaggt cgggcgccga tatcttgaag tcgcagttgg    21360
ggcctccgcc ctgcgcgcgc gagttgcgat acacagggtt gcagcactgg aacactatca    21420
gcgccgggtg gtgcacgctg ccagcacgc tcttgtcgga gatcagatcc gcgtccaggt    21480
cctccgcgtt gctcagggcg aacggagtca actttggtag ctgccttccc aaaaagggcg    21540
cgtgcccagg cttttgagttg cactcgcacc gtagtggcat caaaaggtga ccgtgcccgg    21600
tctgggcgtt aggatacagc gcctgcataa aagccttgat ctgcttaaaa gcccacctgag  21660
cctttgcgcc ttcagagaag aacatgccgc aagacttgcc ggaaaactga ttggccggac    21720
aggccgcgtc gtgcacgcag cacccttgcgt cggtgttgga gatctgcacc acatttcggc   21780
cccaccggtt cttcacgatc ttggccttgc tagactgctc cttcagcgcg cgctgcccgt    21840
tttcgctcgt cacatccatt tcaatcacgt gctccttatt tatcataatg cttccgtgta    21900
gacacttaag ctcgccttcg atctcagcgc agcggtgcag ccacaacgcg cagcccgtgg    21960
gctcgtgatg cttgtaggtc acctctgcaa acgactgcag gtacgcctgc aggaatcgcc    22020
ccatcatcgt cacaaaggtc ttgttgctgg tgaaggtcag ctgcaacccg cggtgctcct    22080
```

```
cgttcagcca ggtcttgcat acggccgcca gagcttccac ttggtcaggc agtagtttga   22140
agttcgcctt tagatcgtta tccacgtggt acttgtccat cagcgcgcgc gcagcctcca   22200
tgcccttctc ccacgcagac acgatcggca cactcagcgg gttcatcacc gtaatttcac   22260
tttccgcttc gctgggctct tcctcttcct cttgcgtccg cataccacgc gccactgggt   22320
cgtcttcatt cagccgccgc actgtgcgct tacctccttt gccatgcttg attagcaccg   22380
gtgggttgct gaaacccacc atttgtagcg ccacatcttc tctttcttcc tcgctgtcca   22440
cgattacctc tggtgatggc gggcgctcgg gcttgggaga agggcgcttc ttttcttct    22500 tgggcgcaat ggccaaatcc gccgccgagg tcgatggccg cgggctgggt gtgcgcggca   22560
ccagcgcgtc ttgtgatgag tcttcctcgt cctcggactc gatacgccgc ctcatccgct   22620
tttttggggg cgcccgggga ggcggcggcg acggggacgg ggacgacacg tcctccatgg   22680 ttggggacg tcgcgccgca ccgcgtccgc gctcggggt ggtttcgcgc tgctcctctt     22740
cccgactggc catttccttc tcctataggc agaaaaagat catggagtca gtcgagaaga   22800
aggacagcct aaccgccccc tctgagttcg ccaccaccgc ctccaccgat gccgccaacg   22860
cgcctaccac cttccccgtc gaggcacccc gcttgagga ggaggaagtg attatcgagc    22920
aggacccagg ttttgtaagc gaagacgacg aggaccgctc agtaccaaca gaggataaaa   22980
agcaagacca ggacaacgca gaggcaaacg aggaacaagt cgggcggggg gacgaaaggc   23040
atggcgacta cctagatgtg ggagacgacg tgctgttgaa gcatctgcag cgccagtgcg   23100
ccattatctg cgacgcgttg caagagcgca gcgatgtgcc cctcgccata gcggatgtca   23160
gccttgccta cgaacgccac ctattctcac cgcgcgtacc ccccaaacgc caagaaaacg   23220
gcacatgcga gcccaacccg cgcctcaact tctacccccgt atttgccgtg ccagaggtgc   23280
ttgccaccta tcacatcttt ttccaaaact gcaagatacc cctatcctgc cgtgccaacc   23340
gcagccgagc ggacaagcag ctggccttgc ggcagggcgc tgtcatacct gatatcgcct   23400
cgctcaacga agtgccaaaa atctttgagg gtcttggacg cgacgagaag cgcgcggcaa   23460
acgctctgca acaggaaaac agcgaaaatg aaagtcactc tggagtgttg gtggaactcg   23520
agggtgacaa cgcgcgccta gccgtactaa acgcagcat cgaggtcacc cacttttgcct   23580 acccggcact taacctaccc cccaaggtca tgagcacagt catgagtgag ctgatcgtgc   23640
gccgtgcgca gccctggag agggatgcaa atttgcaaga acaaacagag gagggcctac   23700
ccgcagttgg cgacgagcag ctagcgcgct ggcttcaaac gcgcgagcct gccgacttgg   23760
aggagcgacg caaactaatg atggccgcag tgctcgttac cgtggagctt gagtgcatgc   23820
agcggttctt tgctgacccg gagatgcagc gcaagctaga ggaaacattg cactacacct   23880
ttcgacaggg ctacgtacgc caggcctgca gatctccaa cgtggagctc tgcaacctgg   23940
tctcctacct tggaatttg cacgaaaacc gccttgggca aaacgtgctt cattccacgc   24000
tcaagggcga ggcgcgccgc gactacgtcc gcgactgcgt ttacttattt ctatgctaca   24060
cctggcagac ggccatgggc gtttggcagc agtgcttgga ggagtgcaac ctcaaggagc   24120
tgcagaaact gctaaagcaa aacttgaagg acctatggac ggccttcaac gagcgctccg   24180
tggccgcgca cctggcggac atcatttttcc ccgaacgcct gcttaaaacc ctgcaacagg   24240
gtctgccaga cttcaccagt caaagcatgt tgcagaactt taggaacttt atcctagagc   24300
gctcaggaat cttgccccgcc acctgctgtg cacttcctag cgactttgtg cccattaagt   24360
accgcgaatg ccctccgccg ctttgggggcc actgctacct tctgcagcta gccaactacc   24420
```

```
ttgcctacca ctctgacata atggaagacg tgagcggtga cggtctactg gagtgtcact    24480
gtcgctgcaa cctatgcacc ccgcaccgct ccctggtttg caattcgcag ctgcttaacg    24540
aaagtcaaat tatcggtacc tttgagctgc agggtccctc gcctgacgaa aagtccgcgg    24600
ctccggggtt gaaactcact ccggggctgt ggacgtcggc ttaccttcgc aaatttgtac    24660
ctgaggacta ccacgcccac gagattaggt tctacgaaga ccaatcccgc ccgccaaatg    24720
cggagcttac cgcctgcgtc attacccagg gccacattct tggccaattg caagccatca    24780
acaaagcccg ccaagagttt ctgctacgaa agggacgggg ggtttacttg gaccccccagt   24840 ccggcgagga gctcaaccca atccccccgc cgccgcagcc ctatcagcag cagccgcggg    24900
cccttgcttc ccaggatggc acccaaaaag aagctgcagc tgccgccgcc acccacggac    24960
gaggaggaat actgggacag tcaggcgagg gaggttttgg acgaggagga ggaggacatg    25020
atggaagact gggagagcct agacgaggaa gcttccgagg tcgaagaggt gtcagacgaa    25080
acaccgtcac cctcggtcgc attcccctcg ccggcgcccc agaaatcggc aaccggttcc    25140
agcatggcta caacctccgc tcctcaggcg ccgccggcac tgcccgttcg ccgacccaac    25200
cgtagatggg acaccactgg aaccagggcc ggtaagtcca agcagccgcc gccgttagcc    25260
caagagcaac aacagcgcca aggctaccgc tcatggcgcg ggcacaagaa cgccatagtt    25320
gcttgcttgc aagactgtgg gggcaacatc tccttcgccc gccgctttct tctctaccat    25380
cacggcgtgg ccttcccccg taacatcctg cattactacc gtcatctcta cagcccatac    25440
tgcaccggcg gcagcggcag cggcagcaac agcagcggcc acacagaagc aaaggcgacc    25500
ggatagcaag actctgacaa agcccaagaa atccacagcg gcggcagcag caggaggagg    25560
agcgctgcgt ctggcgccca acgaacccgt atcgacccgc gagcttagaa acaggatttt    25620
tcccactctg tatgctatat ttcaacagag caggggccaa gaacaagagc tgaaaataaa    25680
aaacaggtct ctgcgatccc tcacccgcag ctgcctgtat cacaaaagcg aagatcagct    25740
tcggcgcacg ctggaagacg cggaggctct cttcagtaaa tactgcgcgc tgactcttaa    25800
ggactagttt cgcgccctttct caaatttta gcgcgaaaaa ctacgtcatc tccagcggcc    25860
acacccggcg ccagcacctg tcgtcagcgc cattatgagc aaggaaattc ccacgcccta    25920
catgtggagt taccagccac aaatgggact tgcggctgga gctgcccaag actactcaac    25980
ccgaataaac tacatgagcg cgggaccccca catgatatcc cgggtcaacg gaatccgcgc    26040
ccaccgaaac cgaattctct tggaacaggc ggctattacc accacacctc gtaataacct    26100
taatccccgt agttggcccg ctgccctggt gtaccaggaa agtccgctc ccaccactgt     26160 ggtacttccc agagacgccc aggccgaagt tcagatgact aactcagggg cgcagcttgc    26220
gggcggcttt cgtcacaggg tgcggtcgcc cgggcagggt ataactcacc tgacaatcag    26280
agggcgaggt attcagctca acgacgagtc ggtgagctcc tcgcttggtc tccgtccgga    26340
cgggacattt cagatcggcg gcgcggccc tccttcattc acgcctcgtc aggcaatcct     26400
aactctgcag acctcgtcct ctgagccgcg ctctggaggc attggaactc tgcaatttat    26460
tgaggagttt gtgccatcgg tctacttaa ccccttctcg ggacctcccg gccactatcc     26520
ggatcaattt attcctaact tgacgcggt aaaggactcg gcggacgct acgactgaat      26580 gttaagtgga gaggcagagc aactgcgcct gaaacacctg gtccactgtc gccgccacaa    26640
gtgctttgcc cgcgactccg gtgagttttg ctactttgaa ttgcccgagg atcatatcga    26700
gggcccggcg cacggcgtcc ggcttaccgc ccagggagag cttgccccgta gcctgattcg    26760 ggagtttacc cagcgccccc tgctagttga gcgggacagg ggaccctgtg ttctcactgt    26820
```

```
gatttgcaac tgtcctaacc ttggattaca tcaagatctt tgttgccatc tctgtgctga   26880
gtataataaa tacagaaatt aaaatatact ggggctccta tcgccatcct gtaaacgcca   26940
ccgtcttcac ccgcccaagc aaccaaggc gaaccttacc tggtactttt aacatctctc    27000
cctctgtgat ttacaacagt ttcaacccag acggagtgag tctacgagag aacctctccg   27060
agctcagcta ctccatcaga aaaaacacca ccctccttac ctgccgggaa cgtacgagtg   27120
cgtcaccggc cgctgcacca cacctaccgc ctgaccgtaa accagacttt ttccggacag   27180
acctcaataa ctctgtttac cagaacagga ggtgagctta gaaaacccctt agggtattag  27240 gccaaaggcg cagctactgt ggggtttatg aacaattcaa gcaactctac gggctattct   27300
aattcaggtt tctctagaaa tggacggaat tattacagag cagcgcctgc tagaaagacg   27360
cagggcagcg gccgagcaac agcgcatgaa tcaagagctc caagacatgg ttaacttgca   27420
ccagtgcaaa agggggtatct tttgtctggt aaagcaggcc aaagtcacct acgacagtaa   27480
taccaccgga caccgcctta gctacaagtt gccaaccaag cgtcagaaat tggtggtcat   27540
ggtgggagaa aagcccatta ccataactca gcactcggta gaaaccgaag gctgcattca   27600
ctcaccttgt caaggacctg aggatctctg caccccttatt aagaccctgt gcggtctcaa   27660
agatcttatt ccctttaact aataaaaaaa aataataaag catcacttac ttaaaatcag   27720
ttagcaaatt tctgtccagt ttattcagca gcacctcctt gccctcctcc cagctctggt   27780
attgcagctt cctcctggct gcaaactttc tccacaatct aaatggaatg tcagtttcct   27840
cctgttcctg tccatccgca cccactatct tcatgttgtt gcagatgaag cgcgcaagac   27900
cgtctgaaga taccttcaac cccgtgtatc catatgacac ggaaaccggt cctccaactg   27960
tgccttttct tactcctccc tttgtatccc ccaatgggtt tcaagagagt cccccctgggg  28020 tactctcttt gcgcctatcc gaacctctag ttacctccaa tggcatgctt gcgctcaaaa   28080
tgggcaacgg cctctctctg acgaggccg gcaaccttac ctcccaaaat gtaaccactg    28140
tgagcccacc tctcaaaaaa accaagtcaa acataaacct ggaaatatct gcacccctca   28200
cagttacctc agaagcccta actgtggctg ccgccgcacc tctaatggtc gcgggcaaca   28260
cactcaccat gcaatcacag gccccgctaa ccgtgcacga ctccaaactt agcattgcca   28320
cccaaggacc cctcacagtg tcagaaggaa agctagccct gcaaacatca ggccccctca   28380
ccaccaccga tagcagtacc cttactatca ctgcctcacc ccctctaact actgccactg   28440
gtagcttggg cattgacttg aaagagccca tttatacaca aaatggaaaa ctaggactaa   28500
agtacggggc tcctttgcat gtaacagacg acctaaacac tttgaccgta gcaactggtc   28560
caggtgtgac tattaataat acttccttgc aaactaaagt tactggagcc ttgggttttg   28620
attcacaagg caatatgcaa cttaatgtag caggaggact aaggattgat tctcaaaaca   28680
gacgccttat acttgatgtt agttatccgt ttgatgctca aaaccaacta aatctaagac   28740
taggacaggg ccctctcttt ataaactcag cccacaactt ggatattaac tacaacaaag   28800
gcctttactt gtttacagct tcaaacaatt ccaaaaagct tgaggttaac ctaagcactg   28860
ccaaggggtt gatgtttgac gctacagcca tagccattaa tgcaggagat gggcttgaat   28920
ttggttcacc taatgcacca aacacaaatc ccctcaaaac aaaaattggc catgcctag    28980 aatttgattc aaacaaggct atggttccta aactaggaac tggccttagt tttgacagca   29040
caggtgccat tacagtagga aacaaaaata atgataagct aactttgtgg accacaccag   29100
ctccatctcc taactgtaga ctaaatgcag agaaagatgc taaactcact ttggtcttaa   29160
```

```
caaaatgtgg cagtcaaata cttgctacag tttcagtttt ggctgttaaa ggcagtttgg    29220
ctccaatatc tggaacagtt caaagtgctc atcttattat aagatttgac gaaaatggag    29280
tgctactaaa caattccttc ctggacccag aatattggaa ctttagaaat ggagatctta    29340
ctgaaggcac agcctataca aacgctgttg gatttatgcc taacctatca gcttatccaa    29400
aatctcacgg taaaactgcc aaaagtaaca ttgtcagtca agtttactta aacggagaca    29460
aaactaaacc tgtaacacta accattacac taaacggtac acaggaaaca ggagacacaa    29520
ctccaagtgc atactctatg tcattttcat gggactggtc tggccacaac tacattaatg    29580
aaatatttgc cacatcctct tacactttt catacattgc caagaataa agaatcgttt      29640 gtgttatgtt tcaacgtgtt tattttcaa ttgcagaaaa tttcgaatca tttttcattc      29700
agtagtatag ccccaccacc acatagctta tacagatcac cgtaccttaa tcaaactcac    29760
agaaccctag tattcaacct gccacctccc tcccaacaca cagagtacac agtcctttct    29820
ccccggctgg ccttaaaaag catcatatca tgggtaacag acatattctt aggtgttata    29880
ttccacacgg tttcctgtcg agccaaacgc tcatcagtga tattaataaa ctccccgggc    29940
agctcactta agttcatgtc gctgtccagc tgctgagcca caggctgctg tccaacttgc    30000
ggttgcttaa cgggcggcga aggagaagtc cacgcctaca tggggtaga gtcataatcg      30060 tgcatcagga tagggcggtg gtgctgcagc agcgcgcgaa taaactgctg ccgccgccgc    30120
tccgtcctgc aggaatacaa catggcagtg gtctcctcag cgatgattcg caccgcccgc    30180
agcataaggc gccttgtcct ccgggcacag cagcgcaccc tgatctcact taaatcagca    30240
cagtaactgc agcacagcac cacaatattg ttcaaaatcc cacagtgcaa ggcgctgtat    30300
ccaaagctca tggcggggac cacagaaccc acgtggccat cataccacaa gcgcaggtag    30360
attaagtggc gacccctcat aaacacgctg gacataaaca ttacctcttt tggcatgttg    30420
taattcacca cctcccggta ccatataaac ctctgattaa acatggcgcc atccaccacc    30480
atcctaaacc agctggccaa aacctgcccg ccggctatac actgcaggga accgggactg    30540
gaacaatgac agtggagagc ccaggactcg taaccatgga tcatcatgct cgtcatgata    30600
tcaatgttgg cacaacacag gcacacgtgc atacacttcc tcaggattac aagctcctcc    30660
cgcgttagaa ccatatccca gggaacaacc cattcctgaa tcagcgtaaa tcccacactg    30720
cagggaagac ctcgcacgta actcacgttg tgcattgtca aagtgttaca ttcgggcagc    30780
agcggatgat cctccagtat ggtagcgcgg gtttctgtct caaaaggagg tagacgatcc    30840
ctactgtacg gagtgcgccg agacaaccga gatcgtgttg gtcgtagtgt catgccaaat    30900
ggaacgccgg acgtagtcat atttcctgaa gcaaaaccag gtgcgggcgt gacaaacaga    30960
tctgcgtctc cggtctcgcc gcttagatcg ctctgtgtag tagttgtagt atatccactc    31020
tctcaaagca tccaggcgcc ccctggcttc gggttctatg taaactcctt catgcgccgc    31080
tgccctgata acatccacca ccgcagaata agccacaccc agccaaccta cacattcgtt    31140
ctgcgagtca cacacgggag gagcgggaag agctggaaga accatgtttt ttttttatt     31200 ccaaaagatt atccaaaacc tcaaatgaa gatctattaa gtgaacgcgc tccctccgg       31260 tggcgtggtc aaactctaca gccaaagaac agataatggc atttgtaaga tgttgcacaa    31320
tggcttccaa aaggcaaacg gccctcacgt ccaagtggac gtaaaggcta aacccttcag    31380
ggtgaatctc ctctataaac attccagcac cttcaaccat gcccaaataa ttctcatctc    31440
gccaccttct caatatatct ctaagcaaat cccgaatatt aagtccggcc attgtaaaaa    31500
tctgctccag agcgccctcc accttcagcc tcaagcagcg aatcatgatt gcaaaaattc    31560
```

```
aggttcctca cagacctgta taagattcaa aagcggaaca ttaacaaaaa taccgcgatc    31620
ccgtaggtcc cttcgcaggg ccagctgaac ataatcgtgc aggtctgcac ggaccagcgc    31680
ggccacttcc ccgccaggaa ccttgacaaa agaacccaca ctgattatga cacgcatact    31740
cggagctatg ctaaccagcg tagccccgat gtaagctttg ttgcatgggc ggcgatataa    31800
aatgcaaggt gctgctcaaa aaatcaggca aagcctcgcg caaaaaagaa agcacatcgt    31860
agtcatgctc atgcagataa aggcaggtaa gctccggaac caccacagaa aaagacacca    31920
tttttctctc aaacatgtct gcgggtttct gcataaacac aaaataaaat aacaaaaaaa    31980
catttaaaca ttagaagcct gtcttacaac aggaaaaaca acccttataa gcataagacg    32040
gactacggcc atgccggcgt gaccgtaaaa aaactggtca ccgtgattaa aaagcaccac    32100
cgacagctcc tcggtcatgt ccggagtcat aatgtaagac tcggtaaaca catcaggttg    32160
attcacatcg gtcagtgcta aaaagcgacc gaaatagccc gggggaatac atacccgcag    32220
gcgtagagac aacattacag cccccatagg aggtataaca aaattaatag gagagaaaaa    32280
cacataaaca cctgaaaaac cctcctgcct aggcaaaata gcaccctccc gctccagaac    32340
aacatacagc gcttccacag cggcagccat aacagtcagc cttaccagta aaaagaaaa    32400 cctattaaaa aaacaccact cgacacggca ccagctcaat cagtcacagt gtaaaaaagg    32460
gccaagtgca gagcgagtat atataggact aaaaaatgac gtaacggtta aagtccacaa    32520
aaaacaccca gaaaaccgca cgcgaaccta cgcccagaaa cgaaagccaa aaaacccaca    32580
acttcctcaa atcgtcactt ccgttttccc acgttacgtc acttcccatt ttaagaaaac    32640
tacaattccc aacacataca agttactccg ccctaaaacc tacgtcaccc gccccgttcc    32700
cacgccccgc gccacgtcac aaactccacc ccctcattat catattggct tcaatccaaa    32760
ataaggtata ttattgatga tgttaattaa tttaaatccg catgcgatat cgagctctcc    32820
cgggaattcg gatctgcgac gcgaggctgg atggccttcc ccattatgat tcttctcgct    32880
tccggcggca tcgggatgcc cgcgttgcag gccatgctgt ccaggcaggt agatgacgac    32940
catcagggac agcttcacgg ccagcaaaag gccaggaacc gtaaaaaggc cgcgttgctg    33000
gcgttttccc ataggctccg ccccccctgac gagcatcaca aaaatcgacg ctcaagtcag    33060
aggtggcgaa acccgacagg actataaaga taccaggcgt ttccccctgg aagctccctc    33120
gtgcgctctc ctgttccgac cctgccgctt accggatacc tgtccgcctt tctcccttcg    33180
ggaagcgtgg cgctttctca atgctcacgc tgtaggtatc tcagttcggt gtaggtcgtt    33240
cgctccaagc tgggctgtgt gcacgaaccc cccgttcagc ccgaccgctg cgccttatcc    33300
ggtaactatc gtcttgagtc aacccggta agacacgact tatcgccact ggcagcagcc    33360
actggtaaca ggattagcag agcgaggtat gtaggcggtg ctacagagtt cttgaagtgg    33420
tggcctaact acggctacac tagaaggaca gtatttggta tctgcgctct gctgaagcca    33480
gttaccttcg gaaaaagagt tggtagctct tgatccggca acaaaccac cgctggtagc    33540 ggtggttttt ttgtttgcaa gcagcagatt acgcgcagaa aaaaggatc tcaagaagat    33600 cctttgatct tttctacggg gtctgacgct cagtggaacg aaaactcacg ttaagggatt    33660
ttggtcatga gattatcaaa aaggatcttc acctagatcc ttttaaatca atctaaagta    33720
tatatgagta aacttggtct gacagttacc aatgcttaat cagtgaggca cctatctcag    33780
cgatctgtct atttcgttca tccatagttg cctgactccc cgtcgtgtag ataactacga    33840
tacgggaggg cttaccatct ggccccagtg ctgcaatgat accgcgagac ccacgctcac    33900
```

```
cggctccaga tttatcagca ataaaccagc cagccggaag ggccgagcgc agaagtggtc  33960
ctgcaacttt atccgcctcc atccagtcta ttaattgttg ccgggaagct agagtaagta  34020
gttcgccagt taatagtttg cgcaacgttg ttgccattgn tgcaggcatc gtggtgtcac  34080
gctcgtcgtt tggtatggct tcattcagct ccggttccca acgatcaagg cgagttacat  34140
gatcccccat gttgtgcaaa aaagcggtta gctccttcgg tcctccgatc gttgtcagaa  34200
gtaagttggc cgcagtgtta tcactcatgg ttatggcagc actgcataat tctcttactg  34260
tcatgccatc cgtaagatgc ttttctgtga ctggtgagta ctcaaccaag tcattctgag  34320
aatagtgtat gcggcgaccg agttgctctt gcccggcgtc aacacgggat aataccgcgc  34380
cacatagcag aactttaaaa gtgctcatca ttggaaaacg ttcttcgggg cgaaaactct  34440
caaggatctt accgctgttg agatccagtt cgatgtaacc cactcgtgca cccaactgat  34500
cttcagcatc ttttactttc accagcgttt ctgggtgagc aaaaacagga aggcaaaatg  34560
ccgcaaaaaa gggaataagg gcgacacgga aatgttgaat actcatactc ttcctttttc  34620
aatattattg aagcatttat cagggttatt gtctcatgag cggatacata tttgaatgta  34680
tttagaaaaa taaacaaata ggggttccgc gcacatttcc ccgaaaagtg ccacctgacg  34740
tctaagaaac cattattatc atgacattaa cctataaaaa taggcgtatc acgaggccct  34800
ttcgtcttca aggatccgaa ttcccgggag agctcgatat cgcatgcgga tttaaattaa  34860
ttaa                                                               34864
```

```
<210> SEQ ID NO 31
<211> LENGTH: 46
<212> TYPE: PRT
<213> ORGANISM: Artificial Sequence
<220> FEATURE:
<223> OTHER INFORMATION: PRRSV gp5a

<400> SEQUENCE: 31

Met Phe Lys Tyr Val Gly Glu Val Leu Asp Arg Val Leu Leu Leu Ala
1               5                   10                  15

Ile Ala Phe Phe Val Val Tyr Arg Ala Val Leu Ser Cys Cys Ala Arg
            20                  25                  30

Gln Arg Gln Gln Gln Gln Gln Leu Ser Tyr Ser Val Asp Leu
        35                  40                  45

<210> SEQ ID NO 32
<211> LENGTH: 174
<212> TYPE: PRT
<213> ORGANISM: Artificial Sequence
<220> FEATURE:
<223> OTHER INFORMATION: VR2332 PRRSV M (matrix protein)

<400> SEQUENCE: 32

Met Gly Ser Ser Leu Asp Asp Phe Cys His Asp Ser Thr Ala Pro Gln
1               5                   10                  15

Lys Val Leu Leu Ala Phe Ser Ile Thr Tyr Thr Pro Val Met Ile Tyr
            20                  25                  30

Ala Leu Lys Val Ser Arg Gly Arg Leu Leu Gly Leu Leu His Leu Leu
        35                  40                  45

Ile Phe Leu Asn Cys Ala Phe Thr Phe Gly Tyr Met Thr Phe Ala His
    50                  55                  60

Phe Gln Ser Thr Asn Lys Val Ala Leu Thr Met Gly Ala Val Val Ala
65                  70                  75                  80

Leu Leu Trp Gly Val Tyr Ser Ala Ile Glu Thr Trp Lys Phe Ile Thr

```
                    85                  90                  95

Ser Arg Cys Arg Leu Cys Leu Leu Gly Arg Lys Tyr Ile Leu Ala Pro
                100                 105                 110

Ala His His Val Glu Ser Ala Ala Arg Phe His Pro Ile Ala Ala Asn
            115                 120                 125

Asp Asn His Ala Phe Val Val Arg Arg Pro Gly Ser Thr Thr Val Asn
        130                 135                 140

Gly Thr Leu Val Pro Gly Leu Lys Ser Leu Val Leu Gly Gly Arg Lys
145                 150                 155                 160

Ala Val Lys Gln Gly Val Val Asn Leu Val Lys Tyr Ala Lys
                165                 170

<210> SEQ ID NO 33
<211> LENGTH: 123
<212> TYPE: PRT
<213> ORGANISM: Artificial Sequence
<220> FEATURE:
<223> OTHER INFORMATION: VR2332 PRRSV N (nucleocapsid protein)

<400> SEQUENCE: 33

Met Pro Asn Asn As

```
Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
            115                 120                 125

Gln Val Val Ser Glu Ala Thr Leu Ser Arg Ile Ser Ser Leu Asp Val
        130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Glu Gln Val Val Ala
            180                 185                 190

Ile Phe Pro Thr Pro Gly Ser Arg Pro Lys Leu His Asp Phe Gln Gln
            195                 200                 205

Trp Leu Ile Ala Val His Ser Ser Ile Phe Ser Ser Val Ala Ala Ser
210                 215                 220

Cys Thr Leu Phe Val Val Leu Trp Leu Arg Ile Pro Met Leu Arg Thr
225                 230                 235                 240

Val Phe Gly Phe His Trp Leu Gly Ala Ile Phe Leu Ser Asn Ser Gln
                245                 250                 255
```

<210> SEQ ID NO 35
<211> LENGTH: 256
<212> TYPE: PRT
<213> ORGANISM: Artificial Sequence
<220> FEATURE:
<223> OTHER INFORMATION: ACF93748.1 PRRSV gp2

<400> SEQUENCE: 35

```
Met Lys Trp Gly Leu Cys Lys Ala Ser Leu Thr Lys Leu Ala Asn

```
Trp Leu Ile Ala Val His Ser Ser Ile Phe Ser Ser Val Ala Ala Ser
    210                 215                 220

Cys Thr Leu Phe Val Val Leu Trp Leu Arg Ile Pro Met Leu Arg Ser
225                 230                 235                 240

Val Phe Gly Phe Arg Trp Leu Gly Ala Ile Phe Leu Leu Asn Ser Arg
                245                 250                 255

<210> SEQ ID NO 36
<211> LENGTH: 256
<212> TYPE: PRT
<213> ORGANISM: Artificial Sequence
<220> FEATURE:
<223> OTHER INFORMATION: AHA83141.1 PRRSV gp2

<400> SEQUENCE: 36

Met Lys Trp Gly Pro Tyr Lys Ala Phe Leu Thr Lys Leu Ala Asn Phe
1               5                   10                  15

Leu Trp Met Leu Ser Arg Ser Ser Trp Cys Pro Leu Leu Ile Ser Leu
                20                  25                  30

Tyr Phe Trp Pro Phe Cys Leu Ala Ser Pro Ser Pro Val Gly Trp Trp
                35                  40                  45

Ser Phe Ala Ser Asp Trp Phe Ala Pro Arg Tyr Ser Val Arg Ala Leu
    50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Thr Lys His Pro Leu Gly
                85                  90                  95

Met Phe Trp His His Lys Val Ser Thr Leu Ile Asp Glu Met Val Ser
                100                 105                 110

Arg Arg Met Tyr Arg Ile Met Glu Lys Ala Gly Gln Ala Ala Trp Lys
            115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Ser Gln Val Phe Ala
                180                 185                 190

Ile Phe Pro Thr Pro Gly Ser Arg Pro Lys Leu His Asp Phe Gln Gln
            195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Ile Leu His Thr
225                 230                 235                 240

Val Phe Gly Phe Arg Trp Leu Gly Ala Ile Phe Leu Ser Asn Ser Gln
                245                 250                 255

<210> SEQ ID NO 37
<211> LENGTH: 249
<212> TYPE: PRT
<213> ORGANISM: Artificial Sequence
<220> FEATURE:
<223> OTHER INFORMATION: CAA01838.1 Lelystad PRRSV gp2

<400> SEQUENCE: 37

Met Gln Trp Gly His Cys Gly Val Lys Ser Ala Ser Cys Ser Trp Thr
1               5                   10                  15
```

-continued

```
Pro Ser Leu Ser Ser Leu Leu Val Trp Leu Ile Leu Pro Phe Ser Leu
             20                  25                  30

Pro Tyr Cys Leu Gly Ser Pro Ser Gln Asp Gly Tyr Trp Ser Phe Phe
             35                  40                  45

Ser Glu Trp Phe Ala Pro Arg Phe Ser Val Arg Ala Leu Pro Phe Thr
 50                  55                  60

Leu Pro Asn Tyr Arg Arg Ser Tyr Glu Gly Leu Leu Pro Asn Cys Arg
 65                  70                  75                  80

Pro Asp Val Pro Gln Phe Ala Val Lys His Pro Leu Gly Met Phe Trp
                 85                  90                  95

His Met Arg Val Ser His Leu Ile Asp Glu Met Val Ser Arg Arg Ile
             100                 105                 110

Tyr Gln Thr Met Glu His Ser Gly Gln Ala Ala Trp Lys Gln Val Val
             115                 120                 125

Gly Glu Ala Thr Leu Thr Lys Leu Ser Gly Leu Asp Ile Val Thr His
130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                 165                 170                 175

Gln Tyr Asn Thr Thr Leu Asp Arg Val Glu Leu Ile Phe Pro Thr Pro
             180                 185                 190

Gly Thr Arg Pro Lys Leu Thr Asp Phe Arg Gln Trp Leu Ile Ser Val
             195                 200                 205

His Ala Ser Ile Phe Ser Ser Val Ala Ser Ser Val Thr Leu Phe Ile
             210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                 245

<210> SEQ ID NO 38
<211> LENGTH: 256
<212> TYPE: PRT
<213> ORGANISM: Artificial Sequence
<220> FEATURE:
<223> OTHER INFORMATION: AAE74522.1 gp2

<400> SEQUENCE: 38

Met Gln Trp Gly Pro Cys Lys Ala Phe Leu Thr Arg Ser Val Asn Phe
1               5                  10                  15

Leu Trp Met Leu Ser Arg Ser Ser Trp Cys Pro Leu Leu Ile Ser Ser
             20                  25                  30

Tyr Phe Trp Pro Phe Cys Leu Ala Ser Pro Leu Pro Ala Gly Trp Trp
             35                  40                  45

Ser Phe Ala Ser Asp Trp Phe Ala Pro Arg Tyr Ser Val Arg Ala Leu
 50                  55                  60

Pro Phe Thr Leu Ser Asn Tyr Arg Arg Ser Tyr Glu Ala Phe Leu Ser
 65                  70                  75                  80

Gln Cys Gln Val Asp Ile Pro Ala Trp Gly Thr Arg His Pro Leu Gly
                 85                  90                  95

Met Leu Trp His His Lys Val Ser Thr Leu Ile Asp Glu Met Val Ser
             100                 105                 110

Arg Arg Met Tyr Arg Ile Met Glu Lys Ala Gly Gln Ala Ala Trp Lys
             115                 120                 125
```

```
Gln Val Val Ser Glu Ala Thr Leu Ser Arg Ile Ser Gly Leu Asp Val
            130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Ile Thr Gly
                165                 170                 175

Ser Asn Val Thr Ile Val His Asn Ser Thr Leu Asn Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Ser Ser Ser Val Ala Ala Ser
            210                 215                 220

Cys Thr Leu Phe Val Val Leu Trp Leu Arg Met Pro Met Leu Arg Ser
225                 230                 235                 240

Val Phe Gly Phe Arg Trp Leu Gly Ala Ile Phe Pro Ser Ser Ser Trp
                245                 250                 255

<210> SEQ ID NO 39
<211> LENGTH: 249
<212> TYPE: PRT
<213> ORGANISM: Artificial Sequence
<220> FEATURE:
<223> OTHER INFORMATION: AAB54503.1 PRRSV gp2
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 39

Met Gln Trp Gly His Cys Gly Val Lys Ser Ala Ser Cys Ser Trp Thr
1               5                   10                  15

Pro Ser Leu Ser Ser Leu Leu Val Trp Leu Ile Leu Xaa Phe Ser Leu
                20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Val Lys His Pro Leu Xaa Met Phe Trp
                85                  90                  95

His Met Arg Val Ser His Leu Ile Asp Glu Xaa Val Ser Arg Arg Ile
            100                 105                 110

Tyr Gln Thr Met Glu His Ser Gly Gln Ala Ala Trp Lys Gln Val Val
            115                 120                 125

Gly Glu Ala Thr Leu Thr Lys Leu Ser Gly Leu Asp Ile Val Thr His
            130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175
```

Gln Tyr Asn Thr Thr Leu Asp Arg Val Glu Leu Ile Phe Pro Thr Pro
                180                 185                 190

Gly Thr Arg Pro Lys Leu Thr Asp Phe Arg Gln Trp Leu Ile Ser Val
            195                 200                 205

His Ala Ser Ile Phe Ser Ser Val Ala Ser Ser Val Thr Leu Phe Ile
210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245

<210> SEQ ID NO 40
<211> LENGTH: 254
<212> TYPE: PRT
<213> ORGANISM: Artificial Sequence
<220> FEATURE:
<223> OTHER INFORMATION: AAE68461.1 PRRSV gp3

<400> SEQUENCE: 40

Met Val Asn Ser Cys Thr Phe Leu His Ile Phe Leu Cys Cys Ser Phe
1               5                   10                  15

Leu Tyr Ser Leu Cys Cys Ala Val Val Ala Gly Ser Asn Thr Thr Tyr
                20                  25                  30

Cys Phe Trp Phe Pro Leu Val Arg Gly Asn Phe Ser Phe Glu Leu Thr
            35                  40                  45

Val Asn Tyr Thr Val Cys Pro Pro Cys Leu Thr Arg Gln Ala Ala Ala
        50                  55                  60

Glu Ala Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Val Pro Ser
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Glu His Gln Leu Ile
130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Thr Leu Arg Pro Thr Pro Pro Gln Arg Gln
210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

<210> SEQ ID NO 41
<211> LENGTH: 254
<212> TYPE: PRT
<213> ORGANISM: Artificial Sequence
<220> FEATURE:
<223> OTHER INFORMATION: AAQ51784.1 PRRSV gp3

<400> SEQUENCE: 41

Met Ala Asn Ser Cys Thr Phe Leu Tyr Ile Phe Leu Cys Cys Ser Phe
1               5                   10                  15

Leu Tyr Ser Phe Cys Cys Ala Val Val Ala Gly Ser Asn Ala Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Ala
    50                  55                  60

Glu Ala Tyr Glu Pro Gly Arg Ser Leu Trp Cys Arg Ile Gly His Asp
65                  70                  75                  80

Arg Cys Gly Glu Asp Asp His Asp Glu Leu Gly Phe Val Val Pro Ser
                85                  90                  95

Gly Leu Ser Ser Glu Gly His Leu Thr Ser Ala Tyr Ala Trp Leu Ala
            100                 105                 110

Ser Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Phe Ile
    130                 135                 140

Cys Ala Val His Asp Gly Gln Asn Thr Thr Leu Pro His His Asp Asn
145                 150                 155                 160

Ile Ser Ala Val Leu Gln Thr Tyr Tyr Gln His Gln Val Asp Gly Gly
                165                 170                 175

Asn Trp Phe His Leu Glu Trp Val Arg Pro Phe Phe Ser Ser Trp Leu
            180                 185                 190

Val Leu Asn Val Ser Trp Phe Leu Arg Arg Ser Pro Ala Ser His Val
        195                 200                 205

Ser Val Arg Val Phe Gln Thr Ser Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Ala Arg Arg
                245                 250

<210> SEQ ID NO 42
<211> LENGTH: 254
<212> TYPE: PRT
<213> ORGANISM: Artificial Sequence
<220> FEATURE:
<223> OTHER INFORMATION: AAE74530.1 PRRSV gp3

<400> SEQUENCE: 42

Met Ala Asn Ser Cys Thr Phe Leu His Ile Leu Leu Cys Cys Ser Phe
1               5                   10                  15

Leu Tyr Ser Phe Cys Cys Val Val Val Thr Asp Ala Asn Ala Thr Phe
            20                  25                  30

Cys Phe Trp Phe Pro Leu Val Arg Gly Asn Phe Ser Phe Glu Leu Met
        35                  40                  45

Val Asn Tyr Thr Val Cys Pro Pro Cys Leu Thr Arg Gln Ala Ala Ala
    50                  55                  60

Gln Ile Tyr Glu Pro Asn Arg Ser Leu Trp Cys Arg Ile Gly Asn Asp
65                  70                  75                  80

Arg Cys Gly Glu Asp Asp His Asp Glu Leu Gly Phe Thr Val Pro Pro

-continued

```
                85                  90                  95
Gly Leu Ser Lys Glu Val His Leu Thr Ser Val Tyr Ala Trp Leu Ala
            100                 105                 110
Phe Leu Ser Phe Ser Tyr Thr Ala Gln Phe His Pro Glu Ile Phe Gly
            115                 120                 125
Ile Gly Asn Val Ser Lys Val Tyr Val Asp Ile Asn His Gln Leu Ile
        130                 135                 140
Cys Ala Val His Asp Gly Gln Asn Thr Thr Leu Pro Arg His Asp Asn
145                 150                 155                 160
Ile Ser Ala Val Phe Gln Thr Tyr Tyr Gln His Gln Val Asp Gly Gly
                165                 170                 175
Asn Trp Phe His Leu Glu Trp Leu Arg Pro Phe Phe Ser Ser Trp Leu
            180                 185                 190
Val Leu Asn Val Ser Trp Phe Leu Arg Arg Ser Pro Ala Ser His Val
            195                 200                 205
Ser Val Arg Val Phe Gln Thr Ser Arg Pro Thr Pro Arg Gln Gln
        210                 215                 220
Ile Ser Leu Ser Ser Arg Thr Ser Ala Ala Leu Gly Met Ala Thr Arg
225                 230                 235                 240
Pro Leu Arg Arg Phe Ala Lys Ser Leu Ser Ala Ala Arg Arg
                245                 250
```

<210> SEQ ID NO 43
<211> LENGTH: 265
<212> TYPE: PRT
<213> ORGANISM: Artificial Sequence
<220> FEATURE:
<223> OTHER INFORMATION: CAA01839.1 PRRSV gp3

<400> SEQUENCE: 43

```
Met Ala His Gln Cys Ala Arg Phe His Phe Leu Cys Gly Phe Ile
1               5                   10                  15
Cys Tyr Leu Val His Ser Ala Leu Ala Ser Asn Ser Ser Ser Thr Leu
                20                  25                  30
Cys Phe Trp Phe Pro Leu Ala His Gly Asn Thr Ser Phe Glu Leu Thr
            35                  40                  45
Ile Asn Tyr Thr Ile Cys Met Pro Cys Ser Thr Ser Gln Ala Ala Arg
        50                  55                  60
Gln Arg Leu Glu Pro Gly Arg Asn Met Trp Cys Lys Ile Gly His Asp
65                  70                  75                  80
Arg Cys Glu Glu Arg Asp His Asp Glu Leu Leu Met Ser Ile Pro Ser
                85                  90                  95
Gly Tyr Gly Gln Leu Lys Leu Glu Gly Tyr Tyr Ala Trp Leu Ala Phe
            100                 105                 110
Leu Ser Phe Ser Tyr Ala Ala Gln Phe His Pro Glu Leu Phe Gly Ile
            115                 120                 125
Gly Asn Val Ser Arg Val Phe Val Asp Lys Arg His Gln Phe Ile Cys
        130                 135                 140
Ala Glu His Asp Gly His Asn Ser Thr Val Ser Thr Gly His Asn Ile
145                 150                 155                 160
Ser Ala Leu Tyr Ala Ala Tyr His His Gln Ile Asp Gly Gly Asn
                165                 170                 175
Trp Phe His Leu Glu Trp Leu Arg Pro Leu Phe Ser Ser Trp Leu Val
            180                 185                 190
Leu Asn Ile Ser Trp Phe Leu Arg Arg Ser Pro Val Ser Pro Val Ser
```

```
              195                 200                 205

Arg Arg Ile Tyr Gln Ile Leu Arg Pro Thr Arg Pro Arg Leu Pro Val
    210                 215                 220

Ser Trp Ser Phe Arg Thr Ser Ile Val Ser Asp Leu Thr Gly Ser Gln
225                 230                 235                 240

Gln Arg Lys Arg Lys Phe Pro Ser Glu Ser Arg Pro Asn Val Val Lys
                245                 250                 255

Pro Ser Val Leu Pro Ser Thr Ser Arg
                260                 265

<210> SEQ ID NO 44
<211> LENGTH: 265
<212> TYPE: PRT
<213> ORGANISM: Artificial Sequence
<220> FEATURE:
<223> OTHER INFORMATION: ABH73414.1 PRRSV gp3

<400> SEQUENCE: 44

Met Ala His Gln Cys Ala Arg Phe His Phe Phe Leu Cys Gly Phe Ile
1               5                   10                  15

Cys Tyr Phe Val His Ser Ala Leu Ala Ser Asn Ser Ser Ser Thr Leu
                20                  25                  30

Cys Phe Trp Phe Pro Leu Ala His Gly Asn Thr Ser Phe Glu Leu Thr
            35                  40                  45

Ile Asn Tyr Thr Val Cys Met Pro Cys Pro Thr Ser Gln Ala Ala Leu
        50                  55                  60

Gln Arg Leu Glu Pro Gly Arg Asn Met Trp Cys Lys Ile Gly His Asp
65                  70                  75                  80

Arg Cys Glu Glu Arg Asp Gln Asp Glu Leu Leu Met Ser Ile Pro Ser
                85                  90                  95

Gly Tyr Asp Asn Leu Lys Leu Glu Gly Tyr Tyr Ala Trp Leu Ala Phe
                100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Trp His Gln Phe Ile Cys
        130                 135                 140

Ala Glu His Asp Gly Ser Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Phe Phe Ser Ser Trp Leu Val
                180                 185                 190

Leu Asn Ile Ser Trp Phe Leu Arg Arg Ser Pro Val Ser Pro Val Ser
            195                 200                 205

Arg Arg Ile Tyr Gln Ile Leu Arg Pro Thr Arg Pro Gln Leu Pro Val
    210                 215                 220

Ser Trp Ser Phe Arg Thr Ser Ile Val Ser Asp Leu Met Arg Ser Gln
225                 230                 235                 240

Gln Arg Lys Gly Lys Phe Pro Ser Gly Ser Arg Pro Asn Ala Val Lys
                245                 250                 255

Pro Ser Ala Leu Pro Asn Ile Ser Arg
                260                 265

<210> SEQ ID NO 45
<211> LENGTH: 254
<212> TYPE: PRT
```

<213> ORGANISM: Artificial Sequence
<220> FEATURE:
<223> OTHER INFORMATION: AAE74526.1 PRRSV gp3

<400> SEQUENCE: 45

```
Met Ala Asn Ser Cys Thr Phe Leu Tyr Ile Phe Leu Cys Cys Ser Phe
1               5                   10                  15

Leu Tyr Ser Phe Cys Cys Ala Val Val Ala Gly Ser Asn Ala Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Thr
    50                  55                  60

Glu Ala Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Val Val Pro Ser
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Gln Val Tyr Val Asp Ile Arg His Gln Phe Ile
    130                 135                 140

Cys Ala Val His Asp Gly Gln Asn Ala Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Ser His Val
        195                 200                 205

Ser Val Arg Val Leu Gln Thr Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Val Val Arg Arg
                245                 250
```

<210> SEQ ID NO 46
<211> LENGTH: 178
<212> TYPE: PRT
<213> ORGANISM: Artificial Sequence
<220> FEATURE:
<223> OTHER INFORMATION: AAE74537.1 PRRSV gp4

<400> SEQUENCE: 46

```
Met Ala Ser Ser Leu Leu Phe Leu Met Val Gly Phe Lys Cys Leu Leu
1               5                   10                  15

Val Ser Gln Ala Phe Ala Cys Lys Pro Cys Phe Ser Ser Ser Leu Ala
            20                  25                  30

Asp Ile Lys Thr Asn Thr Thr Ala Ala Ala Ser Phe Ala Val Leu Gln
        35                  40                  45

Asp Ile Gly Cys Leu Arg His Arg Asp Ser Ala Ser Glu Ala Ile Arg
    50                  55                  60

Lys Ile Pro Gln Cys Arg Thr Ala Ile Gly Thr Pro Val Tyr Ile Thr
65                  70                  75                  80
```

Ile Thr Ala Asn Val Thr Asp Glu Asn Tyr Leu His Ser Ser Asp Leu
            85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
            115                 120                 125

Val Asn Phe Thr Ser Tyr Val Gln His Val Arg Glu Phe Thr Gln Arg
            130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
            165                 170                 175

Ala Ile

<210> SEQ ID NO 47
<211> LENGTH: 178
<212> TYPE: PRT
<213> ORGANISM: Artificial Sequence
<220> FEATURE:
<223> OTHER INFORMATION: AAE74538.1 PRRSV gp4

<400> SEQUENCE: 47

Met Ala Ala Ser Leu Leu Phe Leu Met Val Gly Phe Lys Cys Leu Leu
1               5                   10                  15

Val Ser Gln Ala Phe Ala Cys Lys Pro Cys Phe Ser Ser Ser Leu Ala
            20                  25                  30

Asp Ile Lys Thr Asn Thr Thr Ala Ala Ala Ser Phe Ala Val Leu Gln
            35                  40                  45

Asp Ile Ser Cys Leu Arg His Arg Asn Ser Ala Ser Glu Ala Ile Arg
            50                  55                  60

Lys Ile Pro Gln Cys Arg Thr Ala Ile Gly Thr Pro Met Tyr Ile Thr
65                  70                  75                  80

Ile Thr Ala Asn Val Thr Asp Glu Asn Tyr Leu His Ser Ser Asp Leu
            85                  90                  95

Leu Met Leu Ser Ser Cys Leu Phe Tyr Ala Ser Glu Met Ser Glu Lys
            100                 105                 110

Gly Phe Glu Val Val Phe Gly Asn Val Ser Gly Ile Val Ala Val Cys
            115                 120                 125

Val Asn Phe Thr Ser Tyr Val Gln His Val Arg Glu Phe Thr Gln Arg
            130                 135                 140

Ser Leu Met Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
            165                 170                 175

Ala Ile

<210> SEQ ID NO 48
<211> LENGTH: 178
<212> TYPE: PRT
<213> ORGANISM: Artificial Sequence
<220> FEATURE:
<223> OTHER INFORMATION: AAE74533.1 PRRSV gp4

<400> SEQUENCE: 48

Met Gly Ala Ser Leu Leu Phe Leu Leu Val Gly Phe Lys Cys Leu Leu
1               5                   10                  15

Val Ser Gln Ala Phe Ala Cys Lys Pro Cys Phe Ser Ser Ser Leu Ser

```
                    20                  25                  30

Asp Ile Lys Thr Asn Thr Thr Ala Ala Ala Gly Phe Ala Val Leu Gln
            35                  40                  45

Asp Ile Ser Cys Leu Arg His Arg Asn Ser Ala Ser Glu Ala Ile Arg
        50                  55                  60

Lys Val Pro Gln Cys Arg Thr Ala Ile Gly Thr Pro Val Tyr Ile Thr
65                  70                  75                  80

Val Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
        115                 120                 125

Val Asn Phe Thr Ser Tyr Val Gln His Val Lys Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Thr Ile Leu Leu
                165                 170                 175

Ala Ile

<210> SEQ ID NO 49
<211> LENGTH: 183
<212> TYPE: PRT
<213> ORGANISM: Artificial Sequence
<220> FEATURE:
<223> OTHER INFORMATION: CAA01840.1 PRRSV gp4

<400> SEQUENCE: 49

Met Ala Ala Ala Thr Leu Phe Phe Leu Ala Gly Ala Gln His Ile Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Ala Gly Phe Met Val Leu Gln
        35                  40                  45

Asp Ile Asn Cys Phe Arg Pro His Gly Val Ser Ala Ala Gln Glu Lys
    50                  55                  60

Ile Ser Phe Gly Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Val Asn Phe Thr Asp Tyr Val Ala His Val Thr Gln
    130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
            180

<210> SEQ ID NO 50
```

```
<211> LENGTH: 183
<212> TYPE: PRT
<213> ORGANISM: Artificial Sequence
<220> FEATURE:
<223> OTHER INFORMATION: ABH73415.1 PRRSV gp4

<400> SEQUENCE: 50

Met Ala Ala Ala Ile Leu Phe Leu Leu Ala Gly Ala Gln His Ile Met
1               5

```
              130                 135                 140
Ser Leu Met Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile

<210> SEQ ID NO 52
<211> LENGTH: 73
<212> TYPE: PRT
<213> ORGANISM: Artificial Sequence
<220> FEATURE:
<223> OTHER INFORMATION: AGX46781.1 PRRSV E

<400> SEQUENCE: 52

Met Gly Ser Met Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
            20                  25                  30

Leu Ala Ile Leu Phe Gly Phe Thr Ile Ala Gly Trp Leu Val Val Phe
        35                  40                  45

Cys Ile Arg Leu Val Cys Ser Ala Ile Leu Arg Thr Arg Pro Ala Ile
    50                  55                  60

His Pro Glu Gln Leu Gln Lys Ile Leu
65                  70

<210> SEQ ID NO 53
<211> LENGTH: 73
<212> TYPE: PRT
<213> ORGANISM: Artificial Sequence
<220> FEATURE:
<223> OTHER INFORMATION: AED17147.1 PRRSV E

<400> SEQUENCE: 53

Met Gly Ser Ile Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
            20                  25                  30

Leu Ala Ile Leu Phe Gly Phe Thr Ile Ala Gly Trp Leu Val Val Phe
        35                  40                  45

Cys Ile Arg Leu Val Cys Ser Ala Val Phe Arg Ala Arg Pro Ala Ile
    50                  55                  60

His Pro Glu Gln Leu Gln Lys Ile Leu
65                  70

<210> SEQ ID NO 54
<211> LENGTH: 73
<212> TYPE: PRT
<213> ORGANISM: Artificial Sequence
<220> FEATURE:
<223> OTHER INFORMATION: AED17148.1 PRRSV E

<400> SEQUENCE: 54

Met Gly Ser Ile Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
            20                  25                  30

Leu Ala Ile Leu Phe Gly Phe Thr Ile Ala Gly Trp Leu Val Val Phe
        35                  40                  45
```

```
Cys Ile Arg Leu Val Ser Ser Ala Val Phe Arg Ala Arg Pro Ala Ile
 50                  55                  60

His Pro Glu Gln Leu Gln Lys Ile Leu
 65                  70
```

<210> SEQ ID NO 55
<211> LENGTH: 69
<212> TYPE: PRT
<213> ORGANISM: Artificial Sequence
<220> FEATURE:
<223> OTHER INFORMATION: AGX46783.1 PRRSV E

<400> SEQUENCE: 55

```
Met Gly Ser Met Gln Ser Leu Phe Asp Lys Ile Gly Gln Leu Phe Val
  1               5                  10                  15

Asp Ala Phe Thr Glu Phe Leu Val Ser Ile Val Asp Ile Ile Ile Phe
                 20                  25                  30

Leu Ala Ile Leu Phe Gly Phe Thr Ile Ala Gly Trp Leu Val Val Phe
             35                  40                  45

Cys Ile Arg Leu Val Cys Ser Ala Leu Arg Arg Pro Ala His Glu Gln
 50                  55                  60

Leu Gln Lys Ile Leu
 65
```

<210> SEQ ID NO 56
<211> LENGTH: 70
<212> TYPE: PRT
<213> ORGANISM: Artificial Sequence
<220> FEATURE:
<223> OTHER INFORMATION: AED17156.1 PRRSV E

<400> SEQUENCE: 56

```
Met Gly Ser Leu Trp Ser Lys Ile Ser Gln Leu Phe Val Asp Ala Phe
  1               5                  10                  15

Thr Glu Phe Leu Val Ser Val Val Asp Ile Ala Ile Phe Leu Ala Ile
                 20                  25                  30

Leu Phe Gly Phe Thr Val Ala Gly Trp Leu Leu Val Phe Leu Leu Arg
             35                  40                  45

Val Val Cys Ser Ala Leu Leu Arg Ser Arg Ser Ala Ile His Ser Pro
 50                  55                  60

Glu Leu Ser Lys Val Leu
 65                  70
```

<210> SEQ ID NO 57
<211> LENGTH: 73
<212> TYPE: PRT
<213> ORGANISM: Artificial Sequence
<220> FEATURE:
<223> OTHER INFORMATION: AIS76359.1 PRRSV E

<400> SEQUENCE: 57

```
Met Gly Ser Met Gln Ser Leu Phe Asp Lys Ile Gly Gln Leu Phe Val
  1               5                  10                  15

Asp Ala Phe Thr Glu Phe Leu Val Ser Ile Val Asp Ile Ile Ile Phe
                 20                  25                  30

Leu Ala Ile Leu Phe Gly Phe Thr Val Ala Gly Trp Leu Val Val Phe
             35                  40                  45

Cys Ile Arg Leu Val Phe Ser Ala Val Leu Arg Ala Arg Ser Thr Val
 50                  55                  60

His Pro Glu Gln Leu Gln Lys Ile Leu
```

```
<210> SEQ ID NO 58
<211> LENGTH: 70
<212> TYPE: PRT
<213> ORGANISM: Artificial Sequence
<220> FEATURE:
<223> OTHER INFORMATION: ABU49670.1 PRRSV E

<400> SEQUENCE: 58

Met Gly Ser Leu Trp Ser Lys Ile Ser Gln Leu Phe Val Asp Ala Phe
1               5                   10                  15

Thr Glu Phe Leu Val Ser Val Val Asp Ile Val Ile Phe Leu Ala Ile
                20                  25                  30

Leu Phe Gly Phe Thr Val Ala Gly Gly Leu Leu Val Phe Phe Leu Arg
            35                  40                  45

Val Val Cys Ser Ala Ile Leu Arg Ser Arg Ser Ala Ile His Ser Pro
    50                  55                  60

Glu Leu Ser Lys Ile Leu
65                  70

<210> SEQ ID NO 59
<211> LENGTH: 200
<212> TYPE: PRT
<213> ORGANISM: Artificial Sequence
<220> FEATURE:
<223> OTHER INFORMATION: VR2332 PRRSV gp5

<400> SEQUENCE: 59

Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
                20                  25                  30

Asn Asp Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
    50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
    115                 120                 125

Lys Asn Cys Met Ser Trp Arg Tyr Ala Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Trp Gly Arg Pro
    195                 200

<210> SEQ ID NO 60
<211> LENGTH: 201
```

<212> TYPE: PRT
<213> ORGANISM: Artificial Sequence
<220> FEATURE:
<223> OTHER INFORMATION: CAA01841.1 PRRSV gp5

<400> SEQUENCE: 60

```
Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asp Ser Ser Thr Tyr Gln Tyr Ile Tyr Asn Leu Thr
        35                  40                  45

Ile Cys Glu Leu Asn Gly Thr Asp Trp Leu Ser Ser His Phe Gly Trp
    50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
    130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200
```

<210> SEQ ID NO 61
<211> LENGTH: 200
<212> TYPE: PRT
<213> ORGANISM: Artificial Sequence
<220> FEATURE:
<223> OTHER INFORMATION: ADA15222.1 PRRSV gp5

<400> SEQUENCE: 61

```
Met Leu Gly Lys Cys Leu Thr Ala Gly Cys Cys Ser Gln Leu Pro Phe
1               5                   10                  15

Leu Trp Cys Ile Val Pro Phe Cys Phe Ala Ala Leu Val Asn Ala Ser
            20                  25                  30

Ser Ser Ser Ser Ser Gln Leu Gln Ser Ile Tyr Asn Leu Thr Ile Cys
        35                  40                  45

Glu Leu Asn Gly Thr Asp Trp Leu Asn Lys Asn Phe Asp Trp Ala Val
    50                  55                  60

Glu Thr Phe Val Ile Phe Pro Val Leu Thr His Ile Val Ser Tyr Gly
65                  70                  75                  80

Ala Leu Thr Thr Ser His Phe Leu Asp Ala Val Gly Leu Ile Thr Val
                85                  90                  95

Ser Thr Ala Gly Tyr Tyr His Gly Arg Ser Val Leu Ser Ser Val Tyr
            100                 105                 110

Ala Val Cys Ala Leu Ala Ala Leu Ile Cys Phe Val Ile Arg Leu Thr
        115                 120                 125
```

-continued

```
Lys Asn Cys Met Ser Trp Arg Tyr Ser Cys Thr Arg Tyr Thr Asn Phe
    130                 135                 140

Leu Leu Asp Ser Lys Gly Lys Leu Tyr Arg Trp Arg Ser Pro Val Ile
145                 150                 155                 160

Ile Glu Lys Gly Gly Lys Val Glu Val Asp Gly His Leu Ile Asp Leu
                165                 170                 175

Lys Arg Val Val Leu Asp Gly Ser Ala Ala Thr Pro Val Thr Lys Val
            180                 185                 190

Ser Ala Glu Gln Trp Cys Arg Pro
        195                 200

<210> SEQ ID NO 62
<211> LENGTH: 46
<212> TYPE: PRT
<213> ORGANISM: Artificial Sequence
<220> FEATURE:
<223> OTHER INFORMATION: AFS30909.1 PRRSV gp5a

<400> SEQUENCE: 62

Met Phe Lys Tyr Val Gly Glu Val Leu Asp Arg Val Leu Leu Leu Ala
1               5                   10                  15

Ile Ala Phe Phe Val Val Tyr Arg Ala Val Leu Ser Cys Cys Ala Arg
            20                  25                  30

Gln Arg Gln Gln Gln Gln Gln Leu Ser Tyr Ser Val Asp Leu
        35                  40                  45

<210> SEQ ID NO 63
<211> LENGTH: 51
<212> TYPE: PRT
<213> ORGANISM: Artificial Sequence
<220> FEATURE:
<223> OTHER INFORMATION: AGK45334.1 PRRSV gp5a

<400> SEQUENCE: 63

Met Phe Lys Tyr Val Gly Glu Leu Leu Asp Arg Gly Leu Leu Leu Ala
1               5                   10                  15

Ile Ala Phe Phe Val Val Tyr Arg Ala Val Leu Phe Tyr Cys Ala Arg
            20                  25                  30

Gln Arg Gln Arg Lys Gln Gln Leu Leu Leu Pro Val Asp Leu Gln Leu
        35                  40                  45

Asp Ala Met
    50

<210> SEQ ID NO 64
<211> LENGTH: 51
<212> TYPE: PRT
<213> ORGANISM: Artificial Sequence
<220> FEATURE:
<223> OTHER INFORMATION: AFU75332.1 PRRSV gp5a

<400> SEQUENCE: 64

Met Phe Lys Tyr Val Gly Glu Met Leu Asp Arg Gly Leu Leu Leu Ala
1               5                   10                  15

Ile Ala Phe Phe Val Val Tyr Arg Ala Val Leu Phe His Cys Ala Arg
            20                  25                  30

Arg Arg Gln Arg Gln Gln Gln Leu Ser Ser Ala Ile Asp Leu Gln Leu
        35                  40                  45

Asp Ala Met
    50
```

<210> SEQ ID NO 65
<211> LENGTH: 46
<212> TYPE: PRT
<213> ORGANISM: Artificial Sequence
<220> FEATURE:
<223> OTHER INFORMATION: AGW23843.1 PRRSV gp5a

<400> SEQUENCE: 65

```
Met Phe Lys Tyr Val Gly Glu Met Leu Asp Arg Gly Leu Leu Leu Thr
1               5                   10                  15

Ile Ala Phe Phe Val Val Tyr Arg Ala Val Leu Val Cys Cys Ala Arg
            20                  25                  30

Gln Ser Arg Lys Arg Gln Gln Leu Pro Leu Thr Val Asp Ile
        35                  40                  45
```

<210> SEQ ID NO 66
<211> LENGTH: 152
<212> TYPE: PRT
<213> ORGANISM: PRRSV VR2332

<400> SEQUENCE: 66

```
Met Asp Ala Met Lys Arg Gly Leu Cys Cys Val Leu Leu Leu Cys Gly
1               5                   10                  15

Ala Val Phe Val Ser Pro Ser Asp Tyr Lys Asp Asp Asp Asp Lys Gly
            20                  25                  30

Gly Ser Ser Asn Asp Ser Ser His Leu Gln Leu Ile Tyr Asn Leu
        35                  40                  45

Thr Leu Cys Glu Leu Asn Gly Thr Asp Trp Leu Ala Asn Lys Phe Asp
    50                  55                  60

Trp Ala Val Glu Ser Phe Val Ile Phe Pro Val Leu Thr His Ile Val
65                  70                  75                  80

Ser Tyr Gly Ala Leu Thr Thr Ser His Phe Leu Asp Thr Val Ala Leu
                85                  90                  95

Val Thr Val Ser Thr Ala Gly Phe Val His Gly Arg Tyr Val Leu Ser
            100                 105                 110

Ser Ile Tyr Ala Val Cys Ala Leu Ala Ala Leu Thr Cys Phe Val Ile
        115                 120                 125

Arg Phe Ala Lys Leu Lys His Thr Lys Lys Arg Gln Ile Tyr Thr Asp
    130                 135                 140

Ile Glu Met Asn Arg Leu Gly Lys
145                 150
```

<210> SEQ ID NO 67
<211> LENGTH: 459
<212> TYPE: DNA
<213> ORGANISM: PRRSV VR2332

<400> SEQUENCE: 67

```
atggatgcta tgaaacgggg actgtgctgc gtgctgctgc tctgtggggc tgtcttcgtg      60
tcaccttctg attataagga cgatgacgat aaaggaggaa gtagcaatga cagctcctct     120
cacctgcagc tcatctacaa cctgacccct tgcgagctga atggaacaga ctggctcgct     180
aacaagttcg attgggcagt ggaatccttc gtcatctttc ccgtgctgac tcacattgtg     240
agctatgggg ccctgaccac atcccatttc ctggatacag tggccctcgt gactgtctct     300
accgctggct tgtccatgg acgctacgtg ctgtcaagta tctatgcagt ctgcgccctg     360
gccgctctca cctgtttcgt gattagattt gcaaagctga agcatacaaa gaagcggcag     420
```
atttacactg acattgagat gaatagactg ggcaaatga 459

<210> SEQ ID NO 68
<211> LENGTH: 155
<212> TYPE: PRT
<213> ORGANISM: PRRSV VR2332

<400> SEQUENCE: 68

```
Met Asp Ala Met Lys Arg Gly Leu Cys Cys Val Leu Leu Leu Cys Gly
1               5                   10                  15

Ala Val Phe Val Ser Pro Tyr Pro Tyr Asp Val Pro Asp Tyr Ala Gly
            20                  25                  30

Gly Ser Gly Ser Ser Leu Asp Asp Phe Cys His Asp Ser Thr Ala Pro
        35                  40                  45

Gln Lys Val Leu Leu Ala Phe Ser Ile Thr Tyr Thr Pro Val Met Ile
    50                  55                  60

Tyr Ala Leu Lys Val Ser Arg Gly Arg Leu Leu Gly Leu Leu His Leu
65                  70                  75                  80

Leu Ile Phe Leu Asn Cys Ala Phe Thr Phe Gly Tyr Met Thr Phe Ala
                85                  90                  95

His Phe Gln Ser Thr Asn Lys Val Ala Leu Thr Met Gly Ala Val Val
            100                 105                 110

Ala Leu Leu Trp Gly Val Tyr Ser Ala Ile Glu Thr Trp Lys Phe Ile
        115                 120                 125

Thr Ser Arg Cys Arg Leu Lys Leu Lys His Thr Lys Lys Arg Gln Ile
    130                 135                 140

Tyr Thr Asp Ile Glu Met Asn Arg Leu Gly Lys
145                 150                 155
```

<210> SEQ ID NO 69
<211> LENGTH: 468
<212> TYPE: DNA
<213> ORGANISM: PRRSV VR2332

<400> SEQUENCE: 69

```
atggatgcta tgaaacgggg actgtgctgc gtgctgctgc tctgtggggc tgtcttcgtg      60
tcaccttacc cctatgacgt gccagattac gcaggaggaa gtgggtcaag cctcgacgat     120
ttttgtcacg attcaacagc acctcagaaa gtcctcctcg ccttcagcat cacatacact     180
ccagtcatga tctacgccct gaaggtgagt aggggcagac tgctcggact gctccacctg     240
ctcattttcc tgaactgcgc attcactttt ggctatatga ccttcgccca ttttcagtcc     300
accaacaagg tggctctgac aatgggagca gtggtcgctc tgctctgggg ggtctacagc     360
gccatcgaga catggaagtt tattacttcc cgatgccgac tgaagctgaa gcatacaaag     420
aagcggcaga tttacactga cattgagatg aatagactgg gcaaatga                  468
```

<210> SEQ ID NO 70
<211> LENGTH: 747
<212> TYPE: DNA
<213> ORGANISM: PRRSV

<400> SEQUENCE: 70

```
atgcaatggg gtcactgtgg agtaaaatca gccagctgtt cgtggacgcc ttcactgagt      60
tccttgttag tgtggttgat attgccattt tccttgccat actgtttggg ttcaccgtcg     120
caggatggtt actggtcttt cttctcagag tggtttgctc cgcgcttctc cgttcgcgct     180
ctgccattca ctctcccgaa ctatcgaagg tcctatgaag gcttgttgcc caactgcaga     240
```

```
ccggatgtcc cacaatttgc agtcaagcac ccattgggta tgttttggca catgcgagtt       300
tcccacttga ttgatgagat ggtctctcgt cgcatttacc agaccatgga acattcaggt       360
caagcggcct ggaagcaggt ggttggtgag ccactctca cgaagctgtc agggctcgat        420
atagttactc atttccaaca cctggccgca gtggaggcgg attcttgccg ctttctcagc       480
tcacgactcg tgatgctaaa aaatcttgcc gttggcaatg tgagcctaca gtacaacacc       540
acgttggacc gcgttgagct catcttcccc acgccaggta cgaggcccaa gttgaccgat       600
ttcagacaat ggctcatcag tgtgcacgct ccattttt cctctgtggc ttcatctgtt         660
accttgttca tagtgctttg gcttcgaatt ccagctctac gctatgtttt tggtttccat       720
tggcccacgg caacacatca ttcgagc                                           747
```

<210> SEQ ID NO 71
<211> LENGTH: 249
<212> TYPE: PRT
<213> ORGANISM: PRRSV

<400> SEQUENCE: 71

```
Met Gln Trp Gly His Cys Gly Val Lys Ser Ala Ser Cys Ser Trp Thr
1               5                   10                  15

Pro Ser Leu Ser Ser Leu Leu Val Trp Leu Ile Leu Pro Phe Ser Leu
            20                  25                  30

Pro Tyr Cys Leu Gly Ser Pro Ser Gln Asp Gly Tyr Trp Ser Phe Phe
        35                  40                  45

Ser Glu Trp Phe Ala Pro Arg Phe Ser Val Arg Ala Leu Pro Phe Thr
50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Val Lys His Pro Leu Gly Met Phe Trp
                85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
        115                 120                 125

Gly Glu Ala Thr Leu Thr Lys Leu Ser Gly Leu Asp Ile Val Thr His
130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

<210> SEQ ID NO 72
<211> LENGTH: 795
<212> TYPE: DNA

<210> SEQ ID NO 72
<211> LENGTH: 795
<212> TYPE: DNA
<213> ORGANISM: PRRSV

<400> SEQUENCE: 72

```
atggctcatc agtgtgcacg cttccatttt ttcctctgtg gcttcatctg ttaccttgtt      60
catagtgctt tggcttcgaa ttccagctct acgctatgtt tttggtttcc attggcccac     120
ggcaacacat cattcgagct gaccatcaac tacaccatat gcatgccctg ttctaccagt     180
caagcggctc gccaaaggct cgagcccggt cgtaacatgt ggtgcaaaat agggcatgac     240
aggtgtgagg agcgtgacca tgatgagttg ttaatgtcca tcccgtccgg gtacgacaac     300
ctcaaacttg agggttatta tgcttggctg gcttttttgt cctttttccta cgcggcccaa     360
ttccatccgg agttgttcgg atagggaat gtgtcgcgcg tcttcgtgga caagcgacac     420
cagttcattt tgtgccgagca tgatggacac aattcaaccg tatctaccgg acacaacatc     480
tccgcattat atgcggcata ttaccaccac caaatagacg ggggcaattg gttccatttg     540
gaatggctgc ggccactctt ttcttcctgg ctggtgctca acatatcatg gtttctgagg     600
cgttcgcctg taagccctgt ttctcgacgc atctatcaga tattgagacc aacacgaccg     660
cggctgccgg tttcatggtc cttcaggaca tcaattgttt ccgacctcac ggggtctcag     720
cagcgcaaga gaaatttcc ttcggaaagt cgtcccaatg tcgtgaagcc gtcggtactc     780
cccagtacat cacga                                                      795
```

<210> SEQ ID NO 73
<211> LENGTH: 158
<212> TYPE: PRT
<213> ORGANISM: PRRSV

<400> SEQUENCE: 73

```
Met Ala His Gln Cys Ala Arg Phe His Phe Phe Leu Cys Gly Phe Ile
  1               5                  10                  15

Cys Tyr Leu Val His Ser Ala Leu Ala Ser Asn Ser Ser Thr Leu
             20                  25                  30

Cys Phe Trp Phe Pro Leu Ala His Gly Asn Thr Ser Phe Glu Leu Thr
         35                  40                  45

Ile Asn Tyr Thr Ile Cys Met Pro Cys Ser Thr Ser Gln Ala Ala Arg
     50                  55                  60

Gln Arg Leu Glu Pro Gly Arg Asn Met Trp Cys Lys Ile Gly His Asp
 65                  70                  75                  80

Arg Cys Glu Glu Arg Asp His Asp Glu Leu Leu Met Ser Ile Pro Ser
                 85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Arg His Gln Phe Ile Cys
    130                 135                 140

Ala Glu His Asp Gly His Asn Ser Thr Val Ser Thr Gly His
145                 150                 155
```

<210> SEQ ID NO 74
<211> LENGTH: 549
<212> TYPE: DNA
<213> ORGANISM: PRRSV

<400> SEQUENCE: 74

```
atggctgcgg ccactctttt cttcctggct ggtgctcaac atatcatggt ttctgaggcg      60
```

```
ttcgcctgta agccctgttt ctcgacgcat ctatcagata ttgagaccaa cacgaccgcg      120
gctgccggtt tcatggtcct tcaggacatc aattgtttcc gacctcacgg ggtctcagca      180
gcgcaagaga aaatttcctt cggaaagtcg tcccaatgtc gtgaagccgt cggtactccc      240
cagtacatca cgataacggc taacgtgacc gacgaatcat acttgtacaa cgcggacctg      300
ctgatgcttt ctgcgtgcct tttctacgcc tcagaaatga gcgagaaagg cttcaaagtc      360
atctttggga atgtctctgg cgttgttcct gcttgtgtca atttcacaga ttatgtggcc      420
catgtgaccc aacataccca gcagcatcat ctggtaattg atcacattcg gttgctgcat      480
ttcctgacac catctgcaat gaggtgggct acaaccattg cttgtttgtt cgccattctc      540
ttggcaata                                                              549
```

<210> SEQ ID NO 75
<211> LENGTH: 183
<212> TYPE: PRT
<213> ORGANISM: PRRSV

<400> SEQUENCE: 75

```
Met Ala Ala Thr Leu Phe Phe Leu Ala Gly Ala Gln His Ile Met
1               5                   10                  15

Val Ser Glu Ala Phe Ala Cys Lys Pro Cys Phe Ser Thr His Leu Ser
                20                  25                  30

Asp Ile Glu Thr Asn Thr Thr Ala Ala Gly Phe Met Val Leu Gln
            35                  40                  45

Asp Ile Asn Cys Phe Arg Pro His Gly Val Ser Ala Ala Gln Glu Lys
        50                  55                  60

Ile Ser Phe Gly Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
                100                 105                 110

Met Ser Glu Lys Gly Phe Lys Val Ile Phe Gly Asn Val Ser Gly Val
            115                 120                 125

Val Ser Ala Cys Val Asn Phe Thr Asp Tyr Val Ala His Val Thr Gln
        130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
            180
```

<210> SEQ ID NO 76
<211> LENGTH: 603
<212> TYPE: DNA
<213> ORGANISM: PRRSV

<400> SEQUENCE: 76

```
atgagatgtt ctcacaaatt ggggcgtttc ttgactccgc actcttgctt ctggtggctt       60
tttttgctgt gtaccggctt gtcctggtcc tttgccgatg caacggcga cagctcgaca      120 taccaataca tatataactt gacgatatgc gagctgaatg ggaccgactg gttgtccagc      180
cattttggtt gggcagtcga gacctttgtg ctttacccgg ttgccactca tatcctctca      240
```

-continued

```
ctgggttttc tcacaacaag ccatttttt gacgcgctcg gtctcggcgc tgtatccact    300
gcaggatttg ttggcgggcg gtacgtactc tgcagcgtct acggcgcttg tgctttcgca    360
gcgttcgtat gttttgtcat ccgtgctgct aaaaattgca tggcctgccg ctatgcccgt    420
acccggttta ccaacttcat tgtggacgac cggggagag ttcatcgatg gaagtctcca    480
atagtggtag aaaaattggg caaagccgaa gtcgatggca acctcgtcac catcaaacat    540
gtcgtcctcg aagggttaa agctcaaccc ttgacgagga cttcggctga gcaatgggag    600
gcc                                                                  603
```

<210> SEQ ID NO 77
<211> LENGTH: 201
<212> TYPE: PRT
<213> ORGANISM: PRRSV

<400> SEQUENCE: 77

```
Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asp Ser Ser Thr Tyr Gln Tyr Ile Tyr Asn Leu Thr
        35                  40                  45

Ile Cys Glu Leu Asn Gly Thr Asp Trp Leu Ser Ser His Phe Gly Trp
    50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
    130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200
```

<210> SEQ ID NO 78
<211> LENGTH: 519
<212> TYPE: DNA
<213> ORGANISM: PRRSV

<400> SEQUENCE: 78

```
atgggaggcc tagacgattt ttgcaacgat cctatcgccg cacaaaagct cgtgctagcc     60
tttagcatca catacacacc tataatgata tacgcccta aggtgtcacg cggccgactc    120
ctggggctgt tgcacatcct aatatttctg aactgttcct ttacattcgg atacatgaca    180
tatgtgcatt tcaatccac caaccgtgtc gcacttaccc tggggctgt tgtcgccctt    240 ctgtggggtg tttacagctt cacagagtca tggaagttta tcacttccag atgcagattg    300
```

-continued

```
tgttgccttg gccggcgata cattctggcc cctgcccatc acgtagaaag tgctgcaggt    360
ctccattcaa tctcagcgtc tggtaaccga gcatacgctg tgagaaagcc cggactaaca    420
tcagtgaacg gcactctagt accaggactt cggagcctcg tgctgggcgg caaacgagct    480
gttaaacgag gagtggttaa cctcgtcaag tatggccgg                           519
```

<210> SEQ ID NO 79
<211> LENGTH: 173
<212> TYPE: PRT
<213> ORGANISM: PRRSV

<400> SEQUENCE: 79

```
Met Gly Gly Leu Asp Asp Phe Cys Asn Asp Pro Ile Ala Ala Gln Lys
1               5                   10                  15

Leu Val Leu Ala Phe Ser Ile Thr Tyr Thr Pro Ile Met Ile Tyr Ala
            20                  25                  30

Leu Lys Val Ser Arg Gly Arg Leu Leu Gly Leu Leu His Ile Leu Ile
        35                  40                  45

Phe Leu Asn Cys Ser Phe Thr Phe Gly Tyr Met Thr Tyr Val His Phe
    50                  55                  60

Gln Ser Thr Asn Arg Val Ala Leu Thr Leu Gly Ala Val Val Ala Leu
65                  70                  75                  80

Leu Trp Gly Val Tyr Ser Phe Thr Glu Ser Trp Lys Phe Ile Thr Ser
                85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Ser Ile Ser Ala Ser Gly
        115                 120                 125

Asn Arg Ala Tyr Ala Val Arg Lys Pro Gly Leu Thr Ser Val Asn Gly
    130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170
```

<210> SEQ ID NO 80
<211> LENGTH: 249
<212> TYPE: PRT
<213> ORGANISM: related to Lelystad PRRSV

<400> SEQUENCE: 80

```
Met Gln Trp Gly His Cys Gly Val Lys Ser Ala Ser Cys Ser Trp Thr
1               5                   10                  15

Pro Ser Leu Ser Ser Leu Leu Val Trp Leu Ile Leu Ser Phe Ser Leu
            20                  25                  30

Pro Tyr Cys Leu Gly Ser Pro Ser Gln Asp Gly Tyr Trp Ser Phe Phe
        35                  40                  45

Ser Glu Trp Phe Ala Pro Arg Phe Ser Val Arg Ala Leu Pro Phe Thr
    50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Val Lys His Pro Leu Gly Met Phe Trp
                85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
```

```
                115                 120                 125
Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Val Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

<210> SEQ ID NO 81
<211> LENGTH: 249
<212> TYPE: PRT
<213> ORGANISM: related to Lelystad PRRSV

<400> SEQUENCE: 81

```
Met Gln Trp Gly His Cys Gly Val Lys Ser Ala Ser Cys Ser Trp Thr
1               5                   10                  15

Pro Ser Leu Ser Ser Leu Leu Val Trp Leu Ile Leu Ser Phe Ser Leu
                20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
    50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Phe Lys His Pro Leu Gly Met Leu Trp
                85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
    115                 120                 125

Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ala Leu Arg Tyr Val Phe Gly Phe His
225                 230                 235                 240
```

```
Trp Pro Thr Ala Thr His His Ser Ser
                245

<210> SEQ ID NO 82
<211> LENGTH: 249
<212> TYPE: PRT
<213> ORGANISM: related to Lelystad PRRSV

<400> SEQUENCE: 82

Met Gln Trp Gly His Cys Gly Val Lys Ser Ala Ser Cys Ser Trp Thr
1               5                   10                  15

Pro Ser Leu Ser Ser Leu Leu Val Trp Leu Ile Leu Ser Phe Ser Leu
            20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
    50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Phe Lys His Pro Leu Gly Met Phe Trp
                85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
        115                 120                 125

Gly Glu Ala Thr Leu Thr Lys Leu Ser Gly Leu Asp Ile Val Thr His
    130                 135                 140

Phe Gln Tyr Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Val Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245

<210> SEQ ID NO 83
<211> LENGTH: 249
<212> TYPE: PRT
<213> ORGANISM: related to Lelystad PRRSV

<400> SEQUENCE: 83

Met Gln Trp Gly His Cys Gly Val Lys Ser Ala Ser Cys Ser Trp Thr
1               5                   10                  15

Pro Ser Leu Ser Ser Leu Leu Val Trp Leu Ile Leu Ser Phe Ser Leu
            20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
    50                  55                  60
```

```
Leu Pro Asn Tyr Arg Arg Ser Tyr Glu Gly Leu Pro Asn Cys Arg
 65                  70                  75                  80

Pro Asp Val Pro Gln Phe Ala Val Lys His Pro Leu Gly Met Phe Trp
                 85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
        115                 120                 125

Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Val
    210                 215                 220

Val Leu Trp Leu Arg Ile Pro Ile Leu Arg Tyr Val Phe Gly Phe His
225                 230                 235                 240

Trp Pro Thr Ala Thr His His Leu Ser
                245

<210> SEQ ID NO 84
<211> LENGTH: 249
<212> TYPE: PRT
<213> ORGANISM: related to Lelystad PRRSV

<400> SEQUENCE: 84

Met Gln Trp Gly His Cys Gly Val Arg Ser Ala Ser Cys Ser Trp Thr
  1               5                  10                  15

Pro Ser Leu Ser Ser Leu Leu Val Trp Leu Ile Leu Ser Phe Phe Leu
             20                  25                  30

Pro Tyr Cys Leu Gly Ser Pro Ser Gln Asp Gly Tyr Trp Ser Phe Phe
         35                  40                  45

Ser Glu Trp Phe Ala Pro Arg Phe Ser Val Arg Ala Leu Pro Phe Thr
     50                  55                  60

Leu Pro Asn Tyr Arg Arg Ser Tyr Glu Gly Leu Leu Pro Asn Cys Arg
 65                  70                  75                  80

Pro Asp Val Pro Gln Phe Ala Val Lys His Pro Leu Gly Met Phe Trp
                 85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys His Val Val
        115                 120                 125

Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asn Arg Val Glu Leu Ile Phe Pro Thr Pro
            180                 185                 190
```

```
Gly Thr Arg Pro Lys Leu Thr Asp Phe Arg Gln Trp Leu Ile Ser Val
            195                 200                 205

His Ala Ser Ile Phe Ser Ser Val Ala Ser Ser Val Thr Leu Phe Thr
        210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

<210> SEQ ID NO 85
<211> LENGTH: 249
<212> TYPE: PRT
<213> ORGANISM: related to Lelystad PRRSV

<400> SEQUENCE: 85

```
Met Gln Trp Gly His Cys Gly Val Lys Ser Ala Ser Cys Ser Trp Thr
1               5                   10                  15

Pro Ser Leu Ser Ser Leu Leu Val Trp Leu Thr Leu Ser Phe Ser Leu
            20                  25                  30

Pro Tyr Cys Leu Gly Ser Pro Ser Gln Asp Gly Tyr Trp Ser Phe Phe
        35                  40                  45

Ser Glu Trp Phe Ala Pro Arg Phe Ser Val Arg Ala Leu Pro Phe Thr
50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Leu Lys His Pro Leu Gly Met Leu Trp
                85                  90                  95

His Met Arg Val Ser His Leu Ile Asp Glu Met Val Ser Arg Arg Ile
            100                 105                 110

Tyr Gln Thr Leu Glu His Ser Gly Gln Ala Ala Trp Lys Gln Ala Val
        115                 120                 125

Gly Glu Ala Thr Leu Thr Lys Leu Ser Arg Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

<210> SEQ ID NO 86
<211> LENGTH: 249
<212> TYPE: PRT
<213> ORGANISM: related to Lelystad PRRSV

<400> SEQUENCE: 86

```
Met Gln Trp Gly His Cys Gly Val Lys Leu Ala Ser Cys Ser Trp Thr
1               5                   10                  15
```

Pro Ser Leu Ser Ser Leu Leu Val Trp Leu Ile Leu Ser Phe Ser Leu
            20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
 50                  55                  60

Leu Pro Asn Tyr Arg Arg Ser Tyr Glu Ser Leu Leu Pro Asn Cys Arg
 65                  70                  75                  80

Pro Asp Val Pro Gln Phe Ala Val Lys His Pro Leu Gly Met Leu Trp
                 85                  90                  95

His Met Arg Val Ser His Leu Ile Asp Glu Met Val Ser Arg Arg Ile
            100                 105                 110

Tyr Arg Thr Met Glu His Ser Gly Gln Ala Ala Trp Lys Gln Val Val
            115                 120                 125

Ser Glu Ala Thr Leu Thr Lys Leu Ser Gly Leu Asp Ile Val Thr His
130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
            165                 170                 175

Gln Tyr Asn Thr Thr Leu Asp His Val Glu Leu Ile Phe Pro Thr Pro
            180                 185                 190

Gly Thr Arg Pro Lys Leu Thr Asp Phe Arg Gln Trp Leu Ile Ser Val
            195                 200                 205

His Ala Ser Ile Phe Ser Ser Val Ala Ser Ser Val Thr Leu Phe Ile
            210                 215                 220

Val Phe Trp Leu Arg Ile Pro Ala Val Arg Tyr Val Phe Gly Phe His
225                 230                 235                 240

Trp Pro Thr Ala Thr His His Ser Ser
                245

<210> SEQ ID NO 87
<211> LENGTH: 249
<212> TYPE: PRT
<213> ORGANISM: related to Lelystad PRRSV

<400> SEQUENCE: 87

Met Gln Trp Gly His Cys Gly Val Lys Leu Ala Ser Cys Ser Trp Thr
 1               5                  10                  15

Leu Ser Leu Asn Ser Leu Leu Val Trp Leu Ile Leu Ser Phe Ser Leu
            20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
 50                  55                  60

Leu Pro Asn Tyr Arg Arg Ser Tyr Glu Gly Leu Leu Pro Asn Cys Lys
 65                  70                  75                  80

Pro Asp Val Pro Gln Phe Ala Phe Lys His Pro Leu Gly Met Phe Trp
                 85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
            115                 120                 125

Gly Glu Ala Thr Leu Thr Lys Leu Ser Arg Leu Asp Ile Val Thr His

```
                    130                 135                 140
Phe Gln His Leu Ala Ala Val Glu Ala Asp Ser Cys Arg Phe Leu Ser
145                 150                 155                 160

Ser Arg Leu Val Met Leu Lys Asn Leu Val Val Gly Asn Val Ser Leu
                165                 170                 175

Gln Tyr Asn Thr Thr Leu Asp Arg Val Glu Leu Val Phe Pro Thr Pro
            180                 185                 190

Gly Ala Arg Pro Lys Leu Thr Asp Phe Arg Gln Trp Leu Val Ser Val
            195                 200                 205

His Ala Ser Ile Phe Ser Ser Val Thr Ser Val Thr Leu Phe Ile
            210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245
```

<210> SEQ ID NO 88
<211> LENGTH: 249
<212> TYPE: PRT
<213> ORGANISM: related to Lelystad PRRSV

<400> SEQUENCE: 88

```
Met Gln Trp Gly His Cys Gly Val Lys Leu Ala Ser Cys Ser Trp Thr
1               5                   10                  15

Pro Ser Leu Ser Ser Leu Val Trp Leu Ile Leu Leu Ser Ser Leu
                20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
50                  55                  60

Leu Pro Asn Tyr Arg Arg Ser Tyr Glu Ser Leu Leu Pro Asn Cys Arg
65                  70                  75                  80

Pro Asp Val Pro Gln Phe Ala Phe Lys His Pro Leu Gly Ile Leu Trp
                85                  90                  95

His Met Arg Val Ser His Leu Ile Asp Glu Met Val Ser Arg Arg Ile
                100                 105                 110

Tyr Arg Thr Met Glu His Ser Gly Gln Ala Ala Trp Lys Gln Val Val
            115                 120                 125

Ser Glu Ala Thr Leu Thr Lys Leu Ser Gly Leu Asp Ile Val Ala His
130                 135                 140

Phe Gln His Leu Ala Ala Ala Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Gln Val Glu Leu Ile Phe Pro Thr Pro
            180                 185                 190

Gly Thr Arg Pro Lys Leu Thr Asp Phe Arg Gln Trp Leu Ile Ser Val
            195                 200                 205

His Ala Ser Ile Phe Ser Ser Val Ala Ser Ser Val Thr Leu Phe Ile
            210                 215                 220

Val Phe Trp Leu Arg Ile Pro Ala Val Arg Tyr Val Phe Gly Phe His
225                 230                 235                 240

Trp Pro Thr Ala Thr Arg His Ser Ser
                245
```

<210> SEQ ID NO 89
<211> LENGTH: 249
<212> TYPE: PRT
<213> ORGANISM: related to Lelystad PRRSV

<400> SEQUENCE: 89

Met Gln Trp Gly His Tyr Gly Ala Lys Ser Ala Asn Cys Leu Trp Met
1               5                   10                  15

Pro Ser Leu Ser Ser Leu Leu Val Trp Leu Ile Ser Leu Phe Ser Leu
            20                  25                  30

Pro Tyr Cys Leu Gly Ser Arg Ser Gln Gly Gly Tyr Trp Ser Phe Phe
        35                  40                  45

Ser Gly Trp Phe Ala Pro Arg Phe Ser Val Arg Ala Leu Pro Phe Thr
50                  55                  60

Leu Pro Asn Tyr Arg Lys Ser Tyr Glu Gly Leu Leu Pro Asn Cys Arg
65                  70                  75                  80

Pro Asp Val Pro Ser Phe Ala Phe Lys His Pro Leu Gly Met Phe Trp
                85                  90                  95

His Val Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
        115                 120                 125

Ser Glu Ala Thr Leu Thr Arg Leu Ser Asp Leu Asp Ile Val Thr His
130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Val Ser Val
        195                 200                 205

His Ala Ser Ile Phe Ser Ser Val Ala Ser Ser Val Thr Leu Phe Ile
210                 215                 220

Val Leu Trp Leu Arg Ile Pro Thr Leu Arg Tyr Val Phe Gly Phe His
225                 230                 235                 240

Trp Pro Thr Ala Thr His His Ser Ser
                245

<210> SEQ ID NO 90
<211> LENGTH: 265
<212> TYPE: PRT
<213> ORGANISM: related to Lelystad PRRSV

<400> SEQUENCE: 90

Met Ala His Gln Cys Ala Arg Phe His Phe Phe Leu Cys Gly Phe Ile
1               5                   10                  15

Cys Tyr Leu Val His Ser Ala Leu Ala Ser Asn Ser Ser Ser Thr Leu
            20                  25                  30

Cys Phe Trp Phe Pro Leu Ala His Gly Asn Thr Ser Phe Glu Leu Thr
        35                  40                  45

Ile Asn Tyr Thr Ile Cys Met Pro Cys Ser Thr Ser Gln Ala Ala Arg
        50                  55                  60

Gln Arg Leu Glu Pro Gly Arg Asn Met Trp Cys Lys Ile Gly His Asp
65                  70                  75                  80

```
Arg Cys Glu Glu Arg Asp His Asp Glu Leu Leu Met Ser Ile Pro Ser
                85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Arg His Gln Phe Ile Cys
            130                 135                 140

Ala Glu His Asp Gly His Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
                180                 185                 190

Leu Asn Ile Ser Trp Phe Leu Arg Arg Ser Pro Val Ser Pro Val Ser
                195                 200                 205

Arg Arg Ile Tyr Gln Ile Leu Arg Pro Thr Arg Pro Arg Leu Pro Val
            210                 215                 220

Ser Trp Ser Phe Arg Thr Ser Ile Val Ser Asp Leu Thr Gly Ser Gln
225                 230                 235                 240

Gln Arg Lys Arg Lys Leu Pro Ser Glu Ser Arg Pro Asn Val Val Lys
                245                 250                 255

Pro Ser Val Leu Pro Ser Thr Ser Arg
            260                 265

<210> SEQ ID NO 91
<211> LENGTH: 265
<212> TYPE: PRT
<213> ORGANISM: related to Lelystad PRRSV

<400> SEQUENCE: 91

Met Ala His Gln Cys Ala Arg Phe His Phe Leu Cys Gly Phe Ile
1               5                   10                  15

Cys Tyr Leu Val His Ser Ala Leu Ala Ser Asn Ser Ser Tyr Thr Leu
                20                  25                  30

Cys Phe Trp Phe Pro Leu Ala His Gly Asn Thr Ser Phe Glu Leu Thr
            35                  40                  45

Ile Asn Tyr Thr Ile Ser Met Pro Cys Ser Thr Ser Gln Ala Ala Arg
            50                  55                  60

Gln Arg Leu Glu Pro Gly Arg Asn Met Trp Cys Lys Ile Gly His Asp
65                  70                  75                  80

Arg Cys Glu Glu Arg Asp His Asp Glu Leu Leu Met Ser Ile Pro Ser
                85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Arg His Gln Phe Ile Cys
            130                 135                 140

Ala Glu His Asp Gly Gln Gly Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
                180                 185                 190
```

-continued

Leu Asn Ile Ser Trp Phe Leu Arg Arg Ser Pro Val Ser Pro Val Ser
        195                 200                 205

Arg Arg Ile Tyr His Ile Leu Arg Pro Thr Arg Pro Arg Leu Pro Val
    210                 215                 220

Ser Trp Ser Phe Arg Thr Ser Ile Val Ser Asp Leu Thr Gly Ser Gln
225                 230                 235                 240

Gln Arg Lys Arg Lys Phe Pro Ser Glu Ser Arg Pro Asn Val Val Lys
                245                 250                 255

Pro Ser Val Leu Pro Asn Thr Ser Arg
            260                 265

<210> SEQ ID NO 92
<211> LENGTH: 265
<212> TYPE: PRT
<213> ORGANISM: related to Lelystad PRRSV

<400> SEQUENCE: 92

Met Ala His Gln Cys Ala Cys Phe His Phe Phe Leu Cys Gly Phe Ile
1               5                   10                  15

Cys Tyr Leu Val His Ser Ala Leu Ala Ser Asn Ser Ser Ser Thr Leu
            20                  25                  30

Cys Phe Trp Phe Pro Leu Ala His Gly Asn Thr Ser Phe Glu Leu Thr
        35                  40                  45

Ile Asn Tyr Thr Ile Cys Met Pro Cys Leu Thr Ser Gln Ala Ala Asn
    50                  55                  60

Gln Arg Leu Glu Pro Gly Arg Asn Met Trp Cys Lys Ile Gly His Asp
65                  70                  75                  80

Arg Cys Glu Glu Arg Asp His Asp Glu Leu Leu Met Ser Ile Pro Ser
                85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Arg His Gln Phe Ile Cys
    130                 135                 140

Ala Glu His Asp Gly Gln Asn Ser Thr Val Ser Thr Gly His Asn Ile
145                 150                 155                 160

Ser Ala Ser Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Arg Leu Pro Val
    210                 215                 220

Ser Trp Ser Phe Arg Thr Ser Ile Val Ser Asp Leu Thr Gly Ser Gln
225                 230                 235                 240

Gln Arg Lys Gly Lys Phe Pro Ser Glu Asn Arg Pro Asn Val Val Lys
                245                 250                 255

Pro Ser Ala Leu Pro Asn Thr Ser Arg
            260                 265

<210> SEQ ID NO 93
<211> LENGTH: 265
<212> TYPE: PRT

<213> ORGANISM: related to Lelystad PRRSV

<400> SEQUENCE: 93

Met Ala His Gln Cys Ala Arg Phe His Phe Leu Cys Gly Leu Ile
1               5                   10                  15

Arg Tyr Leu Val His Ser Ala Val Ala Ser Asn Ser Ser Thr Leu
            20                  25                  30

Cys Phe Trp Phe Pro Leu Ala His Gly Asn Thr Ser Phe Glu Leu Thr
        35                  40                  45

Ile Asn Tyr Thr Ile Cys Met Pro Cys Ser Thr Ser His Ala Ala Arg
50                  55                  60

Gln Arg Leu Glu Pro Gly Arg Asn Met Trp Cys Lys Ile Gly His Asp
65                  70                  75                  80

Arg Cys Glu Glu Arg Asp His Asp Glu Leu Leu Met Pro Ile Pro Pro
                85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Gln His Gln Phe Ile Cys
130                 135                 140

Ala Glu His Asp Gly Gln Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Gln Thr Arg Pro Arg Leu Pro Val
210                 215                 220

Ser Trp Ser Phe Arg Thr Ser Ile Val Ser Asp Leu Thr Arg Ser Gln
225                 230                 235                 240

Gln Arg Lys Arg Lys Phe Pro Ser Glu Ser Arg Pro Asn Val Val Lys
                245                 250                 255

Pro Ser Val Leu Pro Ser Thr Ser Arg
            260                 265

<210> SEQ ID NO 94
<211> LENGTH: 265
<212> TYPE: PRT
<213> ORGANISM: related to Lelystad PRRSV

<400> SEQUENCE: 94

Met Ala His Gln Cys Ala Arg Phe His Phe Leu Cys Gly Leu Ile
1               5                   10                  15

Arg Tyr Leu Val His Ser Ala Val Ala Ser Asn Ser Ser Thr Leu
            20                  25                  30

Cys Phe Trp Phe Pro Leu Ala His Gly Asn Thr Ser Phe Glu Leu Thr
        35                  40                  45

Ile Asn Tyr Thr Ile Cys Met Pro Cys Ser Thr Ser His Ala Ala Arg
50                  55                  60

Gln Arg Leu Glu Pro Gly Arg Asn Met Trp Cys Lys Ile Gly His Asp
65                  70                  75                  80

Arg Cys Glu Glu Arg Asp His Asp Glu Leu Leu Met Pro Ile Pro Pro

```
                    85                  90                  95
Gly Tyr Asp Asn Leu Lys Leu Glu Gly Tyr Tyr Ala Trp Leu Ala Phe
                100                 105                 110
Leu Ser Phe Ser Tyr Ala Ala Gln Phe His Pro Glu Leu Phe Gly Ile
                115                 120                 125
Gly Asn Val Ser Arg Val Phe Val Asp Lys Gln His Gln Phe Ile Cys
            130                 135                 140
Ala Glu His Asp Gly Gln Asn Ser Thr Val Ser Thr Gly His Asn Ile
145                 150                 155                 160
Ser Ala Leu Tyr Ala Ala Tyr Tyr His His Gln Ile Asp Gly Gly Asn
                165                 170                 175
Trp Phe His Leu Glu Trp Leu Arg Pro Leu Phe Ser Ser Trp Leu Val
                180                 185                 190
Leu Asn Ile Ser Trp Phe Leu Arg Arg Ser Pro Val Ser Pro Val Ser
                195                 200                 205
Arg Arg Ile Tyr Gln Ile Leu Arg Gln Thr Arg Pro Arg Leu Pro Val
            210                 215                 220
Ser Trp Ser Phe Arg Thr Ser Ile Val Ser Asp Leu Thr Arg Ser Gln
225                 230                 235                 240
Gln Arg Lys Arg Lys Phe Pro Ser Glu Ser Arg Pro Asn Val Val Lys
                245                 250                 255
Pro Ser Val Leu Pro Ser Thr Ser Arg
                260                 265

<210> SEQ ID NO 95
<211> LENGTH: 265
<212> TYPE: PRT
<213> ORGANISM: related to Lelystad PRRSV
<220> FEATURE:
<221> NAME/KEY: misc_feature
<222> LOCATION: (60)..(60)
<223> OTHER INFORMATION: Xaa can be any naturally occurring amino acid

<400> SEQUENCE: 95

Met Ala His Gln Cys Ala Arg Phe His Phe Leu Cys Gly Phe Ile
1               5                   10                  15
Cys Tyr Leu Val His Ser Thr Leu Ala Ser Asn Ser Ser Phe Thr Leu
                20                  25                  30
Cys Phe Trp Phe Pro Leu Ala His Gly Asn Thr Ser Phe Glu Leu Thr
            35                  40                  45
Ile Asn Tyr Thr Ile Cys Met Pro Cys Ser Thr Xaa Gln Ala Ala His
        50                  55                  60
Gln Arg Leu Glu Pro Gly Arg Asn Met Trp Cys Lys Ile Gly His Asp
65                  70                  75                  80
Lys Cys Glu Glu Arg Asp His Asn Glu Leu Leu Met Pro Ile Pro Pro
                85                  90                  95
Gly Tyr Asp Asn Leu Lys Leu Glu Gly Tyr Tyr Ala Trp Leu Ala Phe
                100                 105                 110
Leu Ser Phe Ser Tyr Ala Ala Gln Phe His Pro Glu Leu Phe Gly Ile
                115                 120                 125
Gly Asn Val Ser Arg Val Phe Val Asp Lys Arg His Gln Phe Ile Cys
            130                 135                 140
Ala Glu His Asp Gly Leu Asn Ser Thr Val Ser Thr Gly His Asn Ile
145                 150                 155                 160
Ser Ala Leu Tyr Ala Ala Tyr Tyr His His Gln Ile Asp Gly Gly Asn
                165                 170                 175
```

```
Trp Phe His Leu Glu Trp Leu Arg Pro Leu Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Gln Leu Pro Val
    210                 215                 220

Ser Trp Ser Phe Arg Thr Ser Ile Val Ser Asp Leu Thr Arg Tyr Gln
225                 230                 235                 240

Gln Arg Lys Arg Lys Phe Pro Ser Glu Ser Arg Pro Asn Val Val Lys
                245                 250                 255

Pro Ser Val Leu Pro Ser Thr Ser Arg
                260                 265
```

<210> SEQ ID NO 96
<211> LENGTH: 265
<212> TYPE: PRT
<213> ORGANISM: related to Lelystad PRRSV

<400> SEQUENCE: 96

```
Met Ala His Gln Cys Ala Arg Phe His Phe Leu Cys Gly Phe Ile
1               5                   10                  15

Cys Tyr Phe Val His Ser Ala Leu Ala Ser Asn Ser Ser Ser Thr Leu
            20                  25                  30

Cys Phe Trp Phe Pro Leu Ala His Gly Asn Thr Ser Phe Glu Leu Thr
            35                  40                  45

Ile Asn Tyr Thr Val Cys Met Pro Cys Pro Thr Ser Gln Ala Ala Leu
50                  55                  60

Gln Arg Leu Glu Pro Gly Arg Asn Met Trp Cys Lys Ile Gly His Asp
65                  70                  75                  80

Arg Cys Glu Glu Arg Asp Gln Asp Glu Leu Leu Met Ser Ile Pro Ser
                85                  90                  95

Gly Tyr Asp Asn Leu Lys Leu Glu Gly Tyr Tyr Ala Trp Leu Ala Phe
                100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Trp His Gln Phe Ile Cys
            130                 135                 140

Ala Glu His Asp Gly Ser Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Phe Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Gln Leu Pro Val
    210                 215                 220

Ser Trp Ser Phe Arg Thr Ser Ile Val Ser Asp Leu Met Arg Ser Gln
225                 230                 235                 240

Gln Arg Lys Gly Lys Phe Pro Ser Gly Ser Arg Pro Asn Ala Val Lys
                245                 250                 255

Pro Ser Ala Leu Pro Asn Ile Ser Arg
                260                 265
```

```
<210> SEQ ID NO 97
<211> LENGTH: 261
<212> TYPE: PRT
<213> ORGANISM: related to Lelystad PRRSV

<400> SEQUENCE: 97

Met Ala His Gln Cys Ala Arg Phe His Phe Leu Cys Gly Phe Ile
1               5                   10                  15

Ser Tyr Leu Val His Ser Ala Leu Ala Ser Asn Ser Ser Thr Leu
            20                  25                  30

Cys Phe Trp Phe Pro Leu Ala His Gly Asn Thr Ser Phe Glu Leu Thr
        35                  40                  45

Ile Asn Tyr Thr Ile Cys Met Pro Cys Leu Thr Ser Gln Ala Ala Gln
50                  55                  60

Gln Arg Leu Glu Pro Gly Arg Thr Met Trp Cys Lys Ile Gly His Thr
65                  70                  75                  80

Thr Cys Glu Glu Arg Asp His Asp Glu Leu Ser Met Thr Ile Pro Ser
                85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Arg His Gln Phe Ile Cys
130                 135                 140

Ala Glu His Asp Gly Pro Asn Ser Thr Val Ser Ile Gly His Asn Ile
145                 150                 155                 160

Ser Ala Leu Tyr Ala Ala Tyr His His Gln Ile Asp Gly Gly Asn
                165                 170                 175

Trp Phe His Leu Glu Trp Leu Arg Pro Phe Phe Ser Ser Trp Leu Val
            180                 185                 190

Leu Asn Ile Ser Trp Phe Leu Arg Arg Ser Pro Val Ser Pro Ala Ser
        195                 200                 205

Arg Leu Ile Tyr Gln Ile Leu Arg Pro Thr Arg Pro Arg Leu Pro Val
210                 215                 220

Ser Trp Ser Phe Arg Thr Ser Ile Val Pro Gly Leu Thr Gly Pro Gln
225                 230                 235                 240

Gln Arg Lys Arg Glu Ser Arg Leu Asn Val Val Lys Pro Leu Val Pro
                245                 250                 255

Pro Ser Thr Ser Arg
            260

<210> SEQ ID NO 98
<211> LENGTH: 260
<212> TYPE: PRT
<213> ORGANISM: related to Lelystad PRRSV

<400> SEQUENCE: 98

Met Ala His Gln Cys Ala Arg Phe His Leu Phe Leu Cys Gly Phe Ile
1               5                   10                  15

Cys Tyr Ser Ile His Ser Ala Leu Ala Ser Asp Ser Asn Ser Thr Leu
            20                  25                  30

Cys Phe Trp Phe Pro Leu Ala His Gly Asn Thr Ser Phe Glu Leu Thr
        35                  40                  45

Ile Asn Tyr Thr Ile Cys Met Pro Cys Leu Thr Ser His Ala Ala Ser
50                  55                  60

Gln Arg Leu Glu Pro Gly Arg Asn Met Trp Cys Lys Ile Gly His Ser
```

```
                65                  70                  75                  80
Arg Cys Glu Glu Arg Asp His Asp Glu Leu Leu Met Ser Ile Pro Ser
                85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Arg His Gln Phe Ile Cys
            130                 135                 140

Ala Glu His Asp Gly Gln Asn Ser Thr Val Ser Ile Gly His Asn Ile
145                 150                 155                 160

Ser Ala Leu Tyr Ala Val Tyr Tyr His His Gln Ile Asp Gly Gly Asn
            165                 170                 175

Trp Phe His Leu Glu Trp Leu Arg Pro Phe Phe Ser Ser Trp Leu Val
            180                 185                 190

Leu Asn Ile Ser Trp Phe Leu Arg Arg Ser Pro Ala Ser Pro Val Ser
            195                 200                 205

Arg Arg Ile Tyr Gln Ile Leu Lys Pro Thr Arg Pro Arg Leu Pro Val
            210                 215                 220

Ser Trp Ser Phe Lys Thr Ser Val Ala Ala Gln Gln Arg Lys Met
225                 230                 235                 240

Lys Val Ser Gly Ser Arg Pro Asn Val Ala Lys Pro Ser Ala Pro Leu
            245                 250                 255

Asn Thr Ser Arg
            260

<210> SEQ ID NO 99
<211> LENGTH: 265
<212> TYPE: PRT
<213> ORGANISM: related to Lelystad PRRSV

<400> SEQUENCE: 99

Met Ala His Gln Cys Ala Arg Leu His Phe Phe Leu Cys Gly Phe Val
1               5                   10                  15

Ser Tyr Leu Val His Ser Ser Leu Ala Ser Asn Ser Ser Tyr Thr Leu
            20                  25                  30

Cys Phe Trp Phe Pro Leu Ala His Gly Asn Thr Ser Phe Glu Leu Thr
            35                  40                  45

Ile Asn Tyr Thr Ile Cys Met Pro Cys Thr Thr Ser Gln Ala Ala Gln
50                  55                  60

Gln Arg Leu Glu Pro Gly Arg Asn Met Trp Cys Arg Ile Gly His Thr
65                  70                  75                  80

Ser Cys Glu Glu Arg Asp His Asp Glu Leu Ser Met Thr Ile Pro Ser
                85                  90                  95

Gly Tyr Asp Asn Leu Lys Leu Glu Gly Tyr Tyr Ala Trp Leu Ala Phe
            100                 105                 110

Leu Ser Phe Ser Tyr Thr Ala Gln Phe His Pro Glu Leu Phe Gly Ile
            115                 120                 125

Gly Asn Val Ser Arg Val Phe Val Asp Lys Arg His Gln Phe Ile Cys
            130                 135                 140

Ala Glu His Asp Gly Gln Asn Ser Thr Val Ser Ile Thr His Asn Ile
145                 150                 155                 160

Ser Ala Leu Tyr Ala Val Tyr Tyr His His Gln Val Asp Gly Gly Asn
            165                 170                 175
```

```
Trp Phe His Leu Glu Trp Leu Arg Pro Phe Phe Ser Ser Trp Leu Val
            180                 185                 190

Leu Asn Ile Ser Trp Phe Leu Arg Arg Ser Pro Ala Ser Pro Val Ser
        195                 200                 205

Arg Arg Ile Tyr Gln Ile Leu Arg Pro Thr Arg Pro Arg Leu Pro Val
210                 215                 220

Ser Trp Ser Phe Lys Thr Ser Pro Val Pro Gly Leu Thr Gly His Gln
225                 230                 235                 240

Lys Gly Arg Lys Ala Thr Phe Thr Thr Ser His Leu Asn Val Val Lys
                245                 250                 255

Pro Ser Ala Phe Pro Ser Thr Ser Arg
            260                 265

<210> SEQ ID NO 100
<211> LENGTH: 183
<212> TYPE: PRT
<213> ORGANISM: related to Lelystad PRRSV

<400> SEQUENCE: 100

Met Ala Ala Ala Thr Leu Phe Leu Leu Ala Gly Ala Gln His Ile Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Ala Gly Phe Met Val Leu Gln
        35                  40                  45

Asp Ile Asn Cys Phe Arg Pro His Gly Val Ser Ala Ala Gln Glu Lys
    50                  55                  60

Ile Ser Phe Gly Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Val Asn Phe Thr Asp Tyr Val Ala His Val Thr Gln
130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Ser Leu
                165                 170                 175

Phe Ala Ile Leu Leu Ala Ile
            180

<210> SEQ ID NO 101
<211> LENGTH: 183
<212> TYPE: PRT
<213> ORGANISM: related to Lelystad PRRSV

<400> SEQUENCE: 101

Met Ala Ala Ala Ile Leu Phe Leu Leu Ala Gly Ala Gln His Ile Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Ala Gly Phe Met Val Leu Gln
        35                  40                  45
```

-continued

Asp Ile Asn Cys Leu Arg Pro His Gly Val Ser Ala Ala Gln Glu Lys
         50                  55                  60

Thr Ser Phe Gly Lys Ser Ser Gln Cys Arg Glu Ala Val Gly Thr Pro
 65                  70                  75                  80

Gln Tyr Ile Thr Ile Thr Ala Asn Val Thr Asp Glu Ser Tyr Leu Tyr
                 85                  90                  95

Asn Ala Asp Leu Leu Met Leu Ser Ala Cys Leu Phe Tyr Ala Ser Glu
             100                 105                 110

Met Ser Glu Lys Gly Phe Lys Val Ile Phe Gly Asn Val Ser Gly Val
         115                 120                 125

Val Ser Ala Cys Val Asn Phe Thr Asp Tyr Val Ala His Val Thr Gln
     130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
                180

<210> SEQ ID NO 102
<211> LENGTH: 183
<212> TYPE: PRT
<213> ORGANISM: related to Lelystad PRRSV

<400> SEQUENCE: 102

Met Ala Ala Ala Thr Leu Phe Leu Leu Ala Gly Ala Gln Tyr Ile Met
  1               5                  10                  15

Val Ser Glu Ala Phe Ala Cys Lys Pro Cys Phe Ser Thr His Leu Ser
             20                  25                  30

Asp Ile Glu Thr Asn Thr Thr Ala Ala Ala Gly Phe Met Val Leu Gln
         35                  40                  45

Asp Ile Asn Cys Leu Arg Pro His Gly Val Ser Ala Ala Gln Glu Glu
         50                  55                  60

Ile Pro Phe Gly Lys Ser Ser Gln Cys Arg Glu Ala Val Gly Thr Pro
 65                  70                  75                  80

Gln Tyr Ile Thr Ile Thr Ala Asn Val Thr Asp Glu Ser Tyr Leu Tyr
                 85                  90                  95

Asn Ala Asp Leu Leu Met Leu Ser Ala Cys Leu Phe His Ala Ser Glu
             100                 105                 110

Met Ser Glu Lys Gly Phe Lys Val Ile Phe Gly Asn Val Ser Gly Val
         115                 120                 125

Val Ser Ala Cys Val Asn Phe Thr Asp Tyr Val Ala His Val Thr Gln
     130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
                180

<210> SEQ ID NO 103
<211> LENGTH: 183
<212> TYPE: PRT
<213> ORGANISM: related to Lelystad PRRSV

<400> SEQUENCE: 103

Met Ala Ala Ala Thr Leu Phe Leu Leu Ala Gly Ala Gln Tyr Ile Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Gly Phe Met Val Leu Gln
            35                  40                  45

Asp Ile Asn Cys Leu Arg Pro His Gly Val Ser Ala Gln Glu Glu
50                  55                  60

Ile Pro Phe Gly Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe His Ala Ser Glu
                100                 105                 110

Met Ser Gly Lys Gly Phe Lys Val Ile Phe Trp Asn Val Ser Gly Val
                115                 120                 125

Val Ser Ala Cys Val Asn Phe Thr Asp Tyr Val Ala His Val Thr Gln
130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
                180

<210> SEQ ID NO 104
<211> LENGTH: 183
<212> TYPE: PRT
<213> ORGANISM: related to Lelystad PRRSV

<400> SEQUENCE: 104

Met Ala Ala Ala Thr Leu Phe Leu Leu Ala Gly Ala Gln Tyr Ile Met
1               5                   10                  15

Val Ser Glu Ala Phe Ala Cys Lys Pro Cys Phe Ser Thr His Leu Ser
            20                  25                  30

Asp Ile Lys Thr Asn Thr Thr Ala Ala Gly Phe Met Val Leu Gln
            35                  40                  45

Asn Ile Asn Cys Leu Arg Pro His Gly Val Pro Ala Ala Gln Glu Lys
50                  55                  60

Ile Pro Leu Glu Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
                100                 105                 110

Met Ser Glu Lys Gly Phe Lys Val Ile Phe Gly Asn Val Ser Gly Val
                115                 120                 125

Val Ser Ala Cys Val Asn Phe Thr Asp Tyr Val Ala His Val Thr Gln
130                 135                 140

His Thr Gln Gln His His Leu Val Ile Asp His Ile Arg Leu Pro His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
                180

<210> SEQ ID NO 105
<211> LENGTH: 183
<212> TYPE: PRT
<213> ORGANISM: related to Lelystad PRRSV

<400> SEQUENCE: 105

Met Ala Ala Ala Ile Leu Phe Leu Leu Ala Gly Ala Gln His Ile Met
1               5                   10                  15

Val Ser Glu Ala Phe Ala Cys Lys Pro Cys Phe Ser Thr His Leu Ser
            20                  25                  30

Asp Ile Lys Thr Asn Thr Thr Ala Ser Ala Gly Phe Met Val Leu Gln
        35                  40                  45

Asp Ile Asn Cys Phe Arg Leu His Gly Val Pro Ala Ala Gln Lys Thr
    50                  55                  60

Asn Ser Phe Gly Lys Pro Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Val Asn Phe Thr Asp Tyr Val Ala His Val Thr Gln
    130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Val Leu Leu Ala Ile
            180

<210> SEQ ID NO 106
<211> LENGTH: 183
<212> TYPE: PRT
<213> ORGANISM: related to Lelystad PRRSV

<400> SEQUENCE: 106

Met Ala Ala Ala Ile Leu Phe Leu Leu Ala Gly Ala Gln Tyr Leu Met
1               5                   10                  15

Val Ser Glu Ala Phe Ala Cys Lys Pro Cys Phe Ser Thr His Leu Ser
            20                  25                  30

Asp Ile Lys Thr Asn Thr Thr Ala Ala Ala Gly Phe Met Val Leu Gln
        35                  40                  45

Asp Ile Asn Cys Leu Arg Pro His Gly Val Ser Thr Ala Gln Glu Asn
    50                  55                  60

Ile Pro Phe Gly Lys Pro Ser Gln Cys Arg Glu Ala Val Gly Ile Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Val Asn Phe Thr Asp Tyr Val Ala His Val Ile Gln
    130                 135                 140

-continued

His Thr Gln Gln His His Leu Val Ile Asp His Ile Arg Leu Leu His
145                 150                 155                 160

Phe Leu Thr Pro Ser Thr Met Arg Trp Ala Thr Thr Ile Ala Cys Leu
                165                 170                 175

Phe Ala Ile Leu Leu Ala Ile
            180

<210> SEQ ID NO 107
<211> LENGTH: 183
<212> TYPE: PRT
<213> ORGANISM: related to Lelystad PRRSV

<400> SEQUENCE: 107

Met Ala Thr Ala Ile Leu Phe Leu Leu Ala Ser Ala Gln His Leu Val
1               5                   10                  15

Val Ser Glu Ala Phe Ala Cys Lys Pro Cys Phe Ser Thr His Leu Ser
            20                  25                  30

Asn Ile Glu Thr Asn Thr Thr Ala Ala Ala Gly Phe Leu Val Leu Gln
        35                  40                  45

Asp Ile Ser Cys Val Gln Leu Arg Gly Gly Gln Gln Thr Ser Gln Ser
50                  55                  60

Val Thr His Gly Lys Pro Ser Gln Cys Arg Glu Ala Ile Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
        115                 120                 125

Val Ser Ala Cys Ile Asn Phe Thr Asp Tyr Val Ala His Val Thr Gln
130                 135                 140

His Thr Gln Gln His His Leu Ile Ile Asp His Val Arg Leu Leu His
145                 150                 155                 160

Phe Leu Thr Pro Ser Ala Met Arg Trp Val Thr Thr Ile Ala Cys Leu
                165                 170                 175

Phe Ala Ile Leu Leu Ala Ile
            180

<210> SEQ ID NO 108
<211> LENGTH: 183
<212> TYPE: PRT
<213> ORGANISM: related to Lelystad PRRSV

<400> SEQUENCE: 108

Met Ala Ala Ala Phe Leu Phe Leu Leu Val Gly Ala Gln Tyr Phe Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Ala Gly Phe Met Val Leu Gln
        35                  40                  45

Asp Ile Ser Cys Leu Arg Pro Tyr Gly Val Ser Ala Thr His Glu Asn
50                  55                  60

Ile Ser Phe Gly Lys Pro Ser Gln Cys Arg Glu Ala Val Gly Ile Pro
65                  70                  75                  80

Gln Tyr Ile Thr Ile Thr Ala Asn Val Thr Asp Glu Ser Tyr Leu Tyr
                85                  90                  95

```
Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
            115                 120                 125

Val Ser Ala Cys Val Asn Phe Thr Asp Tyr Val Ala His Val Ile Gln
130                 135                 140

His Thr Gln Gln His His Leu Val Ile Asp His Ile Arg Leu Leu His
145                 150                 155                 160

Phe Leu Thr Pro Ser Thr Met Arg Trp Ala Thr Thr Ile Ala Cys Leu
                165                 170                 175

Phe Ala Ile Leu Leu Ala Ile
            180

<210> SEQ ID NO 109
<211> LENGTH: 183
<212> TYPE: PRT
<213> ORGANISM: related to Lelystad PRRSV

<400> SEQUENCE: 109

Met Ala Thr Ala Val Leu Phe Leu Leu Ala Gly Ala Gln His Leu Met
1               5                   10                  15

Val Ser Glu Ala Phe Ala Cys Lys Pro Cys Phe Ser Thr His Leu Ser
            20                  25                  30

Asp Ile Lys Thr Asn Thr Thr Ala Ala Gly Phe Met Val Leu Gln
            35                  40                  45

Asp Ile Asn Cys Leu Gln Pro Arg Gly Val Ser Ala Thr His Gly Ser
        50                  55                  60

Ala Pro Phe Lys Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
            115                 120                 125

Val Ser Ala Cys Val Asn Phe Thr Asp Tyr Val Ile His Val Thr Gln
130                 135                 140

His Thr Gln Gln His His Leu Ala Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
            180

<210> SEQ ID NO 110
<211> LENGTH: 200
<212> TYPE: PRT
<213> ORGANISM: related to Lelystad PRRSV

<400> SEQUENCE: 110

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asn Ser Ser Thr Tyr Gln Tyr Ile Tyr Asn Leu Thr
            35                  40                  45
```

```
Ile Cys Glu Leu Asn Gly Thr Asp Trp Leu Ser Ser His Phe Gly Trp
 50                  55                  60

Ala Val Glu Thr Phe Val Phe Tyr Pro Val Ala Thr His Ile Leu Ser
 65                  70                  75                  80

Leu Gly Phe Leu Thr Thr Ser His Phe Phe Asp Ala Leu Gly Leu Gly
                 85                  90                  95

Ala Val Ser Thr Ala Gly Phe Val Gly Gly Arg Tyr Val Leu Cys Ser
                100                 105                 110

Val Tyr Gly Ala Cys Ala Phe Ala Ala Phe Val Cys Phe Val Ile Arg
                115                 120                 125

Ala Ala Lys Asn Cys Met Ala Cys Arg Tyr Ala Arg Thr Arg Phe Thr
            130                 135                 140

Asn Phe Ile Val Asp Asp Arg Gly Arg Val His Arg Trp Lys Ser Pro
145                 150                 155                 160

Ile Val Val Glu Lys Leu Gly Arg Ala Glu Val Asp Gly Asn Leu Val
                165                 170                 175

Thr Ile Lys His Val Val Leu Glu Gly Val Lys Ala Gln Pro Leu Thr
                180                 185                 190

Arg Thr Ser Ala Glu Gln Trp Glu
            195                 200

<210> SEQ ID NO 111
<211> LENGTH: 201
<212> TYPE: PRT
<213> ORGANISM: related to Lelystad PRRSV

<400> SEQUENCE: 111

Met Arg Cys Ser His Lys Leu Gly Arg Phe Leu Thr Pro His Ser Cys
 1               5                  10                  15

Phe Trp Trp Phe Phe Leu Leu Cys Thr Gly Leu Ser Trp Ser Phe Ala
                 20                  25                  30

Asp Gly Asn Gly Asp Ser Ser Thr Tyr Gln Tyr Ile Tyr Asn Leu Thr
             35                  40                  45

Ile Cys Glu Leu Asn Gly Thr Asp Trp Leu Ser Ser His Phe Gly Trp
 50                  55                  60

Ala Val Glu Thr Phe Val Leu Tyr Pro Val Ala Thr His Ile Leu Ser
 65                  70                  75                  80

Leu Gly Phe Leu Thr Thr Ser His Phe Phe Asp Ala Leu Gly Leu Gly
                 85                  90                  95

Ala Val Ser Ala Ala Gly Phe Val Gly Gly Arg Tyr Val Leu Cys Ser
                100                 105                 110

Val Tyr Gly Ala Cys Ala Phe Ala Ala Phe Val Cys Phe Val Ile Arg
                115                 120                 125

Ala Ala Lys Asn Cys Met Ala Cys Arg Tyr Ala Arg Thr Arg Phe Thr
            130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
                180                 185                 190

Arg Thr Ser Ala Glu Gln Trp Glu Ala
            195                 200
```

```
<210> SEQ ID NO 112
<211> LENGTH: 201
<212> TYPE: PRT
<213> ORGANISM: related to Lelystad PRRSV

<400> SEQUENCE: 112

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Ser Ser Thr Tyr Gln Tyr Ile Tyr Asn Leu Thr
        35                  40                  45

Ile Cys Glu Leu Asn Gly Thr Asp Trp Leu Ser Ser His Phe Ser Trp
50                  55                  60

Ala Val Glu Thr Phe Val Leu Tyr Pro Val Val Thr His Ile Leu Ser
65                  70                  75                  80

Leu Gly Phe Leu Thr Thr Ser His Phe Phe Asp Ala Leu Gly Leu Gly
            85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Ile
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200

<210> SEQ ID NO 113
<211> LENGTH: 201
<212> TYPE: PRT
<213> ORGANISM: related to Lelystad PRRSV

<400> SEQUENCE: 113

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asp Ser Ser Thr Tyr Gln Tyr Ile Tyr Asn Leu Thr
            35                  40                  45

Ile Cys Glu Leu Asn Gly Thr Asp Trp Leu Ser Ser His Phe Gly Trp
50                  55                  60

Ala Val Glu Thr Phe Val Leu Tyr Pro Val Ala Thr His Ile Leu Ser
65                  70                  75                  80

Leu Gly Phe Leu Thr Thr Ser His Leu Phe Asp Ala Leu Gly Leu Gly
            85                  90                  95

Val Val Ser Thr Ala Gly Leu Val Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
```

```
                130                 135                 140
Asn Phe Ile Val Asp Asp Arg Gly Arg Val His Arg Trp Arg Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
                180                 185                 190

Arg Thr Ser Ala Glu Gln Trp Glu Ala
                195                 200

<210> SEQ ID NO 114
<211> LENGTH: 201
<212> TYPE: PRT
<213> ORGANISM: related to Lelystad PRRSV

<400> SEQUENCE: 114

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
                20                  25                  30

Asp Gly Asn Gly Asp Ser Ser Thr Tyr Gln Tyr Ile Tyr Asn Leu Thr
                35                  40                  45

Ile Cys Glu Leu Asn Gly Thr Asp Trp Leu Ser Ser His Phe Gly Trp
50                  55                  60

Ala Val Glu Thr Phe Val Leu Tyr Pro Val Ala Thr His Ile Leu Ser
65                  70                  75                  80

Leu Gly Phe Leu Thr Thr Ser His Leu Phe Asp Ala Leu Gly Leu Gly
                85                  90                  95

Val Val Ser Thr Ala Gly Leu Val Gly Gly Arg Tyr Val Leu Cys Ser
                100                 105                 110

Ala Tyr Gly Ala Cys Ala Phe Ala Ala Phe Val Cys Phe Val Ile Arg
                115                 120                 125

Ala Ala Lys Asn Cys Met Ala Cys Arg Tyr Ala Arg Thr Arg Phe Thr
130                 135                 140

Asn Phe Ile Val Asp Asp Arg Gly Arg Val His Arg Trp Lys Ser Pro
145                 150                 155                 160

Ile Val Val Glu Asn Leu Gly Lys Ala Glu Val Asp Gly Asn Leu Val
                165                 170                 175

Thr Ile Lys His Val Val Leu Glu Gly Val Lys Ala Gln Pro Leu Thr
                180                 185                 190

Arg Thr Ser Ala Glu Gln Trp Glu Ala
                195                 200

<210> SEQ ID NO 115
<211> LENGTH: 201
<212> TYPE: PRT
<213> ORGANISM: related to Lelystad PRRSV

<400> SEQUENCE: 115

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
                20                  25                  30

Asp Gly Asn Gly Asp Ser Ser Thr Tyr Gln Tyr Ile Tyr Asn Leu Thr
                35                  40                  45

Ile Cys Glu Leu Asn Gly Thr Asp Trp Leu Ser Ser His Phe Gly Trp
```

```
                    50                  55                  60
Ala Val Glu Thr Phe Val Leu Tyr Pro Val Ala Thr His Ile Leu Ser
 65                  70                  75                  80

Leu Gly Phe Leu Thr Thr Ser His Leu Phe Asp Ala Leu Gly Leu Gly
                     85                  90                  95

Val Val Ser Thr Ala Gly Leu Val Ser Gly Arg Tyr Val Leu Cys Ser
                    100                 105                 110

Val Tyr Gly Ala Cys Ala Phe Ala Ala Phe Val Cys Phe Val Ile Arg
                115                 120                 125

Ala Ala Lys Asn Cys Met Ala Cys Arg Tyr Ala Arg Thr Arg Phe Thr
                130                 135                 140

Asn Phe Ile Val Asp Asp Arg Gly Arg Val His Arg Trp Lys Ser Pro
145                 150                 155                 160

Ile Val Val Glu Asn Leu Gly Lys Ala Glu Val Asp Gly Asn Leu Val
                165                 170                 175

Thr Ile Lys His Val Val Leu Glu Gly Val Lys Ala Gln Pro Leu Thr
                180                 185                 190

Arg Thr Ser Ala Glu Gln Trp Glu Ala
                195                 200

<210> SEQ ID NO 116
<211> LENGTH: 201
<212> TYPE: PRT
<213> ORGANISM: related to Lelystad PRRSV

<400> SEQUENCE: 116

Met Arg Cys Ser His Lys Leu Gly Arg Phe Leu Thr Pro His Ser Cys
  1               5                  10                  15

Phe Trp Trp Leu Phe Leu Leu Cys Thr Gly Leu Ser Trp Ser Phe Ala
                 20                  25                  30

Asp Gly Asn Gly Asp Ser Ser Thr Tyr Gln Tyr Ile Tyr Asn Leu Thr
                 35                  40                  45

Ile Cys Glu Leu Asn Gly Thr Asp Trp Leu Ser Ser His Phe Gly Trp
 50                  55                  60

Ala Val Glu Thr Phe Val Leu Tyr Pro Val Ala Thr His Ile Leu Ser
 65                  70                  75                  80

Leu Gly Phe Leu Thr Thr Ser His Leu Val Asp Ala Leu Gly Leu Gly
                     85                  90                  95

Val Val Ser Thr Ala Gly Leu Val Gly Gly Arg Tyr Val Leu Cys Ser
                    100                 105                 110

Val Tyr Gly Ala Cys Ala Phe Ala Ala Phe Val Cys Phe Val Ile Arg
                115                 120                 125

Ala Ala Lys Asn Cys Met Ala Cys Arg Tyr Ala Arg Thr Arg Phe Thr
                130                 135                 140

Asn Phe Ile Val Asp Asp Arg Gly Arg Val His Arg Trp Lys Ser Pro
145                 150                 155                 160

Ile Val Val Glu Asn Leu Gly Lys Ala Glu Val Asp Gly Asn Leu Val
                165                 170                 175

Thr Ile Lys His Val Val Leu Glu Gly Val Lys Ala Gln Pro Leu Thr
                180                 185                 190

Arg Thr Ser Ala Glu Gln Trp Glu Ala
                195                 200

<210> SEQ ID NO 117
<211> LENGTH: 201
```

<212> TYPE: PRT
<213> ORGANISM: related to Lelystad PRRSV

<400> SEQUENCE: 117

Met Arg Cys Pro His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
            20                  25                  30

Asp Gly Asn Gly Asp Ser Ser Thr Tyr Gln Tyr Ile Tyr Asn Leu Thr
        35                  40                  45

Ile Cys Glu Leu Asn Gly Thr Asp Trp Leu Ser Ser His Leu Gly Trp
    50                  55                  60

Ala Val Glu Thr Phe Val Leu Tyr Pro Val Ala Thr His Ile Leu Ser
65                  70                  75                  80

Leu Gly Phe Leu Thr Thr Ser His Leu Phe Asp Ala Leu Gly Leu Gly
                85                  90                  95

Val Val Ser Thr Ala Gly Leu Ile Gly Gly Arg Tyr Val Leu Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
    130                 135                 140

Asn Phe Ile Val Asp Asp Arg Gly Arg Val His Arg Trp Lys Ser Pro
145                 150                 155                 160

Ile Val Val Glu Asn Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200

<210> SEQ ID NO 118
<211> LENGTH: 201
<212> TYPE: PRT
<213> ORGANISM: related to Lelystad PRRSV

<400> SEQUENCE: 118

Met Arg Cys Ser His Lys Leu Gly Arg Phe Leu Thr Pro His Ser Cys
1               5                   10                  15

Phe Trp Trp Leu Phe Leu Leu Cys Ile Gly Leu Ser Trp Ser Phe Ala
            20                  25                  30

Asp Gly Asn Gly Ser Ser Ser Thr Tyr Gln Tyr Ile Tyr Asp Leu Thr
        35                  40                  45

Ile Cys Glu Leu Asn Gly Thr Asp Trp Leu Ser Ser His Phe Gly Trp
    50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Phe Cys Ser
            100                 105                 110

Val Tyr Gly Ala Cys Ala Phe Ala Ala Phe Val Cys Phe Val Ile Arg
        115                 120                 125

Ala Ala Lys Asn Cys Met Ala Cys Arg Tyr Ala Arg Thr Arg Phe Thr
    130                 135                 140

```
Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Tyr Lys Ala Gln Pro Leu Thr
            180                 185                 190

Arg Thr Ser Ala Gln Gln Trp Glu Ala
        195                 200

<210> SEQ ID NO 119
<211> LENGTH: 201
<212> TYPE: PRT
<213> ORGANISM: related to Lelystad PRRSV

<400> SEQUENCE: 119

Met Ser Ser His Lys Leu Gly Arg Phe Leu Thr Pro His

Gln Ser Thr Asn Arg Val Ala Phe Thr Leu Gly Ala Val Ala Leu
65                  70                  75                  80

Leu Trp Gly Val Tyr Ser Phe Thr Glu Ser Trp Lys Phe Ile Thr Ser
                85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Ser Ile Ser Ala Ser Gly
        115                 120                 125

Asn Arg Ala Tyr Ala Val Arg Lys Pro Gly Leu Thr Ser Val Asn Gly
    130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170

<210> SEQ ID NO 121
<211> LENGTH: 173
<212> TYPE: PRT
<213> ORGANISM: related to Lelystad PRRSV

<400> SEQUENCE: 121

Met Gly Ser Leu Asp Asp Phe Cys Tyr Asp Ser Ile Ala Ala Gln Lys
1               5                   10                  15

Leu Val Leu Ala Phe Ser Ile Thr Tyr Thr Pro Ile Met Ile Tyr Ala
                20                  25                  30

Leu Lys Val Ser Arg Gly Arg Leu Leu Gly Leu Leu His Ile Leu Ile
            35                  40                  45

Phe Leu Asn Cys Ser Phe Thr Phe Gly Tyr Met Thr Tyr Val His Phe
    50                  55                  60

Gln Ser Thr Asn Arg Val Ala Leu Thr Leu Gly Ala Ala Val Ala Leu
65                  70                  75                  80

Leu Trp Gly Val Tyr Ser Phe Thr Glu Ser Trp Lys Phe Ile Thr Ser
                85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Pro Ile Ser Ala Ser Gly
        115                 120                 125

Asn Arg Ala Tyr Ala Val Arg Lys Pro Gly Leu Thr Ser Val Asn Gly
    130                 135                 140

Thr Leu Val Pro Gly Leu Arg Asn Leu Val Leu Gly Gly Lys Arg Ala
145                 150                 155                 160

Val Lys Arg Gly Val Val Asn Leu Val Lys Tyr Gly Arg
                165                 170

<210> SEQ ID NO 122
<211> LENGTH: 173
<212> TYPE: PRT
<213> ORGANISM: related to Lelystad PRRSV

<400> SEQUENCE: 122

Met Gly Ser Leu Asp Asp Phe Cys Asn Asp Ser Ala Ala Val Gln Lys
1               5                   10                  15

Leu Val Leu Ala Phe Ser Ile Thr Tyr Thr Pro Ile Met Ile Tyr Ala
                20                  25                  30

Leu Lys Val Ser Arg Gly Arg Leu Leu Gly Leu Leu His Ile Leu Ile
            35                  40                  45

```
Phe Leu Asn Cys Ser Phe Thr Phe Gly Tyr Met Thr His Val His Phe
    50                  55                  60
Gln Ser Thr Asn Arg Val Ala Phe Thr Leu Gly Ala Val Val Ala Leu
65                  70                  75                  80
Leu Trp Gly Val Tyr Ser Phe Thr Glu Ser Trp Lys Phe Ile Thr Ser
                85                  90                  95
Arg Cys Arg Leu Cys Cys Leu Gly Arg Arg Tyr Ile Leu Ala Pro Ala
            100                 105                 110
His His Val Glu Ser Ala Ala Gly Leu His Ser Ile Pro Ala Ser Gly
        115                 120                 125
Asn Arg Ala Tyr Ala Val Arg Lys Pro Gly Leu Thr Ser Val Asn Gly
    130                 135                 140
Thr Leu Val Pro Gly Leu Arg Ser Leu Val Leu Gly Gly Lys Arg Ala
145                 150                 155                 160
Val Lys Arg Gly Val Val Asn Leu Val Lys Tyr Gly Arg
                165                 170

<210> SEQ ID NO 123
<211> LENGTH: 173
<212> TYPE: PRT
<213> ORGANISM: related to Lelystad PRRSV

<400> SEQUENCE: 123

Met Gly Ser Leu Asp Arg Phe Cys Asn Glu Pro Asp Ala Val Gln Gln
1               5                   10                  15
Leu Val Leu Ala Phe Ser Ile Thr Tyr Thr Pro Ile Met Ile Tyr Ala
                20                  25                  30
Leu Lys Val Ser Arg Gly Arg Leu Leu Gly Leu Leu His Ile Leu Ile
            35                  40                  45
Phe Leu Asn Cys Ser Phe Thr Phe Gly Tyr Met Thr Tyr Val His Phe
    50                  55                  60
Gln Ser Thr Asn Arg Val Ala Leu Thr Leu Gly Ala Val Val Thr Leu
65                  70                  75                  80
Leu Trp Gly Val Tyr Ser Phe Thr Glu Ser Trp Lys Phe Ile Thr Ser
                85                  90                  95
Arg Cys Arg Leu Cys Cys Leu Gly Arg Arg Tyr Ile Leu Ala Pro Ala
            100                 105                 110
His His Val Glu Ser Ala Ala Gly Leu His Ser Ile Pro Ala Ser Gly
        115                 120                 125
Asn Arg Ala Tyr Ala Val Arg Lys Pro Gly Leu Thr Ser Val Asn Gly
    130                 135                 140
Thr Leu Val Pro Gly Leu Arg Gly Leu Val Leu Gly Gly Lys Arg Ala
145                 150                 155                 160
Val Lys Arg Gly Val Val Asn Leu Val Lys Tyr Gly Arg
                165                 170

<210> SEQ ID NO 124
<211> LENGTH: 173
<212> TYPE: PRT
<213> ORGANISM: related to Lelystad PRRSV

<400> SEQUENCE: 124

Met Gly Ser Leu Asp Gly Phe Cys Asp Glu Pro Ala Ala Val Gln Lys
1               5                   10                  15
Leu Val Leu Ala Phe Ser Thr Thr Tyr Thr Pro Ile Met Ile Tyr Ala
                20                  25                  30
```

Leu Lys Val Ser Arg Gly Arg Leu Leu Gly Leu Leu His Ile Leu Ile
          35                  40                  45

Phe Leu Asn Cys Ser Phe Thr Phe Gly Tyr Met Thr Tyr Val His Phe
 50                  55                  60

Gln Ser Ile Asn Arg Val Ala Phe Thr Leu Gly Ala Val Val Ala Leu
65                  70                  75                  80

Leu Trp Gly Val Tyr Ser Phe Thr Glu Ser Trp Lys Ser Ile Thr Ser
                 85                  90                  95

Arg Cys Arg Leu Cys Cys Leu Gly Arg Arg Tyr Ile Leu Ala Pro Ala
             100                 105                 110

His His Val Glu Ser Ala Ala Gly Leu His Ser Ile Pro Ala Ser Gly
         115                 120                 125

Asn Arg Ala Tyr Ala Val Arg Lys Pro Gly Leu Thr Ser Val Asn Gly
     130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                 165                 170

<210> SEQ ID NO 125
<211> LENGTH: 173
<212> TYPE: PRT
<213> ORGANISM: related to Lelystad PRRSV

<400> SEQUENCE: 125

Met Gly Ser Ile Asp Gly Phe Cys Asp Pro Ala Ala Val Gln Lys
1               5                   10                  15

Leu Val Leu Ala Phe Ser Ile Thr Tyr Thr Pro Ile Met Ile Tyr Ala
                 20                  25                  30

Leu Lys Val Ser Arg Gly Arg Leu Leu Gly Leu Leu His Ile Leu Ile
          35                  40                  45

Phe Leu Asn Cys Ser Phe Ala Phe Gly Tyr Met Thr Tyr Val His Phe
 50                  55                  60

Gln Ser Thr Asn Arg Val Ala Ile Thr Leu Gly Ala Val Val Ala Leu
65                  70                  75                  80

Leu Trp Gly Val Tyr Ser Phe Ile Glu Ser Trp Lys Phe Ile Thr Phe
                 85                  90                  95

Arg Cys Arg Leu Cys Cys Leu Gly Arg Arg Tyr Ile Leu Ala Pro Ala
             100                 105                 110

His His Val Glu Ser Ala Ala Gly Leu His Pro Ile Pro Ala Ser Gly
         115                 120                 125

Asn Arg Ala Tyr Ala Val Arg Lys Pro Gly Leu Thr Ser Val Asn Gly
     130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                 165                 170

<210> SEQ ID NO 126
<211> LENGTH: 173
<212> TYPE: PRT
<213> ORGANISM: related to Lelystad PRRSV

<400> SEQUENCE: 126

Met Gly Gly Leu Asp Asp Phe Cys Phe Asp His Tyr Ser Ala Gln Lys
1               5                   10                  15

Leu Val Leu Ala Phe Ser Ile Thr Tyr Thr Pro Ile Met Ile Tyr Ala
            20                  25                  30

Leu Lys Ala Ser Arg Gly Arg Leu Leu Gly Leu Leu His Ile Leu Ile
        35                  40                  45

Phe Leu Asn Cys Ala Phe Thr Phe Gly Tyr Met Thr Tyr Val His Phe
    50                  55                  60

Gln Ser Thr His Arg Val Ala Leu Thr Met Gly Ala Val Val Ala Leu
65                  70                  75                  80

Leu Trp Gly Val Tyr Ser Phe Ile Glu Ser Trp Lys Phe Ile Thr Ser
                85                  90                  95

Arg Cys Arg Leu Cys Cys Leu Gly Arg Arg Tyr Ile Leu Ala Pro Ala
                100                 105                 110

His His Val Glu Ser Ala Ala Gly Leu His Pro Ile Pro Ala Ser Gly
            115                 120                 125

Asn Arg Gly Tyr Ala Leu Arg Lys Pro Gly Leu Thr Ser Val Asn Gly
        130                 135                 140

Thr Leu Val Pro Gly Leu Arg Ser Leu Val Leu Gly Gly Lys Arg Ala
145                 150                 155                 160

Val Arg Arg Gly Val Val Asn Leu Val Lys Tyr Gly Arg
                165                 170

<210> SEQ ID NO 127
<211> LENGTH: 173
<212> TYPE: PRT
<213> ORGANISM: related to Lelystad PRRSV

<400> SEQUENCE: 127

Met Gly Gly Leu Asp Asn Phe Cys Tyr Asp Ser Thr Ala Ala Gln Lys
1               5                   10                  15

Val Leu Leu Ala Phe Ser Ile Thr Tyr Thr Pro Ile Met Ile Tyr Ala
            20                  25                  30

Leu Lys Val Ser Arg Gly Arg Leu Leu Gly Leu Leu His Ile Leu Ile
        35                  40                  45

Phe Leu Asn Cys Ser Phe Thr Phe Gly Tyr Met Thr Tyr Glu His Phe
    50                  55                  60

Glu Ser Thr Asn Arg Val Ala Leu Thr Met Gly Ala Val Val Ala Leu
65                  70                  75                  80

Leu Trp Gly Val Tyr Ser Phe Ile Glu Ser Trp Lys Phe Val Thr Phe
                85                  90                  95

Arg Cys Arg Leu Cys Cys Leu Gly Arg Gln Tyr Ile Leu Ala Pro Ala
                100                 105                 110

His His Val Glu Ser Ala Ala Gly Leu His Ser Ile Pro Ala Ser Gly
            115                 120                 125

Asn Gln Ala Tyr Ala Val Arg Lys Pro Gly Leu Thr Ser Val Asn Gly
        130                 135                 140

Thr Leu Val Pro Gly Leu Arg Ser Leu Val Leu Gly Gly Lys Arg Ala
145                 150                 155                 160

Val Lys Arg Gly Leu Val Asn Leu Val Lys Tyr Gly Arg
                165                 170

<210> SEQ ID NO 128
<211> LENGTH: 173
<212> TYPE: PRT
<213> ORGANISM: related to Lelystad PRRSV

<400> SEQUENCE: 128

Met Ala Gly Leu Asp Asp Phe Cys Tyr Asp Ser Thr Ala Val Gln Lys
1               5                   10                  15

Leu Val Leu Ala Phe Ser Ile Thr Tyr Thr Pro Ile Met Ile Tyr Ala
            20                  25                  30

Leu Lys Val Ser Arg Gly Arg Leu Gly Leu Leu His Ile Leu Ile
            35                  40                  45

Phe Leu Asn Cys Ser Phe Thr Phe Gly Tyr Met Thr Tyr Val His Phe
    50                  55                  60

Glu Ser Ser Asn Arg Val Ala Phe Thr Met Gly Ala Val Val Thr Leu
65                  70                  75                  80

Leu Trp Gly Ile Tyr Ser Phe Ile Glu Ser Trp Lys Phe Val Thr Ser
                85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Pro Ile Pro Ala Ser Gly
            115                 120                 125

Asn Gln Ala Tyr Ala Val Arg Lys Pro Gly Leu Thr Ser Val Asn Gly
130                 135                 140

Thr Leu Val Pro Gly Leu Arg Gly Leu Val Leu Gly Gly Lys Arg Ala
145                 150                 155                 160

Val Lys Arg Gly Met Val Asn Leu Val Lys Tyr Gly Arg
                165                 170

<210> SEQ ID NO 129
<211> LENGTH: 173
<212> TYPE: PRT
<213> ORGANISM: related to Lelystad PRRSV

<400> SEQUENCE: 129

Met Gly Ser Leu Asp Asn Phe Cys His Asp Pro Thr Ala Val Gln Lys
1               5                   10                  15

Val Leu Leu Ala Phe Ser Ile Thr Tyr Thr Pro Val Met Ile Tyr Ala
            20                  25                  30

Leu Lys Val Ser Arg Gly Arg Leu Leu Gly Leu Leu His Ile Leu Ile
            35                  40                  45

Phe Leu Asn Cys Ser Phe Thr Phe Gly Tyr Leu Thr Tyr Val His Phe
    50                  55                  60

Asp Ser Thr Asn Arg Val Ala Leu Thr Met Gly Ala Val Val Ala Leu
65                  70                  75                  80

Leu Trp Gly Ile Tyr Ser Phe Ile Glu Ser Trp Lys Phe Val Val Ser
                85                  90                  95

Arg Cys Arg Leu Cys Cys Leu Gly Arg Gln Tyr Ile Leu Ala Pro Ala
            100                 105                 110

His His Val Glu Ser Ala Ala Gly Leu His Pro Leu Pro Ala Cys Gly
            115                 120                 125

Asn Gln Ala Phe Ala Val Arg Lys Pro Gly Leu Thr Ser Val Asn Gly
130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170

<210> SEQ ID NO 130
<211> LENGTH: 70
<212> TYPE: PRT
<213> ORGANISM: related to Lelystad PRRSV -continued

<400> SEQUENCE: 130

Met Gly Ser Leu Trp Ser Lys Ile Ser Gln Leu Phe Val Asp Ala Phe
1               5                   10                  15

Thr Glu Phe Leu Val Ser Val Val Asp Ile Ala Ile Phe Leu Ala Ile
            20                  25                  30

Leu Phe Gly Phe Thr Val Ala Gly Trp Leu Leu Val Phe Leu Leu Arg
        35                  40                  45

Val Val Cys Ser Ala Leu Leu Arg Ser Arg Ser Ala Ile His Ser Pro
    50                  55                  60

Glu Leu Ser Lys Val Leu
65                  70

<210> SEQ ID NO 131
<211> LENGTH: 70
<212> TYPE: PRT
<213> ORGANISM: related to Lelystad PRRSV

<400> SEQUENCE: 131

Met Gly Ser Leu Trp Ser Lys Ile Ser Gln Leu Phe Val Asp Ala Phe
1               5                   10                  15

Thr Glu Phe Leu Val Ser Val Val Asp Ile Val Ile Phe Leu Ala Ile
            20                  25                  30

Leu Phe Gly Phe Thr Val Ala Gly Trp Leu Leu Val Phe Leu Leu Arg
        35                  40                  45

Val Val Cys Ser Ala Leu Leu Arg Ser Arg Ser Ala Ile His Ser Pro
    50                  55                  60

Glu Leu Ser Lys Val Leu
65                  70

<210> SEQ ID NO 132
<211> LENGTH: 70
<212> TYPE: PRT
<213> ORGANISM: related to Lelystad PRRSV

<400> SEQUENCE: 132

Met Gly Ser Leu Trp Ser Lys Ile Ser Gln Leu Phe Val Asp Ala Phe
1               5                   10                  15

Thr Glu Phe Leu Val Ser Val Val Asp Ile Val Ile Phe Leu Ala Ile
            20                  25                  30

Leu Phe Gly Phe Thr Val Ala Gly Trp Leu Leu Val Phe Leu Leu Arg
        35                  40                  45

Val Val Cys Ser Ala Leu Leu Arg Ser Arg Ser Ala Val His Ser Pro
    50                  55                  60

Glu Leu Ser Lys Val Leu
65                  70

<210> SEQ ID NO 133
<211> LENGTH: 70
<212> TYPE: PRT
<213> ORGANISM: related to Lelystad PRRSV

<400> SEQUENCE: 133

Met Gly Ser Leu Trp Ser Lys Ile Ser Gln Leu Phe Val Asp Ala Phe
1               5                   10                  15

Thr Glu Phe Leu Val Ser Val Val Asp Ile Val Ile Phe Leu Ala Ile
            20                  25                  30

Leu Phe Gly Phe Thr Val Ala Gly Trp Leu Leu Val Phe Leu Leu Arg

```
                35                  40                  45
Val Val Cys Ser Ala Ile Leu Arg Ser Arg Ser Ala Ile His Ser Pro
         50                  55                  60
Glu Leu Ser Lys Val Leu
 65                  70

<210> SEQ ID NO 134
<211> LENGTH: 70
<212> TYPE: PRT
<213> ORGANISM: related to Lelystad PRRSV

<400> SEQUENCE: 134

Met Gly Ser Leu Trp Ser Lys Ile Ser Gln Leu Phe Val Asp Ala Phe
 1               5                  10                  15
Thr Glu Phe Leu Val Ser Val Val Asp Ile Val Ile Phe Leu Ala Ile
                20                  25                  30
Leu Phe Gly Phe Thr Val Ala Gly Trp Leu Leu Val Phe Leu Leu Arg
                35                  40                  45
Val Val Cys Ser Ala Phe Leu Arg Ser Arg Ser Ala Ile His Ser Pro
         50                  55                  60
Glu Leu Ser Lys Val Leu
 65                  70

<210> SEQ ID NO 135
<211> LENGTH: 70
<212> TYPE: PRT
<213> ORGANISM: related to Lelystad PRRSV

<400> SEQUENCE: 135

Met Gly Ser Leu Trp Ser Lys Ile Thr Gln Leu Phe Val Asp Ala Phe
 1               5                  10                  15
Thr Glu Phe Leu Val Ser Val Val Asp Ile Ile Ile Phe Leu Ala Ile
                20                  25                  30
Leu Phe Gly Phe Thr Val Ala Gly Trp Leu Leu Val Phe Leu Leu Arg
                35                  40                  45
Val Val Cys Ser Ala Ile Leu Arg Ser Arg Ser Ala Ile His Ser Pro
         50                  55                  60
Glu Leu Ser Lys Val Leu
 65                  70

<210> SEQ ID NO 136
<211> LENGTH: 70
<212> TYPE: PRT
<213> ORGANISM: related to Lelystad PRRSV

<400> SEQUENCE: 136

Met Gly Ser Leu Trp Ser Lys Ile Ser Gln Leu Phe Val Asp Ala Phe
 1               5                  10                  15
Thr Glu Phe Leu Val Ser Val Val Asp Ile Val Ile Phe Leu Ala Ile
                20                  25                  30
Leu Phe Gly Phe Thr Val Ala Gly Trp Leu Leu Val Phe Leu Leu Arg
                35                  40                  45
Leu Val Cys Ser Ala Ile Leu Arg Ser Arg Ser Ala Ile His Ser Pro
         50                  55                  60
Glu Leu Ser Lys Val Leu
 65                  70

<210> SEQ ID NO 137
```

```
<211> LENGTH: 70
<212> TYPE: PRT
<213> ORGANISM: related to Lelystad PRRSV

<400> SEQUENCE: 137

Met Gly Ser Leu Trp Ser Lys Ile Ser Gln Leu Phe Val Asp Ala Phe
1               5                   10                  15

Thr Glu Phe Leu Val Ser Val Val Asp Ile Val Ile Phe Leu Ala Ile
                20                  25                  30

Leu Phe Gly Phe Thr Val Ala Gly Trp Leu Leu Val Phe Leu Leu Arg
            35                  40                  45

Val Val Cys Ser Ala Leu Leu Arg Ser Arg Ser Ala Ile His Pro Pro
        50                  55                  60

Glu Leu Ser Lys Ile Leu
65                  70

<210> SEQ ID NO 138
<211> LENGTH: 70
<212> TYPE: PRT
<213> ORGANISM: related to Lelystad PRRSV

<400> SEQUENCE: 138

Met Gly Ser Leu Trp Ser Lys Ile Ser Gln Leu Phe Val Asp Ala Phe
1               5                   10                  15

Thr Glu Phe Leu Val Ser Val Val Asp Ile Val Ile Phe Leu Ala Ile
                20                  25                  30

Leu Phe Gly Phe Thr Val Ala Gly Trp Leu Leu Val Phe Leu Phe Arg
            35                  40                  45

Leu Val Cys Ser Ala Ile Leu Arg Ser Arg Ser Ala Ile His Ser Ser
        50                  55                  60

Glu Leu Ser Lys Val Leu
65                  70

<210> SEQ ID NO 139
<211> LENGTH: 70
<212> TYPE: PRT
<213> ORGANISM: related to Lelystad PRRSV

<400> SEQUENCE: 139

Met Gly Ser Leu Trp Ser Lys Ile Ser Gln Leu Phe Val Asp Ala Phe
1               5                   10                  15

Thr Glu Phe Leu Val Ser Val Val Asp Ile Val Ile Phe Leu Ala Ile
                20                  25                  30

Leu Phe Gly Phe Thr Val Ala Gly Trp Leu Leu Val Phe Leu Leu Arg
            35                  40                  45

Val Val Cys Ser Ala Phe Leu Arg Ser Arg Ser Ala Ile His Ser Ser
        50                  55                  60

Glu Leu Ser Lys Val Leu
65                  70
```